US011168336B2

(12) United States Patent
Ykema et al.

(10) Patent No.: US 11,168,336 B2
(45) Date of Patent: Nov. 9, 2021

(54) TOMATO PLANT RESISTANT TO TOMATO BROWN RUGOSE FRUIT VIRUS

(71) Applicant: Enza Zaden Beheer B.V., Enkhuizen (NL)

(72) Inventors: Marieke Ykema, Harlingen (NL); Cornelis Walter Verweij, Enkhuizen (NL); Sergio De La Fuente Van Bentem, Amsterdam (NL); Frederic Michel Pierre Perefarres, Roquetas de Mar (ES)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 17/196,655

(22) Filed: Mar. 9, 2021

(65) Prior Publication Data

US 2021/0238627 A1 Aug. 5, 2021

Related U.S. Application Data

(63) Continuation of application No. PCT/EP2019/084272, filed on Dec. 9, 2019.

(30) Foreign Application Priority Data

Jan. 14, 2019 (WO) ................. PCT/EP2019/050830

(51) Int. Cl.
*C12N 15/82* (2006.01)
*C07K 14/08* (2006.01)

(52) U.S. Cl.
CPC .......... *C12N 15/8283* (2013.01); *C07K 14/08* (2013.01)

(58) Field of Classification Search
None
See application file for complete search history.

(56) References Cited

U.S. PATENT DOCUMENTS 7,148,397 B2 12/2006 Osumi et al.
2016/0100538 A1* 4/2016 Aarden .................... A01H 5/08 800/265

FOREIGN PATENT DOCUMENTS

WO WO-2004020594 A2 3/2004
WO WO-2018219941 A1 12/2018
WO WO-2020018783 A1 1/2020
WO WO-2020147921 A1 7/2020
WO WO-2020148021 A1 7/2020

OTHER PUBLICATIONS

"Call for submission of new research proposals for 2016," State of Israel Ministry of Agriculture and Rural Development. Partial English translation included (pp. 1, 2, beginning of p. 3, p. 8 section 4, and pp. 13 and 14 regarding section 4 item 1). 29 pages.
Alignment of genomic sequence of sample 2015-406 with SEQ ID No. 1 of EP3325502. 5 pages.
Alishiri et al., (2013). "Prevalence of Tobacco mosaic virus in Iran and Evolutionary Analyses of the Coat Protein Gene," Plant Pathol. J., 29(3):260-273.
Alliance Seeds, "Tomato—Candela F1," Product sheet of Candela. Available at <https://allianceseeds.co.za/wp-content/uploads/2018/03/tech-sheet-TOMATO-CANDELA-F1.pdf>, 1 page.
Approval of the Research Grant entitled «Coping with Tm-2 resistance-breaking Tobamo viruses in tomatoes» including the allocation of funds, and allocating the grant No. 20-10-0070. Dated Oct. 6, 2015. Partial English translation included (first page). 3 pages.
Confirmation of Research Commencement for the plan N° 2611159 18 / 20-10-0070. State of Israel Ministry of Agriculture and Rural Development. Dated Feb. 11, 2017. English translation included. 2 pages.
Cover page of Volcani Center internal grant. State of Israel Ministry of Agriculture and Rural Development. Dated Dec. 28, 2016. Partial English translation included (first page). 5 pages.
Declaration and CV of Abdullah Ahmad Sa'sa, employee of Rijk Zwaan Export B.V., a subsidiary of the opponent. Dated Mar. 16, 2021. 4 pages.
Declaration and CV of Daniel Ludeking, employee of Rijk Zwaan Breeding B.V., a subsidiary of the opponent. Dated Mar. 16, 2021. 6 pages.
Declaration and CV of Hamzeh Zuhdi Habboub, employee of Rijk Zwaan Export B.V., a subsidiary of the opponent. Dated Mar. 16, 2021. 3 pages.
Declaration and CV of Robert John Dekker, University of Amsterdam. Dated Mar. 2021. 7 pages.
Dombrovsky Declaration, Annex A (CV of Dombrovsky), and Annex B (list of exhibits), dated Mar. 2021, filed in Opposition against EP3325502. 7 pages.
Email confirmation that sequencing of the virus was finished, dated Jul. 8, 2015, from University of Amsterdam to Enza Zaden, 1 page.
Email from Enza Zaden on sequencing of AE50 isolate from Saudi Arabia in Jun. 2015, 1 page.
Email string from Enza Zaden on virus availability from Jan. to Jun. 2015, 4 pages.
Fedex Airway bill 1, dated May 10, 2015 (Annex 1 to D7). 1 page.
Fedex Airway bill 2, dated Jul. 9, 2015 (Annex 2 to D7). 1 page.
Ganz et al., (2014). "Coping with Tomato Tobamoviruses," The Ministry of Agriculture and Rural Development. English translation included. 8 pages.
Ganz et al., (2015). "TMV and ToMV Tomato Viruses Alert," The Ministry of Agriculture and Rural Development. English translation included. 8 pages.

(Continued)

*Primary Examiner* — Elizabeth F Mcelwain
(74) *Attorney, Agent, or Firm* — Morrison & Foerster LLP

(57) ABSTRACT

The present invention relates to a tomato, *Solanum lycopersicum*, plant that is resistant to Tobamovirus, wherein the plant comprises one or more genomic sequences conferring Tobamovirus resistance. More specifically the invention relates to a tomato plant that is resistant to Tomato Brown Rugose Fruit Virus (TBRFV). The present invention further relates to a genomic sequence or locus providing resistance to Tobamovirus. In addition, the present invention relates to methods for proving a tomato plant that is resistant to Tobamovirus.

7 Claims, 6 Drawing Sheets

Figure 1:
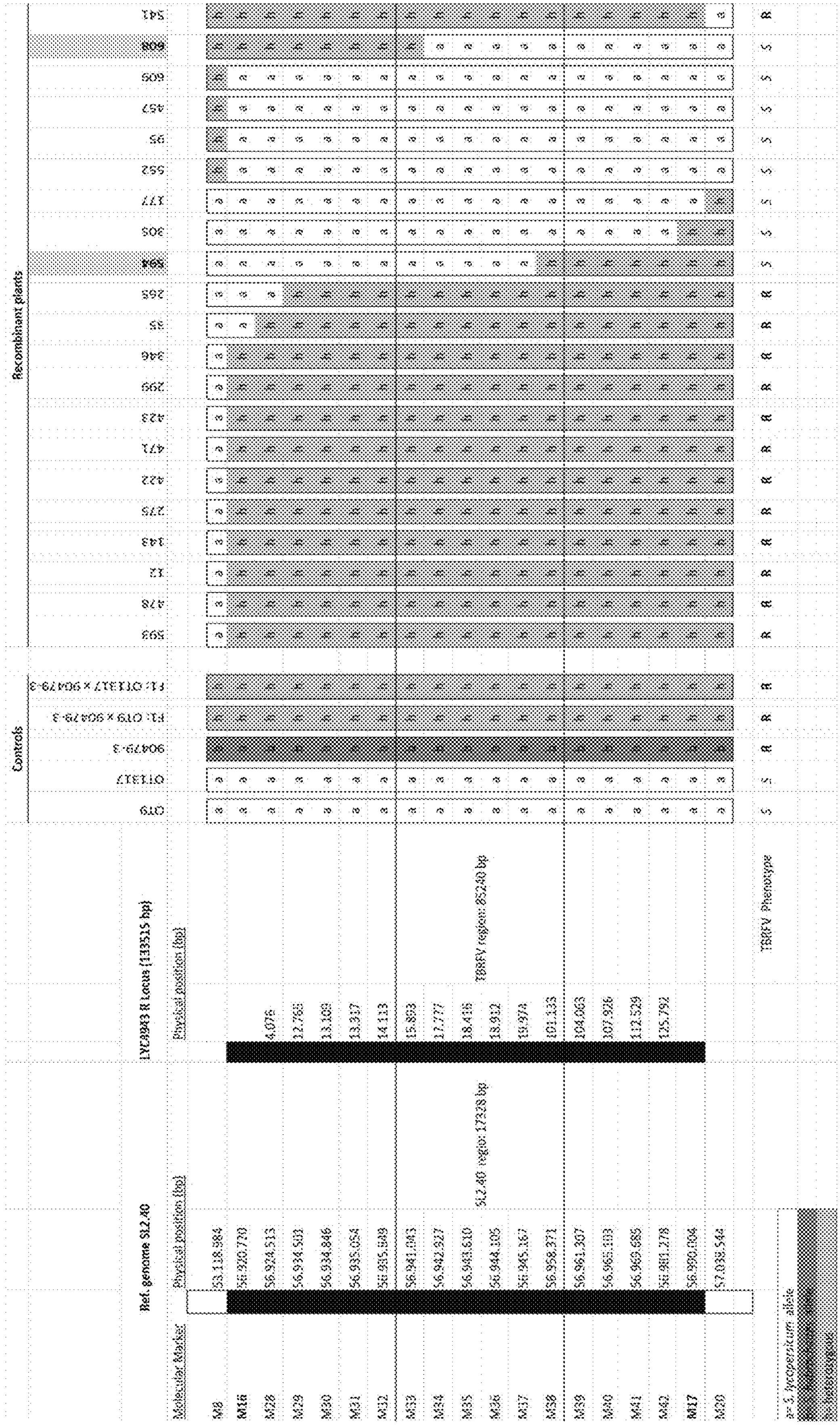

Specification includes a Sequence Listing.

(56) References Cited

OTHER PUBLICATIONS

GenBank deposit: KT383474, “Tomato brown rugose fruit virus isolate Tom1-Jo, complete genome,” Available at <https://www.ncbi.nlm.nih.gov/nuccore/KT383474>, 3 pages.
GenBank deposit: KX619418, “Tomato brown rugose fruit virus-Israeli isolate TBRFV-IL, complete genome,” Available at <https://www.ncbi.nlm.nih.gov/nuccore/KX619418>, 3 pages.
Hudcovicova et al., (2015). “Molecular Selection of Tomato and Pepper Breeding Lines Possessing Resistance Alleles Against Tobamoviruses,” Agriculture (Polnohospodarstvo), 61(1):33-37. DOI:61.10.1515/agri-2015-0008.
International Committee on Taxonomy of Viruses (ICTV), “Genus: Tobamovirus,” Available at <https://talk.ictvonline.org/ictv-reports/ictv_online_report/positive-sense-rna-viruses/w/virgaviridae/672/genus-tobamovirus>, 6 pages.
Invitation to National Conference on Edible Tomatoes on Jun. 30, 2015, for Gantz S, Katari L, Ilani S, Avraham I, Ziger I, dated before Jun. 2015. English translation included. 2 pages.
Lanfermeijer et al., (2005). “The products of the broken Tm-2 and the durable Tm-22 resistance genes from tomato differ in four amino acids,” Journal of Experimental Botany, 56:2925-2933.
Lapidot Declaration, Annex A (CV of Moshe Lapidot), and Annex B (list of exhibits), dated Mar. 2021, filed in Opposition against EP3325502. 6 pages.
Lapidot, Moshe. Request of a Research Grant: Temporary ID code 0781-003, “Coping with Tm-2 resistance-breaking Tobamo viruses in the Tomato (Hebrew title)/New solutions for new resistance-breaking tobamoviruses in tomato (English title),” dated May 18, 2015. English translation included. 6 pages.
Letschert et al., (2002). “Detection and differentiation of serologically cross-reacting tobamoviruses of economical importance by RT-PCR and RT-PCR-RFLP,” J Viral Methods, 106(1):1-10. doi: 10.1016/s0166-0934(02)00135-0. PMID: 12367724.
Li et al., (2013). “Complete Genome Sequence of a New Tobamovirus Naturally Infecting Tomatoes in Mexico,” Genome Announcements, 1(5):1-2.
Moreira et al., (2003). “Characterization of a new Tomato mosaic virus strain isolated from tomato in the State of Sao Paulo, Brazil,” Fitopatol. bras., 28(6):602-607. English abstract only.
Moya et al., (2004). “The population genetics and evolutionary epidemiology of RNA viruses,” Nature Reviews, vol. 2, pp. 279-288.
Notice of opposition by Enza Zaden Beheer B.V., filed in relation to EP3325502, dated Mar. 16, 2021, 29 pages.
Notice of opposition by Rijk Zwaan Zaadteelt & Zaadhandel B.V., filed in relation to EP3325502, dated Mar. 17, 2021, 33 pages.
Notice of opposition by Syngenta Crop Protection AG, filed in relation to EP3325502, dated Mar. 15, 2021, 17 pages.
Notice of opposition by Vilmorin & Cie, filed in relation to EP3325502, dated Mar. 16, 2021, 35 pages.
Panthee et al., (2013). “Novel molecular marker associated with Tm2a gene conferring resistance to tomato mosaic virus in tomato,” Plant Breeding, 132:413-416. DOI:10.1111/pbr.12076.
Partial transcript of genomic sequence of Tobacco mosaic virus strain Ohio V, NCBI sequence database, published Jan. 10, 2012, 1 page.
Partial transcript of sequence of Israel virus 01, NCBI sequence database, 1 page.
Partial transcript of sequence of Jordan virus 03, NCBI sequence database, 1 page.
Rast, A. Th. B., (1975). Thesis titled “Variability of tobacco mosaic virus in relation to control of tomato mosaic in glasshouse tomato crops by resistance breeding and cross protection,” Institute of Phytopathological Research, Wageningen, 88 pages.
Report on sequencing new ToMV virus, Jul. 2015, “Identification of viruses by small RNA sequencing,” University of Amsterdam. 5 pages.
Run report of sequencing project performed by University of Amsterdam on new virus isolate, dated Jul. 7, 2015, 5 pages.
Screenshot of Enza Zaden database transcript, showing the dates of receipt of virus isolated from Jordan and Saudi Arabia, 1 page.
Screenshot of the FASTA file created on Jul. 13, 2015 by the University of Amsterdam, on the virus genome sequence, 1 page.
Sequence alignment of KT383474 against SEQ ID No. 1 of EP3325502 using NCBI Blast, 5 pages.
Sequence alignment of KT383474 and KX619418 against SEQ ID No. 1 of EP3325502, 14 pages.
Sequence alignment of KX619418 against SEQ ID No. 1 of EP3325502 using NCBI Blast, 6 pages.
Sequence alignments of KX619418 and KT383474 against MS838349 (SEQ ID No. 1 of WO2017/012951) using NCBI Blast, 14 pages.
UPOV, (2011). Guidelines for the conduct of tests for distinctness, uniformity and stability: Tomato. TG/44/11. 71 pages.
UPOV, Technical Committee (2015). Partial revision of the test guidelines for sweet pepper, hot pepper, paprika, chili (Document TG/76/8). TC/51/30. 25 pages.
UPS Airway bill 3, dated Jul. 7, 2015 (Annex 3 to D7). 1 page.
Vegetables Bulletin—Field and Vegetables No. 285. Oct. 2015. The Vegetable Growers Organization. Partial English translation included (p. 1; p. 9 partially, pp. 10-11, 26 and 27 completely). 51 pages.
Weber et al., (1998). “Tm-22 Resistance in Tomato Requires Recognition of the Carboxy Terminus of the Movement Protein of Tomato Mosaic Virus”. MPMI, vol. 11, No. 6, pp. 498-503.
Bolger A et al., (2014). “The genome of the stress-tolerant wild tomato species Solanum pennellii,” Nat Genet., 46(9):1034-1038, 6 pages.
Fraiture M et al., (2019). “MinION sequencing technology to characterize unauthorized GM petunia plants circulating on the European Union market,” Scientific reports, 9(1):7141, 8 pages.
GenBank Accession No. AP009297.1, “Solanum lycopersicum genomic DNA, chromosome 8, clone: C08SLe0082C24, complete sequence,” Dec. 11, 2006, 28 pages.
Huang C et al., (2012). “Virus-induced gene silencing and its application in plant functional genomics,” Sci China Life Sci., 55(2):99-108.
Kadirvel P et al., (2012). “Mapping of QTLs in tomato line FLA456 associated with resistance to a virus causing tomato yellow leaf curl disease”, Euphytica, 190(2):297-308.
Li J et al., (2018). “Linkage between the I-3 gene for resistance to Fusarium wilt race 3 and increased sensitivity to bacterial spot in tomato,” Theoretical and Applied Genetics, 131:145-155.
Luria N et al., (2017). “A New Israeli Tobamovirus Isolate Infects Tomato Plants Harboring Tm-22 Resistance Genes”, PLOS One, 12(1):e0170429, 19 pages.
Maayan Y et al., (2018). “Using genomic analysis to identify tomato Tm-2 resistance-breaking mutations and their underlying evolutionary path in a new and emerging tobamovirus”, Archives of Virology, 163(7):1863-1875, 13 pages.
Oosumi T et al., (2009). “Gene Rpi-bt1 from Solanum bulbocastanum Confers Resistance to Late Blight in Transgenic Potatoes,” Am. J. Potato Res., 86 (6):456-465.
Salem N et al., (2015) “A new tobamovirus infecting tomato crops in Jordan”, Archives of Virology, 161(2):503-506, 4 pages.
Shi A et al., (2011). “Molecular Markers for Tm-2 Alleles of Tomato Mosaic Virus Resistance in Tomato”, American Journal of Plant Sciences, 2(2):180-189.
Song J et al., (2006). “Gene RB cloned from Solanum bulbocastanum confers broad spectrum resistance to potato late blight,” Proc Natl Acad Sci USA, 100(16):9128-9133.
Tiwari J.K. et al., (available in NCBI database, Nov. 28, 2019). “Whole genome sequencing of Interspecific potato hybrid MSH/14-112,” Crop Improvement, ICAR—Central Potato Research Institute, 5 pages. (Relevant portion of sequence only).
Van der Vossen E et al., (2003). “An ancient R gene from the wild potato species Solanum bulbocastanum confers broad-spectrum resistance to Phytophthora infestans in cultivated potato and tomato,” The Plant Journal, 36(6):867-882.
Van Lieshout N et al., (2020). “Solyntus, the new highly contiguous reference genome for potato (*Solanum tuberosum*),” G3: Genes, Genomes, Genetics, 10(10):3489-3495.

(56) References Cited

OTHER PUBLICATIONS

Workman R et al., (2018). “High Molecular Weight DNA Extraction from Recalcitrant Plant Species for Third Generation Sequencing,” Nature, Protocol Exchange, 15 pages. (Preliminary version of a manuscript).
Arens et al., (2010). “Development and evaluation of robust molecular markers linked to disease resistance in tomato for distinctness, uniformity and stability testing,” Theor Appl Genet, vol. 120, 655-664.
Declaration of Jochem Altena, dated Jul. 30, 2021, submitted in Opposition proceedings for EP3325502, 1 page.
Luria et al., (2018). “A local strain of Paprika mild mottle virus breaks L(3) resistance in peppers and is accelerated in Tomato brown rugose fruit virus-infected Tm-2(2)-resistant tomatoes,” Virus Genes, DOI: 10.1007/s11262-018-1539-2, 10 pages.
Reply of the patent proprietor to the notice(s) of opposition, filed on Aug. 9, 2021 in Opposition proceedings for EP3325502, 86 pages.
Turina et al., (2016). “First report of Tomato mottle mosaic virus in tomato crops in Israel,” New Disease Reports 33, 1. <http://dx.doi.org/10.5197/j.2044-0588.2016.033.001>, 1 page.
Van Esse et al., (2020). “Genetic modification to improve disease resistance in crops,” New Phytologist, 225: 70-86, doi: 10.1111/nph.15967.
Vosman et al., (2006). “Minutes of first project meeting: Development and evaluation of molecular markers linked to disease resistance genes for tomato DUS testing (option 1a),” Available at <https://cpvo.europa.eu/sites/default/files/documents/techreports/Apendices_final_report_CPVO_tomato_project.pdf>, 4 pages.

* cited by examiner

| | Chromosome 8_SL2.40 | LYC4943 R Locus (133516 bp) | Controls | | | Recombinant plants | | |
|---|---|---|---|---|---|---|---|---|
| Molecular Marker | Physical position (bp) | Physical position (bp) | OT9 | 90479-3 | BC2: OT9 x 90479-3 | 15321-02 | 15321-03 | 15321-07 |
| M33 | 56.941.043 | 15.893 | a | b | h | h | h | a |
| M34 | 56.942.927 | 17.777 | a | b | h | a | h | h |
| M35 | 56.943.610 | 18.416 | a | b | h | a | h | h |
| M36 | 56.944.105 | 18.912 | a | b | h | a | h | h |
| M37 | 56.945.167 | 19.974 | a | b | h | a | h | h |
| M-SEQ 10 | | 36.480 | - | + | + | - | + | + |
| M-SEQ 11_1 | | 48.748 | - | + | + | - | + | + |
| M-SEQ 11_2 | | 52.303 | - | + | + | - | + | + |
| M-SEQ 14 | | 77.410 | - | + | + | - | - | + |
| M38 | 56.958.371 | 101.133 | a | b | h | a | a | h |

SL2.40 regio: 17.328 bp

TBRFV region: 85.240 bp

| | OT9 | 90479-3 | BC2: OT9 x 90479-3 | 15321-02 | 15321-03 | 15321-07 |
|---|---|---|---|---|---|---|
| TBRFV Phenotype | S | R | R | S | S | R |
| TBRFV ELISA (absorption at 405nm) | 1527 | | | 1109 | 1547 | 893 |
| TBRFV qPCR (Ct value) | 22,6 | | | 23,4 | 22,4 | 36,6 |

a = *S. lycopersicum* allele
b = *S. habrochaites* allele
h = heterozygous
+ = *S. habrochaites* allele present
- = *S. habrochaites* allele absent

Figure 4

TOMATO PLANT RESISTANT TO TOMATO BROWN RUGOSE FRUIT VIRUS

CROSS REFERENCE TO RELATED APPLICATIONS

This application is a continuation application of International Application No. PCT/EP2019/084272, filed Dec. 9, 2019, which claims priority to International Application No. PCT/EP2019/050830, filed Jan. 14, 2019, each of which is incorporated herein by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 701802018401SEQLIST.TXT, date recorded: Feb. 3, 2021, size: 446 KB).

DESCRIPTION

The present invention relates to a plant of the *S. lycopersicum* species that is resistant to Tobamovirus, wherein the plant comprises one or more genomic sequences. More specifically the invention relates to tomato plants (*S. lycopersicum*) that are resistant to Tomato Brown Rugose Fruit Virus (TBRFV). The present invention further relates to a genomic sequence or locus providing resistance to Tobamovirus. Furthermore the present invention relates to methods for providing a *S. lycopersicum* plant that is resistant to Tobamovirus.

Tobamovirus is a genus in the virus family Virgaviridae that infects plants, including plants of the Solanaceae family, such as tobacco, potato, tomato, and eggplant and are among the most serious threats to vegetable crops in the world. Tobamoviruses are particularly a problem in tomato crops grown in protected environments and are transmitted over long distances through external seed contamination, and mechanically from plant to plant through common culture practices through workers' hands, clothes, tools, and are capable to preserve infectivity in seeds and contaminated soil. Furthermore, common weeds, often asymptomatic when infected by the virus comprise a cryptic reservoir between growth cycles.

Tobamovirus infections can have disastrous effects in crops when they become contaminated. Prevention of infection, by, for example, raising seedlings in a virus free environment is generally costly and/or unfriendly to the environment. In addition, these methods do not always provide satisfactory results.

Tobamoviruses are non-enveloped, with helical rod geometries, and helical symmetry. Viral particles are rod-shaped and have a diameter of around 18 nm, and a length of 300 to 310 nm. Their positive-sense single stranded RNA genomes are linear and non-segmented, and around 6.3 to 6.5 kb in length. There are over 35+ virus species in this genus including Tomato Mosaic Virus (ToMV) or Tobacco Mosaic Virus (TMV), Tomato Mild Mottle Virus (ToMMV), and the recently newly discovered Tomato Brown Rugose Fruit Virus (TBRFV).

In tomato, naming of the four strains of Tobamovirus (more specifically ToMV) currently recognized (Tm-0, Tm-1, Tm-2 and Tm-$2^2$) is based on the introgressed resistance (R) genes Tm1, Tm2 and Tm$2^2$ from related wild species. The Tm1 gene was introgressed from *Solanum*

*habrochaites* and is incompletely dominant. The Tm2 and Tm$2^2$ genes were introgressed from *Solanum peruvianum* and confer dominant complete resistance to ToMV. However new strains of Tobamovirus have emerged as resistance is overcome and recently resistance-breaking Tobamovirus species have been reported in commercial fields in Mexico, Jordan, and Israel.

In the end of 2014 and beginning of 2015 an outbreak of a new disease infecting tomatoes occurred in Israel and Jordan. Symptomatic plants showed a mosaic pattern on leaves accompanied occasionally by narrowing of leaves and yellow spotted fruit. Research showed that this new disease was a new Tobamovirus, called TBRFV. TBRFV infection is associated with necrotic lesions on leaves and tomato plants show mild foliar symptoms at the end of the season but strong brown rugose symptoms on fruits, making the fruit unsuitable for consumption. Furthermore, regarding to other members of the Solanaceae family, it seems that the TBRFV is capable to infect pepper plants as well, e.g. when planted on contaminated soil from a previous growth cycle of infected tomato plants in high temperatures above 30° C.

In the battle against Tobamovirus, resistance was introduced in tomatoes by introgression of the R genes Tm2 and Tm$2^2$, resulting in resistance to ToMV. However, these R-genes do not provide resistance to the new TBRFV, since different domains in the viral proteins comprised of different protein structure and a new resistance mechanism and/or resistant genes are required for a different resistance mechanism. Furthermore, it is highly likely that over time resistance will be broken, since the virus will adapt and evolve, resulting in viral breakthrough. Therefore, new resistance genes need to be identified and/or combined to provide resistant crops, especially against the new TBRFV.

Considering the above, there is a need in the art for TBRFV resistant tomato plants, more specifically TBRFV resistant *S. lycopersicum*. In addition, there is a need in the art to provide methods and means for providing TBRFV resistant *S. lycopersicum* plants.

It is an object of the present invention, amongst other objects, to address the above need in the art. The object of present invention, amongst other objects, is met by the present invention as outlined in the appended claims.

Specifically, the above object, amongst other objects, is met, according to a first aspect, by the present invention by a plant of the *S. lycopersicum* species that is resistant to Tobamovirus, wherein the plant comprises a TBRFV resistance gene that encodes for a TBRFV resistance protein, wherein the protein has at least 90%, preferably at least 95%, more preferably at least 98%, even more preferably at least 99%, most preferably 100% amino acid sequence identity with SEQ ID No. 116. It is predicted that the TBRFV resistance gene encodes for a NBS-LRR resistance protein.

According to a preferred embodiment, the present invention relates to the plant, wherein the TBRFV resistance gene comprises a coding sequence that has at least 90%, preferably at least 95%, more preferably at least 98%, even more preferably at least 99%, most preferably 100% nucleotide sequence identity with SEQ ID No. 115.

According to another preferred embodiment, the present invention relates to the plant, wherein the plant comprises one or more genomic sequences selected from the group consisting of SEQ ID No. 1, SEQ ID No. 2 SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17 and SEQ ID No. 18, or having at least 95% sequence identity with any of said SEQ ID No's. The genomic sequences encode for one or more genes or genetic elements that provide resistance to Tobamovirus. Sequences have been examined on gene homology using public database of the National Center for Biotechnology Information (NCBI). Six genomic sequences have homology with sequences that encode for NBS-LRR resistance proteins (SEQ ID No. 7, 8, 9, 10, 11 and 14). Four genomic sequences have homology with LRR receptor-like serine/threonine-protein kinase (SEQ ID No. 5, 6, 12 and 13).

Pathogen recognition by plants takes place via two relevant groups of host receptors involving two main types of proteins, namely Receptor-like kinases or proteins (RLK or RLP) and nucleotide-binding site leucine-rich repeat proteins (NBS-LRR resistance proteins). The first group are pattern recognition receptors (PRR) specializing in the recognition of pathogen associated molecular patterns (PAMPS). RLPs or RLKs are attached to the cell membrane and are extracellular immune receptors. Plant RLKs are involved in plant-pathogen interaction and defence responses and plant receptor kinases (PRKs) can be defined as proteins that contain an extracellular domain, a single-pass transmembrane domain and a cytoplasmic serine/threonine (Ser/Thr) protein kinase domain. Plant LRR-RLKs (leucine rich-repeat receptor-like kinase) possess a functional cytoplasmic kinase domain, and all of the plant LRR-RLKs analysed to date possess Ser/Thr kinase activity. The resistance to pathogens provided by these receptors is called PAMP-triggered immunity (PTI). The other group mainly comprises intracellular receptors called resistance proteins (R proteins). The majority of disease resistance genes in plants encode nucleotide-binding site leucine-rich repeat proteins, also known as NBS-LRR proteins. These proteins are characterized by nucleotide-binding site (NBS) and leucine-rich repeat (LRR) domains as well as variable amino- and carboxy-terminal domains and are involved in the detection of diverse pathogens, including bacteria, viruses, fungi, nematodes, insects and oomycetes. The majority of the identified genomic sequences that provide Tobamovirus resistance comprise multiple LRR domains. It is thought that these domains determine effector recognition and therefore disease susceptibility/resistance.

Pathogens develop counter strategies to overcome PTI through modifying or changing PAMPs or MAMPs. Then, plants will develop a way to recognize these effectors and trigger a faster and stronger secondary defence response known as effector-triggered immunity (ETI). ETI is mediated by R proteins and accompanied by localized cell death around the site of infection. The presence of these newly identified resistance gene and/or genomic regions encoding NBS-LRR proteins and/or plant receptor kinases will decrease the chances of the pathogen overcoming the resistance, or when combined with other resistance genes, disease resistance may even be further improved.

According to a preferred embodiment, the present invention relates to the plant, wherein the plant comprises the genomic sequence represented by SEQ ID No. 3. The genomic sequence SEQ ID No. 3 comprises multiple sequences that have homology with sequences that encode for NBS-LRR resistance proteins and LRR receptor-like serine/threonine-protein kinase.

According to yet another preferred embodiment, the present invention relates to the plant, wherein the plant comprises SEQ ID No. 8, SEQ ID No. 9, SEQ ID No. 10 and SEQ ID No. 11.

According to the present invention, Tobamovirus resistance of the plant may be affected by one or more genomic sequences encoding a NBS-LRR protein selected from the group of SEQ ID No. 8, No. 9, No. 10, No. 11 and No. 14, for example a combination of SEQ ID No. 8 and SEQ ID No. 9, or SEQ ID No. 8 and SEQ ID No. 10, SEQ ID No. 8 and SEQ ID No. 11, SEQ ID No. 9 and SEQ ID No. 10, SEQ ID No. 9 and SEQ ID No. 11, SEQ ID No. 10 and SEQ ID No. 11. Furthermore or alternatively, the resistance may affected by one or more genomic sequences encoding a LRR receptor-like serine/threonine-protein kinase selected from the group of SEQ ID No. 12, SEQ ID No. 13, or SEQ ID No. 12 and SEQ ID No. 13.

According to yet another preferred embodiment, the present invention relates to the plant, wherein the plant comprises the genomic sequences of SEQ ID No. 8, SEQ ID No. 11 and SEQ ID No. 14.

According to a preferred embodiment, the present invention relates to the plant, wherein the plant comprises SEQ ID No. 8, SEQ ID No. 9, SEQ ID No. 10, SEQ ID No. 11, SEQ ID No. 12, SEQ ID No. 13 and SEQ ID No. 14.

According to another preferred embodiment, the present invention relates to the plant, wherein the plant is resistant to Tobamovirus strains Tm-0, Tm-1 and Tm-2. In tomato, four strains of Tobamovirus have been identified; Tm-0, Tm-1, Tm-2 and Tm-$2^2$.

According to yet another preferred embodiment, the present invention relates to the plant, wherein the plant is resistant to Tomato Brown Rugose Fruit Virus (TBRFV).

According to yet another preferred embodiment, the present invention relates to the plant, wherein the TBRFV is virus isolate AE050.

According to yet another preferred embodiment, the present invention relates to the plant, wherein the plant is a tomato plant (*Solanum lycopersicum*).

According to yet another preferred embodiment, the present invention relates to the plant, wherein the one or more genomic sequences and/or TBRFV resistance gene is heterozygously or homozygously present in the genome of said plant. From the experimental data it can be concluded that the resistance is dominant and that the TBRFV resistance gene and/or genomic sequence must be at least heterozygously present in the genome of the plant to provide resistance against the Tobamovirus.

The present invention, according to a second aspect, relates to plants, plant parts, tissues, cells, and/or seeds derived from the plant of the present invention.

The present invention, according to a further aspect, relates to a resistance gene (TBRFV resistance gene) for providing resistance to a Tobamovirus in a *S. lycopersicum* plant, wherein said resistance gene is represented by a coding sequence having at least 90% nucleotide sequence identity with SEQ ID No. 115.

The present invention, according to a further aspect, relates to a genomic sequence for providing resistance to a Tobamovirus in a *S. lycopersicum* plant, wherein the genomic sequence is selected from the group consisting of SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17 and SEQ ID No. 18, or having at least 95% sequence identity with any of said SEQ ID No's. Preferably the genomic sequence is SEQ ID No. 8, SEQ ID No. 11 or SEQ ID No. 14.

The present invention, according to a further aspect, relates to a resistance locus for providing resistance to a Tobamovirus in a *S. lycopersicum* plant, wherein the locus is represented by SEQ ID No. 1, SEQ ID No. 2, SEQ ID No. 3 or SEQ ID No. 4, preferably SEQ ID No. 3.

According to a preferred embodiment of present invention, the resistance gene, genomic sequence or resistance locus provides resistance to a TBRFV.

The present invention, according to a further aspect, relates to a method for providing a plant of the *S. lycopersicum* species that is resistant to Tobamovirus, wherein the method comprises the steps of;

a) selecting a *S. habrochaites* plant that is resistant to Tobamovirus, wherein said selection comprises establishing the presence of the resistance gene genomic sequence or resistance locus of present invention, b) transferring the identified genomic sequence or locus of step a) into a *S. lycopersicum* plant thereby conferring Tobamovirus resistance to said *S. lycopersicum* plant.

Transferring can be done by crossing the selected *S. habrochaites* plant with a *S. lycopersicum*. Subsequently, a Tobamovirus resistant *S. lycopersicum* plant can be selected.

According to another preferred embodiment, the present invention relates to the method, wherein after step b) a first *S. lycopersicum* plant is selected that is resistant to Tobamovirus and is crossed with a second *S. lycopersicum* plant that is not resistant to Tobamovirus, and subsequently selecting *S. lycopersicum* plants that are resistant to Tobamovirus.

According to a preferred embodiment, the present invention relates to the method, wherein in step a) establishing the presence of the resistance gene (TBRFV resistance gene), resistance conferring genomic sequence or the resistance locus in a *S. habrochaites* plant is performed by one or more markers selected from the group consisting of SEQ ID No: 83, SEQ ID No: 84, SEQ ID No: 85, SEQ ID No: 86, SEQ ID No: 87, SEQ ID No: 88, SEQ ID No: 89, SEQ ID No: 90, SEQ ID No: 91, SEQ ID No: 92, SEQ ID No: 93, and SEQ ID No: 94, SEQ ID No. 105, SEQ ID No. 106, SEQ ID No. 107, SEQ ID No. 108, SEQ ID No. 109, SEQ ID No. 110, SEQ ID No. 111, and SEQ ID No. 112, preferably SEQ ID No. 105, SEQ ID No. 106, SEQ ID No. 107, SEQ ID No. 108, SEQ ID No. 109, SEQ ID No. 110, SEQ ID No. 111, and SEQ ID No. 112.

The present invention, according to a further aspect, relates to a use of a marker for establishing the presence of the TBRFV resistance gene, the TBRFV resistance conferring genomic sequence or the resistance locus in a *S. lycopersicum* plant, wherein the marker is one or more markers selected from the group consisting of SEQ ID No: 83, SEQ ID No: 84, SEQ ID No: 85, SEQ ID No: 86, SEQ ID No: 87, SEQ ID No: 88, SEQ ID No: 89, SEQ ID No: 90, SEQ ID No: 91, SEQ ID No: 92, SEQ ID No: 93, and SEQ ID No: 94, SEQ ID No. 105, SEQ ID No. 106, SEQ ID No. 107, SEQ ID No. 108, SEQ ID No. 109, SEQ ID No. 110, SEQ ID No. 111, and SEQ ID No. 112, preferably SEQ ID No. 105, SEQ ID No. 106, SEQ ID No. 107, SEQ ID No. 108, SEQ ID No. 109, SEQ ID No. 110, SEQ ID No. 111, and SEQ ID No. 112.

The present invention will be further detailed in the following examples and figures wherein:

FIG. 1: Shows an overview of the mapping of the locus providing resistance against Tobamovirus, more specifically TRBFV in *S. lycopersicum*. F1 plants were created by crossing *S. habrochaites* line 90479-3 that was selected for resistance phenotype with *S. lycopersicum* lines OT9 and OT1317 to create two populations for mapping. Over 700 plants were tested on TRBFV resistance and several recombinant plants (21 plants) were selected and the results of the disease test were combined with the marker data. Several molecular markers (M1 to M42) have been used to determine the position and size of the genomic sequence providing resistance to TRBFV. A clear segregation was observed between resistant (R) and susceptible plants (S). The results indicated that a genomic region located between markers M16 and M17 was providing the TRBFV resistance; the corresponding locus (named LYC4943 R Locus) is 133.515 bp in length and comprises several putative genes. Based on further fine mapping, the size and location of the genomic sequence that was harbouring the TBRFV resistance was determined to be between markers M33 and M38 and was approximately 68.000 bp larger compared to the SL2.40 reference genome of *S. lycopersicum* (85.240 bp vs. 17.328 bp, respectively). It is therefore most likely that one or more genes that are located within this region, indicated as "TBRFV region", are providing the TBRFV resistance.

Figure 2:
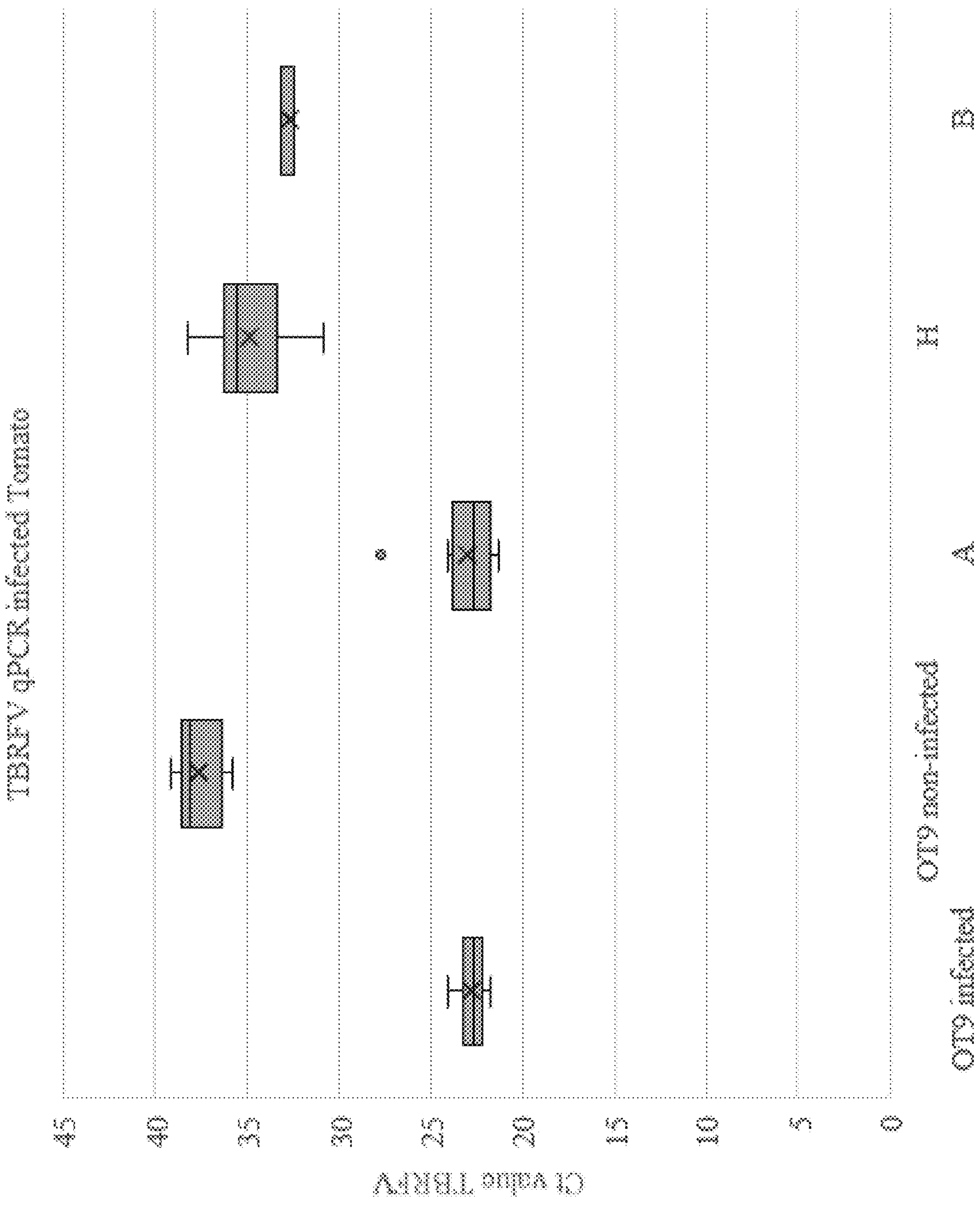

FIG. 2: Shows the results of a qPCR for the detection of TBRFV in infected and uninfected tomato plants (*S. lycopersicum*) of the present invention and plants that do not comprise the TBRFV resistance locus. Low Ct values (i.e. below 30) indicate the high presence of viral RNA present in the samples. OT9 is a tomato plant that does not comprise the TBRFV resistance locus. The control sample (OT9 uninfected) showed a Ct value of between 35 and 40 cycles and the infected control sample (OT9 infected) showed a Ct value of between 20 and 25. Plants that show a Ct value above 30 cycles, preferably around 35 cycles were considered resistant, whereas plants that show a Ct value below 30 were considered susceptible. Tomato plants comprising the TBRFV resistance locus, homozygous (B) or heterozygous (H) have a Ct value above 30 cycles and were considered as being resistant. Furthermore, the results showed that the resistance is dominant Plants that did not comprise the TBRFV resistance locus (A and OT9 infected) showed a Ct value of between 20 and 25, indicating that the plant was susceptible to TBRFV infection.

Figure 3:
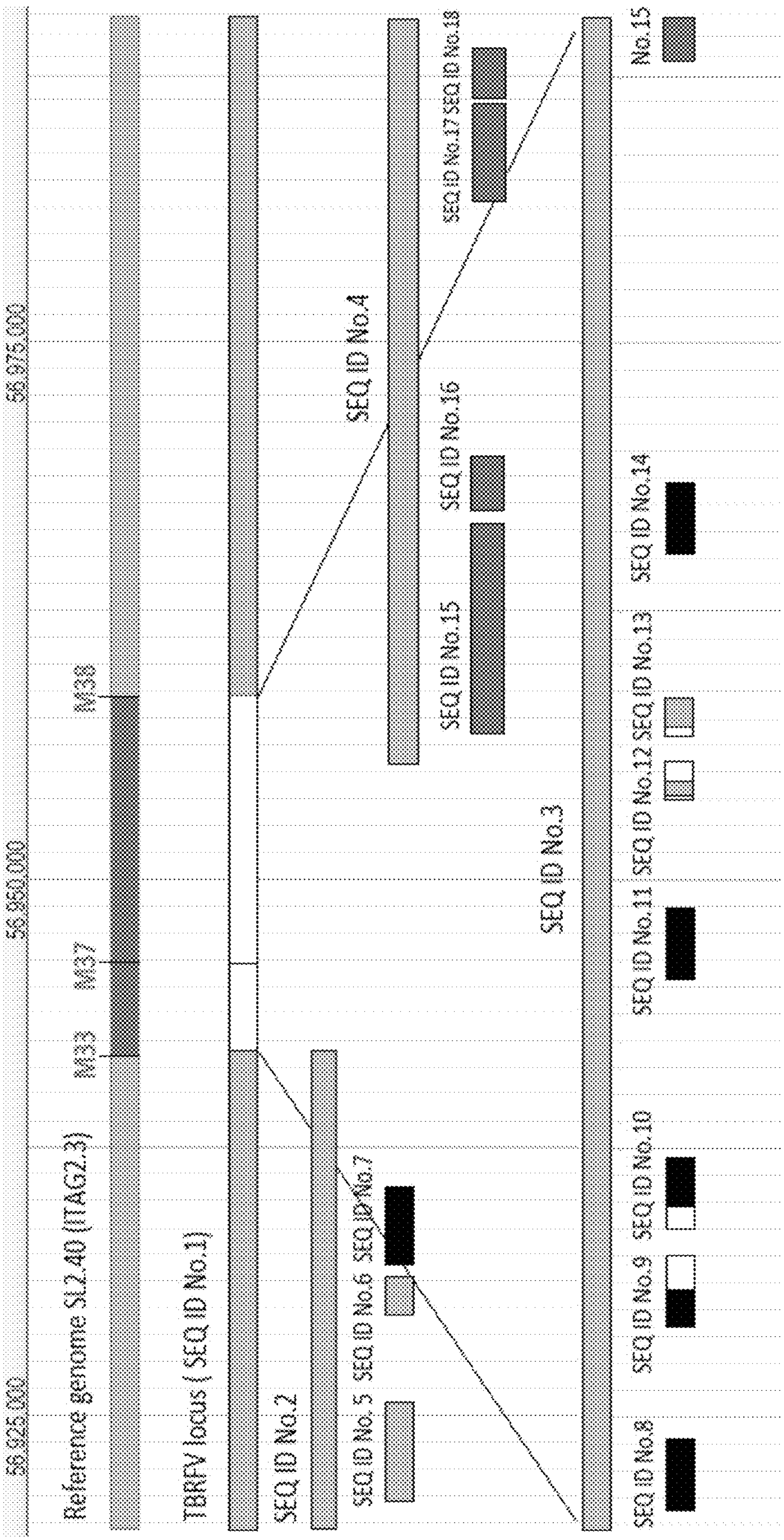

FIG. 3: Shows a schematic overview of the genomic sequences SEQ ID No. 1 to SEQ ID No. 18 of the present invention that encode for one or more genes or genetic elements that provide resistance to Tobamovirus.

FIG. 4: Shows an overview of a further mapping of the locus providing resistance against Tobamovirus in addition to FIG. 1. A further recombinant selection has been performed by further genotyping plants with M33 and M38 to identify recombinant plants in the identified TBRFV region and further limit this TBRFV region. Recombinant plants have been further genotyped with markers (M-SEQ 10, M-SEQ 11-1, M-SEQ 11-2, and M-SEQ 14) covering the TBRFV locus and were specifically designed to eliminate candidate regions in the TBRFV locus, i.e. the genomic sequences SEQ ID No. 1 to SEQ ID No. 18 of present invention that encode for one or more genes or genetic elements that provide resistance to Tobamovirus. Recombinant plants 15321-02, 15321-03 and 15321-07 were screened for resistance by inoculation with TBRFV isolate AE50. Based on these recombinant plants in combination with phenotyping, ELISA and qPCR data for the determination of TBRFV infection, it was concluded that the gene conferring resistance is part of genomic SEQ ID No 14. Plants 15321-02 and 15321-03 do not comprise SEQ ID No 14 and were shown to be susceptible to TBRFV, with high ELISA scores and low qPCR ct-values that correspond to the values obtained with the susceptible control line OT9, indicating virus infection. Plant 15321-07 comprises the SEQ ID No 14 and was shown to be resistant to TBRFV, with low ELISA scores and high qPCR ct-values.

Figure 5:
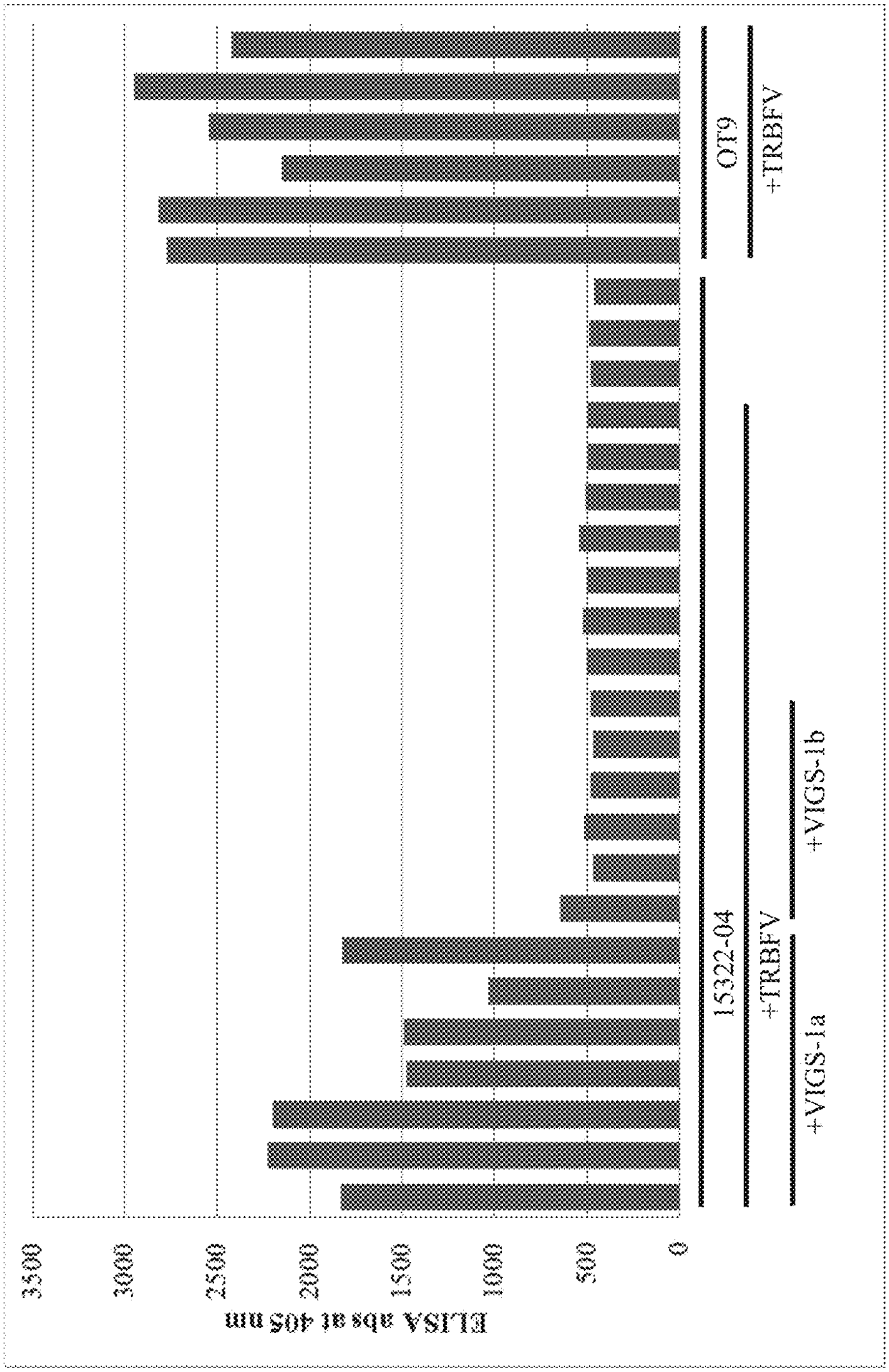

FIG. 5: Shows the TBRFV infection by ELISA in a homozygous TBRFV resistant line (15322-04) as well as a susceptible control line (OT9). Plants were infected with TBRFV (+TBRFV) and infiltrated with construct VIGS-01a that specifically targets the TRBFV resistance gene or with construct VIGS-01b which targets a different region within the identified TRBFV region. ELISA reading was done by measurement of absorption at 405 nm. Control plants OT9 infected by TBRFV resulted in absorption levels of 2000 abs or higher, whereas the resistant plant lines infected with TRBFV resulted in absorption levels of approximately 500 abs. In cases where the TRBFV resistance gene was silenced by VIGS-01a in the resistant plant lines, absorption levels of between 1500 and 2250 abs were measured, indicating viral infection. Silencing by VIGS-01b in the resistant plant lines, resulted in similar absorption levels as was observed in the infected resistant plant lines that were not silenced by VIGS.

Figure 6:
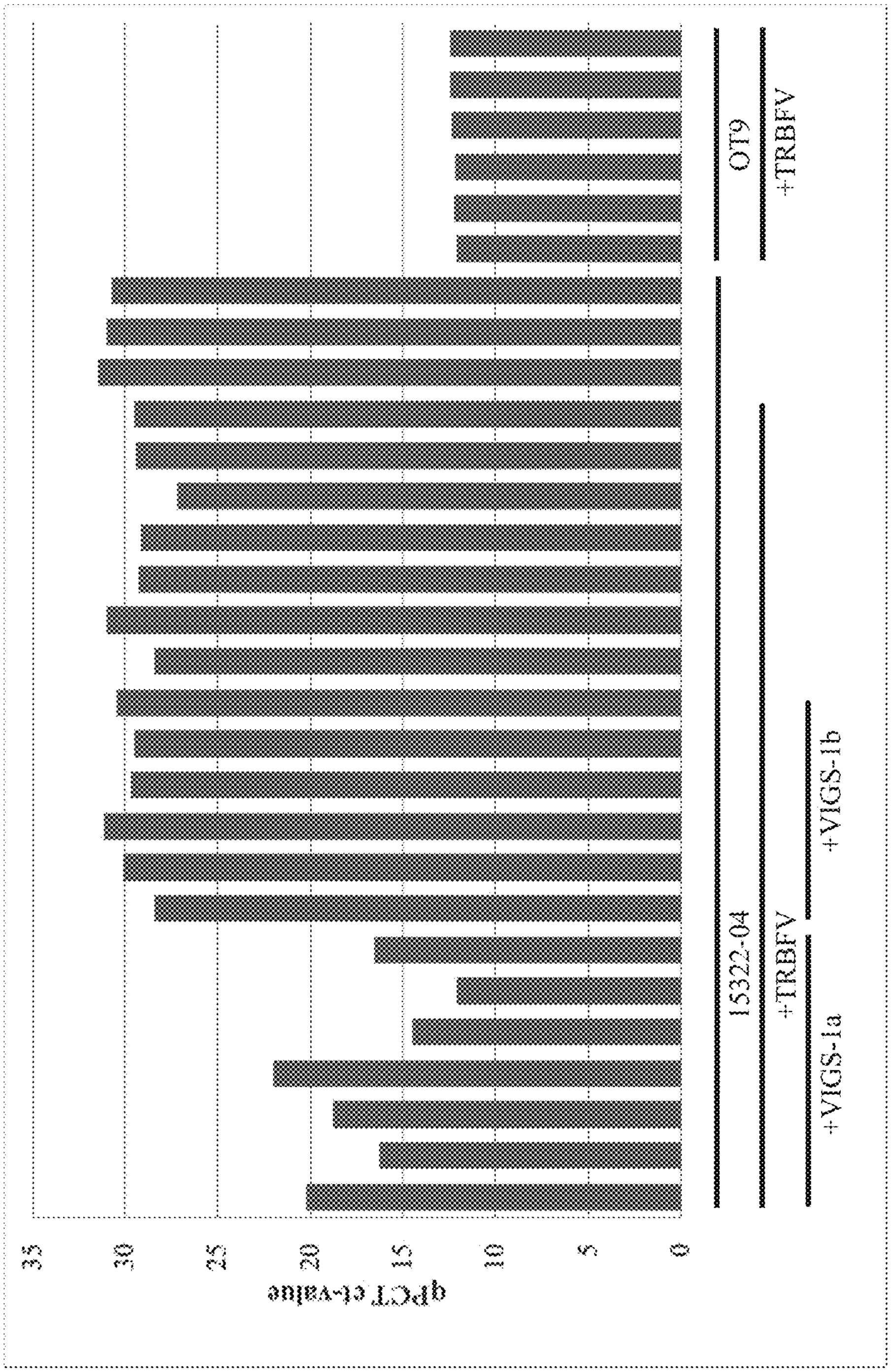

FIG. 6: Shows the TBRFV infection by qPCR in a homozygous TBRFV resistant line (15322-04) as well as a susceptible control line (OT9). Plants were infected with TBRFV (+TBRFV) and infiltrated with construct VIGS-01a that specifically targets the TRBFV resistance gene or with construct VIGS-01b which targets a different region within the identified TRBFV region. The infected control sample showed a Ct value of approximately 12 or 13. The resistant plant lines infected with TRBFV showed a Ct value of approximately 30, indicating TBRFV resistance. In cases where the TRBFV resistance gene was silenced by VIGS-01a in the resistant plant lines, Ct values were observed to drop to between approximately 12 to 20, higher than the infected control cells, and clearly indicating viral infection. Silencing by VIGS-01b in the resistant plant lines, resulted in similar Ct levels (Ct value of ~30) as was observed in the infected resistant plant lines that were not silenced by VIGS.

EXAMPLES

Inoculation of a tomato plant with TBRFV

The TBRFV isolate AE050 (Origin: Saudi Arabia) was used to perform the disease assays. As plant material, the Line OT9, which is a plant line susceptible for TBRFV, was used for virus maintenance. Symptomatic leaves received from the original samples were used for sap-mechanical inoculation on the Line OT9. The virus was maintained on systemically infected tomato plants OT9 by monthly sap-mechanical inoculation on new 3 weeks-old seedlings.

The tomato plants of the species of *Solanum pennellii, S. peruvianum, S. chilense, S. habrochaites, S. pimpinellifolium, S. neorickii, S. corneliomulleri, S. chmielewskii, S. cheesmaniae, S. galapagense* have been screened (~800 out of 912 wild *Solanum* accessions in total). Twelve plants of each accession were infected with TBRFV isolate AE050.

Seeds were sown in vermiculite, seedlings were transplanted in rockwool blocks and inoculated at 4 weeks after sowing. As starting material symptomatic leaves from infected-OT9 were collected and ground in a mortar and pestle in chilled demi water with carborundum (1 gr/100 mL). The oldest leaf from 3 weeks-old seedlings of each test plant was mechanically inoculated with AE050 by gently rubbing the leaf once with one finger.

The plants were phenotyped by visual scoring of the plants and the leaves. Plants were scored for visual symptoms at regular time intervals. Symptoms were visually assessed at 2, 4 and 6 weeks after inoculation, and ELISA tests on remaining plants were done from 6 weeks onwards, with 1 month intervals. More than 50% of the plants showed already symptoms at 2 weeks after inoculation.

Visual scoring was performed on a weekly basis. Plants were scored for visual symptoms. The presence of yellowing, mosaic pattern on leaves, leaf deformation (narrowing, mottling) was recorded on a weekly basis at the plant level. First symptoms were typically observed 12-14 days post-inoculation. Plants were categorized as "resistant" when no such symptoms on leaves were observed. Plants displaying any of the symptoms on leaves were categorized as "susceptible". Leaf samples were collected from asymptomatic plants (i.e. resistant) to test for the presence of virus by ELISA.

The screening allowed the selection of several candidates for resistance breeding, with the best candidate being LYC4943, a *S. habrochaites* accession from Peru. LYC4943 was symptomless and tested virus-free by ELISA for more than 15 weeks after inoculation.

Determination of TBRFV Infection by ELISA

Infection was determined by ELISA. One apical leaf (fully expanded) of every plant was collected. Leaves were crushed using a Type R302 D63N-472 machine (VECTOR Aandrijftechniek B.V., Rotterdam, The Netherlands) and sap was collected by adding 2 mL of PBS-Tween buffer. 100 μL of the extract was used for ELISA with antibodies against ToMV (supplier Prime Diagnostics, Wageningen, The Netherlands). ELISA reading was done by measurement of absorption at 405 nm with a FLUOstar Galaxy apparatus. Plants that gave absorption values more than 1.5 times of the clean control plants were considered infected (susceptible).

Bioassays and Mapping of TBRFV Resistance Genomic Sequence

The original LYC4943 (*S. habrochaites*) seed lot was segregating for the resistance. Nine different F1 families were sown for bioassay in order to identify the F1 families which were completely resistant (resistance is fixed) and which would be used for further backcrosses. Four F1 families germinated and were tested in bioassay. F1 plants created with LYC4943 plant 3 (90479-3) were selected for resistance phenotype to create two populations for mapping, choosing the *S. lycopersicum* lines OT9 and OT1317 as backcross lines. Markers M1 to M42 (respectively SEQ ID No. 19 to SEQ ID No. 102) that have been used in the mapping are listed in Table 1.

298 plants (OT9×90479-3)×OT9) and 484 plants (OT1317×90479-3)=total of 782 plants were inoculated with the TBRVF isolate AE050. Two to three weeks after inoculation the TBRFV symptoms were present and phenotyping by eye was done. A clear segregation was observed between resistant (R) and susceptible plants (S) and resistant phenotypes could be linked with marker M1 (see Table 1) located on chromosome 8 at 2673609 bp on the reference genome SL2.40 (*S. lycopersicum*). 92 plants have been genotyped with 26 markers in order to flank the QTL (M2 to M27, see Table 1). Based on these results the resistance could be mapped between 53118984 bp and 57038544 bp on the reference genome SL2.40 (between M8 & M20, See Table 1 and FIG. 1).

TABLE 1

| Primer name | Primer sequence | Pos. SL2.40 | Pos on Locus | SEQ ID No. |
|---|---|---|---|---|
| M1_F | GGTACAACAATTGACCAAGG | 2672994 | | 19 |
| M1_R | GCTAATTAAAAAGGAACATCAGC | | | 20 |
| M2_F | GCTATGGCGGAGAAGTCAAG | 18124 | | 21 |

TABLE 1-continued

| Primer name | Primer sequence | Pos. SL2.40 | Pos on Locus | SEQ ID No. |
|---|---|---|---|---|
| M2_R | AGTCACCTCCATAGTAGACC | | | 22 |
| M3_F | GGATCCAAGTTGTGTTCGAAC | 881036 | | 23 |
| M3_R | CTTCTCATCAATGTATGTGATTTC | | | 24 |
| M4_F | TGTATAACACCTGGTGCTCC | 15384575 | | 25 |
| M4_R | CCATTTTCTGTTACAAAATTTCAG | | | 26 |
| M5_F | GCTTCCCAATTTATGCTGAAG | 47887679 | | 27 |
| M5_R | GAGCCTCCCACTATAGTAATC | | | 28 |
| M6_F | AGAATTATCATTTGCAGGATCG | 50957946 | | 29 |
| M6_R | CTATGGTTCGCATGTCATGC | | | 30 |
| M7_F | CACAACGGCAATATACCTTGC | 53082561 | | 31 |
| M7_R | TGGAAGTATTAGAAAGGTCCAG | | | 32 |
| M8_F | CCATTGAGAATAACTACTGTAC | 53118984 | | 33 |
| M8_R | CCACAGGATGACTAACTTGG | | | 34 |
| M9_F | TGCAGTATTGATCGCATCTTCTA | 53452252 | | 35 |
| M9_R | GTTTGTTGCTGCCCTCAAA | | | 36 |
| M10_F | TGATCAAGAATTTTGTTTTAGCATAGA | 55664335 | | 37 |
| M10_R | TAAAGCATCAATTTTGCATTGTCT | | | 38 |
| M11_F | TCGAAGACTAACAAAGTCCTTGTAGA | 55720872 | | 39 |
| M11_R | GACACTCCGGCAGTTCCTT | | | 40 |
| M12_F | TTCTTATGTGAAAAATTGGGTGG | 55776574 | | 41 |
| M12_R | ACTACGCAGTCCCACAGCTT | | | 42 |
| M13_F | TTGTTTGGTGGATCCATGTG | 56448988 | | 43 |
| M13_R | AGGGAAAGGGCAAGGATG | | | 44 |
| M14_F | GATCTACCAATGGCTATTCATC | 56781521 | | 45 |
| M14_R | GCAAAACTTAACCGGTCTAAG | | | 46 |
| M15_F | TCTCGATGGTTGATAATTTGTTC | 56874054 | | 47 |
| M15_R | GGAATCGATTAACACTGGTTC | | | 48 |
| M16_F | CATCTTATTGAAGCTCTGCTG | 56920720 | | 49 |
| M16_R | CAAACAGTCCCTATTCAACAC | | | 50 |
| M17_F | GGTCTTGCGCTAATCAAAAG | 56990004 | | 51 |
| M17_R | GCGTTGTGGTGAAAGTTTTATC | | | 52 |
| M18_F | CTTGTTTGGATGGTTGTCAC | 57003163 | | 53 |
| M18_R | CAACAAAAAATATACAATCCGTCC | | | 54 |
| M19_F | GAGATAGAAGGAAACTTACCG | 57024614 | | 55 |
| M19_R | CAATTATCCCCTCAGTTCTG | | | 56 |
| M20_F | TATGCCTGTCCCTGAAAAGG | 57038544 | | 57 |
| M20_R | AGGGTCTTGGATCAAATCTTGA | | | 58 |
| M21_F | TGTGGACTTGGAGTGGTATC | 57427631 | | 59 |

TABLE 1-continued

| Primer name | Primer sequence | Pos. SL2.40 | Pos on Locus | SEQ ID No. |
|---|---|---|---|---|
| M21_R | GTAGAAAGGGTAGGCATGTTC | | | 60 |
| M22_F | TACCAAAGCAAACACTGCCAC | 57441418 | | 61 |
| M22_R | AGCCACGAGATATATATTGGAG | | | 62 |
| M23_F | GATAAGACCGCCAATAACTAG | 60844273 | | 63 |
| M23_R | GTGATCTCCATGAGCAAATG | | | 64 |
| M24_F | TGAGTTGAGATGCTGTTCTAG | 61412883 | | 65 |
| M24_R | AGTCCACCAAGACTTAAAGAG | | | 66 |
| M25_F | GTCTGCCTTCTCTTGCATGC | 62277547 | | 67 |
| M25_R | GTTGCTCCAGACAGAATAAGC | | | 68 |
| M26_F | CATCGAAGAGATGTGTAGGG | 62418391 | | 69 |
| M26_R | TGCAGTTGAAGTAGACTTCAG | | | 70 |
| M27_F | TCAACGTTAGTGGTGATGCTAG | 62783214 | | 71 |
| M27_R | CAATTGCAGAAAGTGAAGCTG | | | 72 |
| M28_F | GTGGATTCAGTTAAACCAGAAC | 56924513 | 4076 | 73 |
| M28_R | GACATGTGGAACTTGACAAAAC | | | 74 |
| M29_F | GCGAGAGAAAAGATTCTCTAC | 56934501 | 12765 | 75 |
| M29_R | CATTCTTCACTCTCTCAAGATG | | | 76 |
| M30_F | CGTTTGGTGATCTGCCTTGTCTT | 56934846 | 13109 | 77 |
| M30_R | TCTTCTTGTAGGGAATCCAGAATC | | | 78 |
| M31_F | GTGTCCTGTGCTTGTTATTCC | 56935054 | 13317 | 79 |
| M31_R | CCTCAAACCTATTGCATCTGACA | | | 80 |
| M32_F | CGGCTCAGCGAGGAAGTGCAG | 56935849 | 14113 | 81 |
| M32_R | CGTTGACTGTTTTTCTTTATG | | | 82 |
| M33_F | GTAAGCTCCTTCATGTCAGC | 56941043 | 15893 | 83 |
| M33_R | CAAGTATTGTCTGCCGAGTAAC | | | 84 |
| M34_F | GCGTACAGACATATTTATGCAAC | 56942927 | 17777 | 85 |
| M34_R | GAACAGCTAAAAGTAAGAGCAC | | | 86 |
| M35_F | GTTCATGTGTGTTTATGGACC | 56943610 | 18416 | 87 |
| M35_R | CTTCACTAAATAAATAAGTGGTAG | | | 88 |
| M36_F | TATGGATTTGTGTCTCAGAAGA | 56944105 | 18912 | 89 |
| M36_R | TGTGGTCACCAAGTGGGTTTC | | | 90 |
| M37_F | GTCTTCCAGAGCAGTTATGCAAG | 56945167 | 19974 | 91 |
| M37_R | TGAGACTGCTAAGTTGACTTGTTTG | | | 92 |
| M38_F | GTACACCAAATCACAGACATCG | 56958371 | 101133 | 93 |
| M38_R | CCCAATTTGGTTTGTGTTGGAC | | | 94 |
| M39_F | GAAATTCCTTGCCTCCTCTC | 56961307 | 104063 | 95 |
| M39_R | GTGGAAGCCATAGTGTACAAG | | | 96 |
| M40_F | CATATTATACAGTGAAAGCTTTG | 56965103 | 107926 | 97 |
| M40_R | GAATTGCAGTTCACTTGCTTC | | | 98 |

TABLE 1-continued

| Primer name | Primer sequence | Pos. SL2.40 | Pos on Locus | SEQ ID No. |
|---|---|---|---|---|
| M41_F | CCACAAAGCTAAAAAGGGATTG | 56969685 | 112529 | 99 |
| M41_R | TCCATGTGAGTTTTGTGTGTG | | | 100 |
| M42_F | GCCACATAAATTACATATAGCTG | 56981278 | 125792 | 101 |
| M42_R | GAACTATTCAACAAGCATAATAC | | | 102 |
| M-SEQ 10_F | GTCTTACAATAGTAAAATGCGCAG | | 36480 | 105 |
| M-SEQ 10_R | GCGGTTCGTTGATATTCCAAC | | | 106 |
| M-SEQ 11_1F | AGCGAAAGCGGAAGGAGTAC | | 48748 | 107 |
| M-SEQ 11_1R | TGTGGTGAGTAAGCAATGAATC | | | 108 |
| M-SEQ 11_2F | GTGTATAATTCGCCAGAATATACGG | | 52303 | 109 |
| M-SEQ 11_2R | CGTTTAGATAATTGTATATTACACATATG | | | 110 |
| M-SEQ 14F | CAAATTATTACTTATGTTGTGATTTG | | 77410 | 111 |
| M-SEQ 14R | ATTAAGCCATGATACACAAATTAC | | | 112 |

The whole population of 782 plants have been genotyped with the flanking markers M8 & M20 in order to find the recombinant plants for further fine mapping. This resulted in 21 recombinant plants (See FIG. 1). These 21 recombinant plants have been selected and genotyped with 11 markers M9 to M19 in order to further fine map the region (Table 1). The resistance could be fine mapped between 56920720 and 56990004 (marker M16 and M17) on the reference genome SL2.40.

Sequencing the resistant LYC4943 region using Oxford Nanopore sequencing technology resulted in a locus of 133.515 bp. The 21 recombinant plants have been genotyped with extra markers in this specific locus (M28 to M42) of LYC4943. Based on the recombinant plants, plants 594 and 608, it was determined that the resistant region was located between positions 56941043 and 56958371, based on the reference genome SL2.40, corresponding with positions between 15.893 and 101.133 on the LYC4943 locus (between M33 and M38, see FIG. 1).

Based on the fine mapping, the size and location of the genomic sequence that was harbouring the TBRFV resistance was determined to be between markers M33 and M38 and was approximately 68.000 bp larger compared to the SL2.40 reference genome of *S. lycopersicum* (85.240 bp vs. 17.328 bp, respectively). It is therefore highly likely that one or more genes are located within this region, indicated in FIG. 1 as “TBRFV region”, providing the TBRFV resistance and is indicated as SEQ ID No. 3 in this application. Based on the reference genome SL2.40 and in silico prediction analysis (ITAG 2.3), at least one gene is located in the fine mapped region that encodes for a CC-NBS-LRR resistance protein. Blasting the fine mapped TBRFV region against the database of National Center for Biotechnology Information (NCBI), resulted in seven genomic fragments of which five have homology with NBS-LRR resistance proteins (SEQ ID No. 8, No. 9, No. 10, No. 11 and No. 14) and two have homology with LRR receptor-like serine/threonine-protein kinases (SEQ ID No. 12 and SEQ ID No. 13).

Next, further fine mapping was performed and a recombinant selection has been performed by genotyping 668 BC2 plants ((OT9×90479-3)×OT9×OT9) with M33 and M38 in order to identify recombinant plants in the TBRFV region, which resulted in three plants 15321-02, 15321-03 and 15321-07 (see FIG. 4). These three plants were tested for resistance by inoculation with TBRFV isolate AE50. Approximately three weeks after TBRFV inoculation the plants were phenotyped by observation, and ELISA and qPCR was performed to monitor virus infection. The recombinant plants have been genotyped with markers (M-SEQ 10, M-SEQ 11-1, M-SEQ 11-2, and M-SEQ 14, respectively SEQ ID No. 105 to SEQ ID No. 112) covering the TBRFV locus and were specifically designed to eliminate candidate genes in the TBRFV locus. This approach provided insight into which of the candidate genomic sequences SEQ ID No. 1 to SEQ ID No. 18 of present invention specifically provides resistance to TBRFV. Based on the recombinant plants and phenotyping by disease tests, ELISA and qPCR, we concluded that the gene conferring resistance is encoded by genomic sequence of SEQ ID No 14, more specifically the coding DNA sequence of SEQ ID No. 115 encoding the protein of SEQ ID No. 116.

Validation Tm0, Tm1 & Tm2 Strain Resistance in Plant Comprising the TBRFV Resistance Locus A tomato plant of the present invention (*S. lycopersicum*) comprising the TBRFV resistance locus (SEQ ID No. 1) was tested for resistance against the Tm0, 1 and 2 strains. The presence of the TBRFV resistance locus was determined by markers M16, M17 and M33. It was furthermore confirmed that the plant does not contain the $Tm2^2$ gene (is a known gene that provides resistance against Tm0, 1 and 2 strains). In some case the plant did contain the Tm1 resistance gene. As a control, plants were selected that did not contain the TBRFV resistance locus.

Eight plants (See Table 2, 1 to 8) of which six plants comprise the TBRFV resistance locus (heterozygous), and two plants (7 and 8) do not have the TBRFV resistance locus have been inoculated with the Tm0 isolate. Eight plants (See Table 2, 9 to 16) of which six plants comprise the TBRFV resistance locus (heterozygous), and two plants (15 and 16) do not have the TBRFV resistance locus, have been inoculated with the Tm-1 isolate. Eight plants (See Table 2, 17 to 28) of which four plants comprise the TBRFV resistance locus (two homozygous 17, 18+two heterozygous 19, 20), and four plants not have the TBRFV resistance locus have been inoculated with the Tm2 isolate. As control the susceptible cultivated tomato line OT95 was also inoculated with all three strains.

First symptoms were typically observed after 12-14 days post-inoculation. Plants were categorized as Resistant (R) when no mosaic pattern symptoms on leaves were observed; plants displaying any of the symptoms on leaves were categorized as Susceptible (S). The phenotype of every single plant has been compared with the TBRFV genotype. Results are summarized in Table 2 below.

TABLE 2

| Plant | Isolate | Phenotype | M16 | M33 | M17 | Tm2 | Tm1 |
|---|---|---|---|---|---|---|---|
| 1 | Tm0 | R | h | h | h | a | a |
| 2 | Tm0 | R | h | h | h | a | a |
| 3 | Tm0 | R | h | h | h | a | a |
| 4 | Tm0 | R | h | h | h | a | h |
| 5 | Tm0 | R | h | h | h | a | h |
| 6 | Tm0 | R | h | h | h | a | h |
| 7 | Tm0 | R | a | a | a | a | h |
| 8 | Tm0 | R | a | a | a | a | h |
| OT95 | Tm0 | S | a | a | a | a | a |
| OT95 | Tm0 | S | a | a | a | a | a |
| 9 | Tm1 | R | h | h | h | a | a |
| 10 | Tm1 | R | h | h | h | a | a |
| 11 | Tm1 | R | h | h | h | a | a |
| 12 | Tm1 | R | h | h | h | a | a |
| 13 | Tm1 | R | h | h | h | a | h |
| 14 | Tm1 | R | h | h | h | a | h |
| 15 | Tm1 | S | a | a | a | a | a |
| 16 | Tm1 | S | a | a | a | a | h |
| OT95 | Tm1 | S | a | a | a | a | a |
| OT95 | Tm1 | S | a | a | a | a | a |
| 17 | Tm2 | R | b | b | b | a | a |
| 18 | Tm2 | R | b | b | b | a | a |
| 19 | Tm2 | R | h | h | h | a | a |
| 20 | Tm2 | R | h | h | h | a | a |
| 21 | Tm2 | S | a | a | a | a | a |
| 22 | Tm2 | S | a | a | a | a | a |
| 23 | Tm2 | S | a | a | a | a | a |
| 24 | Tm2 | S | a | a | a | a | a |
| OT95 | Tm2 | S | a | a | a | a | a |
| OT95 | Tm2 | S | a | a | a | a | a |

R = resistant,
S = susceptible,
a = no resistance locus present,
h = heterozygous,
b = homozygous Result Tm0

All plants that contained the TBRFV resistance locus were resistant. Plants 7 and 8 did not contain the TBRFV resistance locus but were also resistant. A reason that could explain the results is that the Tm1 gene is causing the resistance to ToMV isolate Tm-0. In addition, plant 1, 2 and 3, did not contain the Tm1 gene, but did contain the TBRFV resistance locus, showed to be resistant.

Result Tm1

The resistant phenotypes are linked with the TBRFV genotypes, providing resistance against ToMV isolate Tm-1.

Result Tm2

The resistant phenotypes (hetero-, homozygous) are linked with the TBRFV genotypes, providing resistance against ToMV isolate Tm-2.

Determination of TBRFV Infection in Tomato (*S. lycopersicum*) by qPCR

Tomato plants comprising the TBRFV resistance locus (heterozygous or homozygous) and plants not containing this region have been selected for TBRFV bioassay using markers (M16 and M17). Plants were infected with TBRFV and the susceptible tomato line OT9 has been included as control (OT9 non-infected and infected).

After 3 weeks of inoculation, one leaf from the top of the plant of every single plant was collected in a 2 ml tube which contain a 6.35 mm metal bullet. The tube was frozen in liquid nitrogen. The tubes were shaken with high speed to pulverize the plant material. After spin down the tube, the standard RNA extraction using Macherey-Nagel™ NucleoSpin™ RNA Plant was carried out. RNA concentration was measured using DropSense 96 (Trinean) and was diluted to a concentration of 100 ng/μl. 900 ng have been used for cDNA synthesis using M-MLV Reverse Transcriptase (Invitrogen). 10 ng cDNA was used for Real-time PCR using LC green as Intercalating dye. Two primer combinations for amplifying the TBRFV strain were used, see Table 3 (SEQ ID No. 103 and SEQ ID No. 104, respectively).

TABLE 3

| qPCR primer name | Sequence |
|---|---|
| TBRFV-3 Fw | ACCGTTCAACGGCAATTTAGC |
| TBRFV-3 Rev | CCTATACACCTTAAAACCACTG |

The more viral RNA present in the samples the lower the Ct value in the qPCR, since less PCR cycles are required to amplify the cDNA (of the viral RNA) and pick up a signal. The control sample (OT9 uninfected) showed a Ct value of between 35 and 40 cycles and the infected control sample (OT9 infected) showed a Ct value between 20 and 25. Therefore plants that show a Ct value above 30 cycles, preferably around 35 cycles were considered resistant, whereas plants that show a Ct value below 30 were considered susceptible (see FIG. 2).

Tomato plants comprising the TBRFV resistance locus, homozygous (B) or heterozygous (H) all have a Ct value above 30 cycles and can be considered as resistant. The results are showing that the resistance is dominant. Plants that did not comprise the TBRFV resistance locus (A) showed a Ct value of between 20 and 25, indicating that the plant was susceptible to TBRFV infection.

Sequencing of Genomic Sequence of Resistant Tomato Plant

Genomic DNA was isolated from a resistant plant (*S. lycopersicum*) of the present invention, i.e. comprising the TBRFV resistance locus, according to the protocol as published on 27 Apr. 2018 in Nature, Protocol Exchange (2018), Rachael Workman et al,. "*High Molecular Weight DNA Extraction from Recalcitrant Plant* Species *for Third Generation Sequencing*". The sequencing libraries were prepared using the PCR free, no multiplex, DNA Ligation Sequencing Kit-Promethion (SQK-LSK109). The isolation procedure resulted in high quality sequencing libraries to be used in the Oxford Nanopore system for sequencing (ONT sequencing). Promethion Flowcell Packs (3000 pore/flowcell) version R9.4.1. were used for sequencing.

Furthermore, to further resolve the TBRFV locus and identify the gene providing the TBRFV resistance, we performed ONT sequencing on a resistant line (LYC4943). Sequencing of the entire transcript isoforms of the resistant LYC4943 line was done using the Iso-Seq analysis application (Pacific Biosciences of California, PacBio). This resulted in only one candidate resistance transcript/gene located in region between markers M33 and M38, more specifically the TBRFV resistance gene of SEQ ID No. 115. This transcript was predicted to encode for a CC-NBS-LRR resistant protein of SEQ ID No. 116.

Gene Validation Using VIGS

To confirm that the TBRFV resistance gene (SEQ ID No 115) was indeed the gene conferring resistance to TBRFV, a Virus Induced Gene Silencing (VIGS) analysis was performed. Tobacco rattle virus (TRV)-derived VIGS vectors have been abundantly described to study gene function in plants such as *Arabidopsis thaliana, Nicotiana benthamiana, Lycopersicon esculentum* and other plants (see for example Huang C, Qian Y, Li Z, Zhou X.: Virus-induced gene silencing and its application in plant functional genomics. Sci China Life Sci. 2012; 55(2):99-108).

As such, two VIGS constructs were developed (Table 4), one construct VIGS-01a to specifically target SEQ ID No 115 and a control construct VIGS-01b that targets SEQ ID No. 7, i.e. a sequence also located within the previously identified TBRFV locus.

TABLE 4

| VIGS construct | Sequence |
|---|---|
| VIGS-01a (SEQ ID No. 113) | GGAAGATTTTAATGAAAAGAGGTTGATAAAGA AAATTGTAGAATCTATTGAAGAAAAGTCACTT GGTGACATGGACTTGGCTCCACTTCAAAAGAA GCTTCAGGACTTGCTGAATGGAAAAAAATATT TGCTTGTCTTAGATGATGTTTGGAATGAAGAT CAAGATAAGTGGGCTAAGTTAAGACAAGTCTT GAAGGCTGGAGCAAGTGGTGCTTATGTTCTAA CCACTACC |
| VIGS-01b (SEQ ID No. 114) | AGAAGATTTTGATGAGAAGAAGTTGATAAAGG CAATTGTTGAATCTATCGAAGGAAACCCACTT GGTGACCACATGGATTTGGCTCCACTTCAAAA GAAGCTTCAGGACATGTTGAATGGAAAGAGAT ACTTTCTCGTTTTGGATGATGTTTGGAATGAA AATCAAGAAAAGTGGGATAAGATAAAAGCAGT CTTAGAGGTTGGAGCACGAGGTGCTTCTGTTC TAACCACCACT |

The VIGS fragments were synthesized (IDT, gBlocks) and subsequently cloned into a TRV vector. The DNA sequences were confirmed by Sanger sequencing. The vector contained all sequences encoding for proteins that are required for a functional TRV particles including the target sequences. The VIGS vectors including the VIGS-01a and VIGS-01b constructs were transformed into *Agrobacterium tumefaciens* strain GV3101 and used in VIGS experiments to reduce endogenous mRNA levels in tomato plants used in this experiment. A homozygous TBRFV resistant line (15322-04) as well as a susceptible control line (OT9) were used in the VIGS experiment, in which plants were *Agrobacterium* infiltrated at seedling stage (cotyledons) followed by TBRFV isolate E50 inoculation three weeks after *Agrobacterium* infiltration. Two weeks after TBRFV inoculation the individual plants were phenotyped by ELISA and qPCR and this revealed that susceptibility was found in resistant plants infiltrated with construct VIGS-01a whereas no susceptibility had been detected in resistant plants infiltrated using construct VIGS-01b. Results of the ELISA and qPCR are shown in FIGS. 5 and 6, and results have been summarized in Table 5.

TABLE 5

| Plants | # plants | VIGS-construct | TBRFV infection | # S plants | # R plants |
|---|---|---|---|---|---|
| R line 15322-04 | 7 | VIGS-01a | Yes | 7 | 0 |
| R line 15322-04 | 6 | VIGS-01b | Yes | 0 | 6 |
| R line 15322-04 | 10 | No | Yes | 0 | 10 |
| S line OT9 | 6 | No | Yes | 6 | 0 |

In the OT9 line all plants were susceptible, as expected. The R line which was shown earlier to be fully resistant became susceptible to TBRFV in cases where the suspected TBRFV resistance gene was silenced using the VIGS-01a construct designed to specifically target this gene, whereas silencing using the VIGS-01b construct (control construct) did not result in any susceptibility of the plants tested. Based on these results it can be concluded that gene SEQ ID No 115 is the conferring resistance to TBRFV.

The invention claimed is:

1. A Tobamovirus resistant *Solanum lycopersicum* plant, wherein the plant comprises a Tomato Brown Rugose Fruit Virus (TBRFV) resistance gene encoding a TBRFV resistance protein comprising polypeptide sequence SEQ ID NO: 116.

2. The plant of claim 1, wherein the resistance gene comprises nucleotide sequence SEQ ID NO: 115.

3. The plant of claim 1, wherein the plant is resistant to Tobamovirus strains Tm0, Tm1, and Tm2.

4. The plant of claim 3, wherein the plant is resistant to Tobamovirus strain Tm0.

5. The plant of claim 3, wherein the plant is resistant to Tobamovirus strain Tm1.

6. The plant of claim 3, wherein the plant is resistant to Tobamovirus strain Tm2.

7. The plant of claim 1, wherein the plant is resistant to Tomato Brown Rugose Fruit Virus (TBRFV).

* * * * *

SEQUENCE LISTING

```
<160> NUMBER OF SEQ ID NOS: 116

<210> SEQ ID NO 1
<211> LENGTH: 133515
<212> TYPE: DNA
<213> ORGANISM: Solanum habrochaites
<220> FEATURE:
<223> OTHER INFORMATION: TBRFV resistance locus

<400> SEQUENCE: 1

tctgtggttt gatgctttca aatcacagca atcctctgta taattatggt ttatatttta     60

ggggttttca gtttacaaag tcattttatc cttccaatca ccaaaagtat tatcttggct    120

ctagtgacta gtaacaagtt agttttgtgt tatgtggaaa tttacaacag atcaccttca    180

tactgaggag ggagatgatc attttgtcgt ggctcggccc gtctgtcttt tagccaaatg    240

ctgcgggaga gagtgggatt ataacagtaa gtattttgtg ttttaatact gcttctatca    300

gctaatgttt catagaaatg acagtgtgaa tgaaattgca aattttgtgt ggtaaatagt    360

ttcaggctcc aatctagtga tcattttttc tgggtaatca gttaacaaga tctctttaag    420

cattcaaatt tatgtatggt aggtaagtgc acatcatgtt aggaccgaaa ataagcgggt    480
```

-continued

```
gtaaatgcgg aagctagcaa agcaaacctc gaaagatcac gagtaagaag ataacgagaa    540
atataccaaa agacacaaag atttaacgtg gttcggtcaa ttgacctacg tccacaaagg    600
agatgagcaa tccactataa atatgagagt acaaaatata gagagaaaca acctcaacca    660
attcactcgg aatacatggg aggttcacac aagtgataac gtatcaagct tgtgacccac    720
aaattctccc tctaaccaaa actctcaaaa ctctttaaga ctacattgtg aatgctgatt    780
aagttagaag gaacatgtct ctatttatag agtcctaaac tttttcatac tagaaaaaag    840
attagtcaat tcaaaacctt ttcctaaaag gaaaacctat ttatggtaag aaatcagggc    900
aaataaaacc caacacatca tggtttgaac cgtactacat aagaaaagtt ctagtattta    960
aattgagaag gatagagggg aggggcctat ccttaaatct gttaaagttt tacgtactag   1020
cccaactatt tgtgcgcgtg aagaaaagat gtgacagctc cactatagat ttcagcacta   1080
ccatttagtt tgttacaaca ttttgctgaa attgagttag gatcttcttg agtcgcagag   1140
taatatcttc catgcgaatt ctctcttcag gcaaatcatt tgtacattca agagctaatt   1200
ccatgattga tttgaagcat ctatctttag aagtaaaatt ttcttcgttc agtgaaaata   1260
gattaatgtc cactacatcc accaatcggt ctggtaatga ttggcatatc catcttttca   1320
aggtgaagtc tccaacgaat agatcatcca cagggctctt tcttgtaaaa gtctccatta   1380
acaatatacc aaagctataa acatctcccg aagttgatac tttgccttca gacccatact   1440
ctacaaaaaa aataaatcac gccatcatta atgaaaataa ttaacaacat ttaaaatcct   1500
caagtgaact tgataataac atttacctgg tgccatgtag ccgatagtac ccaaagtctt   1560
ggtatgtgct attagcgtct cagatgtaag aagtttggat atcccaaaat cactcacttt   1620
tgccaccata tcttcatcca aaagtatgtt acttggtttc aaatcacaat ggacgactac   1680
aaacaaatgt cctccatgta aatactccac agcagaagcc acatcaatca tcacctttag   1740
tctttgagtt atatccaaaa ctttgtcagt agagtgaagc caacattcga ggttttcatt   1800
aggcatgtac tctagcacca acactttata atcgaaattt gcacaactac ttatcacctt   1860
aacaaggttt ctgtgtcgaa tgctacctaa aacttgacat tccacctcga aacttctaaa   1920
tgcaagttgc agttctgtat tgaatacctt tatcgccaca accattccat ctgctagtgt   1980
ccctttatac accaaaccaa ggctccccct tccaatcaag tttgcttcat caaagttgtt   2040
tgtcccttga gaaatatcat agtacgaaat cctcttatgt acctgaccaa atgtatcaac   2100
tagaggaagt tccgtactcc tttttcggca tttcagaaac caaatgataa aaatggttgt   2160
gactacaatt cctgaggaaa ctgatgcaag aacagaagtt aggactctgt tctttctttt   2220
tctttcaaga cttgtcactc tgcattgcat cacatggaag cgtgatgatc cacataatgc   2280
agggttaccc atgaatgatt cagctgtaaa atttacgaat ggccctccat ctggaatttc   2340
acccatgagc ccattgaacg agacattgaa atgcatgaga tgttcaagat tcctcaagga   2400
cttggggatc atgcctgata gattgttgct agatagatcc aaatattcca acgaaaccaa   2460
atcttcaaat acttcaggta tggaaccatc taacatattc tttgacaatg aaaggctaac   2520
caagctttgt agttggccaa tcgtgctagg aatctgacca gagaactgat taccatgtaa   2580
atgtaatatc cgcaaactcc ttaaattccc catttctact gcaagagacc cattcagcaa   2640
attggaggcc aaagtgagaa ttgaaatatc tttgttcctc caaaaagttg atggaatatg   2700
ggaaattagt gcattggaat ctaagtagag ttctcttaaa gatgaaagat ttccaaaaca   2760
atttggtaat tcaccagtaa gttgattttt ccccaagata atttggtaca agttttccat   2820
gttacacaag ctagttggta taattccatc taaattgttt ttctctaggc taaatctttt   2880
```

-continued

```
caacttcctc aagttcccca aatctggagg aatagatcct ataagtttat tgtctcccaa   2940
gcttaaccac tccaggttcc taaagttact gatgttaggt ggtatttttc ctgtgatacc   3000
attttgaagg gcaatgaaat attcaaggga aaaggaccag tttcctgaac ctaaagatgt   3060
tggaagactt ccattaaatt ggttacctcc tatttgaacg gttttcatat acttgcaatt   3120
agataatgaa gtcaggaaac ttaactcgcc tgtagattga tcattcgtca attggtttat   3180
ttgcaagttg atgaattgta gctgttgtag ctttccaaga ttcataggta caggtccact   3240
aaacagattg cggccaaaat caagctggat aagcatggtg gaattcacaa tggaggtagg   3300
aatcagcccg gtgaactggt tatccccaag gtaaaggcct tcaaggtttg gaagagtatg   3360
gcctatgttt gagggaagtg ttcctgaaag ctcatttgct acaaatgaaa tctttttag    3420
tccagaaatg ttgtacaaac gccttggaac ttcacccgat aatctgtttg gaccaagata   3480
cacttctttc aaatttacaa gatgttcaaa ctcctgagga attccaccat ataaactgtt   3540
gtcacctagg tctatcatct ctagatttga caaatttcca attgatggtg gaagaattcc   3600
caccaaattg ttccgtcgta gacttaatct tcgaattgct gataggttat cgatttcact   3660
tggtatatgt cctgtaaaat atatgtcgaa ttgtgtggtt actacactga aatgtccaat   3720
actgtataac agctttatag tcactaagtt actataaata acagaaactg ttagttgtat   3780
gccttttaaa tagttcagca atcctcacaa actgttttga tgtcctttttg aagatgggac  3840
taaatggatc aacatggata attaggattc atatagcaga cacaaactag aattgagcca   3900
atgtagtagt tactgttgtt gtttgaaaat gaagaacaaa gagctatacc aacatttttt   3960
gctactaccc tttgaaatgc aaatactaat ttcttataaa tgagttgaag agcaagtttt   4020
taaatatcaa agatctctag tgctacaagg tgagaagtcc agcaataaag ttaggtggat   4080
tcagttaaac cagaacatta taaatacctg ttatgttatt ccatccaaga aatagatgtt   4140
gaagttttgt caagttccac atgtctctag gcaagtttcc tgtaatagga tattacgata   4200
agttatatgt acctctcacg gcctatgatt gtttaactaa aaaattgttg caatctttgt   4260
tgtcaatatg aaccaaaagt agcagagaaa gaagttggtt ccgttttttt ttacctgtga   4320
agtggttata tgacaaggac aaatatatta gctctttgca tttgtctaaa ttgcttggta   4380
gttggccaga gagttgattt cttgctattt gtaatccctc cagccgcgga agattatggc   4440
aaatgtcatt cggcaaagtc ccagatagtg cattataaat caaattgatg accttcaaag   4500
aagagacatt gaagatagac gaaggaacag atccaaagag atcattttca gaaagatcca   4560
acaactcgag ccttctcagt aatccaagac tttctggaat ttgacctgtg agattattca   4620
ttgacaagga caagtgcttc agcctcctca aatagccgag ttcatcaggg atttcaccgt   4680
tgatgctgtt gttgccaatg tccaagaaac taagaaagga gaggttccca atatctgtcg   4740
cgattgaacc tcttagtctg agaccattga ggtctagtga tgtcactctt tgatgccttt   4800
tactgcaaga tatgcctatc caattgcaaa cgtgagtccc ctttgtccag tttttcgaca   4860
acattccatt tggatctgaa gttatatgag ctttgaaagc taaaagagca gcctcatcag   4920
ttgaaatgtt cgatgcatta gtattcgaga ggtacgttaa caaaactagc aatcctataa   4980
tcatagccac ggaaaccgtt ttgtgcaact tctcttgcag ctatttgtgg gggaaattta   5040
taagtgcctg attttttatt tttcaagtga cattaatata tatttctata attaaaggca   5100
ataaagaatc atgtattagc actggaatat atagaatcta gagttcaatg tcaatgatca   5160
acatatatac gtaatatgtt ttgagacatt tttttttaaa ttgaatgttg ctgaacttga   5220
```

-continued

```
ctgcaattca ttgctgaagg gaaatcattg gttgtgggat tctgtagtga tagtaaaata   5280
atttacttgg atttataagc cttgtatatt cattattcaa gaatattaaa gactaaaatc   5340
atgatataat gtcatcattc gaatgtatat agcctccgct gaatagatgt ttgacaaaag   5400
aacgtgaagt gttacggtca aattagtgaa tctaacgtgt aatgttggat ttacgtgaat   5460
tcaatagctt ttattcctat cttttatata tattaagtaa tttattaaaa atctaaaatt   5520
atcgtatatt actatcttgc agtctgtgtg agaatactat tttgataatc gtcaaataat   5580
tatctataaa tttcaaatct tgaatcacac ttatttaata ggaggaaatg gtaaaaagga   5640
agtgaggttg acaagatctc aagactcttt cttaattttg atgaaatgtt gtaaaaactt   5700
gaattagtag attgcatggc atcactatac acgtgtcagt ctagtgttta gagaaattta   5760
atcaaagaat ataagttata atatatatta tccatgagaa tcttgagaaa gattttctgt   5820
atctgtctga tgaaatagaa attggagttt cccaattcta tattacttgg cttattctaa   5880
cttctagtgc agaatctgca gatggtcaat attctttgaa tatataatag caaatttgat   5940
tattagtttc atttttaaac tattgatagt tttaaaaata tttattattt aactaattaa   6000
atttaaatat atcctcgatc ttgcaatatg agagaaatac atctctaaat tctttccttt   6060
tcaacatttc tttcgttttt ctaattaaaa gcctcatact tatacaagag tttgaaacca   6120
cttgatatgt cacgtgacaa aaaagaattg tatctaagtt tggctactca tgtagagaag   6180
tatttttaaa gcggtcaata tctcaaaaga gaaacaaata aattatgtat ctacaaatta   6240
taaaaaaagg agtctacctt tattgggaaa gtcatatgca attcatgtat gctttcctaa   6300
ttggggatac aaagtcaatc ttgttaaacc cctaaactat tacaatcatt ttaagaatta   6360
tatatatatg tactatttga gtgttgacaa aagccttaaa ttatcataaa actcatatta   6420
aaatatctct tagagtaata tgacatgtca tgtgaatatt atgtttgaca aactcaattt   6480
caaagagttc aaagtggtta tacacgtagg ttttagaaaa attctaaact cactgttttg   6540
tgactttcat acctaaaatt gttaggtgtt tatataacca cccctgaatt ataccatgaa   6600
attattgtgc caggtggcct aatttgaaat ttaatagggc tgaattaaga tttttgaagt   6660
caattaaaga aaatattttt ttaatttatc ctgaataagc ttgctatttg aggggtttga   6720
gaaatatcgg tagggcggta catgggctaa taaaattgat taaaaatata atatgatatt   6780
aaatttaaaa ttaaagagaa tccaaactca aaacaattag gttaatattt ctatttagct   6840
atttatcttt gttatcttga aaaaaactta ataaatatta taaagataat tttatttgtg   6900
gatttgatta acaagtagta acattaacat catgtaatat tgttttgtgg atatttttcg   6960
ataatatttt ttaaattata atttataatt taatttaata attataaaaa aataaaaaaa   7020
aagtgggcca cggcaagttc tgtagctctc acgtacttat gggttggacc gacccatttt   7080
ctgacccata caaaaaatga gctagcctag cttaacccat aaaatatcaa aacatgtatg   7140
gattagccca ggatgagata tgttagccca tattgacagc tctattccca catcaacaag   7200
gtatttaata tgtcaacttg aaaagaaaag atattccaaa attaatctgc ttatactcta   7260
tcaattccat atctcactta gtgaaatttc gcagaatata tcgttgaata tattgttgtt   7320
gtcgttgtcc tctcccatca ttctaaattt aaagaacatg caatgtaaga ggtaatttag   7380
aaaacttagt tcggccgtag aagaaggatc atctgtaaat ttattcctct gcaagttgat   7440
gctctgttgg aaatttatta ctacaagata gattggttaa tttgaccgta aaacagttga   7500
cattcttttg tcaaggatct attctgggga ggttatagat atacatttga ataatgacat   7560
tgtcaagtaa attatttaac tgtcaataca gaattccaca accaatggtt tatttccctt   7620
```

-continued tagcaatgaa ttgcagtcaa gttcagctag caatatacga ttaaaagttg tttcaaatca 7680
ttggtattaa ttagataagt attgactcaa ttacaagtat acacacagta tatatagaat 7740
ggcgtttgaa aacgaaaaca taggcacaaa tagcagctaa agaagttgaa caaatccaaa 7800
tggttgcgaa gactattatt atagcatgcc tagttttgtt agcatgcctc tcagttacta 7860
atgcatcaaa cattacaact gatgaggctt ctcttttagc tttcaaagct catataactt 7920
cagatcccaa tgaaatgttg tcgaaaaact ggacaaaagg aactcacatt tgcaattgga 7980
taggcatatc ttgcagtaaa aagcatcaaa gagtgacatc attagtcctc aaaggtttaa 8040
ataaatgcac caaacttgaa gttctgtcct tgtcttataa caaattcact ggtaattaac 8100
taacttgtaa acttttcatt tactaatttc ttcttgaatt aatcatcatt tttgtgtgtg 8160
tctgtcattt tataattgat aggaaattta ccaagagaca tgtggaacat gtcaaaggtt 8220
caagaactgt ttattggatg gaataacttt acaggtacgt gattcttgta tgtattaaat 8280
cttgaatact cttcacgaag ttcctaattt cactagatat agtcaatttg tgcattgtct 8340
agtaacaaac aaagattaat atatgttgtg gagaacattt tcgaaagaca ctctatgtct 8400
gatctttagc atgataacca tgtacttatt ttcaaaatga atttgcagga aatataccaa 8460
atgaaatgaa cctaccatct atttgcagga aagttaacaa agcttgagca tctcaactat 8520
ctgaaagtct cttacaatga gttatcaggt gaaataccag atggagggcc ttttggtaat 8580
tttcacagct gaatcattca tcggcaacga agagttatgt ggaccgccta gattccaagt 8640
caaggtgtgt gaaatccaga acaacgtgac aagaagaaac aggaagaaaa cagtactaaa 8700
atttgttctt ggaccagttg cagctggagg tttagtcata ggggttttag gcatgatatg 8760
gttgttgaat tatcggagac gtaacaacca acttattcct ttaactgatt ggtatgatca 8820
gttatcacac aaaaggtttt cttactatga acttgttcga gggactaaca actttgacga 8880
atcaaatttg attggaaagg gaagccttgg tatggtttat aaggggacat ttacaaatgg 8940
gaccatagct gctgtaaagg ttttcaatgc acaactgcaa gatgcattca agaggtttga 9000
tttggagtgt aaggttttgc gtaacactcg aaataggaat cttgttaagg tgataagtag 9060
ttgtgcaaat cttgatttta aggcattggt gtttgagtac atgcctaatg gagatcttga 9120
ttattggctt tactcacaca acaatttctt ggatttaaac aagaggctga aaattatgtt 9180
tgatgtggct tgtgtcgtag agtatctaca ccaaggccat tcacttgtag tggtccattg 9240
cgacttgaac atacttttgg atgaagacat ggttgccaga gtaagtgatt ttggtatatc 9300
caaactcttg accgcgtatg atccagtggc attgacaaag actttaggca ccattggcta 9360
cacggcagca ggtactgatc aaacttttat ttactaatta ctttcttcaa cttgtattcg 9420
atatgcatat atgatgtatt tcattttaat ggcagagtag ggatagtgtc aactatgggg 9480
gatgtttaca gctacggcat tttattgatg gaaaccttca caagaaagaa accagtagat 9540
gatgagtttg ttggagacct tacattgaag agatgggtcg cggaatcata tcctcataga 9600
gtcattgtta tgaaataaaa acgaatacac gctgaacgtc acttatgagt catttatcta 9660
atatgatcca ttaacaattg attaatgtaa cgcaaggaag aagaaaacaa tttgcattgt 9720
tatgaatgaa tgtgtttgta ctacaatata tacagtactg acaagtccag caaactttct 9780
aaccaactta ttctaaccaa ctctactcat tattaattta gctcacttaa tcaagaaatt 9840
aaacttaaca actaactacc attactcatt caactgatca cggaacatca acacattttg 9900
ttgatttctt tcacacacac cctctgcttc gaaaacccct ctttttaaca tgtaagcgac 9960

-continued

```
aatatctttt ttttaggaga gtgttcaaca ttgagcataa aaataataaa atagagaaca  10020
aaaaagatga gtataaaata aataataata taagatcgat tttaccgatt gtcaattttg  10080
tgtatggact aaagaaataa cagcttcaca tatctaatat taaatgtaat actgaatttc  10140
acatatggtc agaggtgaat ccacctgcac ccgatatatt ctttttttaaa aaaattatat  10200
gtatatatat agattgttga taagacggta atatatttaa ttgtgcactc ttataacgaa  10260
caaatgattt gacttgtcca ttggaaaaac gaaaagtgtc acataaattg agacatgggg  10320
agtaacattt ctttcttaaa tttttcgtgt gaagtcaaac taattcatat aaaatgagac  10380
ggaaggagta ctgtttaata ttaattgcat atggtagtaa atttgataga catggtcccg  10440
tgggagtgtg tgttatttcc attgaataat tgagtttgta attgttacaa gtccattcta  10500
atttccaaca ccttacttca tttcaaaaat atactctatg gctgaagctt tccttcaaat  10560
tatgttagag aatctgactt gtttcatcca agggaacttg gattgattct tggttttaag  10620
gatgagttca aaaagcttca aagcacgttt actacaatcc aagctgtggt acaagatgct  10680
cagttgaagc aattgaagga caaggcaatt gaaaattggt tgcagaaact caatggtgct  10740
gcatatgaag ctgatgacat cttggacgaa tgtaaaactg aggcaccaat tatacagaag  10800
aagaataaat atgggtgtta tcatccaaac gttatcactt tccgtcacaa gattgggaaa  10860
cggatgaaaa agattatgga gaaactagat gcaattgcag cggaacgaat taagtttcat  10920
ttggatgaaa ggactataga gagacaagtt gctatacgcc aaacaggtaa atatttttct  10980
aaataacagc tttatatcat caaattcatg tgtgttttgg ggattttgtc taagtagata  11040
agtggttcaa aatctattat ctaaatctgt ttggtgaagt ctttaacata tatataaatc  11100
catagcttac tcatatgccc caaagtctaa atgacaggat aaagccagag ttgttttaga  11160
ttttataaat taacaaagat aataatgtaa attcaaaata gtgcatttgt tttatatttg  11220
aaatatgtct gctgcttctg atcaagctga tcattgtctt ttgcaaaatt cttctttgtt  11280
ttttttgctg actcttaccg atcttggacc aggttttgtt ttaaatgaac cacaagttta  11340
tggaagagac aaagataagg atgagatagt gaaaatcctg ataaacaatg cccaaacact  11400
ttcagtcctc ccaatacttg gtatgggggg actaggaaag acgacccttg cccaaatggt  11460
cttcaatgat cagagagtaa ttgagcattt ccatcccaaa atatggattt gtgtctcgga  11520
agatttaatg aaaagaggtt gataaaggaa attgtagaat ctattgaaga aaagtcactt  11580
ggtgacatgg acttggctcc acttcaaaag aagcttcggg acttgttgaa tggaaaaaga  11640
tacttgcttg tcttggatga tgtttggaat gaagatcaag ataagtgggc taagttaaga  11700
caagtcttga aggttggagc aagtggtgct tctgttctaa ccactactcg tcttgaaaag  11760
gttggatcaa ttatggcaac attgcaacca tatgaattgt caaacttttc tcaagaagat  11820
tgttggttgt tgttcatgca acgtgcattt gggcactaag aagaaataaa tcttaatctt  11880
gtggctatcg gaaaggtgat tgtgagaaaa tgtggtggtg tgcctctagc agctaaaact  11940
cttggaggta ttttgcgctt caagagagaa gaaagacagt gggaacatgt gagagatagt  12000
gagatttgga aattgcctca agaagaaagt tctattctgc ctgccctgag acttagttac  12060
catcaccttc cacttgattt gagacaatgc ttttcatatt gtgcagtatt cccaaaggat  12120
accaaaatgg aaaaggaaaa tctaatctct ctgtggatgg cacatggttt tcttttatca  12180
aaaggaaact tggagctaga ggatgtaggt aatgaagtat ggaatgaatt atacttgagg  12240
tctttttttcc aagagattga agttaaatat gatcgaactt atttcaagat gcatgatctc  12300
attcatgatt tggcaacatc tctattttca gcaagcacat caagcagcaa tatccgagaa  12360
```

```
ataaatgtag aaggttacct acatatgatg tcgattggtt tcgcaaaagt ggtgtcttct  12420
tactctcctc ctcacttgca aaagtttgtc tcattgaggg ttcttaatct aagttccatg  12480
ggacttaagc agttaccgtc ctccattgga gatctagtac atttaagata cttgaacctc  12540
tctctcaata acatgcgtac tcttccaaag cagttatgca agcttcaaaa tctgcagact  12600
cttaatgtag agtattgctg gtcactttgt tgtttgccaa aagaaacaag taaacttggt  12660
agtctccgaa atctcttact tgatggttgc gatggattgg attctatgcc accaaggata  12720
ggatctttga catgccttaa gactctaagt ttctttgtta ttggcgagag aaaagattct  12780
ctacttggtg aattacgaaa cctgaatttg tatgggtcag ttgaaatcac gcatcttgag  12840
agagtgaaga atgataggga tgcaaaagaa gccaatttat ctgcaaaaga aaatctgcat  12900
tctttaagca tgagatggaa aaaaccacat agatatgaat cagaagaagt tgaagtgctt  12960
gaatccctca aaccacaccc taatttgact tctttactaa tcactggctt cagaggattc  13020
cgtcttccaa agtggatgaa tcactcagtt ttgaaaaatg ttgtctctat tgcaattaga  13080
ggttgtgaaa actgctcatg cttaccaccg tttggtgatc tgccttgtct tgaaagtcta  13140
gagttaggag atgggtctgc ggaactgaag tatgttgaag attctggatt ccctacaaga  13200
agaaggtttc catctctgag aaaacttatt atagtcaatt ttgataatct gaaaggattg  13260
ttgaaagagg caggagaaga gcaattcccc gtgcttgaag agatgacaat tagctggtgt  13320
cctgtgcttg ttattccgac cctttcttct gtcaagaaat tggtagttta tcggaacatg  13380
tcagatgcaa taggtttgag gtccatatat aatcttaggg ctcttacttc cctcaacatt  13440
agccataact tgacagctac ttcgctccca gaagagatgt tcaaaagcct tgcaaatctc  13500
aaatacttgg aaatctcttt catcttcaat ctcaaagagc tgccaaacag cctggctagt  13560
ctcaatgctt tgaagcatct gaaaattgaa tattgtgacg cactcgagag tctccccgag  13620
gaaggggtga aaggtttaac ttcactcaca gaattatcca taacaaattg taagaggcta  13680
aaatgtttac cggagggatt gcagcaccta acaaatttat cagttaggga atgtccaaca  13740
ctggccaagc ggtgtgagaa gggaatagga caagactggt acaaaattgc tcacattcct  13800
catctgctta ttactaatga gatgtaattt tctgattttt cttttggaaa caaatcaact  13860
atttgtaacc aattcgtatt ggacttttga gccctgcatt tgttcgaata cgcctttcaa  13920
cctgtatatc agtgtataac aaatgtatac aatatgtata ctgctgctca aatctgcaga  13980
tttgattttc cagcaacaca tttgctgatt cttccgacct gtaaattaat ttccagcagc  14040
tcattttttt gtgttcaacc tgtacgccag ttgtgagggt ctaagacttg aggaggaggt  14100
ttgagccttt acggctcagc gaggaagtgc agggatacgg gcgaaatccg ttaggactca  14160
tggcgaatgc acgtgaaacg gatcaaaagg aaacataaag aaaaacagtc aacgatgaaa  14220
acaattctgc atttatacgc ataactaagg caatgtaaat caaattgaag aatgggcagc  14280
caagataaat gaaagcaaat aaagccacaa tgcatgtttt aaaatactat aaccctgcca  14340
tgctgcatag acacacattt atattcaaga ttcaagtcat aacaaaatat aatttgaaag  14400
tttaaagctc tggatatcag cttactacag ttcaatcttc ttacttaaaa aagatgctaa  14460
aaaaaaacaa aattcaactc ttccaggcaa ctaacaatat caaacctaca aactaacata  14520
tgagcaaaaa aaaatcattg aaataaaggc atacaaatac taaaatgaca accactagtt  14580
catgaaaaac aaaatggagc aggcaataaa taataaacaa gataatagat aaatatgtct  14640
tttaatttta ttttatttta tatttgtatc cttcaaattt gaatgtacac ataatttgat  14700
```

-continued

```
attttaactt gtatataatt gaacaagtac atagttaagt catatgtagc ataaatatat  14760
atatatatat atatatatat gaaacaccac ctatgacaca atttccatga agcatgtaca  14820
cttttatttg ttcatttcaa tactgagttt aagtatttta ctttgtttca tattatagtt  14880
gaacaccata aatataaaat aatatcaaat ttaaaaaata tatttatgta ttatgcttta  14940
aaaaatattt tttaaaaatc tagtaattgc cccaccataa aagagatgcc cattatacgc  15000
cgaaagaatg tttaaaatca aaagcaactg ttagttattg gattgaaaaa taaaaccaaa  15060
tactccaatt gagagacatg gcggccccat ggtggaataa ttattacaac acaccttcca  15120
taattaaagt ttgaccttac acctagagac aatcaaattt tggatttggg tcttatttta  15180
ctagttaaca tttcagataa tcacttaatt ttaaataatt tatttcgata gtcattcaac  15240
tttgaattat tctgttagaa agtcattcaa ttctatttta aagtcaaaag tcactaatat  15300
ttgagttgtt ggtttaaaag gtcattcaac tctctttata attcaaaagt aacataatta  15360
tttttgttt cacttaaaag acatccgatc aacttaaata tttttcata aaatcttatt  15420
tttatgttaa actattcttt ttaaaaataa taagatattt attttagaaa aagggaaaat  15480
atgttaaaaa gttagttatt ccaaaaaaga agaaagaagt tggaattgaa aagaaataat  15540
ataaaaaccg cagcacagtg cctttttttct tattactttt tatttaaaag atagttataa  15600
agaaatatta tacttcaaca aaatttaata aaataattaa aagcagctta taattttatt  15660
ttatttttgt attcagtcaa atttaataaa aaatttcatt ttaaaataat tgtctgactt  15720
tctaagtaaa attagttgag taatttttag gttataaaac aaaattgagt gactttcgaa  15780
gttaactcaa atctgagtga ctttctaagt gaattattcg aagttgagtg aatattaact  15840
ccttatacaa gttcgaggaa gatattgaaa aagattgtac atatggggtt cgtaagctcc  15900
ttcatgtcag cttataaaag gcttcacaca agtatatata gcgggtaaaa ttttattttg  15960
tgagaggtag aaatgttact cggcagacaa tacttgtatg acatgcttaa agcttcattt  16020
ttttctcttt cacctatttc tatcttcttc ttctctcttt ttttctccgt gcttcataaa  16080
attttatttt atttttcatc aaaaacttga tacttaatat attttattga atgaaaattg  16140
atttaataat tttattttc aaatgttaaa atcaagacaa atcaattaag ttgatttttt  16200
tcattacttt atttttttc cttgcgattt gtttttgtg gacttctcga aaatatataa  16260
taatataaaa ttatcctctg aaaaaattat gcattacgaa gaatttaatc attactaaga  16320
aatttgataa aaaattccca atgattttac tatattctta caaaaattaa agatttaagg  16380
ctgatatatt aaagatgtct tgttaatatt ttatttaaat aaaataatca attaaattac  16440
gagttatttt gaacatgaaa aaacactttc aattttatct aaataaaaat ataaattaaa  16500
ttacaaagta aaaagaataa ttattataaa gagaaacaca tgagtactca caaagagaac  16560
aaaaaaaata tttataataa tttttttagc ttcagagaag gttatacgta taatcaaaat  16620
tattacggat catttattaa taaaataata aaataaaaat tctcctaaaa aattaatgta  16680
tgatcttttt ataagcaaac acaaaaatta tttaattaca ctatattaaa tttctttaat  16740
ctcactaaaa aactattttt tctcgtttca tttactttaa gttttcctta aataaataat  16800
ataaaaataa aatagttaaa cattgtggct aattttttt aaaaaaaaca caaaagacta  16860
caaaggagaa caagagaatg agaaacaaaa gtttacggga aaagagtctg atataccccct  16920
taactttgtc atttggagct aatatatccc tcgttataaa agtggctcat atatgccctt  16980
accgttatac aaacggctca tatatacccc tgtcgttata aaatgactca catataccct  17040
taatttgtgg aagttaaaaa ttagttttaa atttatattt aatacttcta atttttaaaa  17100
```

-continued

```
aaaattattt agaggtatat atgattcttc tatcaaagtt caaggtatat tttaattttt  17160
ttttcataca taaactattt ttgacttctt ttattataat tatttgagtt tcttattctt  17220
attttatttt tttttctttc attccttagt ttaaagagag agaaaaatta aactattttt  17280
tttgtatgta ttgtaattta atttcgtatt caaagaaaaa aatttagtca tctacaataa  17340
gttttacaag aatattagtg aaaaaataaa taaatttgat tatcaaaata ataattataa  17400
attagtcatt gaaaaaaaaa gtcaaaaaaa aatgtttttg agaattaaat ttattcatat  17460
gagattatat tttatagaaa aaataataaa aatttagatt aaaattatat tttttcattt  17520
ccgttagatt aaagggatat ctcgagccat ttgtttacaa gtagggtata tatatgctac  17580
tttcatgtta ggtatatcag ctctaaataa caaaattgat gggtatatca gaccctttttc  17640
tcaagtttaa attaatgtga aaaagtttta agtgtgggtc ccatgttgta catttaaaat  17700
tctcatacaa cagacaaaag gttagctttt cacaaaataa aatttttccc atgtgaaact  17760
caaaataaaa taattgcgta cagacatatt tatgcaacac aacattaatt tatttattta  17820
cccattcaat aagtaaagga ataattataa agctttgtgc tcttactttt agctgttcat  17880
atttcattcc aacatcgatc ttatagattt attgctaatt cacaacaatt ccagcaatct  17940
acatggctga agctttcctt caaattttgt tgaaaaattt gacttctttc atacaagagg  18000
aacttggatt gttttttggt tttaagaacg agtttgaaaa tcttaaaagc acgtttacta  18060
cgatccaagc tgtgcttgaa gatgctcagg agaagcaact gaaggacaag ccactagaaa  18120
attggttgca gaaactcaat attgctgcat atgaagttga tgacatcttg gatgaatgtc  18180
aaactgaggc agcaagactc aaagagacta aatatgggag ttatcatcca aaggctatcg  18240
ctttccgtta caagattggg aaaaggatga aagagataat ggagagacta gatgcaattg  18300
ctgcagaacg aagcaagttt catttggaaa aaaggactac agagagagaa gctgctagac  18360
gagaaacagg tgctcatctt taattagttt atattcattt ttttgcgatt atcaagttca  18420
tgtgtgttta tggacccaag ggactttttt ctaatctaat gtttgtctca agtctaaaca  18480
gatttgtaat tctaccactt atttatttag tgaagttctt aaacatatat acatggtgta  18540
agccagctca gataaatcca tagtcagttg tttcggactg aacttaactt ggatgtcaat  18600
ttttcaaagt caatcatgtt ttcaactcct ccccctgatt ctcatctctt tgtagtgcaa  18660
aaatcttctc tctgttttc gctaaacata ttctcgtgtg aacatatatt gcttgaaaca  18720
ggttttgttt taactgaacc agaaccttat ggaagagaca aagaagaaga tgagatagtg  18780
aaaatcctga taaacaatgc ccaacaactt tcggtcctcc caatacttgg tatggggggg  18840
ctaggaaaat cgactcttgc ccagatggtc ttcaatgatc agagagtaac tgaccatttc  18900
catcccaaaa tatggatttg tgtctcagaa gattttgatg agaagaagtt gataaaggca  18960
attgttgaat ctatcgaagg aaacccactt ggtgaccaca tggatttggc tccacttcaa  19020
aagaagcttc aggacatgtt gaatggaaag agatactttc tcgttttgga tgatgtttgg  19080
aatgaaaatc aagaaaagtg ggataagata aaagcagtct tagaggttgg agcacgaggt  19140
gcttctgttc taaccaccac tcgtcttaaa aggttggatc aattatggga actttgcaac  19200
catatgaatt gtcaaatctg tctcaagaag attgttggtt gttgttcatg aaacgtgcat  19260
ttgagaacca agaaaaaaat aaatcctaac cttgtggcta tcggaaagga gattgtcaaa  19320
aaaagtggtg gtgtgcctct agccgccaag actcttggag gtcttttgcg cttcgtggat  19380
caagaaagag aatgggaaca tgtgagagat aatgagattt ggaatctgcc tcaagatgaa  19440
```

-continued

```
agttctattc tgcctgccct gagacttagt tatcatcatc ttccagttga tttgacacaa  19500
agttttgcat attgtgcagt attcccaaag gacacggtaa tggaaaaagg aaatctaatc  19560
tctctctgga tggcacacgg ttttctttta tcgaaaggaa acttggagct agaggatgta  19620
ggtaatcaag tatggaatga attatattta aggtcttttt tccaagagat tgaagttaaa  19680
gatggtaaaa cttatttcaa gatgcatgat ctcatccatg atttggcaac atctctattt  19740
tcggcaagag catcaagcaa caatatccgt gaaataaatg taaaacggaa cccacatatg  19800
atgtcgattg gttttgcaaa agtggtgtct tcttactctc cttctcactt gcaaaagttt  19860
gtgtcgttga gggtgcttaa tctaagtgaa ttaagactta agcatttacc gtcttccatt  19920
ggagatctag tacatttaag atacttgaac ctctaccgca ataacatgcg tagtcttcca  19980
aagcagttat gcaagcttca aaatctacag actcttgatc tacagtattg cgccttactt  20040
tcgtgtttgc caaatcaaac aagtcaactt agcagtgtca gaaatctttt acttcatggt  20100
tgctataaat tgaattctat gccaccaagg ataggatctt tgacatgcct taacactctt  20160
ggttgctttg ctgtgggaag gaagaaaagt tgtcaacttg gtgaattacg aaacttgaat  20220
ctctatggct caattcaaat cacacatctt gagagactga agaatgatag ggatgtaaaa  20280
gaagccaatt tatctgcaaa agaaaatctg cattctttaa gcatgacttg gaaaggacca  20340
catagatatg aattagaaga agttgaagtg cttgaagccc tcaaaccaca ctccaatgtg  20400
acttgcttaa caatccatgg cttcagagga atccgtttcc cagagtggat gaatcactca  20460
gttttgaaaa atgttgtctc tattgatatc cggggttgcg aaaactgctc gtgcttacca  20520
ccctttggtg agctgccttg tctaaaaagt cttaagttac aggacgggtc tgcggaaatg  20580
gagcatgttg attctggatt ccctacaaga aggaggtttc catctctgag aaatcttatt  20640
atagtcaatt ttgataatct gaaaggattg ctgaaagagg caggagaaga gcaattcccc  20700
gtgcttgaag agatggatat ttggtggttc cctgtgtttg ttattccgac cctttcttct  20760
gtcaagaaat tgttagttca ttggaacatg tcagatgcaa taggtttgag ttccatatca  20820
aatctcaggg ctcttacttc actccacatt agaactaact tcatagctac ttcgctccca  20880
gaagagatgt tcaaaagcct tgcaaatctc aaatacttga aatctcttt cttctacaat  20940
ctcaaagagc tgccaaacag cctggctagt ctcaatgctt tgaagcatct ggagatgaat  21000
tgttgtccca aactggagag tctccccgag gaaggggtga aaggtttaac ttcactcaca  21060
cagttatcca ttacatactg tgagatgcta aaatgtttac cagagggatt gcagcaactc  21120
acaaatttat caattaagaa ttgtccaaca ctggccaaga ggtgtgagaa gggaatagga  21180
caagactggt acaaaattgc tcacattcct catctgctta ttactaatga gatgtaattt  21240
tctgattttc ttttggaaac aaatcaacta tttgtaaaat ctatttgtat tatacttgat  21300
ttttcttggt tatgtaacaa taaatatttg aaaattttca tataaaaata gttacatttc  21360
tatatgtata attcgccaga ataatacata tatatgtata atatacaatt atttaaccga  21420
tatacatata taattcacct ctctcccact ctctgtcctc tctcactcgc ctctctcctc  21480
cctctctcaa tttcgctttc catatataca aatacaatta tctaaaagat atatatatat  21540
atatgcaatt catctctctc ccactctttg cttcacttga caactatgac atttaacatt  21600
ggacaagcac aaattgacac ttaaaaactg gttacagaaa ctcaacgctg ctgcgtataa  21660
agttgatgac ttattgaatg aatgagaata cgaggcagca agactaaagc agtctcgact  21720
aggacggtat catccaaagg ctatcaatac aaactcagtt gtttagacca cgaaaagact  21780
gtgaattcaa tacaggagta gttaacgatt actctaattc tatgtcacag aaagtaattt  21840
```

```
cataagcgag aaaatcctct agcatttttc catttctctt tatggcgtgc aaatatcgtt  21900
atctattttc tgctgtctcc tagctaatta tcttgaatgt acgtaacact ctctatttat  21960
ttccaagaga ttgaactaaa atctggtaaa acttatgatc tctgttttca gcaaacacat  22020
caagcagcaa tatctgcgaa attaaacaca tatgatgatg tcttcttact caccgagtta  22080
ttagttatgc taaaatgttt acccgaggga ttgcagcacc taacaaatct cacaattttt  22140
ttttattagt gaaagcatag ttatcaaaat aaaaacaaaa aatgagcaat atttatacaa  22200
cagacaaaaa aaagaatgat ttttcatatt ctttgcttat gttaccgatt cataacccat  22260
ataaaaacaa atttcaatca cccattaaac caaaaatgat taaacaaaaa aaatcttcta  22320
gatatctaac taatgaataa taacatattc agtgtagtcc cacaagtgga atctgggtta  22380
actatccaac taatcataga tcaaaattgc agtgaaaggt attttattag accacttcca  22440
atctcaacta tttcaacaca aaacttatat tcaatctttg atggataata gaccatctat  22500
ttttaattcc cttttctcac caacaaattg aaatgtcagt gatgtttctg agcaacaaaa  22560
agtactttaa gatgatattc taaatgtgca caatttcatg ctccaacaat cgaccaatta  22620
gattaaaaaa tatactcatt gagtatttct tctgtcacat ggtcaatacc atagaaaatg  22680
aaaaatataa tcacaattta acaacataac tattgagatg gaatatgttt catctagtta  22740
aaaaaaattt acttgagaat gttgtttgtg agcattacac taatagacgt cagatgattt  22800
tcggatggtg gtcaaatgac acttgttact ggttcaagca gagtaatggg atgtgaaatt  22860
gcccttcaat cgtagaaaat ggaatatata aagcaaagtt acacaattta atcgtactct  22920
tgaaacttat ctctctataa tccatgtttg ctataaacaa taatattgtc ttacacatat  22980
tcaacaatta catatcctat ttaaactaat atacgaaata tattcaataa aaagtgcatg  23040
cagacgattt ttctacaata aagactccag gtttagagtg tttagcgact cctgataaag  23100
acaatgagat tatagtaaac aggagaaaca gagcagctct tcataaataa agaggaggaa  23160
aaaatctacc gattgatgca cgtaaaagag taaatgtgag actaatgaca ataacctgtt  23220
gttggagaga tttatataga tgagtatttg aaaagtttac gatcaaatga acttgagcgt  23280
cagaaaagtt gtcgcttgag cagtaactgt tatagtgatc aatgaggcat tttttggaga  23340
attaaattag gtctcaaact atgagcaaat ttaatttata ataaattaat acttattaaa  23400
actgtagggt taaaacggta aatcaagttt atgattaaac tcttcccact tataataata  23460
taagattaaa aataatcata aaatagaatg gtgcattggt atcaaacaag aaatatgtga  23520
aactaattaa gagaatatag tctctaaggg tatgaatata tcgatgaatg cttgattgaa  23580
aaataataat aaatgtatat aagtctttaa tgaaataaca aaggcacgag ataaatttat  23640
tagaaatata aatctacata ttctaggtat tacaaaaaag atcctaaaat atgtagcaaa  23700
caaatgactt attcttctat aaagcacgta accatcgaag tttaatgtta atacgataag  23760
attgccttga gaatgcattt acttgtgata agtccacggg tctacgtata agtatagttt  23820
attgtattct tataaaataa tagtaaaaat aatagtctct ttttatttca aatttaattt  23880
ttaataaaca gaaaataaat taataaaata agacaaaaaa caataataat attatagaca  23940
tgtttatgat gagtacgtat aatttgaagg ggaaaactac aaattcaaac tcaagagaaa  24000
ataataaagg tttggaataa aatatctaag atacggaaag attaaaatgt gttctctaac  24060
taaaatcttc atcttcatga ataattaaca tgaaaataga ggatccacca aaaattaaat  24120
aggagaagga aagagactta ttagaaaaat gatgaattat aaaatctaaa agcctatatg  24180
```

-continued

```
tgaaaataag agaacaagaa tattgcataa aaaaaaatta tagctacgaa aaatactatg  24240
tgtgatttta aagataaaat ctattttatt gttacatgta tcatatttat tgttgaaatt  24300
tcacctttta aaaaatgaaa aacaagctaa gaaaaaaaaa gtaaaaagag gaaaatgaac  24360
aaataaaaga ttaatagaga aaagggaaaa ataccaatga atatcctgat tgaaactgca  24420
ttatataaat cttcggatca atccatttac cttgaatttc aagaacactg caaattcgat  24480
cataaattaa tctaaaaaga ggcatgttta tgataaaagg ggggaaaaca gtgttagaag  24540
aaaacaataa agaaatagtg ttagaagttt gaaatcttca tgtttcaaaa aagaacaaat  24600
taatcttcaa tgtcaagtaa aatctcaaga tctctagtaa agaaaattta tttttatact  24660
acaaacaaat taatggcatt ttaaacatat aaagaaatat gaggatcaac atattataga  24720
ttaactacaa gttttcatgt ccttaaaaga taacttatca accacaaaca aaagtaaatt  24780
gaagggcaag agatgaagaa gtcttcagtt tgttaactta attggtgttt ctatcttcca  24840
tgtcttttga aatgtgtatg aagatgaaat gtttcaagta cttgaagatg aaatatagtt  24900
tcttacttgg atgcttaaca atgttattac ttcaaaaaga acctgaaaaa aatcattatt  24960
cacttggttg cttaactatt ctattacttc aaaagattta ttactttcaa ttggcttttc  25020
acttacccta ttcatggtga ttaatatgta agtttcatgc aatgtctttt caattatcct  25080
aattattgta attgaaatgt gaatttattt ttcagataat taaaatatta tgtttttttt  25140
catataataa tgttcaagaa taaattggta attcaacttt aagctaaagg gcttcccact  25200
tataataata tgatatgata tgatgattat tagatgtaat tttctgattt ttcttttgga  25260
aacaaatcaa ctatttgtaa catctatttg tattatactt gatttttctt gggtctgtaa  25320
aaataaatat ttgaattttt tcatattaag attcataatt agtcttatag cttaactgta  25380
agaaagaaat tacaaattaa atttgacaaa taattaagct acttaaataa cttaattgtt  25440
caatataaaa ttttaaggat tgcctaaact tagaaaaaaa aaacaattaa atttagttat  25500
atggttgcaa tgtgtaatca aatagtaata aatatgtggc tgtttgtaca gctacaatat  25560
gacatgagat aattaaaata tatgtgtctt taagctctcc tctttttgtt tgttttgagg  25620
aaaatctgtt gtattttgat gtgtataatt ggttaattat acactctttt agaaacaaat  25680
agtgttgaat ctacaataac atgtgaatac atagatttga taaaatataa aatcgtaaat  25740
agattagacc atctttttta ttgacagagg tgaaagacaa agcaacccca caagaaaaga  25800
taggtatgaa actagctagc agttttatga acaattaata taaaatataa aacacttttt  25860
attttactca acaattaatt tataagctat ttttatttta aaacacttaa aataagttaa  25920
ttcgaacatg tactataaat caaaacaaat aaggaaaaaa aggaaaagct aaaggtgtgt  25980
ttggtatgaa ggaaaatgtt ttcctaaaaa ataaatagat tttggattta ttttctcatg  26040
tttgattggt aagtagaaaa tattttcctg tgtttgattt atgaatgaaa ttaatttttg  26100
gggggtgggg gtgggtgggg gctggtaggg gtggataggg ggctggccgg gtggaggagg  26160
gtaggagttt aaaaataaaa atttgaagtt gaaaatattt taaaaagcaa aattaatttt  26220
tggggagggt gaggtttagg ggctggtcgg tggtgggtgg acgggggtca aggatcgagt  26280
gaaaaaataa attttaaaat tgaaaatatt tttattaata ttgatatttt cctaaatttt  26340
tgaagggaag tcattttcct taatttttag gaaaatgagt tgatttgaaa aatattttct  26400
aaaactttta ttccaaccaa acatgaaaaa attgaaaaat attttccaga aaatgttttt  26460
cttcatacca aacacactca aaaagagact cttttaatca agtattattg ctaaaaaaaa  26520
aagagacaaa gaataataat ttaccccata aatttcgcaa atcaatctat aaaagattga  26580
```

-continued

```
gggtgagata ttgataagat aaaacaatca aaataataga taaatatgtc ttttagttta  26640
atttaatttt atatttatat tccttaattt agaatggaca cataatttga tatcttaact  26700
tgtatataat taaacaagta tgtatatata tatatatata tatatatata tatatatata  26760
tatatatata tatatatata tataacacca cctatgacac aatttccatg aaggatgtgc  26820
acgtttattt tattgattct atacaagttt aagtatacgc ttattcatac tatagttgaa  26880
taatataaat ataaaataat atcaaattta aaagatatat ttatatatta tcttaaacaa  26940
atatgtttta aaaaaaaata aaatctagta actaccccac cataaaagtg atgcccttat  27000
acgccgaaag aacgtttaaa atcaaaagca actgttagtg ttattggatt gaaaaataaa  27060
accgaatact ccaattaaga gacatggcgg ccccatggtg gaataattat tacaacacac  27120
cttccataat taaagtttga ccttatacct aatgacaatc aaattttgag ttcggatcct  27180
atttcatgag ttaatatctc atataatcac ttaattttaa ataattcatt tagtatgtta  27240
ttcaagttta aattgttcac ttaaaaagtc attcaactct attttataag taaaaaatca  27300
ctaatatttg agttgttcat ttagaaagtc attcaactct ctttataatt caaaagtaac  27360
tcaattattt ttgtttcact taaaaagtca cccgatccca acttaaatat tttttttca  27420
taaaatctta tttttatgtt aaactattct tttaaaaaaa aaataagata tttattttag  27480
aaaaggggaa aacatgttaa aaagttagtt attccaaaaa agaagaaaga agttggaatt  27540
gaaaagaaat aatataaaaa aaaaacgcag gacagtgcct ttttttctta ttacttttta  27600
tttaaaagat aggtataaag aaatattata cttcaacaaa atataataaa taattaaaat  27660
aagcagctta taattttatt ttatttttgt attcagccaa atttaattaa aaaatcattt  27720
aaaaataatt gaatgacttc ttaagtaaaa ttagttgagt aatttttaag ttataaaata  27780
aaattgagtg actttcaaag tgaactcaaa gctgagtaac tttctaagtg aactattcga  27840
aattgagtga acatctgaga tattaacacc ttattttata cgtgaaacaa tttaaactat  27900
attacaaaag ttggaggaag atattgaaga aagattgtac atatgttcgt aagctccttt  27960
atgtcagctt ataaaaggct taacacaagt atatatagcg ggtaaaattt tattttgtga  28020
gaggtacaaa tgttacttag cagacaatat ttgtatgaca ttctctcagc ttttgccaag  28080
tggagtttgg gtctcactta cagaaaatgt gcttaaagct tcattttttt ctctttcacc  28140
tatttctatc ttcttcttct ctcttttttt ctccgttctt cataaatttt attttatttt  28200
ctgtcaacaa acatcgatac ttaatatatt ttattgaatg aaaattgatt taataatttt  28260
tatttttcaa atgttaaaat caagacaaat caattaagtc gatttttcat tacttttttt  28320
ttccttgcga tttgtttttt gtggacttct cgaaaatata taataatata aaattatcct  28380
ctgaaaaaat tatgcattac gaagaattta atcattacta agaaatatga taaattattt  28440
ccttacaaaa aaattaaaga tttaaggctg atatattaaa gatgtcttgt taatatctga  28500
tttaaataaa ataatcaatt aaattacgag ttattttgaa cataaaaaaa cactttcagt  28560
attatctaaa taaaaaatata agttaaacta caaagtaaaa aaaaataatt attataaaga  28620
gaaacacatg agtactcaca aagagaacaa aaaaaaatatt tataatgatt tttttagctt  28680
tagataaggt tatacatata accaaaatta ttacggacca tttgttaatg aaataataaa  28740
atataaagat tctcctaata aattaatgta tgatcttttt taaacaaaca caaaaaattag  28800
ttaattacac tatatttaat ttctttaatc tcactaaaaa aactattttt tctcatcaca  28860
tttactttaa attttcctta aataaataat ataaaaataa aatagttaaa cattgtggct  28920
```

```
aattttttttt tttttttaca aaaaaacaca aaagactaca aaggagaaca agagaatgag  28980
aaacgaaagt ttaaagggaa aaaagtctga tatacttctc aactttttca tttggagctg  29040
atatatttct cgttataaaa gtgactcata tatgccctta tcgttataca aacgactcat  29100
atatctgagt catttgttta caagtaaggt atcactttct taaaaaagca atgatatcat  29160
ctctaaaacg acaaagattg aggggtatat cgatcctttt tcaaagttta aatgaatgag  29220
aaaaagtttt aagtgtgggt cccatgttgt acatttaaaa ttctcataaa ctgacagaag  29280
gttagctttt cacaaagtaa aatttttccc atgtgaaact caaaataaaa taattgcgta  29340
cagacatgtt tatgcaacac aacattaatt tatttattta cccattcaat aagtgaagga  29400
ataattataa tgctttgtgc tcttactttt agctgttcat atttcattcc aacatcgatc  29460
ttatagattt attgttaatt cacaacactt ccagcaatct acatggctga tgctttcctt  29520
caaattttgt tgacttcttt catacaagag gaacttggat tgaaaatcta aaaagcacgt  29580
ttactacgat ccaagctgtg cttgaagatg ctcaggagaa gcaactgaag gacaagccaa  29640
tagaaaattg gttgcacaaa ctcaatgttg ctgcatatga agttgatgac atcttagatg  29700
aatgtcaaac tggaattttt aaccaaatta agtcattata taaaataatt taccaaagta  29760
aaatattttt ctaaaagttt acaaaactaa tataaacgta tttcatggta acgttttagg  29820
gtatatttta ttttttaaaa actaatgact ttaggttgat atcgttcttt gtaagtaacg  29880
ttttactcct aaaacgttat tttcaataac attttactct taaaacgtta ctcatagtaa  29940
cgttttactc ctaaaacgtt attttcaata acattttact cctaaaacgt tactatgagt  30000
aacgttttag gagtaaaacg ttactgtgag taacgtatat caatctgacg ccatcaactt  30060
ttaaaaaata aaatatatcc taaaacgtta ctgtggaata cgtttatact agttttgtaa  30120
aattttagaa aaacatatta ttttggtgaa tgactttata taatgactta gtttggttaa  30180
aacctcgtca aactgaggca gcaagactca atcagactaa atatgggagt tatcatccta  30240
aggctatcac tttccgttac aagattggga aaaggatgaa agagataatg aagaaactag  30300
atgcaattgc tgcagaacga agcaagtttc atttggaaaa aaggactaca gagagagaag  30360
cttctagacg agaaacaggt gctcatctta aatatattag tattaattac aacaatttaa  30420
ttagtttata ttcatttttt tgctattatc aagttcatgt gtgtttatgg acccaaggga  30480
ctttttttcta atctaatgtt tgtctcaagt ctaaacagat ttgtaattct accacttatt  30540
tatttactga agttcttaaa catatataca tggtgtaagc cagctcagat aaatccatag  30600
tcagttgttt cggactgaat ttaacttgga tgtcaatttt tcaaagtcaa tcatgttttc  30660
aactcctccc cctgattctc atctctttgt agtgcaaaaa tcttctctct gtttttcgct  30720
aaacatattc tcgtgtgaac atatattgct tgaaacaggt tttgttttaa ctgaaccaga  30780
accttatgga agagacaaag aggaagatga gatagtgaaa atcttgataa acaatgccca  30840
acaactttcg gtcctcccaa tacttggtat gggagggcta ggaaattcga cgcttgccca  30900
gatggtcttc aataatcaga gagtaactga ccatttcaat cccaaaatat ggatttgtgt  30960
ctcagaagat tttgatgaga agaagttgat aaaggcaatt gttgaatcta tcgaaggaaa  31020
gtcagttggt gaaaacatgg atttggctcc acttcaaaag aaggcattgt gtcgatttga  31080
gataatacga gaaaaatata catgcgaaaa acaagacaac agatttcgtg gttcaccaat  31140
aaattggctc gtccacggga agagggcggg ttttattatg gaggcaaaaa ccaattctga  31200
gaatagggtt tgccatagcg tctatatata gtgtaaacta agcccctaac aggcttgggc  31260
ccaaaatata aattgaatga taattaaggg cccaattcaa ggcattcaac aaatctccac  31320
```

```
cttgacttga attctccaag cagattcttg ggcgcactat gatagtgcca ggcctccccc  31380
ctcttcctcg ggttgccctt gagtataatt acttgacacg atgttgagca agtcaaacga  31440
gtgttgaaac ttgctcacgt ggagccaagc tttgtgaaca tatcagcggg attatcaaca  31500
gttctacttt cttcaccttg attctcttct cacttctcgg gaaaatgata cctccgtcaa  31560
tatgcttggt tctctcatga tggacttgat ccttggctag acaaattgcg ctcaaaagct  31620
gtcaatacac acgtgctttg agtcatgatc gagaccaaga tcactaacca gccccttca  31680
accaaatccc ttcttttgca gcctctgtca aggccatgta ctccgcttcc gtagtagaca  31740
aagtcccatg taggttgcaa agttgccttc aatgacgcgg atcctcaagg gtaaacactt  31800
gagtcatccg atcttcttgt gtcaacatct ccaaagatag tctgaatcag aatagccaat  31860
aaccaagcac tgagtatcac ctccataaat gggaccagcg tcggatgtac ctctaaggca  31920
ccgaaaaatt ctcttctgac tgccaatgtt ctctccacgt tgtcccatga atgctcacta  31980
cactaatttg catgtactaa atctggcctt atacagacca tagcatacat caaacttcct  32040
cagcactggc ataagggact cgtgacatat actccttctc ttcttctgac tgtggagccg  32100
aacatggcga gtgggatgga taaaggcgtg gggtatcaat gggcttagat gaagacatgc  32160
caaacctagc caagaccttg aatgtaacct tctctgtgac aagaaaagtt tccttctctc  32220
tctgtctcta atgatctcca tccctaaaat cttcggctcc cggatccttc atctcaaact  32280
cagactaagt aaacccttga cttctgagat gtcatacttc ttctttgcag ctatcaatat  32340
atcatctaca taaagcacta gatagatgaa tgaatcatcc ttgagcctat tgtagtagac  32400
acaacaatca tatgagctcc gagtatagcc caacttcacc atatagctgt caaacctttt  32460
ataccacatc cttggagact gcttaagtcc atataaggac ttcttcaact tcaggacgtg  32520
attttccttc tggaacttgg aaaccatcct ttgagtcatg tatatctctt cctccaactc  32580
tccatgtaga aacgctgtct tcacatcaag ttattcaagc tccattctga tgtgtaacta  32640
tcgctagtaa cactcggatg gaagtatgtc tgaccactgg tgagaagatc tcattgtagt  32700
ccactccctc tctttggttg aaacctctgg caacaaccct ggctttatac ttgactcctt  32760
ctgctggtga tatcccttcc ttcttcttga aaacccattt gcaagtaata atctttctcc  32820
ccgaaggctg tatgaccaga tcccatgtct gattcttgtg tagggactcc atctcatctc  32880
ccatagcggc aaaccatttt tcagaatcag aacttaaaat ggcttctttg taagtagacg  32940
gctcagatgt atctacctct tcagcaacct gcagtgcata acccaccatg tcctcaaaac  33000
catacctcgt aggtggccga actccaaccc tccttggccg atcttgagct aaactctgat  33060
ggatatctga tggcatagat tctggaatat cagtttctgt ctgtggctct tgatcctcct  33120
cttcaggttc tttcaaatcg ctctcgttct gaatgacttg aaactccacc tgtttatcaa  33180
gactcccagt ttctgacgta gttgtaggct tcacaatggt tctaagcaga gaactttcat  33240
caaagacaac gttcctgctc ataataaccc tcttttctgg agccggatta cgaaaccttt  33300
cactccatct catgccccaa atactccttt ttggctcttg gtttctaact taccttcact  33360
gacgtgatag taagccgtac aaccaaaagc tttcagattt gaataatcgg cagcttttcg  33420
accacatctc cataggtgtt ttgcactgtg gctgtatgtg gtcccttgat tatcagtagc  33480
aaagctgtac taaccgcttc ttgagaatct tctatcccca gcattgaaag catgcacctt  33540
gctctctcca gaagtgtttg attcatccgc tcggctacac cgttctcttg tggtgtattt  33600
ctaagcacat gcgatgtcgg gcaatccttc atccttacga attgatcaaa ttcagaccaa  33660
```

```
cagaattcca gcccattatc agttcgcaac ctcttgatct tcttccctgt ttgattttcc  33720
atcaaaattt tccactcctt gaacttctgg aaagcttcac ttttatgctt catcatgtac  33780
acccaagtca tccttgagta gtcatcaatc atggacacaa aaaatgggcg acctcccaaa  33840
gactcaacac ggcatggacc ccaacaatca gaatggatat aatcaagtgt gccttttgtt  33900
ctttgaatgg cctttggaaa cttgttgcga tgtagttttc caaagacaca atgttcacaa  33960
aactctaggc tcttaacctt atgaccagca agaagatcct ctttttgatg aatttgcatc  34020
cctctttcac ccatatgacc aagtctattg ccataactta gtcatatcct tctggtgaaa  34080
ttctgacgat gcaacatggg ctgaacctgt aaccggaacc ttgtagaaaa tataaaagta  34140
ccacatgaca cctttcaaga atcaatttga acctttccag accccaagac tccatctttt  34200
cccgaccatt tgaatccctt gctgtcaaaa gactgagaga tatcagattt tcgtcatcaa  34260
tggaacgtgc tgaccctcgt tcaatgtgcc aaaactaaat cgtcgtgtcc ttatcttgat  34320
cagcctgtcc caaccacctt gcggtgaaac tgttggccat cgagatcttg cctcaaatct  34380
accactcata agtcgtgaac cactctccct aggacagatg tgataggatg ccccagaatc  34440
gagaacccac atatctgaat gatgagtgtg ctcatcgtca actagggcaa tatcttcttg  34500
aattggtgtc ttcttgacta gcaacagcag agaccactga ttgttttcga ttgcttcttc  34560
ttcttggaca atcaaatttc aatgtccctt ctccttgcag taattacaaa catcatccct  34620
ttgcaccttc gacatcggct tatttttctt tccgccgttt tccttccctt tccgctcttg  34680
gtcagcaggc ccggaaggta taatgtcgta cttgtgccgt tagccttatg ccgtaattcc  34740
ctgctatgaa gggccgatct gacttcttcc agtgacacag tatctttccc aacaatgaac  34800
gattgaacaa aattctcaaa cgacattggg agagatacta acaatcaggc gacatcttca  34860
tcctcgatct tcacatcgat attcgcaatt ctaataacaa agtattcaat tgctctaagt  34920
gttccctgag ttgtaccttg accattcgta aaccgaatag gcgttgtttg aagcagcttg  34980
ttggttagag attttgtcat gtacaaactc tccgacttca accgagacca gacggtctct  35040
tcatccgaga cctctgcgtg atgacgtcat ccgcgagaca caaagatgat cgtcagtgcg  35100
cctttcctcc ggaatctcca tctcgggagt aacgacggcg ttcttgtctt tcgacaacgg  35160
cgcccgtaaa accttgttgt ttcaacaaag cccgcatctt gatcgccata aaccaaactg  35220
gctattcctc caccgtgaat ttgtcgattt tcacgttcaa agcgtacatc tcaattctca  35280
agaacacccg attaaccgag aggctcgata ccaatttgtt gtgcggaatt tgagataata  35340
cgagaaaata taaacgcgaa aaacaagaca acagatttac gtggttcacc aataaattgg  35400
ctacgtccac gggaagaggg aacattttat tatggaaggc aaaaaccgta attacgaata  35460
gggtttgcca taagcgtcta tatataacta aactaagccc ttaatgcttg ggccaaaata  35520
tagaattgac agataattaa gggcccaatt caaggcattc aatgaagctt caagatatgt  35580
tgaatggaaa gagatacttt ctcgttttgg atgatgtttg gaatgaaaat caagaaaagt  35640
gggataagat aaaagcagtc ttagaggttg gagcacgagg tgcttctgtt ctaaccacca  35700
ctcgtcttaa aagggttgga tcaattatgg acactttgca accatatgaa ttgtcaaatc  35760
tgtctcaaga agattgttgg ttgttgtgca tttgagaacc aagaaaaaat aaatcctaac  35820
cttatggcta tcggaaagga gattgtcaaa aaaagtggtg gtgtgcctct agccgccaag  35880
actcttggag gtcttttgcg cttcgtggat caagaaagag aatgggaaca tgtgagagat  35940
aatgagattt ggaatctgcc tcaagatgaa agttctattc tgcctgtcct gagacatagt  36000
tatcatcatc ttccagttaa tttaacacaa agttttgcat attgtgcagt attcccaaag  36060
```

-continued

```
gacaaggtaa tggaaaaagg aaatttaata tctctctgga tggcacacgg ttttctttta  36120
tcgaaaggaa acttggagct ggaggatgta ggtaatcaag tatggaatga attatacttg  36180
aggtcttttt tccaagagat tgaagttaaa gatggtaaaa cttatttcaa gatgcatgat  36240
ctcatccatg atttggcaac atctctattt tcggcaagag catcaagcag caatatccga  36300
gaaataaacg tagaaggtta cccacatatg atgtcgattg gtttcggaaa agtggtgtct  36360
tcttactctc cttctcactt gcaaaagttt gtgtcgttga gggtgcttaa tctaagtgaa  36420
ttaagactta agcgtttacc atctttggag atctagtaca tttaagatac ctggatttgt  36480
cttacaatag taaaatgcgc agtcttccaa agcagttatg caagcttcaa aatctgcaga  36540
ctcttgatct aaagtattgc tggtcactat gttgtttgcc aaaagaaaca agtaaacttg  36600
gtagtctccg aaatctttta cttgatgatt gcgatggatt gaattctatg ccagcaagat  36660
taggatcttt gacatgcctt aagactctaa gtagatttgc agtggggagg agaaaaagtt  36720
gtcaacttgg tgaattctga aacctgaatc tgtatgggtc aattgaaatc acgcatcttg  36780
agagagtgaa gaatgatagg gatgcaaaag aagccaattt atctgcaaaa gaaaatctgc  36840
attctttaag catgagttgg aatatcaacg aaccgcgtag atatgaatca gaagaagttg  36900
aagtgcttga agccctcaaa ccacactcca atgtgacttg tttaacaatc aaaggcttca  36960
gaggaatccg tctcccagag tggatgaatc actcagtttt gaaaaatgtt gtctctatta  37020
caattggagg ttgtgaaaac ttctcatgct taccactgtt tggtggtctg ccttgtctag  37080
aaagtctaga gttatggaat gggtctgcgg aattggagta tgttgaagat tctggattcc  37140
ctacaagaag aaggtttcca tctctgagaa aacttattat agtgaatttt gataatctga  37200
aaggattgct gaaagaggca ggagaagagc aattccccgt gcttgaagag atgaaaatta  37260
gctgttgtcc tgtttttgtt attcagaccc tttcttctgt gaagaaattg aatgcttatt  37320
ggcacaagtc agatgcaaca ggtttgagtt ccatatcaaa tcttagggct cttacttccc  37380
tcaacattag ccataactcc acagctactt tgctcccaga agagatgttc aaaagccttg  37440
caactctcaa atacttgaaa atctcttact tcgataatct caaagatctg ccaaacagcc  37500
tggctagtct caatgctttg aagcatctgg agattaattg ttgttatgta ctagagagtc  37560
tccccgagga aggggtgaaa ggtttaactt cactcacaca gttatccatt gcatactgtg  37620
agatgctaaa atgtttatca gagggattgc agcaactcac aaatttatca attacgaatt  37680
gtccaacact ggccaagcga tgtgagaagg gaataggaca agactgatac aaaattgctc  37740
acattcctca tctgctgatt acatagtgtc atactaaatt aaatgattct tatagcaata  37800
ttattggttc aaccaacaaa actaaatctc taattatatt acttaattgc ttttagtttg  37860
ctacaattat cactcatgac taacattatg tatcaattac gtggtttgtc ttcaattttg  37920
tataattagt catgttttta tatgtataat tcgctagaat aatacagata tatgtataat  37980
atacaattat ttaactgata tacatatata attcacctct cttccactct ctgtcctctc  38040
tcacttgcct ctgtcctctg ccaatcgacg agatgagcct acgaaagatt tcaagttcag  38100
actatgatga ctgacatcct cacttacgca acgaaatgga gttgatggag tagccagtgc  38160
ccttgagtca ttctcttcgg tatcgccttc tctcatcgtt aatggcgccg caaggcactc  38220
gactagcaag ttagacctta gttagggcga aagatttctt ggatggttca tttcagtctg  38280
aagtcgggtc aagtcatgga attgatgtga agttctctca atttcgcttt ccatatatac  38340
aaatatatat gtataacata caattatcta aatgatatat atatatatat atatatatat  38400
```

-continued atatataagc aatttatctc tctcccactc tttgtttcac ctgacaacta tgacaactat 38460
gtttgttagg gctggaaggt ctaacttcac tcaccgagtt atttgttgaa catatgctaa 38520
aatgtttacc cgaggaattg caccacctaa caaacctcac aattttttt ttataagtga 38580 aagcatagtt aaactctcaa atgtagatga taattaagct cttgaagatt attgctgaat 38640
taagtgaatt cgtcaagcta tatttgtaaa attcttatgg ccaaacaagt aatattgcaa 38700
caaattgtag aaggattatt atactcttaa cactaactaa aagattcttc caattctcaa 38760
agcaatttat attcctttcc aaccaaagag gttttccaaa tttgctttct agcaaaaaac 38820
aattttctgc acgataggaa tagatctcat atatactccc tccgtttcat tttatgtgaa 38880
gtagtttaac tgagtacgga atacaaaaat aaaagaaaga catttaaaat ttatggtcta 38940
aaatgaaggg aaaaaggtcg atatctcctc aactttgtca ttttagaaat gatatacctt 39000
gttatgaaag tggctcatat atacccctac ttgtaaacaa atggctcaca tataccttt 39060 tcctctaacg ggaaatgaaa aataataatt ttcaatctaa atttttatt tttttctaa 39120 aaaatataag tccatatgag taaatttaat tctcgtcaaa caattttttt tttttactt 39180 tttttttgtt tcaatgacta atttataatt attagtttga taatcaaatt tatttatgtt 39240
tcactaatat tcttgtaaaa cttattgtag atgaaaaaaa aaaaatttga atacgaaatt 39300
aaattacaat aaacacaaaa aaatagttta tttttttttt tctttaaact aaggaatgat 39360
agaaaaaaat aaaataagaa taagaaactc aaataattat aataaaagaa gttaaaaata 39420
atttatgtat gaaaaaaaaa ttaaatatac tttgaacttt tattgaagaa tcatatatac 39480
cactaaataa tttttttaaa attttttaag taataaatat aaatttaaaa ctaattattt 39540 aaaatttgt taaatgaagg gtatatttga acaattttgt aacggcaggg gtatatgtga 39600
gccgtttgta taacggtaag ggtatatacg agccactttt ataacgagag tatatcagat 39660
tcaaatgaca aagttgaggg gtatatcaaa ccctttccc ctaaaatgaa taataaaaaa 39720
ttgtgtgagt ataaatcatt tcattaagag taaatggaca atttaaaatt aaattgttac 39780
ttaatatagt aacgtatctt ttttgttttt gagtctgctt taaaaagaaa ataaaccata 39840
taaattggaa catagggagt atctacttac aaagtaaaag ttgtgtgtag aagattttgg 39900
catacaaatc aaatcatata tcatatcata tatcatcata tcatatatca catcatatca 39960
tatattagta aaagcatgaa taaaaaaagt tgaaagttga attacggttt tattccttct 40020
attaattaac ttgttataaa atatttaaat atttgatttt acaagtttaa ttaaaatgtt 40080
aaatgacttt tagacttcct acgattaatt tctaattaaa tatctaattt attaatattt 40140
atcatttata atctatatgt atataataat tataattttt taaaataaaa gtctaattat 40200
aattttaatg actttttaga cttcctaaca ctaattccta attaaatatc taatttatta 40260
atatttttat catctataat gttataataa gcatctttag aaggtttctc tgaaatactc 40320
tttaaaagaa tgcttggact atgccatcct aaggttgaaa ccagtaggca aaagaaggtc 40380
gttatgggga gtaaacaaag ttgaggcgct gttagggtaa ccaattaaag aagaaagctg 40440
tagtagtgac taggcgagat gattattaaa tcattattat tacataataa gtaagtataa 40500
tttattaaga ggtcggaagg aataaaactt ttagcaaaaa tgaataagat gactacctac 40560
ctaattgatg atgatgatga atataagata ttattacttt atatattaaa aaatcttaat 40620
actgatcaag ttagcagtct caaaaatctt tttttacttc atggttgcca taaattgaat 40680
tctatgccac caagtatagg atctttgaca tgccttaaga ctctaggtca ctttgttgtg 40740
ggaaggaaga aaggttctca acttgatgaa ctacgaaacc taaatctcta tggatcaatt 40800

-continued

```
tcaatcacac aactagagag agtaaagaat gatagggatg caaaagaagc caatttatct  40860
gcaaaagcta atctgcattc tttaagcatg agttggaata tcaacgaacc gcgtagatat  40920
gaatcagaag aagttgaagt gcttgaagcc ctcaaaccac actccaatgt gacttgttta  40980
acaatcaaag gcttcagagg aatccgtctc ccagagtgga tgaatcactc agttttgaaa  41040
aatgttgtct ctattacaat tggaggttgt gaaaacttct catgcttacc actgtttggt  41100
ggtctgcctt gtctagaaag tctagagtta tggaatgggt ctgcggaatt ggagtatgtt  41160
gaagattctg gattccctac aagaagaagg tttccatctc tgagaaaact tattatagtg  41220
aattttgata atctgaaagg attgctgaaa gaggcaggag aagagcaatt ccccgtgctt  41280
gaagagatga aaattagctg ttgtcctgtt tttgttattc agaccctttc ttctgtgaag  41340
aaattgaatg cttattggca caagtcagat gcaacaggtt tgagttccat atcaaatctt  41400
agggctctta cttccctcaa cattagccat aactccacag ctactttgct cccagaagag  41460
atgttcaaaa gccttgcaaa tctcaaatac ttggaaatct ctttcttcga taatctcaaa  41520
gagctgccaa acagcctggc tagtctcaat gctttgaagc atctgaagat tagttgttgt  41580
cccaaactgg agactctccc cgaggaaggg gtgaaaggtt taacttcact cacactgtta  41640
tccattacat actgtgagat gctaaaatgt ttaccagtgg gactgcagac actcacaaat  41700
ttatcaatta agaaatgtcc aacactggcc aagcgatgtg agaagggaat aggacaagac  41760
tggtacaaaa ttgctcacat tcctcatctg ctgattactg attagatgta attttctgat  41820
ttttcttttg gaaacaaatc aactatttgt aacatctatt tgtatgatac ttgatttttc  41880
ttggttatgt aacaataaat atttgaaatt tttcatatta aagattcaga atgagtttta  41940
tagctaactc tatattttca cagtttaata acgtaaaaat gtgatattta tatcaaatta  42000
ttacttatgt tgtcatttat caacatgttg gagatgattt tgacagttta ttaaagaatt  42060
tctaagtttt tattgtttgc acaagtaaca agccataaat taagtttcga gataaaagtg  42120
atttgtgtat catggcttaa ttagtcggaa tttcaagttt ttttctcaag ttatatatat  42180
gacaatttgt aaaaaataga tagtattgat tttgatttaa ttcaagcatt tttaaaaata  42240
taaacattat aatatgggag atacacacgc taaacgcgta cccagaaact agtatataaa  42300
gaatcatgac cgaaaaataa aatgaagttc tgtcaacaac tatctcgaca tctttgctga  42360
tatatatata tatctaacta gtgtacttat tcggacttga catggtataa aaagatatta  42420
aatatatttt taaataatta ataaatgata taataaaaag aaagaaatac aaattcagtt  42480
atgattctga taaaagggaa actaattttc tgatttttct tttggaaaca aatcaactat  42540
ttgtattata cttgttaatg ttgcaattat tagtgaacag ttgtattttg gattatcact  42600
tacagcagat gtctaaaatg tgaataagat aatacttaga ataatttatg caatatactt  42660
ttgtttaaat acaagaaatt taaataaaga ttgctaaaga ttattatttt gaatgaaaga  42720
ttttgatttt gttactttgt cgcctatgta acatagtact gttgcaaaca tatacatatg  42780
tgttcatttt tccccttgtg tttcatttta ttttctacaa ctcataaata ctaaaaagaa  42840
aacgttagga atgagtttta actagattta aattttaaca aaaacaacgt gattatattt  42900
cactaaattg acttaaatat atttatactt aaaaaaaaat tattaattta taatattaat  42960
gggaccatat atttatataa aaattttcta taaatatatt atcttatatc tcctctaaat  43020
tcatttcacg agaattaaaa ccatcctaac ggatgacgtt gccaaaaaga atagaaattt  43080
tctttgaaag cgtgttaagt ttttttaaa aaaaagtaat ggtctcactt tgtatatatg  43140
```

```
aagaaaaaaa aaacccaccc ctttcttctt cttcttcaaa cccccacccc cgctttttca  43200
aaacccacca gccccccttta cctgcttgtc ttttcttcct catattcccg acgtcaccct  43260
atccccaacc caccccatcc tctttctcat ttttcgaact ctacattcaa agcacataaa  43320
taaaaagaat cacatttaag attcatataa tttttttact ctttactttt gagatttgat  43380
ttttcttaaa aagttatgat ttttttgaaa ataaagaata gggcataaaa gaagatgagg  43440
ttttgtcaac caatctataa tgttaatggc tgggaatggt gattgaagca atggatagag  43500
aaagattttt ttttaaaaaa aaaagagaag aaaaatcact acaatcagta accgcaattg  43560
cagtaggctt acatcatgga gtatcccaat gagtctcttc actgttcaat cggccatcgg  43620
taaccgcatt acaatgggct ttgggtcacc cacccaattt cttataaata gaaagagaca  43680
tgagatttat gattgcacct agatcacata gtgatttggc aaagtgtaat aatacgaatg  43740
gtacatgaaa tagtgaaagc gccaggatct tccttcttct gcacaagagt tcttgtgaca  43800
atagcactac aatgctgcat tcagttatca tcctcaaaac ttaccgatct cttctttgta  43860
actatatcct tcatgaactt ggcataaccg gaccatttgc tccaaagctt ctatcaaagg  43920
gacattgatg gaaagttgct tcaacatagt gataaaatgt tggtatttac cattctcact  43980
attcttcacc aatctaaaag tggtggtggt ctaggaatgg ggaccacttt ctagggtatc  44040
tttgcttttt tcgccgcttt gtccaccaat tcaccactag tttccaccac ctcttcatct  44100
tttctcatct catcttctac cacagacgac ataggtgaat caatagtttg catacctcct  44160
caagtagtga ctgtcatgca atgtccatca tttttaggat ttgaatggaa ttactatgaa  44220
aagtgacagt tgtcgcgggt tctgatagtg aacaattgga ccatttataa ttcaagatgc  44280
ttaatcgaga ccgcatgtgc atccaccttt ttcccgatat tagccaaatc acctctcaat  44340
ttcttggcgt gctcatcact agcatcaaac cttctcatca tctttagcaa catatcttca  44400
acttgcgccg tactacctcc accatctcaa ggagcaactt tctgattttg aggtggaaca  44460
tagggcacac ttcaatcatt tctattacca tagttacccc ggttgaagtt gttatctcgg  44520
ttgtagtttc ttctcgaact tactggccct cttgttgtaa ttcccattct gcattttcaa  44580
tttaaaattg ttgataaaaa agacaaaaac ataaaaattg atatgaaaga gctttggtta  44640
agtaacaatc taattatcat agtgtcatat tcaattcaat gattcttata gcaatattgt  44700
tggttcaaca gtttaacttt actcgctgag ttttctattt atgatgttaa aatgtttacc  44760
gaagggttat tatacttgtt tttaatgttg taactattag gggtagatta tcactttatg  44820
aatgaatatt ttggcacatt ggaaaaacac caaatatagc gcgcaaaagc taaacaagga  44880
aattttcata tattggatat agtctttgtc atttccaaag gtctccaaca tagagatagt  44940
aattgagaga aaacttctat tgctattaaa tagaatctgc aattaaaaaa aaaataaatt  45000
attattatat tttatattat aagtgggaag atgcttagtc taaaggtgga ttaagaaaac  45060
gccttcaact tttttaatta tcattattat attatattat aaataataat taattatttt  45120
tctataagtg tgaaactatt aaagttgaat aacctttttaa ttctacaaga actcaccatt  45180
aagttgaatg actttttaac tcttcaagaa atcactaata agtcttttta cacgtcgtct  45240
tataatgata atattgtaca tttgaatttg gtttagagag cataaatccc ttattatact  45300
atgtgttttc aagcatttct ttacatttag atttttttta tttttgcta taattcaagt  45360
tatattctta aattgatatt taagtgtttg atttctcaca tgaaaatata cagttaaaat  45420
tttgttttat gaactcatga tgtaattttt tctcaggtat aattttaatg tgattctttt  45480
gcagacaatt gactaaaatt tttagtagaa attgcaccaa tacaaataag gtatgcggca  45540
```

-continued

```
tgtctctcca acaattttac attttttgca tgattatttt ttaataaatt tgatatacat  45600
acgattattg tatttttaac tagattttaa taacttaatg catgtttttt tttataatag  45660
agcctccttg ataactttac aattacttat tgaaatttat ttttcttcaa tctcctagct  45720
tccgagataa aatgggtaac taatatttct ccctcaacaa catggagcaa aaaaaatcga  45780
gaaaatctat gaagaagaca tattctaaca aatggagtaa tttaatttaa tttaaaggag  45840
tacttaatag tcaaatatga atagtaaagt aagagaaaaa aaaataaaaa aattagaata  45900
tgacaagtat gaaagacaac catgaacaaa ttattggagt tttttgttca tgctacaaag  45960
aacaataaag ttactatgtc atttgaatgt aatatgtaga caacatatat acttgttaca  46020
agtatatatg gtaattcaaa ttttggtaca aattgagcag gtgtgttatg tgtgtattgt  46080
tcctttctta gaaaagtaac aaactaatat attgtagatt tcgacctaat aacataaaaa  46140
tgtaaattat ttatcacatt aaattttgtt gtccaaattt gacaagttat tggaatatct  46200
aattatttga catttacatt ttacaataaa gaagtcattt ttataggttg attgtccatt  46260
tatttcgttt atattttttt cgttaaatca tttttgaaaa ttttcaaact gtgattttaa  46320
tatatttttt tagtttaatg taattttaat ataactccta caatatataa tatttttgtg  46380
ggactgacat gcaaaacacg tgtcttggac tagtctttca cataaagaca gacaactaag  46440
aagattgtat cgcggataaa cgctactgga atagccctat tatgaagagt gtttgtcaaa  46500
cagccaaatg actgtagttt tttcttttcc agaaatatga ctgaaggact atatcttgga  46560
tcgatcagag tgcatgaatc actcagtttt ggaaaataaa gttttgcttg ataaacacaa  46620
atttatctat tcacaccaca agcaatggta agtcatcata aaaaaaaaga gagagagaga  46680
aatttgttgt tagatcgaga aagattttga taattgacga atagacgaac aaatgaaaga  46740
aacaggttgc atgtacatgt tcctttcaaa ccaaatccga ctgggattgt caaccatgcg  46800
aattagaagt tataaagtaa tggaagggtt gctttttcga cccgaacgaa gagtgcaaaa  46860
ggtttccttt cataaagaaa tcctaagcaa agtgggaagt gtaaacgaag taggtagcat  46920
aagcgagtag gaagtataac gacgtgaata aatttcaaat ctgaatggag tagatgatca  46980
gatatgtaaa acaagtacaa gatgaaaaag gttttgaaga gtccaaagtt tataaatagg  47040
gcaatatttt ctttggagaa aattgtgcac ttaaacagag agttacaagc aaaatacaat  47100
caaatagagg gagtttatat ttgagtgaat tctgattacg aactgcagcc aacacaagaa  47160
aacaagaatt gaagaactca ttcattggct tatgttttat agttcttaag tcaagttttt  47220
ttgtattgag tttttatcga gttgtatatt taaccctttc taaatccagt gaagtataaa  47280
ctggagtaga aatagagtct ttaagttaaa gacttggaaa cataaacctt gggggatttt  47340
gttggagtct aggaattaga atcagttcta gtattgcaag agttggaatc cgaattcata  47400
acttgaagtg ggatcgacga tctagttggt tgttggtagg gccgactcaa caagattgag  47460
ggcctaaagt caaaccttaa agagggctcc aatatttttt taattctttt taaaaaaaaa  47520
aaaaaaaaaa ctaataatca tgtatatatt atttaaaatc tattttctag cttttctaga  47580
tgtgaagtca ttaattacta ttttctaatg gatttgtttt aataattctt tttcaattga  47640
taatatagct aatacattca atctcattgt tgatattaca tatataagat tttatcaatt  47700
taaattttaa aaaattcttt cggccgaaac aatagttctg gattgttaac tttattcgtt  47760
aagcaatata tgcattagga ttagaatcaa gtctttttat tagattgcgt atttccatta  47820
aatcattatc ttctacttgt attatttctc ttaataataa taactaaagc gagcatgtat  47880
```

-continued

```
acttactatg aatatcaaca acaacaaaag ttcaagaaaa attacaaaat aagttagtat  47940
aataaaactt ggcttgcgaa tttgataaat tgatataaca atactgaaat agtgtttcat  48000
ttcttcaata taatgactgt ttgtttaaac aagacactca aaaacaaatt ttattttttt  48060
taacatgtaa gcgacaataa cttttttttta ggagagtgtt caacattgag cataaaagta  48120
ataaaataga gaataaaaaa gatgagtata agataaataa taatataaga tcgattttac  48180
ctattgtcaa ttttgtgtat cgactaaaga aataacagct tcacatatga atttgtattt  48240
taggctgctg taagtactaa aagatagtta ttcaaccagt agaagagatg aaggtggggg  48300
gcagctgttg gcaatcaata agggcatatt gagccaattt ttttcttctc tgaaaaactt  48360
tggcagagaa attaaggcta acgaaaagtc tttgtgcagt tgtttcccaa aactttgtga  48420
attgtatttc aaaaaataca ttatttaata ctccaacaac tttgtgattc cactctagac  48480
taccatcaca tatctaatat taattataat agtgaatttc acatatggcc agaggcgaac  48540
ccacctgcac ccaatatatt tttaaaaaaa attcatatgt agattgttga taagacgcta  48600
taatatattt aattgtgcac tcttataatg aacaaatgat ttgacttgtt cattgaaaaa  48660
acaaaaagtg tcacataaat tgagacatga aaaataatat ttctttttta aatttttcgt  48720
gtgaagtcaa actaattcat atataaagcg aaagcggaag gagtactgtt taatattaat  48780
tgcatatggt agtaaatttg atagacatgg tcccgtgggg tgtgtgttat ttccattgaa  48840
taattgagtt tgtaattgtt acaagtccat tctaatttcc aacaccttac ttcatttcaa  48900
aaatatagat tcattgctta ctcaccacat actcgatggc tgaagctttc cttcaaattc  48960
tgttagaaaa tttaacatct ttcatacaag gggaacttgg attgtttttt ggttttaagg  49020
acgaatttga aaatctgaaa agctcgttta ctacgatcca agctgtgctt gaagatgctc  49080
aggagaagca actgaaggac aagccactag aaaattggtt gcagaaactc aatgttgctg  49140
catatgaagt tgatgacatc ttggatgaat atcaaactga ggcagcaaga ctcaatcaga  49200
ctaaatatgg gagttatcat ccaaaggcta tcgctttccg ctacaagatt gggaaaagga  49260
tgaaagagat aatgaagaaa ctagatgcaa ttgctgcaga acgaagcaag tttcatttgg  49320
aaaaaaggac tacagagaga gaagctgcta gacgacaaac aggtgctcat cttaaatata  49380
ttagtcttag ttacaacaat ttaattagtt tatattcatt ttttggcgat tatcaagttc  49440
atctgtgttt atggactgaa cttaacttgg atgtcaattt ttcaaagtca atcatgtttt  49500
caactccccc ctgattctta tctctttgta gtgcaaaaat cttctctctg tttttcgcta  49560
aacatattct cgtgtgaaca tatgttgctt gaaacaggtt ttgttttaac tgaaccagaa  49620
ctttatggaa gagacaaaga ggaagatgag atagtgaaaa tcctgataaa caatgcccaa  49680
caactttcgg tcctcccaat acttggtatg ggggggctag gaaaatcgac gcttgcccag  49740
atggtcttca atgatcagag agtaactgac catttccatc ccaaaacgtg gatttgtgtc  49800
tcagaaggtt ttgatgagaa gaagttgata aaggcaattg ttgaatctat cgaagaaaac  49860
ccacttggtg acgacatgga tttggctcca cttcaaaaga agcttcagga taggttgaat  49920
ggaaagagat actttctcgt tttggatgat gtttggaatg aaaatcaaga aaagtgggat  49980
aagataaaag cagtcttaga ggttggagca cgaggtgctt ctgttctaac caccactcgt  50040
cttaaaaggg ttggatcaat tatgggaact ttgcaaccat atgaattgtc aaatctgtct  50100
caagaagatt gttggttgtt gttcatgaaa cgtgcatttg agaaccaaga aaaaataaat  50160
cctaaccttg tggctatcgg aaaggagatt gtcaaaaaaa gtggtggtgt gcctctagcc  50220
gccaaaactc ttggaggtct tttgcgcttc gtggatcaag aaagagaatg ggaacatgtg  50280
```

agagataatg agatttggaa tctgcctcaa gatgaaagtt ttattctgcc tgccctgaga 50340
cttagttatc atcatcttcc agttgattta acacaaagtt ttgcatattg tgcagtattc 50400
ccaaaggata cggtaatgga aaaaggaaat ctaatctgtc tctggatggc acacggtttt 50460
cttttatcga aaggaaactt agagctggag gatgtaggta atcaagtatg gaatgaatta 50520
tacttgaggt ctttttttcca agagattgaa gttaaagatg gtaaaactta tttcaagatg 50580
catgatctca tccatgattt ggcaacatct ctatttttgg caagagcatc aagcagcaat 50640
atccgagaaa taaacgtaga aggttaccca catatgatgt cgattggttt cgcaaaagtg 50700
gtgtcttctt actctccttc tcacttgcaa aagtttgtgt cgttgagggt gcttaatcta 50760
agtgaattaa gacttaagcg tttaccatct tccattggag atctagtaca tttaagatac 50820
ttgaacctct ctcgcaataa catgcgtagt cttccaaagc agttatgcaa gcttcaaaat 50880
ctacagactc ttgatctaca gtattgctgg tcactttgtt gtttgccaaa tcaaacaagt 50940
caagttagca gtctcagaaa tcttttactt catggttgcc ataaattgaa ttctatgcca 51000
ccaaggatag gatctttgac atgccttaag actcttggtt gctttgctgt gggaaggaag 51060
aaaagttgtc aacttggtga attacgaaac ctgaatctgt atggctcaat tcaaatcaca 51120
catcttgaga gagtgaagaa tgatagggat gtaaaagaag ccaatttatc tgcaaaagaa 51180
aatctgcatt ctttaatcat ggaatgggac gacgatgaac gtccacatag atatgaatca 51240
gaagaagttg aagtgcttga agctctcaaa ccacactcca atgtgacttg tttaaaaatc 51300
tatagattca gaggaatccg tctcccagag tggatgaatc actcagtttt gaaaaatgtt 51360
gtctctatta gaattggagg ttgtgaaaac tgctcatgct taccaccgtt tggtgatttg 51420
ccttgtctag aaagtctaga gttatggagt gggtctgcgg aagtggagta tgttgaacat 51480
tctggattcc caacaagaag aaggtttcca tctctgagaa aacttattat agacaatttt 51540
gataatctga aaggattgct gaaagaggca ggagaagagc aattccccgt gcttgaagag 51600
ttgacaatta gttgttgtcc tgtgtttgtt attccgaccc tttcttctgt caagaaattg 51660
gtagtttatg ggaacatgtc agatgcaaca gtttttaggt ccatatataa tcttagggct 51720
cttacttccc tcaacattag ccttaactcc atagctactt cgctcccaga agagatgttc 51780
aaaagccttg caaatctcaa atacttggca atctctttct tcgacaatct caaagagctg 51840
ccaaacagcc tggctagtct caatgctttg aagcatctga aaattgaatc ttgttatgca 51900
ctcgagagtc tccccgagga agcggtgaaa ggtttaactt cactcacaca gttatccata 51960
gaatactgtg agatgctaaa atgtttaccg gaggaattgc agcaactcac aaatttatca 52020
attacgaatt gtccaacact ggccaagcga tgtgagaagg gaataggaca agactggtac 52080
aaaattgctc acattcctca tctgctgatt acatagtgtc atactaaatt aaataattct 52140
tatagcaata ttattggttc aaccaacaaa actaaatctc tagttatatt atttacttgc 52200
tcatcatagc tatagtttgc tataatcatc actcgcgatt aacattatgc atcaattacg 52260
cgggctgact tcgattttgt ataattagtc acgtttttat gtgtataatt cgccagaata 52320
tacggatata tgtataatat ataattattt aaccgatata catatataat tcacctctct 52380
cccactctat gtcatctctc actcgcctct ctcctccctc tcttaatttt gcttttcata 52440
tatacaaata catatgtgta atatacaatt atctaaacga tatatatata tgcaattcat 52500
ctctctcccg ctcttttgct tcacctgaca actatgacat ttaactttgg atatgcacat 52560
ttaaaaactg gttacagaaa ctcaatgttg ctgcgtataa agttgatgac ttattggatg 52620
aacgtgaata cgaggcagca agactaaagc agtctcgatt aggacgttat catccaaagg 52680
ctatcaaata cgaactcagt tgtttagacc acaaaaagac tgtgaattca atacaggagt 52740
agttaacgat ttagaagaga tctactctta acgctaacta aaagattatt ccaattctca 52800
aagaaaattt atattccttt ccaaccaaag aggttttcca aatttgcttt ctagtaattt 52860
ttttttttt ctgcacgata ggaatagatc tcatatactc cctccgtccc attttatgtg 52920
aagtagttta actcgtacgg aatacaaaaa tgaaagaaag acatttaaaa tttatggtct 52980
aaatgaataa taaaaaatcg tgtgactata aatcatttca ttaagagaaa atagacaatt 53040
taaaattaaa ttgttactta gtatagtaac gtgtcttttt ttttttaaac tgtctaaaaa 53100
agaaaataaa ttatataaat tggaacatag ggagtatcta cttacaaagt aaaagttatg 53160
tgtagaagat tttggcatac aaatcatatc atatatcatc atatcatata tcacatcata 53220
tcatcatata ttattataag catgaagttc aaaacttaaa agttgaatta ccattttagc 53280
cttatactaa attaaaatat tataaaataa ttaattaatt aaatattaaa tatgcttaaa 53340
ttgttaatta agttgattca cttattgtta aaataaatag gagaatgaat agttgtaaaa 53400
ataattaatt ataaagttat tacaaaaact tattagagaa acgtttcatt tctctatcga 53460
tcgattttag gtgtaatttt gtcataatgt gtattaatac cacacctcca ctatctcatc 53520
attaatatcc acaccttcat aatcttccac actctcaaga agttgatggc ataattatga 53580
gacttttgat tttactcaat gatgtcctat aaattgcggt atttgacaca acaatctata 53640
cactttgaag atatttaggt acagtttgga agaaattaaa aaaaatgtct atatttctat 53700
tgtttttatc ctttagtata tatttaaatc actttttaaa ctgctcataa caccgattca 53760
ttaattttcc ttatcttcat ttgttgttta taggaaggaa atgtgtacaa attgttagat 53820
cttctaatgg agtttacaac gagagaaggg atgttcaagt cttccggagg ttgaaatcaa 53880
ttttaatttc aagtattata ttcatgcttt tagatgttta tatatatata tatatatata 53940
tatatatata tatatatata tatatattca aatgagtcaa catagactaa tatgagactt 54000
aaaggtcgga aaattggagt atcacaatta gtagtaaaac aaagtaagaa atctcaatta 54060
gatatatttt attatttttt aagaaataat acactcatgg gtataagtgt gaagctccaa 54120
aatgcaaaaa gttgaattac tattgtatcc ctataatagt taattatttt taaatattag 54180
ttcatatgat attattaaat tatacttctt tgaaattaat aacataataa aaaccaaatt 54240
catctttgaa gtgcaaattt atcgtccttc attattgata atttgaatgc actaaaaact 54300
atttaatatc ccggaaggtg gaagagtgaa agtattcata attaatttct agataaaatt 54360
ttactagata aaaaagtata catgcattgg aattaataat ttaaaaataa agaaataatg 54420
atttagcctt ttaagttacc tacttttatt atgctcttta aaccattgtt attattttt 54480
aaaaaaaaaa ctcatattaa ggtgttagct tgattagtct aaagatatca aaatgtcatt 54540
tcttggatca cttaatttgt aacgttttta tcttctatta gcgtgattct ccattttcct 54600
atattatata ttatactttc tcatgtaatc atgttatcta tatttatttt tttatataag 54660
tttgttatgc tcaatgtttt atttatcttt atttgaactc atctaaattg ttgaatattt 54720
caactactaa taaatttttt aaatttgact ttttttttat gaaaatacaa ttaagaaatg 54780
acgctaatat ttcatagtga tgatgcagta agtgaagcaa cacagattga actgtttcaa 54840
gtggtatcaa ttttcaggta ataaatcatt gttccttata tgcaattaat tatttttgtg 54900
taagttgata tgttcttaat aaaattttgg tttgattttt aaataaaaat tattttatag 54960
aagttgagac ggtacactta attggattat ccaaaaaaag aatcttttac acaaggacaa 55020

```
gaagaaagac ttctagcttt atcactgcat tcatgacaat caatggaata tcctacaaga  55080
caaaaagttg atgtgattct gtacaagtga atccaactca ctaacaaaaa aattaaagaa  55140
agaaaaaaat gaacatgaag agaataaaaa tgaagatgaa gagaatcaat ggtgtcttat  55200
aagttgatga accactgtaa cttcattatt ttttaaattt acgaggaaat gaattattga  55260
cgaaatttat gaaatgtaca tatatacctt tgggtcggta acaaatgtga ttgaaagtag  55320
tattttttca tgcataatag ctaattcttg atatatatat tgtttaaatt tattatttgt  55380
actacaaaca ttgtatgata tattttagga taagcgtaac gcatgcgacg tggaaactag  55440
tatattagta aaagcatgaa taaaaaagtt gaaagttgaa ttacgatttt attccttcta  55500
taattaactt gttataaaat atttaaatat ttgattgtac aagtttaatt aaaatgttaa  55560
atgactttta gacttcataa gattaattta taattaaata tctattttat taatatttat  55620
catttataat ctatatgtat ataataatta tatttttttt taaataaaag tctaattaaa  55680
atattaatga cttttagact tcctaacact aatttctaat taaatatcta atttattaat  55740
atttttatca tctattatct ctctctatat aataatttta caaaaattaa caaaaaaagt  55800
ctctacgtaa atttttatac tttttttttt attctcataa atttttccta aataacaaaa  55860
tttaataatt tgaaggatgc aaatctgcaa aatggagaca cacacatttg ataatgtcct  55920
cttaattatc attaaagaat gactctaact agcttcacaa atttaaattc attgatactt  55980
aattactcgg agaaaagtag atgaagactc ttaattttga tagtatatgg aaggagtcaa  56040
taaagtttcg tagatttatg caataatttt gtacttattt tttcatctac atatacatag  56100
tcttatgaga atgatgtcta cattgtattt tttcttaaat ctgtttcttt tgtcttttat  56160
ccccaattag acttcttaat ttaattttat acaaatgttt tattgtcata agtctttata  56220
cttattttgt aattgtagca ttttattgtt cattacaatt tgcatatata tatttccatg  56280
aaatattagt aattctatca tatctataaa aattcacatg aaatacacgt gcaaagcacg  56340
tgttcagaaa ctagttagga aaacaacaca aatatacatc tgaactatcg taaatgatat  56400
acagatacca tcatcatact tttgggacat tggtgtccat gtcgtcaaaa aaatagagca  56460
aatatattaa tggacatcac gtgtcagaat catatcaatt gatccaacat ttattaaatg  56520
tttgatcgaa gaatagattg tgtcacatgt ccctatttag tcatctgtta aaatgaatga  56580
catatgggtt gggccgacca ttttctgacc cacacaaaaa atgggctagc ccggtttaac  56640
ccgtaaaata tcaaaacatg tatggattag cccggataag gtgtgttagc catattgaca  56700
gctttatccc cacatcaaga aggtatttat atgtcaactt gaaaagaaaa aattttccaa  56760
atatgatctg cttatactct atcaattcca tatctcactt agtgaaattt cactgaatat  56820
attgttgttg ttggtgtcct ctcccatcat tataaattta aagaacatgc aatgtaagac  56880
gtaatttaga aaacttggtt cgcccgtaga agaaggatca tctgtaaatt tattcctctg  56940
caagttgatg ctttgaatct gttggtacat ttcctctaaa catgttagat tggattgaat  57000
cttaagtcat catgtgttac tatctgaaag accaatattt aaatttattg ctcacaagta  57060
aaaattagaa ctaaaaatat acaaacatga agttcaacat atattataac ttaattcata  57120
aaagaaaaat tatttgcatg cataatattt gtttattcat ttcttagtgt acatatttta  57180
actttatcag cgtagtaatt tggtttgatt tgtttgtttg ttataatgta attacaagtg  57240
tacttagctt gtttgattac acaagtgtaa tcatataatt atactgaatt ttaaagataa  57300
aagttaatta tttgaaacaa aaaaattata ttaggcaaat aagagccttt ataaatgata  57360
```

ttcaattgaa tatttaagat atatagtgtc ttttaaaaaa tatgttattt aataaacata 57420
tgttcttaat taatattata aaaaaagcaa atgatttata tatttcaatg tagtattttt 57480
aaagtaaatt aatcataaaa attaaaaatg catgaacatc atgaaatgct tgtttcacaa 57540
aaaaattaat attataaata taatgtcata aaatcataga aaaataattg acaaaagaac 57600
taatttatca agtctaactt aaaaagaata ggttgcaatg gaatatcaag tcaatactcc 57660
taaaacaaat gaaattgaaa atataatata agttctaaat ttaaaataaa aaatttaaca 57720
taatactttt atgtcaaatt tcaacataat atgattaaaa gaaaaggaaa atttaagtcc 57780
gtaactttgt tcaacaataa attctacttt aattcaaaaa ttagaatact aacaaaatta 57840
tactaataat ttttttagat attatgaaga attgcatgaa atcacatgaa gtaaaagtta 57900
aaaataagaa ggaaatgaaa tataaataat aaaggaaaac tttcatatat agccacttaa 57960
aaataattaa ttactctcca tagctatagt ttgataatta caatttgtag ctacatgtta 58020
tgtggaggag agagaggcga gcgtcacttg gagagagagg cgagagagag agggggaaaa 58080
gagtgggaga aaggtgaatt gtatatgtat attggctaga taattgtata ttatacatat 58140
gtaattgtat atatggcaag agagattgag agagggagga gagaggcgag tgagactgtg 58200
agagagagag agaggcgagc gagatcaaga gagggaggag agaggtgagc gagagagggc 58260
agagagtgag agggatgtga attgtatatg tatataattt tatataactg tatattatac 58320
atatacattt gtataaatgg caagcgagat tgggagaggg atgagagaga cgagcgagag 58380
agggcagaga gtgggagaga ggtgaattgt atatgtatat aggctaaaaa attgtatatt 58440
atacatattt atttgtatat cctggcaaat tatacatata taaacatgat aattatacaa 58500
acatgaagtc aacccacgta attaatgtat aatgttagtc gcgagtggta attataacaa 58560
actatagtta tgatgcataa ttaaaataat ataagtttgt ttattcgcat aatttttcct 58620
tttttaaatt cctccttcta ttcaacttgc atttttttgtc aaatataatc atcgttaaaa 58680
attatttgat gttgaattaa caaacatcca tctttattat atcacatgtt gtgacatgca 58740
ccaaaacgat aaaaacgaca ccttcaaaat gattttttttt aaaataagcc tagttaattg 58800
atgtttaaca tataaataat caactaataa ggttaaaggc ttacacatac aaactaaaaa 58860
ttagatcaaa tgcactaaaa ataaataata tgaggaaaat ctgttttagg gattatagtg 58920
tcccccaacg accaagtctt atttttaatg gagcatcatt gattggtcta ttgacaaaga 58980
aaatttggaa attaatgatt ttgttttatc ctctggaaat ttattatgtt atcacaacta 59040
tttgttaatt tgaactgcat aaaagttttt gttcgaactt catatatgaa aattctaaac 59100
aagaattgga aacttgaaat gaatccaaca tttaaatcaa tagataatta ttgattgaat 59160
ttcttaatac gtatatatac aaaagatctg aataaaagct attgaataca ttacatgtta 59220
tattggttaa tttgaccgta aaacagttga cattcttttg tcaagcatct attctgggga 59280
ggttatatat atatacattt gaataatgac gttatactat agcctaaaac tacataaaaa 59340
atgtcaagta aattatttaa ctgtcaatac agaattccac aaccaatagt ttatttccct 59400
ttagcaatga attgcagtca agttcagcta gcaatataca attaaaagat gtttcaaatc 59460
attggtatta attagataag tattgactca attacaagta tacacacagt atatatagat 59520
ggcgtttgaa aacgaaaaca taggcacaaa tagcagctaa agaagttgaa caaatcaaaa 59580
tggttgcgaa gactattatt atagcatgcc tagttttgtt aacatgcctc tcagttacta 59640
atgcatcgaa cattacaact gatgaggcac aaatgactat atctagtgaa attaacatgc 59700
agatgaatag gcatatcttg cagtaaaaag catcaaagag tgacatcatt agtcctcaat 59760
agctttggat ttagaggttc aatcgcgaca gatattggga atctctcctt ccttaacttt 59820
ttggacattg gaaacaacag tttccatggc caaatacctg atgaaatagg gcgtttgagg 59880
cgtttaaaat acatgtattt gcagatgaat aatctcgctg gtcaaatccc agaaagcctt 59940
ggatttctca caaggcttca agttcttcat ctttctgaaa atcgtctatt tggaaatgtt 60000
ccagcttcca ttttcagcgt gtcttcttta aaggacattg atttgtctca gaattacgag 60060
ttaactggga gtttaccaaa tgagatatgc actaatcttc cagtgttgga atatatatcc 60120
ctgcaagata atcaatttgt aggtgaactt cctaaaggtt taaataaatg ctccaaactt 60180
gaagttctgt ccttgtctta taacaaattc actggtaatt aactaacttg taaacttttc 60240
atttactaat ttcttcttga attaatcatc atttttgtgt gtgtctgtga ttttataatt 60300
gataggaaac ttaccaagag acatgtggaa catgtcaaag gttcaagaac tttttattgg 60360
atggaataac ttaacaggta cgtgattctg tatgtattaa atcttgaata ctcttcacga 60420
agttcctaat ttcactagat atagccaatt tgtgcattgt ctagtaataa acaaagatta 60480
atatattttg tggagaacat tttcgaaaga cactctatgt atgatcttta gcatgataac 60540
catatactta ttttcaaaat gaatttgcag gaaatatacc aaatgaaatg aacctaccat 60600
ctatttgcag gaaagttaac aaagcttgag catcttgttg ggttatgggt ctttttccct 60660
tcctatttgg ataactaaaa gcccaatttg gaccaatcca tttttgccta taagcccatt 60720
cttatgaggc aaatataaac tgattttagg gtctgatttt cagaacatat agagagttct 60780
tcagcagcca aaaagagaga aagagagatt ttcgcaggca aaattcagat ctaatagaca 60840
acttcaaatt gcgattcccg cttcttttct tatccgattg agttgatttt tggacagcat 60900
attgtcttca tctcaatctt tgattagaaa ctgacagagt tggatttggt ggcctgcgac 60960
tttcagtttt gcttttgtcg tgagcgaagc tgcaaaattg gtgattttgc tcctttaatt 61020
ttctagattt ggtgcaatct tattttgttg ttgctcgttg tttggcactt gttttgtggc 61080
caattttgga gaacaatatt gtaactcttg gtgattatag tggagctttt ggtccgtggt 61140
ttttactctt cacatgaagg gttttcaacg taaatcttgg tgtcttatgt gattggtttc 61200
acattgtctt gttatatttg tttggttgaa ttggaatcgc cttactatca tattgcttgt 61260
ggttgtttgt cttctcttgg ttcaaatcga aaaagggaaa gtatagactt ggatattctt 61320
ccgttatctg tcgtcagcat tcttggtagt gtcttgtctt tcccaacaaa gtggtatcag 61380
agcattgggt attgttgatt gtcgttttga atgatggaga caaatatgag caaaatggtg 61440
tttttaaatg gtagtaacta tcatatttgg aaaggcaaga tgaaagatct tctatttgtc 61500
aagaagatgc atttacctgt gtttgtttct aataagccta agtctttgaa tgatgaagaa 61560
tgggaatttg agcatcatgc aggtttggct atattataca atgggttgaa gataatgtta 61620
ttagaaatca gtattgtgaa tgagacatgc caaaagtttg tggacaagtc gagacacttt 61680
atgcttcaag attgtgtaac aactgctcct attgaacaat taatgaatat cgtataaaga 61740
gggcactcct atttctgatc atattaatga ttttaggggg ttcttgaccg gctgtccgaa 61800
atgggtgtaa agtttgatga tgagatacag ggactttggc ttcttaatac cgccagatct 61860
tgggaaactc ttcagtttct ttgaccaatc tgctcccaaa gggtgttgta accatcggaa 61920
tatactaaaa gtagtgtctt gaatgaagaa ataagaagaa gatctgacct catcttcaga 61980
cttctacact ccgatgtttt tccactgaag atagggggag aaacaagtcg gtaggaggaa 62040
tgatagaggt aaaagtgtat gtcaaagtct aagtctaaca caagaatatt acatgtgact 62100

```
attgccacaa gaatgggcat atcatgaaat attgttacaa gcctgagaga tatgagacaa  62160
caaaaaagag aaggcgataa tgaaaatcgt gttgttgttg ttgctaatga tcttctttct  62220
tttttcttg atgcaaatgc cattaatctt gttcgtgatg agtctagctg gtttgtggat  62280
tcgggtgcta cttctcatgt catgccaaag aaggaattct atttcttata ctccggggta  62340
attttgaaac gttgaaatgg gcaataatca tgaagttgaa gttattggca ttgggacagt  62400
ttgtttggaa aataacaatg gttcaaaact agttctcaat aatgtcaagc atactccgga  62460
tgttcgcttg aatttgattt acgtaggata tcttgatgat gaggttatgt taaacacatt  62520
tggtgttggc tagtggaagc ttactagagg tttgatggtt gtggcccgtg gtgacaagtt  62580
gtctaacttt gtatgtattt ggggctccgt ttcgagagac tcaagaattt ggtagagaat  62640
gatacttatc gaagttatgg catgtaaaat ttgagtcata tgagcgagaa gaggattgat  62700
agtttggcta agaaaaattt gctttctgga gtgaaacaag caaagttgaa gaaatgtgtt  62760
cattgcttag ccggtaaaca taaagagttt cttttgaaat catccgcctt caagaaagct  62820
tgatttgctt ggagttggta cattcccgat tttgtggtcc ttttaaggta agatcccata  62880
gtggtgcaat tttactttgt gactttttat tgatgatcat tctcgcaaac tcggggtatt  62940
tcctttgaag tccaaggatc aagtacttga tgtgttcaag agttttcagg ccttggttga  63000
aagacaaaca ggaagacatt gaaatgcatc cgctcgaata atggtggtga gtatattggt  63060
ccttttgat agatattgaa gagagcgggg tattaggcac gaaaactcct ccaaaactcg  63120
cggttaaatg gtttagcaag gaggatgggc agaactctag ttgagaggct tagatgtatg  63180
ctctcggatg ctaatttgcc attcctttag gcggaagcac ttaatctgcc gcttatgtta  63240
tcgatttatc tcctttgttg ctttagatag atggtgatgt cacagcggag tttgggtggt  63300
aagaatgttt cttatgatca tcttagagtc tttgggtgta aagcctttgt acatgtttct  63360
aaggatgaaa ggtcaaagtt ggatgttaaa actaggcgag gtatcttcat tggttatagt  63420
caagatgaat ttggctatcg tttctatgat ctgttgagaa gaaacttgtt agaagccatg  63480
atgttgagtt ctttgaagac caaacaattg aagattttga caaaagtgac aaggctgatt  63540
ttcgagtagt gagagcttag ttgatgttga tccggttcct ttgactattg ccgaagaaaa  63600
tcttcttaat gaagaaaatc aagttgataa tgaagatggt gatcatgttc taatgaccgg  63660
catgatgttg tttatgctcc caagaagatg atgtggttgt ccaacaacca attatagatg  63720
ctccggagag ttctctcgca cgatctagta gagaattcct tcatctcgtg attctcctaa  63780
tgagtatgta cttgacttac ggggagaacc cagagtcttg atgaggccat ggaaagtgaa  63840
gaaaaagaaa ggtggtttga tgctatggaa gatgagatta aatccttgca tgataatcat  63900
acctttgatt tgttgttacc taaactgaaa aacttttga aaaaaggtgg gtttttcgg  63960
gtgaaacatg aagatggtaa tccggttcca ccagacaaag ctagattagt tgtcaaggga  64020
tttaatcaga aaagggagtt gattttgatg aaatattctc tccgattgtg aagatatcat  64080
ccattcggtg tggttctagg tcagctgcaa gtctagattt agaggttgag caaatggatg  64140
ttaaaaaccg ctttcctcca tggtgactta gactaagaaa tttatatgga gcaaccggaa  64200
ggttttgaag tcaaggtaaa agagaattat gtttgcaaat taaagaagag cttgtatggt  64260
ttgaaacaag ctcccgtgca aaggggtaca gtgaagtttg gttttttatg agtcaaaggg  64320
gcttcaagaa gacttcttaa ccattgtgtt ttgtgcaaag ttctctgatg gtgactttta  64380
ttgttgcggt tgctttatgt tgatgacacg cttgttgtcg ggtcataata cttgcagtag  64440
gatcaagttg aagcaaggag tcgaggcaag tctttttgca tgaaagactt agaccaaaga  64500
```

-continued

```
aggcagattc ttggcatgca gattgcccgt gatagaaaaa gccaagaaat tggtattatc  64560
acaagagaaa gtacattttt aaagtacttc aagcagattc aaagatggac aaagctaagg  64620
ttgtcaagac accttagcta tgccttcaaa ttgaaagcat ggaaatgctg tcctttctag  64680
cgatgatgga aaggaagata tgaagaaagt tccttatgct tcaaattggt agtttgatgt  64740
atgcgatggt ttgtacaaga ccgatattgc tcacgctgtt gagttgttaa gcgggtttct  64800
ttctaatcca ggaagagaac attggaatct ttgtgaagtg ggttatgaga tatctcatgg  64860
cacttctagt ccgagtttgt ttttggcagg gaagcctatt tttttgattt atcttgatta  64920
ggacatggtt ggtgatgttg atactcgcaa gtctacttgg tgcttggtta cttttagggg  64980
agtattgtct tggcaatcta gattgcaaaa tgtgttactc tatctctact atggaaggct  65040
tattcttttc gtgaagcttg taaagaattg ctttggatga agagattatt aagaacttgg  65100
tttgtgctca aagaggtatg tactttattg tgaccggtca aagtgctata catcttggca  65160
agaattctac gttccatggt cggttaaaca cattgatgtg agataccatt tgattcgaga  65220
tgtattggat tctaagttgc ttgagcttga aaaagattca tacaaatgac aatggttccg  65280
atatgatgac taaagctttg ccaagaggaa gtttgaagat tgttgcatgg tcgtggggac  65340
gggcggtcct ccacatagtc gtgagggaga attgttgggt tatgggtctt ttttccttct  65400
atgtggataa ataaaagccc aatttggacc aacctatttt tgcctataag cccattctta  65460
tgaggcaaat ataaactgat tttagggtct gattttcaga acatatagag agttcttcag  65520
cagccaaaaa gagagaaaga gagattttcg caggcaaaat tcaaatctaa tagccaactt  65580
caaattgcga ttcccgcttc gtttcttatc cgattgagtt gatttttgga cagcatattg  65640
tattcatctc aatatttgat taggaactga cagagttgga tttggtggcc tgcagcttca  65700
gttttattgt gaggaattag ctgcaaaatt ggtgattttg ctcctttaat tttctagatt  65760
tggtgcaatc ttattttgtt ttgttgctca ttgtttggca cttgttttgg ccaattttgg  65820
agaacaatat tgtaactctt ggtgattata gtggagcttt tggtcccgtg gttttactct  65880
tcacatcgaa gggttttcca cgtaaatcgt ggtgtcttgt gtgattggtt tcatattgtc  65940
tcgttatatt tgtttggttg aattacctgc tgccttagta tcatattgct tgtggttgtt  66000
tgtcttctct tggttcaaat cgaaaaaggg aaagtataga cttgggtatt cttccgctgt  66060
tatcctgtca ggcattcttg gtagtgcctt gtctttccca acacatctca actatctgaa  66120
tgtctcttac aatgagttat caggtgaaat accagatgga gggccttttg gtaattttca  66180
cagctgaatc attcatcggc aatgaagagt tatgtggacc gcctagattc caagtcaaga  66240
tttgtgaaat ccgaacaacg tgacaagaag aaacaggaaa aaacaagact aaaatttgtt  66300
cttggaccag tgcagctgga ggtttagtca tggggtttta ggcatgatat ggttgttgaa  66360
ttatcggaga cgtaacaacc aacttattcc tttaactgat tagtatgatc ggttatcaca  66420
caaaaagttt tcttactatg aacttgtttg agggactaac aactttgact ttaatcaaat  66480
ttgattggaa agggaagcct tggtatggtt tataagggga catttacaaa tgggactata  66540
gccaactgta aaggttttca atgctggcgc aagatgcatt caagaggttt gatttggagt  66600
gtaaggtttt gcgtaacacc gaaataggaa tcttgttggg tgataagtag ttgttcaaat  66660
cttgatttta aggcattggt gtttgagtac atgcctaatg gagatcttaa ttattggctt  66720
tactcacaca acaatttctt ggatttaaac aaaatttgaa aattatgttt gatgtggctt  66780
tgtgtcagag agtatctaca ccaaggccat tcaaaacata gtggtccatc atgacttgaa  66840
```

-continued

```
catacttttg gatgaagaca tggttgccga gtaagtgatt ttggtatatt caaactcttg  66900
accgccagat gatccaaagg gcattgacaa agactttagg caccattatc ctggcactgt  66960
gcccgatcaa atttttattt actaattact ttcttcaact tgtattcgat atgcatatat  67020
gatgtatttc attttaatgg tagagtacgg gtcagaaggg atagtgtcaa ctatggggga  67080
tgtttacagc tacggcattt tatttatgga aaccttcata agaaagaaat gatagatgat  67140
gagtttgttg gagaccttac attgaagaga tgggtcatgg aatcatatcc tcatagagtc  67200
attgttatga aataaaaacg aatacaagtt gaacgtcaat tatgagtcat ttatctaata  67260
tgatccatta acaattgatt aatgtaacgc aggaagaaga aaacaatttg cattgttatg  67320
aatgaatgtg tttgtactac aatatataca aagatcgaca agtctagcaa actttctaac  67380
caacttattc taaccaactc tactcattat tcatttagct cacttaatca agaaattaga  67440
cctaacaact aactaccatt aactcattca actgattgtt gggttatagg tctttttccc  67500
ttcctatgtg gataaataaa agcccaattt ggaccaaccc atttttgccc ataggcccat  67560
tcttatgagg caaatataag cctatttagg gtcttatttt cagacaaaac agatcagttt  67620
ttcagcagcc aaaaagagag aaagagagat tttcgcaggc aaaaatttag atctaatagc  67680
taacttcaaa ttgcgatttt cacttcgttt cttatccgat tgagctgatt tttggacagc  67740
atattgtctt catctaaata tttgactagg aactgacaga gttggatttg gtggcctgta  67800
gcttcagttt tgctgtcgtg aacagtagct gcgaaattgg tgattttgct ccctttaatt  67860
ctctagattt ggtgcaatct tattttgttg ttgctcattg tttggcactt gttttgtggc  67920
caattttgga gaacaatatt gtaactcttt ggtgattata gtggagctgt tggtccgtgg  67980
tttttactct tcacatcaag agttttccac gaaatcttgg tgtctttgtg attggtttca  68040
cattgtcttg ttatatttgt ttggttaaat tacttgccgc cttactatca tattgcttgt  68100
ggttgtttgt cttctcttgg ttcaaatcga aaagagaagt atagacttgg atattcttca  68160
tttgttatcc cgtcgagcat catttgttat tgccttgtct tttcccaaca aagtggtatg  68220
tcaggagcat tggttattgt tgattgtcgt tttgaatgat ggaggcaaat atgagcaaaa  68280
tggtgtgttt aaatggtagt aactatcata tttggaaagg caagatgaaa gatctttatt  68340
tgtcgaagat gaatttacat gtttgcttct aataagccta agtctttgaa tgatgaagaa  68400
ttggaatttg agcatcctgg gtttcggcta tattagacaa tgggttgaag ataatgttag  68460
aaatcatatt gtgaatgaaa cacatgccaa agtttgtggg acaagctcga gacactttat  68520
cttgaagacg gcaacaaaca agttgttcta ttgaaacaat taatgaatat cggtataaag  68580
agggcactct atttctacga tcatattaat gattttcagg gtgttcttga ccagcctgtc  68640
cggaatgggt gtaaagtttg atgatgagat cacaggggac tttggcttct taatactcat  68700
ccggactctt gggaaacttc ttctagtttc tttgactaat tgctcccggt ggtgttgtaa  68760
ccatggaata tactaagagt ggtgtcttga atgaagaaaa tgagaagaag atcttgcctc  68820
atcttcttaa acttcactcc gatgttttgg ttcttgaaga tggggagaaa caagtcagta  68880
gatcgaatga tagaggtaaa agtagaagca agtcaaagtc taaatacaag aatattactt  68940
gtgactattg ccacaagaat gggcatatca tgaaatattg ttacaagcac aagagatatg  69000
agacaacaaa acaagagaag gcgataatga aaatcgtggt tgctgttgtt gctaatgatg  69060
atcttctttt ttcttgtgat gcaaatgcca ttaatcttgt tcatgatgag tctatttggt  69120
ttgtggattc ggtgctactt ctcatgtcac gccaaagaag gaattatttt cttcttatac  69180
tccgggtaat tttgaaacgt tgaaaatggg caataatcat gaagttgaag ttattggcat  69240
```

-continued tgggacgttt tgtttggaaa gtaacaatgg ttcaaaacta gttctcaata atgtcaagca 69300
cacccaaatg ttcgcttgaa tttgatttcc gtgggatatc ttgacgatga gggttatgtt 69360
aatacacttg gtgttggcgg tggaagctca ctagaggttt gatggttgtg gcccgtggtg 69420
acaagttgtc taacttgtat gtatttaggg gctccatatc cggagactcc aagaatttgg 69480
tggagaatga tacttcatcg agttatggca tgaaggtcga gtcatagaga aggggattga 69540
tagtttggct aagaaaaatt ttctttctgg attgaaacaa gcaaagttga agaaatgtgt 69600
tcattgctta gcgggtaaat agaaaagagt tttttttag tcatccgcct tcaagaaagc 69660
ttgatttctt tggagttggt acattccgat tttgtgtggt cctttaaggt aagatctcat 69720
ggtggtgcac tttactttgt gacttttatt gatgatcatt ctcgcaaact ctaggtattt 69780
cctttgaagt ccaatgatca agtacttgat gtgttcaaga gttttcgtgc cttggtttaa 69840
agacaagcag tggaagacat tgaaatgcat ccattaagat aatggtggtg agtatattgg 69900
tccttttgat agatatttgc agagcggggt attaggcatg aaaaacctcc aaagactccc 69960
tcggttaaat ggtttagaag cagaggatga gcgagaactc tagttgagag ggttagatgt 70020
atgcttttag atgttgtcgt cgattccttt tgggcggaag cacttaacat cgctgcttat 70080
gttatcaatt tatctccgtt gctttagatg gtgatgtcct cgatgtagtt tggatcgtaa 70140
gaatgttttt acatcatctt gtagtctttg ggtgtaaagc ctttgtacat gttcctaagg 70200
atgaaaggtc aaagttggat gttaaaacta ggcaaagata tcttcattgg atatggtcaa 70260
gatgaatttg gctatcgctt tctatgatcc cgttgagaag aaaacttgtt agaagtcgtg 70320
gatgttatgt tcttttgaag accaaacaat tgaagatttt gacaaactga caaggctgat 70380
tttgagagta gtgagagctt agttgatgtt gatccggttc ctttgactat caacttggga 70440
agaaaatttt cataatgatg aaaatcaagt tgataatgaa gatggtgatc atgttcagta 70500
atgacctatg acgatgacgc tttttgatgc tcgatgcaga agatgacggg ttgtccaaca 70560
accaattata gattctccga gagttctctc agacgcatct agtagagaga gatttcttca 70620
tctcgttatt ctcccaatga gtatgtactc ttggtgacgg ggagaacccg agagtcttat 70680
gaagccatgg aaagtgaaga aaaagaaagg tggtttgatg ctatggaaga tgagattaaa 70740
tccttgcatg ataatcatac ctttgatttg gttaagttac ctaaaagcgt aaaaagcttt 70800
gaaaaaaaag ggtttttttt gttgaaacat gaagatggta atcaagttcc acggtataaa 70860
agtagttgtc aagggattta atcggaaaag ggagttgatt ttgatgagat attctctccg 70920
ggttgtgaag atgtcatcca ttcgtgtggt tctaggcttg gtacgcaagt ctagatttaa 70980
gttgagcaaa tggatgttaa accgcttccc atggtgactt agatgaagaa atttatatgg 71040
agcaaccgga aggttttgaa gtcaagggta aagagaatta tgtttgcaaa ttgaagaaga 71100
gcttgtacgg gtttggaaac aagctcccaa agcaaattgg tacagaagtt ttggttcttt 71160
atgctgggga aaggcttcaa gaagacttct tcagaccatt gtgtttttgt gcaaaagttc 71220
tctgatggtg actttattat tgtgttgctt ttatgttgat gacatgcttg ttgttgggtc 71280
ataatacttg cggggattca gaagttgaag caagagttga gtaagtcttt ctttatgaaa 71340
gacttaggac caaagaagac agattcttgg catgcagatt gtccgtgtga tagaaaggct 71400
aaaaattggt attatcacaa gagaagtaca ttcagaaagt acttccacag tattcaagat 71460
ggacaaagct aaaggttgtc agtgacacac ttttagctat gcacttcaaa ttgagcacta 71520
gcttaggtgt ccttctagtg acagatgaga aggaagatat gaagaaagtt cttatgccta 71580

-continued

```
gctgggttgg tagtttgatg tcacgatggt tttgtacaag accggatgtt gctccatatt  71640
tggggttatt aaccgttttc ttttctaatc gggaagagag aacattggaa tctttgtagt  71700
gggttatgag atatctttgt ggcacttcta gtaaagtttg tgttttagtg cagaagccta  71760
ttctttgtgg ttatccggat tcggacatgg ctggtgatgt tgatactacg caagtctact  71820
tgatgcttaa ttcttttttg tggggagctg tgtcttggca atctaggttg caaaatgtgt  71880
tgctctatct actctctgct ggaggcttat tctttatcgt tgaagcttgt aaaattactt  71940
tggatgaaag attaacacgg gaacttggtt gtgctcaaga gaggtatgtg ctttattgtg  72000
gtcaaaagtg ctatacatct tggcaagaat tccacgttca atagtcggtc taaacacgtt  72060
gatgtgagat accattggat tcgagatgtg ttggattcta agttgcttga gcttgaaaag  72120
attcatacaa atgacaatgg ttacgatatg atgactaaag ctttgccaag agggaagttt  72180
caagattgtt gcatggtgct tgggatggcg ggcctccaca tagtcgtgag gggggagaat  72240
tgttgggtta taggtctttt ttccttccta tgtgataata aaaagcccaa tttgaccaac  72300
ccatttttgc tcatagccca ttcttatgag gcaaatataa gccttattta ggatcttatt  72360
tcggaaaatg acagttagtt ttttggtgag ccaaaataga gaaagagaga ttttcgcagg  72420
caaaaattca gatctaataa ccaactttaa attgtgattc ccgcttcgtt tcttatccga  72480
ttgagctgat ttttggtcag aatattgtct tcatctcaat ctttgactag gaaccgacag  72540
agttggattt ggtggttcgg taacttcagt tttctttgcg aatgagcgat ggctaaattg  72600
gtgattttgc tcctttaatt ctctagattt ggtgcaatct ttttgttgtt gtcgttgttt  72660
gacacttgtt ttgtggccaa ttttggagaa caatattgta actcttggtg attactggtg  72720
ggagcttttg gtcctgtggt tttttactct tcacatcggg ccgattttcc gtaaatcttg  72780
atgtcttgtg tgattggttt cacattgtct tgttatattt gtttggttga attcttgctg  72840
ccttactatc atattgcttg tggttgtttc ttctcttggt tcaaatcaaa aggaagtata  72900
cttgggtatt cttccatcgt tatcctgtcg aggcattctt atttgtgcct tgtctttcct  72960
aacactgatc acggaacatc aacacatttt gttgatttct ttcacacaca cctcctcaaa  73020
aaaccctctt ttttaacatg taagcgacaa tatctttttt aggagagtgt tcaacattga  73080
gcataaaaat aataaaatag agaacaaaaa aagatgagta taaaataata aataataata  73140
taagatcgat tttaccgatt gtcaattttg tgtatgaact aaagaaataa cagcttcaca  73200
tatgaatttg tattttaggc tgctgtaagt actaaaaata gttattcaac cagtagaaga  73260
gatgaaggtg ggggccagct gttggcaatc aataagggaa agaaaagaca aggaatattg  73320
agccaatttt ttttcttctg tggaaaactt tggcagagaa attaaggcta acgaaaagtc  73380
tttgtgcaat gaccccatgg gcatgtgcag ttgtttccca caactttgtg aattatattc  73440
caaaaaatac aaattcatta tttaatactc caacaacttt ttgattccac tctagactac  73500
catcacatat ctaatattaa atgtaatact gaatttcaca tatggtcaga ggcgaatcca  73560
tcagcacctg atatattctt tttttaaaaa aattatatct atatatacag attgttgata  73620
agacggtaat atatttaatt gtgcactctt ataacgaaca aatgatttga cttgtccatt  73680
ggaaaaacaa aaagtgtcac ataaattgag acatggcgaa taatatttct ttcctaaatt  73740
tttcgtgtga agtcaaatta attcatataa aattagacga aaggagtaat gtttaatagt  73800
aattgcatat ggtagtaaat ttgatagacg tggtcccgtg ggagtgtgtg ttatttccat  73860
tgaataattg agtttgtaat tgttacaagt ccattctaat ttccaacacc ttacttcatt  73920
tcaaaaatat actctatggc tgaagctttc cttcaaatta tgttagagaa tctgacttgt  73980
```

ttcatccaag gggaacttgg attgattctt ggttttaagg atgagttcga aaagcttcaa 74040
agcacgttta ctacaatcca agctgtggta caagatgctc agttgaagca attgaaggac 74100
aaggcaattg aaaattggtt gcagaaactc aatggtgctg catatgaagc tgatgacatc 74160
ttggacgaat gtaaaactga ggcaccaatt atacagaaga agaataaata tgggtgttat 74220
catccaaacg ttatcacttt ccgtcgcaag attgggaaaa ggatgaaaaa gattatggag 74280
aaactagatg caattgcagc ggaacgaatt aagtttcatt tggatgaaag gactatagag 74340
agacaagttg ctacacgcca aacaggtaaa tatttttcta aataacagct ttatatcatc 74400
aaattcatgt gtgttttggg gattttgtct aagtagataa gtggttcaaa atctattatc 74460
taaatctgtt tggtgaagtc tttaacatat atataaatcc atagcttact catatgcccc 74520
aaagtctaaa tgacaggata aagccagagt tgttttagat cttataaatt aacaatgata 74580
ataatgtgaa ttcaaaatag tgcatttgtt ttatatttga aatatgtctg ctgcttctga 74640
tcaagctgat cattgtcttt tgcaaaattc ttctttgttt tttttgctga ctcttaccga 74700
tcttggacca ggttttgttt taaatgaacc acaagtttat ggaagagaca aagataagga 74760
tgagatagtg aaaatcctga taaacaatgc ccaaacactt tcagtcctcc caatacttgg 74820
tatgggggga ctaggaaaga cgacccttgc ccaaatggtc ttcaatgatc agagagtaat 74880
tgaacatttc catcccaaaa tatggatttg tgtctcggaa gattttaatg aaaagaggtt 74940
gataaagaaa attgtagaat ctattgaaga aaagtcactt ggtgacatgg acttggctcc 75000
acttcaaaag aagcttcagg acttgctgaa tggaaaaaaa tatttgcttg tcttagatga 75060
tgtttggaat gaagatcaag ataagtgggc taagttaaga caagtcttga aggctggagc 75120
aagtggtgct tatgttctaa ccactacccg tcttgaaaag gttggatcaa tcatggggac 75180
attgcaacca tatgaattgt caaatttgtc tcaagaagat tgttggttgt tgttcatgca 75240
atgtgcattt gggcaccaag aagaaatgaa tcttaatcta gtggctatcg gaaaggtgat 75300
tgtgaaaaaa tgtggtggtg tgcctctagc agctaaaact cttggaggta ttttgcgctt 75360
caagagagaa gaaagacagt gggaacatgt gagagatagt gagatttgga atttacctca 75420
agatgaaagt tctattctgc ctgccctgag acttagttac catcaccttc cacttgattt 75480
gagacaatgc ttttcatatt gtgcagtatt cccaaaggat accaaaatgg aaaaggaaaa 75540
tctaatctct ctctggatgg cacatggttt tcttttatca aaaggaaact tggagctaga 75600
ggatgtaggt aatgaagtat ggaatgaatt atacttgagg tctttttttcc aagagattga 75660 agttcaatat gatcgaactt atttcaagat gcatgatctc attcatgatt tggcaacatc 75720
tctattttca gcaagcacat caagcagcaa tatccgagaa ataaatgtag aaggttacct 75780
acatatgatg tcgattggtt ttataaaagt ggtgtcttct tactctcctc ctcacttgca 75840
aaagtttgtc tcattgaggg ttcttaatct aagttccatg ggacttaagc agttaccgtc 75900
ctccattgga gatctagtac atttaagata cttgaacctc tctctcaata acatgcgtac 75960
tcttccaaag cagttatgca agcttcaaaa tctgcagact cttaatgtag agtattgctg 76020
gtcactttgt tgttttccaa aagaaacaag taaacttggt agtctccgaa atctcttact 76080
tgatggttgc gatggattgg attctatgcc accaaggata ggatctttga catgccttaa 76140
gactctaagt ttatttgtta ttattagaga aaagattctc tacttggtga attacttaaa 76200
cctgaatctg tatgggtcaa ttgaaatcac gatcttgaga gagtgaagaa tgatagggat 76260
gcaaaagaag ccaatttatc tgcaaaaaag aaaatctgca ttctttaagc atgagatggg 76320

-continued

```
aaggaccaca tagatatgaa tcagaagaag ttgaagtgct tgaatccctc aaaccacact  76380
ccaatgtgac ttgtttaaca atcactggct tcagaggaat ccgtctccca gagtggatga  76440
atcactcagt tttgaaaaat gttgtctcta ttgcaattag aggttgtgaa aactgctcat  76500
gcttaccacc gtttggtgat ctgccttgtc tagaaagtct agagttacgg agtgggtctg  76560
cggaagtgga gtatgttgaa gattctggat tcccaacaag aagaaggttt ccatctatga  76620
gaaaacttac tatagaaaat tttgataatc tgaaaggatt gctgaaagag gcaggagaag  76680
agcaattccc cgtgcttgaa gagttgacaa ttagatgttg tcctgtgttt gttattccga  76740
ccctttcttc tgtcaagaaa ttggtagttc atgggaacaa gtcagatgca atagttttga  76800
ggtccatata taatcttagg gctcttactt ccctcaacat tagccataac ttcacagcta  76860
cttcgctccc agaagagatg ttcaaaagcc ttgcaaatct caaatacttg gaaatcgctt  76920
tcatctccaa tctcaaagag ctgccaaaca gcctggctag tctcaatgct ttgaagcatc  76980
tgtttattaa ttgttgtttt gcactagaga gtctccccga ggaagcggtg aaaggtttaa  77040
cttcactcac acagttatcc ataacatact gtaagaggct aaaatgttta ccagagggat  77100
tgcagcaact aacaaattta tcagttaggt attgtccaac actggccaag cgatgtgaga  77160
agggaatagg acaagactgg tacaaaattg ctcacattcc tcatctgctg attactgatt  77220
agatgtaatt ttctgatttt tcttttggaa acaaatcaac tatttataac atctatttgt  77280
attatacttg atttttcttg attatgtaac aataaatatt tgaaattttt catattaaag  77340
attcagaatg agttttacag ctaactctat attctcacag tttaataacg taaatatgat  77400
atttatatca aattattact tatgttgtga tttgatttat caacatgttg gagatgattt  77460
tgacagttta ttaaagaatt tctaagtttt tattgtttgc acaagtaaca agccataaat  77520
taagtttcga gataaaagta atttgtgtat catggcttaa ttagtcggaa tttcaagttt  77580
tttctcaagt tatatatatg gcaatttgta aaaaatagat agtattcatt ttgatttaat  77640
tcaagtattt ttaaaaatat atacaaataa tatgggggat acacacgcta aacgcgtacc  77700
caaaaattag tatataaaga ataatgacga aaaaataaaa tgaagttcta tcaccaacta  77760
tctctacatc ttttgctgat atatatatat atatatatat atatatatat atatatatat  77820
atatatatat atatatatat atatatatat atatatatat atatatatat atatatatat  77880
atatatatat atatatatat atatatatat ctaactagtg tacttattcg gacttgacat  77940
ggtataaaaa gatattaaat atattttaaa taattaataa atgatataat aaaaagagaa  78000
atacaaaata agttatgatt ctgataaaag gaaacttaca taaatgtgtt ataataaaaa  78060
aatatttacc atttatagct ataatttttt ttttcactcg atcactttta attaatttat  78120
aatacaagtt taatatatat tacaaagaac aatttattat tcacatacaa tacaagtttt  78180
aatgatggat tttatcacac attttaatac acttataata taatgttact attttttacc  78240
aaacaaacac aatatatttc aaaaacaatt ataattcaaa tatattgcat aaataattca  78300
cttttaataa atattacaga tttatcacaa tattgctata aatgataata aacaaaagta  78360
tcgctaaaat cagtaattat tttttaacat atattaattc atgtaatttt tcttattatc  78420
tattcagaaa aattgcttaa aaaatctcat ttgacatttt caatttaaaa ttgttgataa  78480
aaaagacaaa aacataaaaa ttgatatgaa agagctttgg ttaagtagca atctaattac  78540
atagtggcat actaaattaa atgattctta tagcaatatt attggttcaa ccaacaaaac  78600
taaatctcta gttatattac ttaattgctc atcatagcta tagtttgtta taatcatcac  78660
tcgcggttaa cattatgcat caattacgtg ggctgacttc gattttgtat aattagtcat  78720
```

```
gtttttatat gtactagatt ctgagaacat gccttgcacg tttgtccttt attattatta  78780
actttttata tactaaaaag ttaagtaatt aaaaagatgc ttaaataaac aataatagtt  78840
taaccattta tcttttattc gctaaataat aactaatata atatgaagaa cattaaatag  78900
atgataatat ctaccttagt aattggttct taaaaagcat attaaaaatt taattctcaa  78960
agtgttttta cataaatagt ggagaatgac tcttcacatt gagcttttaa ttttaaaaaa  79020
ttatgtgtat gagaaataat taacattcaa taattaggta gaataatatc acattatcat  79080
aaataaaata atatctctaa gtcaaaagta gacattctag tttggaaaat aattactact  79140
aactatttat gggtccagct ccaatcaata atctatagat gggagtttga caatttttca  79200
gctatagtta aaattttaca tcaacaataa ataacttatt atcacagtag atagacgttt  79260
gatgcataaa agttataaat gctaaaagat tttgtcaatg tagtacatat gcaaacttat  79320
gataaaaaca cttggtatat tacgaaacac acttgaagcc attaccatga ttaacatatc  79380
aattattttt atcattatat cacatatacg tcttcttttt aaccttaaaa gtattgtaca  79440
catgatttat gaagagaaaa gaatagtact cctttttttca tgtaacgacc tgtttagtcg  79500
ttttgagcag cagaatttat ttctggaaaa actgtctgag tcaacggaac ccacgacgga  79560
ccgtcatggg cacgacggac cgtcgatggt gtctcattcc aaaacactta gaattttgaa  79620
atttgggtct gaaatcgact ctccaacttc gtgcttgaga tggccggggc gaacaagtaa  79680
gtggagccgc acggctgcac cgtcacaaat cttccatggg gaagtgatcc gaatgtgtgg  79740
atttggcggg gagatgccgt ccacgatcca cgacgggacg tcactgttgc gcgtaatccc  79800
ggtgggtcgg atttctgtta agtgatttaa ggggcgtttt ggactattcc tgctttaatt  79860
ataaagttag tgggttaatg ttaataagtt taattacttg ggggttaaaa gaggtaacct  79920
tgagttaatt agtgggttat tattgacatc tttatactta attatattct aattagggta  79980
aaagaaagag ggtttgaata agaaacaata gaaagaacaa tgagagggaa agagaaacga  80040
gaaagagaga aacgaacgaa gaggaaaaca caagctttgg gaaaattgct ttcttgatca  80100
aaattcttcg gtggaggtag gttattgttt ttatactatt cgtagtaaac tcttaatagc  80160
gaatgatatg tgttgggttg tattgtaaag tcttctatat gcttaattgt atgcttgtat  80220
aaatgtgatt atataattgt gataaaaataa gcaagataaa gctattgaat cccaaatctt  80280
gaaaacccct tgttaatgat gatgccttgg tataaaagaa ggcttgatga actaaagtaa  80340
tgatattgat gatgtcttgg tataaaagaa ggcttgatga actaaagtaa tggggttgat  80400
gatgccttgg tataaaagaa ggattgatga attaatagaa tgagattagt ggagcgggtg  80460
tcacgaaccg acacatagta ttagggggac cgggtgtcac gaaccgacac gtagtattag  80520
ggggaccgag tgtcacgaac cgacacatag aattagggga tcgggtgtca cgaaccgaca  80580
cgtagaatta ggggatcggg tgtcacgaac ccacatgtat aattggggat cgggtgtccg  80640
aaccgacacg tgggaattag gagatcggtg tcacgtgcgg acaaatagta gtaggggcgg  80700
gtgtcacata ccaaaccaag aggaataaag ataatgaatc ttgaaagatg ttaatatact  80760
caatctaatg aacctaatcc caaataggta tggtattgag gcttgagtct catgtgaact  80820
tggcggtgct tattaatgat tatagtactt gttgttgtta cacatattga gtattgtagt  80880
tgatttatga tattatcagt atatcttttg ttttctattt tgagttggcc gatgatacct  80940
acctcgatgc ccgtgtttta tcttgaccct acttgtattt gttttctttg ttatttgtgg  81000
agtgtagcaa gcgtaccgtc gtcttcaact cattgccaac tctgtgatct tcattacacc  81060
```

ggattttagg gtgagctaat gcttctagct tggactggat cttcttcctc atgtcttgat 81120
gccttgaagt tccggcatgg actagatttt gtttatttta gcttctttag aatactctta 81180
gtttagtaat ttgatcatag atgttcttgt ggtgatgacg ggattttggg gaatactagt 81240
tgttgaattt tagaagttat tgaattggtt ttattaatga gtttaagtct tcatattact 81300
tctgttgata ttatattgaa atgttggggt ttagattggt tggttcgcta acataggatg 81360
gtaagtgtgg gtgcgttggc tcggttttgg gtcgtgacaa acttggtatc gagcattagg 81420
ttcgttggtc tcatcacaca agagaaccag tctagtagag tcttaaggag cgtagggggg 81480
gccttttact tttctttgag aggctataag actttaggaa attttccttt cttttctttt 81540
tctttattac ttggatccaa ttggtatcta ggtgatacaa attggtaatc gaccatcttc 81600
actctatttt tcgcaaatgg ttagaacaaa agcgacgact aacaacagca ccgatagcgc 81660
gggcggagcg aggtgcgtcc cgggcgtgct ggggagtaca tggctgggaa ggcggctgac 81720
agaggccgtg gtgaaattag gtggggagac gtctacaggg gacaaacacc gccccatagt 81780
actgggcggt gactcactcc acccggtagg tggtaagaga gggtgaggaa ggaggcccgg 81840
caagtgcgag gagatgagga actaccgctg acctacccgg agatgataaa tcaggttctg 81900
cttaccttag taggttgctc tgatcaaggt caaacacctc gatgtttctg ctgcttctct 81960
cgggttttgg aaatacgacg ggcaaaatct gtttcacgca tggatatgcc attggaagcg 82020
aaactatttc ctcgtttgac tacggggcct atgatgacaa gcggtgacaa agatgaacca 82080
agaagggatt gaaattgaaa cctccgtctt caagggtgct aaccgggatg cctacgattt 82140
tccgtcgatt gtcatgagtt accaagataa aatgggcata gtggaacgat tcggtgttga 82200
gtttttggac ttatcagttt caaaggaacg ccaaatgcgc ggcggtcaca tgttgagtgt 82260
caaccaacgg aggaaccacc tatgacttgg ccattctcta gcttatttat ggaagtatat 82320
cccctgacct tgagggatag gaggagatga gttttttggc ttagagcaag tagaacgacg 82380
gtcacttcat atgaaggcta agtttcgtgc attatctagg tatgtcactt tgcgcccggg 82440
ttcacaagaa gcggattcaa accgttttgt gaaaggggtt gaggtcagtt ttcagccctt 82500
ttgtagcggt ggcaaaatga aatccttcca gaaagtggta gacttctgtg atagaggtgg 82560
aggagtaaag taggatgact tcaccatggc atcgacatca aaaaggtttg aaaagggaga 82620
ggtttaatgg ttcttacact acagggcgag agttcgagga ttttcggtgg gccgttgtct 82680
gctcaggagg ctgtggtggg gtccgctacc ggaccgtgac atttctgcgg gagtagggtc 82740
attccagacc tcaatcattc tcacaaatac tatactgggc tccagagaat gttatggatg 82800
tgggaggctg gaccataatg ggaagttatg acgaggtccc atgggccagg ccagctaggt 82860
ggggtggtgg taggagaggc agttgataag gaggccagtg gccaggtaat gggtgagtcc 82920
tgaaggcagc caggagtgag gacaagtgaa ctacaacctt accacatggt gagggcagcc 82980
gaggcagcag gcaaattagt aggggctacg gctgtgcagc ctcgcagtct ggcggggaca 83040
tcagatgttg ttatcaccgg taatcttttg gtttgtgatt gcatggctac gtcattatcg 83100
gatcctgatc cacatttcat atgtatcttc ctatttgtta ctggtgtaat ttacattgtg 83160
aattgcttga catgctattt gtgtttctac tccgttggtg agtcatgata gttgaaaagg 83220
tatataggtc ttgtccgtga cttttgtggg gagcacactc atgtagattt ggttatttta 83280
gaaatggttg atttctgatg taattacggg tatgacttgc tttccaaatt ttgcaatctt 83340
agattgtaat gctaaaagcg taacgttggc caagccaggg acatccagat tagtaatggg 83400
agtgtgacta cacttccgct ccagataaat atcatatcct ttttcgtgct aagagaatgg 83460

-continued

```
ttagtaaagg gtgtttagcc ttcttggcac ctcagtgatg atactaagta ccttcgagtg  83520
agcctggggt ttcggtagtt cgtgagtttt agacgtgttc cctcgcacct tctccggtat  83580
gccaccgacg aggatattga cttttgcatt gatttgggcc gagtactcat tcccatttcc  83640
ccccttata gaatggctca aacgagttaa ggagttaaaa gcccaacttc aaaaactgtt  83700
aggggaagag ctttattagg ccgagtgcat cccctaggg tgctttgttt ttgtttgtga  83760
agaagaagat gggagtcttc ggatgtgcat agattactgg caactaaata aagtaactgt  83820
taagaacagg taccctcttc cctcgcattg atgacttgac cgatcgattt ctaaggtgct  83880
atgtcttctc taagattgac ttgagatggt tatcatcaat tgaaaatcca ggcgtgagat  83940
atgccaaggc ccttttcgaa gacggtatgg gcattatgaa ttcttggtaa tgtcctttgg  84000
actaacaaaa tgcccctgct actttctgcg agcttgatga gcattttta agccatatct  84060
atggatctct ttagatcgta tttattgatg atatcttgat atactcaaga gaaagaagga  84120
acatgaggag catttgagag ttgtgttgga aatgttgagg agaaaaagct ttatgccaaa  84180
ttctccaagt atgagttttg gctagattga ttgtccttct tgaggcaacg tagtttctaa  84240
gggaggagtg atgtagatcc ttctaagatc aagtagttag aagaattggg taagacctac  84300
taatatgtcg taaataagaa gctttgttgg tttaaccatt ctaccgtcga tttgtcaagg  84360
gattctcttc cattgcttcc caattcgaac ttaactaagc agaatgttcc atttgtatgg  84420
tcggatgaat gtgaggaaat ctttcgtaaa ctcaagacct tgtttgactt caccgcacct  84480
atccttacct ttccaaagag agagggtaag aacttcattg tgtattgtga tgcatcatat  84540
tctggttcgc aaaaaaaaaa aaaaaagtgc taatgcaaga gaagaacgta attgtgtatg  84600
cttcgaggca attaaaggtg catgaacgta attatccaac ccacgtattt ggagttggtc  84660
atggatagtg tttgcattaa acaatggaga cactatctat atggggggtt aagtgaagtc  84720
tatcacggat catcgtagcc tacagtatgt ctttaccgga aagatttgaa tttgagacgg  84780
agggaggtgg atggaactaa tgcgaaggat tatgatgttt accatcttgt atcacccaga  84840
aaggctaatc ttgtggcggt ataggtagaa aaagcaggag catggtagtt tagctcactt  84900
gcaagcttct aggcgcccat tggcctagag aggtgagact acggctaata actttatgag  84960
attggaagta aaaaatgaga agggagtgat tttttggcgg tgtggaggcg tagatattct  85020
tttcttgaca agatcaaagg aaaaacagtt tttaatgatg agaaattgat ccgaattagg  85080
gatatggtgt tatgagggag agtctaaaaa agcaacaatc gatgaggaag gtgttttgag  85140
aatcaaggga agggtgatgt gtaccctgcg ttgatgactt gatcaacact attatgagag  85200
gctcatagtt caaggtattt tatacacctg gtgcaaccaa gatgtatcgt gacctaaagc  85260
aacacttttg gtggagtaga atggtagcga cattgttgat tttgttgcca aatgtccaaa  85320
ttgtcaacaa gtaaagtatg aacaccggag gcaggaggaa cactttcaga gaatgcccat  85380
tctgaatgga aatgggagaa attgcaatgg atttcgtggt tggtcttcca aagacaatgg  85440
gtaaatgact ctatttgggt gattgttgat aggttaacta agtctgctca tttcattcgt  85500
caaggtgact tacaatgctg agaaattagc caaactttac atccagtaga ttgttaggtt  85560
catggagttc cactctccat catatcggat aaattaccag tttactttaa gttttggaga  85620
acattgcatg cggaattagg tactaggttg aaccttagtg cgcatttcac ccctcgagac  85680
gatggagatg atcggcgagc gattcaagtg ttggaggata tgccgtgcat gtgtgataga  85740
atttggtggc catgggatag cttcttaccc ttagcggagt tttcatacaa taatagctat  85800
```

cactcaagta ttgacatggc cccatttgaa gcattgtatg gtaggagata taggtctccc 85860
attgggtggt ttgatgcatt tgaggttaga ccttgggggt cttgaccttt tgaggttatt 85920
agaggcggtg aaatctattc agaaaagctt ttaagcggta aagtaggcaa aaataatgtc 85980
cggatcgaag gttagagact taaggtttat ggagggtgag caagtcttct ttgaaggttt 86040
tcgccaaaga aaggggtgat gcggtttggt aaagaggtaa gctaagccca aggtatattg 86100
gaccatttga agtacttagc gaatagggga ggtggcttat gaattagcct tgcctcgggg 86160
ttgtcagagt gcatccggta tttcatgtgt ctatgttgaa aagttaccat ggggatggaa 86220
acacatcatc gttgggattg atctggcttt gatgagaatt tgtcccataa gtatgagcct 86280
ttgtgccatt ctagatagag aaattcgcaa gttaagatca agtgagattg catccatcaa 86340
agttcaatgg aagaatcgac ccgattgaag aggccacttg gggagaagga agtcgatgtg 86400
caaagaaaga tacccacaac ctacttacgt attcgtgtac tcccgctttt tttttggcg 86460
tgatcgttcg aggacgaacg atgggtaaat tggtatctat tgtaacgact gcttagtcgc 86520
ttttgagtat tgattttatt tccccgaaaa actgaagtca tcggaaccca cgacggaccg 86580
tcacgggcac acgacggacc gagggtgtct cattccaaaa cacttagaat tctggaattt 86640
gggtaccgaa tcgactctct cgaacttcgt aacgatggcg acggaccgtc gtgagcggcg 86700
gaccgtcaca catcttccat aggaattgag tctacgaact tctgtgtgac ggcggcggag 86760
acggaccgtc gcagtacccg tcactgcaat cccgtaatcc cagctggccg gtcacattaa 86820
gtgatttaag gggcgttttg gactattccc tttaattata aagttagtgg gttaatgtta 86880
ataagtctaa ttactgaggg ttaaaaagag gtaaccttga gttaatttgg gttattattg 86940
acatctttat acttaattat attctaatta gggtaaaaga aagagggttt gaataagaaa 87000
caatagaaaa gagcgagagg aagagaatga gaaagagaga aaacaagcga gcgaaaaaac 87060
acaagatttg aaattgcttt ttgcttgatc aaaattcttg attggaggta ggttattgtt 87120
tttatactat tattagtaaa ctcttaatag cgaatgatat gtgttgggtt gtattgtaaa 87180
gtcttctata tgcttaattg tatgcttgta tgaatgtgat tatataattg tgataaaata 87240
agcaagataa agctattgaa tcccaaatct tgaaaacccc ttgttaatga tgatgccttg 87300
gtataaaaga aggcttgatg aactaaagta atgagattga tgatgccttg gtataaaaaa 87360
agggttgatg atgccttggt ataaaagaag gattgatgaa ttaatagaat gagattagtg 87420
gagcgggtgt cacgaaccga cacgtagtat tagggggacc gggtgtcacg aaccgacacg 87480
tagtattagg gggaccgggt gtcatgaacc gacacataga attaggggat cgggtgtcac 87540
gaaccgacac gtgggaattg gggggatcgg gtgtcacgaa ccggccacgt ataattgggg 87600
gatcgggtgt caccgaaccg agccgcgtag aattagggga tcggagtgtc acgcatcgac 87660
cacatagtag taggggagcg ggtgtcgtcg caccgacaca agaggaataa agataatgaa 87720
tcttgaaaga tgttaatata ctcaatctaa tgaacctaat cccaaatgag tatggtattg 87780
aggcttgagt ccgcatgtgt gaacttggcg gtacttatta atgattatag tacttgttgt 87840
tgttacatgt tgagtattgt agttgattta tgatattatc tgatatatat actattttct 87900
attttgagtt ggccgatgat acctactcag tacccgtgtt ttgtactgac ccctacttgt 87960
atttgttttc tttgttattt gtggagtgta gcaaacgtac cgtcgtcttc aactcaaccg 88020
caactctagc cagtcttcat tacaccggat tttagggtga gctaatgctt ctagcttgga 88080
ctggatcttc ttcctcatgt cttgatgcct tgaagttccg gcatggacta gattttgttt 88140
attttagctt cttagaatac tcttagttta gtaatttgat catagatgtt cttgtggtga 88200

-continued

```
tgacttccag attttgggga atattagttg ttgaatttta gaagctattg aattggtttt  88260
tattaatgag tttatgtctt ccgcattact tctgttgata ttatattgaa atgttaaggt  88320
ttagattggt tggttcgctc acataggagg gtaagtgtgg gtgccagtcg cggctcggtt  88380
ttgggtcgtg acatttcata acattactct ttgaataatt aatataaatt gagcaatata  88440
aacttttcaa aatgacttat tctagatata tgatcaattt gaggaatgaa tgttccaaca  88500
aacatataat agactaataa gatcaataaa ttatacatat aaacgaaaag tttaaataaa  88560
aatacaacct caaaatcaca tatatactac atagaatatg attcattctt tatctccaat  88620
taggtgggtc atttttattt tagttcatat atatatgtgt gtgtgtgtgt gtgtgcgtgt  88680
gtgtgtgtgt gtggcgtctt ggcgtcttgg cgtgtcttgg tgtgttaatg tgcgtgtgcg  88740
tgtgtgtgtg tgtgtatgaa tttcatcagt aattaagata catagtagaa catgaattgt  88800
atattactat tttcttcatg taggatacaa aatattctaa taaaaaaatc taagaaagta  88860
catcaacata tataaaaagg aaatatataa tacttaggac ggacaaaagg agcggataaa  88920
aacaaaaaat aattactaca catacaaaat gatttgcaaa gttcattttt gcatgataat  88980
ctctcatcct cttcttgtca tatacatgaa gatcatgcta gataatttat agaagtagct  89040
atgatgacct ttgaatagat aattaatttg cattaaatta gttcaatggt tttagtccat  89100
atcaaatttg tttaatggaa aaaattttca aatactcctg attttcacaa tagagtaatt  89160
aattattaat gtgaatttga tacatgcatc aatctaaatg agttatttat caaaaataaa  89220
atgaaataga gtagactaaa aataataaaa tagctaatga attctaaaac ttttaaataa  89280
caaaaattaa agaaagaaat agttctagtt tataagaata gtggaacttc ctcaataact  89340
aacaaaaaca taaacaaatc tatatctttt ttattgcata tgttatgaac aattacattc  89400
atcaacaatt atccatcaat aattatacat tagaataaca aagcatatgc atcaacaaaa  89460
agtaattgtg ttgaacaatg tgtcaagtgt aattacatcc accaataatt attcataaac  89520
aattatacat cggaataact aagtgtgcat taatataaag tgattttgaa gataattttt  89580
tggtatttat agttacaagt ttggaattgt aaaagtcatt taaaaattaa tgatatacat  89640
aacgtttatg agaattagat tgtttaaagt tgagcatatg taaagtttct tactaaaatc  89700
taaatgtgtc atattaagat gtatggtaat tcaaaggaca tttttgttct ttaatgttaa  89760
ttgatatttt gaatataatt tatcatcttt ttgttatgaa atacttcatc tcttgaactc  89820
tattttagaa taaaagacaa attaaacatt tctttaatta tttctaccta gaaacataat  89880
ggattaatac catataagta ttatttaagt aatattttat taattatttc tttaataata  89940
tttaaattag taaaagggta gaatcataat cctattttaa agttaagatc ttctcactta  90000
taataaaata ataataattt acggactagc cccgcttgtt tacctatatt agtcaataca  90060
tttttaaaaa aaagtataaa tattattaat aatattgttt tatgtttaaa aattaaaagg  90120
agtatatact ccttaaaatg agtaaaagaa tctatgagat tttttatcca aatacttttt  90180
ttttctagat agaataaatg aaataataag ttctaaattt aatcaataaa aacataaagt  90240
tgcagaatat aaaaatattt agcaatactg tttttcttct tcaacgctac ctcgtctttc  90300
gttattaggg gtatttattt acaaacatga aatcacacca tgattttatt ttcatacaag  90360
tagtaaatca tttataaatt ctaaaaaaac acattaaata taatgcatgc taattttttg  90420
tagatttaat tatgagaaaa aactaattac atcaattatt caattctctt atccaataac  90480
ctagagtgtt cactacatga taatcaactt gttataacaa acataatctt taaaagaaga  90540
```

-continued

```
tttgtacatc agacatgtaa atgaaaaatt ttcttttctt ttttcactgc cattattcaa  90600
gaaaaagtag tcaatttacc ttccttcaac cgaaaaattg aatgtaacaa ataatgaact  90660
aagtaaaaat atgcaacatt gaaatgaaaa ataatactta ccaaacaaca aataaatgtc  90720
catgacgcct ttaaccttct tgaagaatgc atcgaatgca ctgaaatgat taaattctaa  90780
ttcagatact atattctcca agatttaccg tcaataaatt aacaaaacaa catacatatt  90840
ttttctcaca caagtaggtt tgttttacct catgaacgtt gagcagacta tttgtccaaa  90900
tgaaaaactc tctagaatta tttatcacct gtttgcgttg aaaacataaa ttttcgatga  90960
aaagaataaa acaaaacatg taatattagt tctatctata tacatatatg cctaaaattt  91020
attgatcaaa agaaacatga aaattttgaa gaagaatttt tgagataaat caattcacat  91080
gctattgtca tgagaagaca tcaaaataat gtattttgtt ggaaaaatca tgtatataat  91140
tttatcaatg gaactcttca aattctttaa cttaaaatta aataaaagat gttttgaaat  91200
gtttgaactt catttgtttg aatgactatt tatctttcat tatatcttta ttactttaaa  91260
gtttattatc taattattta ttaaaaatac ttttacattt taaaaaatag aaaaaattta  91320
agtgaatggt aaaatggtaa tttaactttg aggttaggag cttcccactt ataataatat  91380
atgatgataa ttcgccagaa taatacagat atatgtataa tatacaatta tttaaccgat  91440
atcatatctg attcctctct tccactctct ctcctctctc acccgcctct ctcctcccac  91500
tctcaatttt cctttccata tatacaaata catatgtata atatacaatt atctaaacga  91560
tatatatata tatatgcaat tcatctctct ctcactcttt gcttcacttg acaactatga  91620
cacttaactt tggatatgca caaattgaca tttaaaaact ggttacagag aaacttaatg  91680
ctgttgcgta taaagttgat gacttattgg atgaacttga atatgaggca gcaagactct  91740
gtttttcagc aaacacatca agcagcaata tctgagaaat taaacacata tgatgatgtc  91800
ttcttactca ccgagttatt agttatgcta aaatgtttac ccgagggatt gcagcaccta  91860
acaaatctca caattttttt tgataagtga aagcatagtt aaactctcaa atgtagatga  91920
taattaagct cttgaagatt atcgctgaat taagtgaatt cgttattagt ttcaaaatgt  91980
ttagcctcct tgggacctga cgaatgattt aaatttcaaa cacaaggtca agctatattt  92040
gtaaaattct tatggccaaa caagtcatac tgcaacaaat tgtaaaagga ttattatact  92100
ccaaaagtaa agatttagaa gagatctact cttaacacta actaaaagat tattccaatt  92160
ctcaaagcaa atttatattc ctttccaacc aaagaggttt tccaaatttg ctttctagta  92220
attttttttt tctgcacgat aggaatagat ctcatatact ccctccgttc catattatgt  92280
ggtgtagttt aattcaatac ggaatataaa aatgaaagaa agacttttaa aatttatagt  92340
ctaaaatgaa taataaaaaa ttgtatgact ataaatcatt tcattaagag taaatgtaca  92400
atttaaaata aaattgttac ttaatatagt aacgtgtctt tttttttgga aactgcctaa  92460
aaaaaaaaaa atagtcatat aaattgaaca cagggagtat ctacttacaa agtaaaagtt  92520
gtgtgtagaa gattttggca tataaatcat atcatatatc atcatatcat atattagtaa  92580
aagcatgaat taaaaaaagt caaaaagtta aattacgatt ttatcccttc tattaattaa  92640
cttgttataa aatatttaaa tatttgattg tacaagttta attaaaatgt taaatgaatt  92700
ttaaacttcc taatattaat ttctaattaa atatctaatt tattaatatt tatcatttat  92760
aatccatatg tatataataa ttataatttt ttaataaaag tctaatcaaa atattaatga  92820
cttttagact tcctaacact aattcctaat taaatatcta atttattaat atttttatca  92880
tctataatct ctctatatat aataatttta caaaaattaa taaaaagtct ctacgtaaat  92940
```

ttttatactt ttcttattct cataactttt accctaaata acaaaattta ataattttaa 93000
gggtgcaaat cttcaaaatg gagacacaca cattgataat gtcctcttaa ttattattaa 93060
agaatgactc tagcttcaca aatttaaatt cattaatgct taattactta gagaaaagta 93120
gatgaagact cttaattttg atagtatatg gaaggattgt gtactaattt tgtacttatt 93180
ttttcatcta catatacata gtcttataaa aatgatgtct acattgtatt ttttcttaat 93240
ctgtttcttt ttgtcttttt cccccaatta gacttcttaa tttagttttc tacaaatgtt 93300
ttattgtcgt aagtctcttt acttattttg taattgtagc attttattat tcattataat 93360
ttgcatatat gtatttccat gaaatattag taattctatc atatctataa aaattcacat 93420
gaaatacacg tgctcagaaa ctagtaagga aaacaacaca aatatacatc cgaactatcg 93480
taaaaatgat atgcagatac catcctcata cttttgggac attgctgtcc attacgtcaa 93540
aaaaatatag catatatatt aacggacatc acgtgtcata atcatatcaa ttgatccaac 93600
atttaataaa tattcgatcg acgaatagat tgtgtcacat gtccctattt agtcatatgt 93660
taaagtgaat gacatatatg ctctagtttt gaaactttct tgtaaaattt aagtatatgc 93720
cctaaatttt taacaatatt ttgctacatt ttacgttttt tccattcacg tattttctta 93780
tttactaaac aagtttctat cgtcctcaga gtatttcctt aattagcact aaatgttgtg 93840
atgtttttct tcaactaagt ttcattgaag gattgagatt aaacctattt cggtatccac 93900
gatctttgaa tgaatcgcca aactctatct atgaatttaa tagcaaaagc tcagattttg 93960
ttccaaattg agatataata tttctataaa gaaatttaaa ttaatgatgt gatataatga 94020
taatgaattc agtttttaca ttagaaagac tctatttttc tctcttactt cacaacaatg 94080
caagaattct taaagaccta aaaatggggt aggggtgggg gaagggggcc aacaacaaca 94140
agattctaaa ttcttgaata tttttaacta aaaaattaat tcttttccca atggattcaa 94200
attgaaaagg aaaactacaa ctttgtgatt atcgcgcttt caaaatgttg aatagattgt 94260
cttcaggtgt gagaagaatg agagtgagat ggagaaccat acgaataaag aaattctcaa 94320
gtacgattcc aatggaagga attgaactac ctattttgat cggagataac aagtcattcg 94380
atagagagat tttgaaactg catatgtttc ctaaatgaaa gttatatatt agctagatag 94440
ggatatagat gggttgaatt ctcaaaatct aagaataatt ttggatatgt ctaaagtgat 94500
tggaaagtga atatatttag gacaaattac atgattcgat atacttcact attatatata 94560
ttatttttac atatactttt aaaacactag tttctggaca cgtgcattga acgtgtatct 94620
caaatatatg aaatagatat ttttgaaatt gtaagacaat tctaaaatat ggttgtgatg 94680
tttagttatg tatgagagca atttaataaa atatgtatga gactttttta atttgtttcc 94740
catttggtgt tccgctagct aattcaaatt catgtgtgac attccacttt gaggatactt 94800
cctataaagt ctttccatca tcaagaattg aattcaaaag attgaattta gaacgaacga 94860
atatttatca atcaatcaac ttatttgatg aaaacatata tgaatttcag tttgcacata 94920
ttataaaagg gcaaacttca tatttcaagg gtactaccta taaggtcttt ccattatcaa 94980
gaattgaatt caaaagattg aatttagaac gaacgaatat ttatcaatca accaacatat 95040
tcgatgaaat atatatgaat ttcggtctgc acatatttta aaagggcaaa cttcaaaatt 95100
tatcgtatat gccccaaatt tttaacaata ttttgctagt ttttagtttt ttccattcac 95160
gcattttctt atttactaaa caagttccta tcgtcctcag ggtattttct taattcagca 95220
ctaaatgttg cgatgtttct cttcaacaaa gttttcattg aaggactgag attaaaccta 95280

```
tttgggtatc catgatcttt gaatgaatcg ccaaactcca tctaagaatt taatagcaaa  95340
agctcagatt ttgttcaaaa ttgagatata acatttctat atagaaattt aaatcaatga  95400
tgtgatataa tgataaatat gaattcagtt tttacattag aaggattctt tttttctctc  95460
ttatttcaca acaatgctag aattcataaa aacctaaaaa tgggaatatt atcatattat  95520
aattaaaagt aaaactctat tttagaaata gtggactaaa catctaaact aataattcaa  95580
tggcctacgt tgatgtaagt tacgttattt tagcaaaatt aagaagaaat tccttcattt  95640
gagggtagaa tcataaaaat aaaaaataga aaaatacata tgaaatatct taccgcaatc  95700
atgtgccctc tttgtatttt tcattactat tgtctctccc cccaacttga tcaattactt  95760
tttttaggaa aaataatcca cgatgaatgt attcgtcaat tttcactgat tatgtgaaca  95820
caaattatta agttctctct tgaatgaaaa caaaaaaaaa agaaattatt taaagaatca  95880
aaaaaaatta aacgtaaatc cccttgcact atttagagaa attttctatg tgaagcatat  95940
ttcacaatta attgcacatt tctctgttct cttcttctct tcttgaataa aaagtcaata  96000
cctaaattcc catgataaga gtatcaaaga aacatattac tggattaggg atgaatcatt  96060
tatgaaattg tgaagtgatt ttagatactc acagaaaaaa aatcaccaag aatttataag  96120
gagtggatga ttgtgattta tgatcgaaaa aagatgaagg ttaaaattgt tgtgactatt  96180
aatacgaaat atgtcttctt taacaaataa aagtttattt aattttaaat gatacaaata  96240
atattgaagt atgtacatga tgaaaatcgt aagaagaaat acaagtatga ttgatgaata  96300
agttgctata atttattcac cgattctttc ttatgtagta cctcgagttt ggttgaattt  96360
cgaacttgat caatagttgc aaacaacact tgagatattt taagaagaag aaatataaaa  96420
atgtgaagaa acacttcaat ttatagctaa caaattgtgt tatgaatatg tgttaattgt  96480
gtctttttag taaagctaca acccttcgaa aaaggcattg ctcatgagaa agtcacaata  96540
ctgagaaaaa gttacaactt atcaaaaaag acacaatgct ttcgaaaact caaaaccttt  96600
tgaaaaaatc acaacccttc tgaaaagtca caactcaccg aaaatgtcac aactgtcaat  96660
ttcaaccctt caaaaagtta caattcatag caaaaattca caaaccgttt aatgaaaaaa  96720
aactatctat atttaatata atataagtaa ataaaataaa aataaattaa ttgtgtattt  96780
ttttttaatt ggggatatta tagtaattta acattcattt tgggagttca tgctttttag  96840
gtagtgctag tttcgagcac gtgttttgca cgtgtgatcc atgtgaattt tatagatatg  96900
ttagaatgac taaaaattaa tggcaatata tatgtaaatt gtaatgaaaa ataaaatgta  96960
acaattacaa atctagtata aagacttacg gcaataaaac attcatagaa aactaaatta  97020
agaagtctat agagagaaaa aaagacaaaa agaaacagat ttaagaaaaa tacaatgtag  97080
acattattct tataagactg ataaatatat agctgaaaga ataagtataa aattagtaca  97140
tataactctc tgagttcttc aactcctttc atatcctatc aaaattcaag agtcttcttc  97200
atctacttta acaatagaat aaaattaata gcctaataat cttggtaggg gtttcatgag  97260
ataaaaagtt gaattttata gatagagtag aaggaatatc aaaagatatc tttaagttta  97320
agtttagata tttggaagtt atgaatatga aaagattaga gttatgaatg ttgagagtaa  97380
aaaagttgaa taagtaatta taaaataata ataaataagt aaataatatg aaaaagaaaa  97440
ttaaaggtag caaaccatgt agaaagaaca actaaagttc ttatcacgta attaatttta  97500
atttaaattt gttaagctag agtcattctt taataataat caagaggaca ttatcaatgt  97560
gtgtctccat tttgcagatt tgcacctttt aaattactaa atttcgttat ttatcataaa  97620
gaataatact ttatccacat aaattatatt attcatgaga ggggttaagg aaagttatga  97680
```

```
gaagaggaaa agtatagcaa tttaggtata gactttttaa ttttattttt tttttataat  97740
tattatatac atatagatta tatgataatt attaataaat tagatattta attaggaatt  97800
aatcttagaa agtctaaaag tcattaagat tttaattaaa taaacaatca aatatttaaa  97860
tattttataa catttaattt atagaagaga taaaaccgta attcaacttt caactttttt  97920
tgttcttgct tttagtaata ctagcaatta taacaaactc atcagcatca actcgacctg  97980
tatatttcat aatcaataat gtcttgtaaa tattcatcga tgtgtcgaaa caaagccccc  98040
cacgtataat acaatcatct tctaattaat tgagctcaag cactttgatg aaaaatcgaa  98100
tggcaggatt ccacaagtaa atatgcttgt ttataccaat cagtataaaa ctatgactgt  98160
taggttgtgg agcctgatta atatttgatg tattatttat tctctgtaac taaatatact  98220
ctgaattatt aatatatacc ccaccgccgt ggaagtttac ccacgggggt gttaccacga  98280
aatattggtt tctctctttc tagatctctc tagatctctc atctctctca aaagtttttg  98340
tgttcttcat tcatcaagtg tgtgtggatt cgatcctaac aacgacaaga acctaaaatc  98400
atacaagttg ggggaaaagc tcattatcat gacttagagg ataggtgagt tcttccacaa  98460
tgagttgttg gtttatttat tgaaagcaag ggttagagtt ctacgttgca ttgacaattg  98520
ctcctccttc tcgacgttga tttgagagat gaataaaatt tggacttgaa attcaagaat  98580
gtcatgatcg tgaaacacac ttgaatcgta atagagattt cacagataaa attgaaagaa  98640
ttatcataat ggtttcattg ggtagataca ccatcttgac aagtagtaga ttttctgggt  98700
aattttaatt ctcgtatttc tgatatagac atatgctcac aaattgacgt gaaaccgcat  98760
gcgaaattta ggaacttatg caggtgtttg ggcgcagttt tgactgtcta ttgttgttcc  98820
ctaattaaat atacaccttc tctgtttcaa ctttccaaca gttttgtgct aaagtatttg  98880
ttgttgcatt tatttattca aacttaattt gttccaaaat atcatcagag tacaaactaa  98940
aggattcaac atgccttgag tacattttat actgtcaatg gcaatgctac agcaattaag  99000
caccagtaca tgaagcaacc gtttattggt tgagatttga gtgtcagtgt cattcctttt  99060
ccattctttg tttttggtag taactatgat attgccattg tttataactt caatgatctg  99120
ctgatattgt ggagcatgca aaactaaaag ctatcgagta aaagtgatca taatgtgcta  99180
gttcatataa gaccatctaa aagctatcaa ttaaaactta tcgcagtgtg ctaggaagtt  99240
aagggtgtac atatatttgc aattggcagc aaaacagagc aaaagcaaag cattaagatc  99300
agaaaaagta gattaacctt aacaaatcga gctcgcctat tgtcccctac agcaaagtta  99360
aacacctgca gtgtttaaaa accacaaaca acatttaaca aaagtgaatg attaaaagta  99420
aaaaaagaaa aaatcgagaa agataaaaaa gaacagaaga cggcataaac tacaatatat  99480
gttttccatc acaggttatt catatcatcc cccataaaac tttctacttg agcactacca  99540
agaaactatt gaggatgtgg gaccttggga tggttagtca aaatgagctt ctattatatc  99600
cttctgtgtc cttctattaa agctctcctc ttcttgttta ttttgtggag tcccaatttt  99660
ggcgtggcca attccatgat gccaaattgg taacaaatac ttgaaagagt gatgactcaa  99720
gagagatggt gaagaaagta gacatagttc aacgaattga agtcatattc gagaacaata  99780
ttatccagat agttcaatga agtcatttat tcaaaattca taagcaaata ttaatgtgga  99840
aaagttctat tcatttccaa attgaacaaa agaagcaaac aatagataag gtctccaaca  99900
tggagataat aattgagagt aaaaacttct attgctatta aatagaatct gcaattaaaa  99960
aaaaaattac atagatacaa tatggaactt caatatgtac aacttggaaa ccctttcaat 100020
```

-continued gcttgaggtc tcagttttta ccacattcag atacaaaaat gtagtaacaa tggcaattgt 100080
gcgcgattct aaaatggcaa aaaaataatg ccaacttaac tatggaaatt atgtacagat 100140
ataactaact ataaaactta aatcgtacag tggcatatca acagagcctt cttaggctct 100200
gctgctatca tcaaaaaaag cttttgactg attctggcag ttcatggagt agtataagct 100260
tcggacgatt tgaactgatt cacacagcat gtaactgatt taaaaattca gttttactct 100320
atcagagtca ccaactcctt tcttcccaga agaactagca gccgcttgtt ccttcaaagc 100380
ttccttctcc agtttcttct tttcagcatc agctgcttgt tcattctcat cacgtgattt 100440
tttaaacatc ttcatgaaca ccaccaaaat ttgtgtcact gcatccagaa agtaaggaaa 100500
tgaaaactga caaagttcgt cacaaacatt gtccggttaa agagttggtg aggaaaaatc 100560
tgttgaagca attctcacac cagttaaaac aagatctcaa ggacaaacgc aattcgagaa 100620
atctagccga tggctatatg cactcaacaa aagctacaaa ggccataaat gttgcatccc 100680
ataatcttca cataaagata gacaactaaa aagcatcact gataaacgct actggaatat 100740
ctatattacc aagactgttt gaacgactgt agttttttct tttccagatg actgataagt 100800
gataatacag caagaaaata acgtatgtat ctctaacctt gctcaaaggg gcatcgagct 100860
ggatcttcgc caaaatacag ggatagggag tctgcactcc ttccctgcag atttacagga 100920
tagaaaaaca atcaataaac ttggcatggc ttatacatcc aggaggcttt aaaatatgac 100980
ataatggatg caagaaactc accacttcaa tataaagagt agtgagagac ttgacttcag 101040
cctcagcagt atcaaggaaa ttctttaaca cctgagaagg aatgcacgag tcacaaaccg 101100
catatttcag atgtttataa caaaattata tgtacaccaa atcacagaca tcgcaatcaa 101160
gtttgactgc atcaccagac tccactctaa aaccatgtcc aacacaaacc aaattgggag 101220
ttttcccagc gcaagccttt ttcacttgac cttgttaaga acacaaatgt catccatcca 101280
ttggggacac ctatcactct tctaaaacag tggtacactg cttccttact ttgttttctc 101340
aaactatcta gaataaagct ttttgatagt aaatagggat ccttgtaatg tataatgaag 101400
gaaacctggg gaaagaggaa tccgcacaac gccgttcatt tcatatctgg cgtaagaaaa 101460
tctcgagaat ttgataatac atttaggggt cgtttggtag agcgtattaa gaaaaatcat 101520
ggatgcatta gccttgttta ttgctagtac catgtttggt actcttttct aaactatgta 101580
caactagtgt tgcattagtt atacactatc gtttattaaa gtagattatg atatgacctt 101640
caaagttaaa atttaaaact aaaaagaaac attatcttgg aagtacaagt aactcatttg 101700
gtttgtagga ataattcaca tgttaccatt ctcttttctc accttctgaa atcctgaaga 101760
tattgtacca tcattgtcgg atgcagtaag ttcttgttca actttctcaa gacctttact 101820
cactgcttgc atttcttcag ccaaagactt cagttgaatc taaccatata atatgatgta 101880
aacaaacatt tcagttcacc aaaataccag tagtactgca aaggaagacc ataataaata 101940
gcaagggtac cttagaagca gcttccaagt gaagaagatc cttgtcaaaa tcaagcaact 102000
ctggcatttt ctcagcaagg agctgacaaa aaaacgaatt tacacatttg gcatcacatt 102060
gagaagtgca aacatatata tgccgaagag taaagactaa ggctggtcaa gccagctata 102120
gttgatagct aaaggctatc aactaaagtt cactgatggt tgggcaaaag aacagcataa 102180
acgtagaata ctgaaagtag aaaataaata caaaaacata tagttttcta cagaactcaa 102240
ccttctatat tacaggaacc tcatgggtgc accaaaaagc aataagggac aagaggctat 102300
tccttaactg tgcaaattac tctacacttt caaaagctct cctaattctc actctccaca 102360
aaacccacat aagtgcaaaa gcatcacttt cacgccttgt gtctcctcct tcatcttccg 102420
ccatttcagt tgagcaacat tacttataca gtgacgggca tcacccaaat ttaccaaacg 102480
aacaccacat ttcccaccat aaccgagaag ttatcgcaca atctagaaga cgattcgcgt 102540
cttcacctga ccccttaca cataaaacac cgcccaacat aagtagttct cctcttcatt 102600
cttttatcat ccatcaagat cacccctctt gttcctaacc aagtgaaaaa acctaccttt 102660
ctcagtacct tagggatcca tatcaaaata tatggaaggc tatctttctt ctcattgatc 102720
aaaaatttgt ccaaagaaaa ggactttagc aaatttattc ttaggcggcc aaaatgaaac 102780
ttagattaca atgaaacctt aacaaagaca agaattcaat gaaacctaaa caaagacaag 102840
gaccagacaa tagagtctag ctaaaaagaa tctgggcttg ctttttcaat tcaaatctgt 102900
gagcgaggat tcctctttct cttctccaca aaaatttgaa gtggtttata acttacggag 102960
tatccgataa tctcttgcaa tcttgtataa gcctgtgcag atgaaataac ttgaacattt 103020
ccaggagtca atcgatttgc accagtcgac cagtgggagc gataatttta agatataaac 103080
atcatataac cttcctttta gcctattccc acttgagcgt acttcacagc tgatacgctc 103140
ataatacttg acgccccgaa ataatgaaca gggatagata tggagataca atttaagaaa 103200
atgaacctta ggcacttcaa tataagagaa gagagaagta gaacaaaata aagaacaatg 103260
caactggaaa aatgttgaaa ataaagtgaa cgatataaga tggattagtt ttcagatttt 103320
catctttaag agctgctgac tctcaaaaat ctgctacacc gccttgccgc cgccttcttg 103380
tttgagtgct caacagaagc acctatacgc acttggactt tccttagggt gatttaatag 103440
attttttgtg tattttattt ccaattgttt catttggcaa gatactctaa gcttgaaatt 103500
tttaatttct atttagatag tcttgtatgc ctaatttcat gtttgatctt ctatttcatt 103560
ttagagtatt ggagttgata ctggatctag ctatcaccga cctactgtcg tactagcgtc 103620
aagtgcagca cttagccaat aatccccaat aataggggct acacttagac aaagtatgaa 103680
tcaagaagtt gtaagtgtta gatgcatgtg tggcatttag ctatgtttaa cctcttttgc 103740
tggagtaatc tctcctttgt aaatgatatg gatcaatcaa cccaccaata gttctagtaa 103800
ttcctgaact actaagtgta ctaccaagca ttctaaagcc tcatgcatct tccttgattg 103860
tgtagaacat gccatactta tgtggtgagc cttgcttgtg cactatggct cccacttgtg 103920
catcaccatg cctcgtgcat gctacatcat cagaccatgc tcttgtgcta acactatcac 103980
cataccagcc cagccatgcc tccatgaaac agttcctaat tttctttgcg ttactactaa 104040
gacaacgaat cgtttgatct tgaaattcct tgcctcctct ctgttagcct ggtccatggc 104100
tttgttgcac ttgcgcatca tgccacactt atgtttgtga accgtgcttg tacactatgg 104160
cttccactag tgcttcttca ccatgcctca tgcatgcttc atcttagtag catcctcttg 104220
tgccaaaaca accacgccta ccagccatgc ctaacatgga actgttcccc aatttcttta 104280
actttctaat taaaacttaa acaaagaatc atttggtttt tgagtgttga aaccttgaaa 104340
gcgctcgcct cctctaaagt agcccccttc atggttttag atgggttatg acatagacct 104400
caaatacact tggcactttt tcaatccaat catgagctac tcaacaatta ttactgagcc 104460
aaaactaatc tgattcaact tacgcttaag tcacctccaa ctcttcccaa ttcagagcta 104520
attgatcaat actaattaca taaaggtaaa aacagaaagg catcataatg cagtaattct 104580
accttgcaca gataatgcat caaggtcatt ttgttgtttc tcgcacgagt gtcagaaagc 104640
ttaagaagac tgtccaactt gaaccctaca gcagatcctg taacgtaatt acaaaacaaa 104700
gatgttagtc acgatgcctc cacccaacaa ctgattattt tcttatagag atatagatct 104760
tagaaaactg tacctcgtgc tgtaccctga ttcagtgcat tacccaatgt tagaatggtc 104820
tgcattatct gacgtaattt ggcagattct ttcacctact tgaccaggaa attcagttag 104880
agcctagtta aatcagaatg tgccaaatca aacttcataa ggtattaaaa atacctctct 104940
agtagcatca ttgattgtac tcaggttact tctcaagtcc ttcacctgaa caattcaaca 105000
tattatagtc aacagaaaat taatggcaga atccatagac attagatcac taagaagtac 105060
aagagaaaat acctgattag agaaagtgat agtaaatgaa aacactcgta acttggactc 105120
aactcgtggg accttcatca gctccaggaa aaactgaaac gggtattact tatccggtta 105180
attacttata acttaaagga taggaaaact tgtacttccc cacatatatg gtcaaaatgg 105240
agaagacctg ctcacacttt ccaagcatcc ccttgtcccc attatagttc tggaaaatag 105300
aacataacca gtaagatcaa attgtgaaat caagaataac aattaaatat caaattgcaa 105360
gtatagactg tcaagaaact aacataacta agttcacaaa gagaggggga aatcaagcag 105420
aaacaagtat ggatctacat acacaaaaga ctaagatata tgcctatgtt tatacacatc 105480
cacacccacc gggaaaggaa gttcccagga aaaggtatct gcatgattag acattgaaac 105540
agacacatga gcatgcacgc acagcataga tgcaagtaca tactgtataa gcatgaaacc 105600
gccaaatggg tcattgactt atgggcatca acctacacag ctacttgcaa caaatggcac 105660
atcaacaaaa ctataggctc ctgctgttcc tacgactcac ttaactattc ttacgttaag 105720
tacaattgca gaatgtgaag gttccgactc ttgtttccaa atactatggg caaaaaactt 105780
caatatggag tattttctct aaacgggaaa agttaaaaga agaatcaaag caaacttcag 105840
aacatacctc taatattact tgtgaactca aaataaatga ctagacacac attataagca 105900
tattattgta acttaaactt tgccatgata ggcaagcaca gtaggatgag aaagagatta 105960
taccctcagt gtctccattt cttcttttgt tgggcaaaat tttatcagat tttcaacctg 106020
atcaatgtcc agagctgatg aatccaaagc caaaatagca ttctgtatga catgcataca 106080
aatataattt gtaagaaatc cgcggtaaat tttcctttgt aaacagaaat tttatttgca 106140
tttgcataat actggccgcg agttcaaata gcggaccccca acttgtctgg aactgaggcg 106200
caactgttgt tataatatta gtaaaaagaa atccatggca aatatttcat tcatttcaat 106260
gtacctccat taaaactcaa aataaggaaa aaagaacttc caaagaaacc atgcatgagc 106320
atcctaaaga aatgctcgtc agtcattaca cttattgaac acatgcatga atcagcatat 106380
tgatactgtg cattatgaaa catgattttg accaaaggcc aaaggataga atattttata 106440
caatttctat catgattcct ttgaatttca aaggaaaaat atccataaga gttcaatttt 106500
gaactcttca agttcggtga aattacatga tcttttcaac acaataaaat tatcaaaaat 106560
ataaaaaata agaaagtctt ttggataaat agttctacag ctacttccat agaaagctcc 106620
ttttctcctt gtacaaaata aaggtttctt tatccatttc attgaactcc ggctaaaaaa 106680
tatttctaat aacgatagtg tctgatccta cttgtgctcg tatcttgact aatttatagg 106740
gtacttgaca cctcctatca acataggtat ggggaactat gccctccaaa atgcaatcag 106800
atgaggaaaa ccaccaagtc ttagttttgg tcgctactag aaaaaccact tggccacact 106860
ctaaagtgct cattgaactc caccaatatg agaaaagcat aactaacttg aaactgaatt 106920
acaaggagaa ctgttatagg ttaatggcta acataaaaat agtcaaacta ccaaactcct 106980
ctgtgtatga cctaaatgtt atgtgtagtt aaccgattta tacgttcttc attcctttgt 107040
tgagaaaaaa tatagatagt taatcaatat attgtacttc tattaagcag aaacgaagat 107100
acttcaattt agagttcagt acataatata atctttttga tctagtaaaa agattatagc 107160
atgaagagtt caatacatac aagatacaac aatcttttcc tttttttgt tgttgagaat 107220
ggacttttag tcaaacccat taagctgatt caataatttt gcagatctat ttgattcatc 107280
agatacatac ttctatagtt ttagcaaatg tacaaaggga ttaaaaaaaa ctaaaatact 107340
aaattgtaat cttttggaaa ataaagtcaa acaacatatg cattcaattg catatgtaat 107400
ttgttacttg atttcaattg ataaacacat caggattcgt taattttaat ggctgtttag 107460
tttgtgttac tttttaaatt attagcagct caatttccaa atatctgatt gtcctaaagc 107520
ccaagtaaag atcacataat ctaatagttt catctgataa acaataatag attattatca 107580
aaagacccac ctgttggcta gaagacataa attagtgcgc aatagataaa agtatcgaag 107640
ctcatagtag aaacgagaag acacaaaaag aactcacaag catatcaggc aggggaatct 107700
tgatttttgt aagcatgatt tcacaattgt atgccctgcg caaatcaatc tggcaaaagc 107760
atatgttaag aaatcatccc ggtcttttaa cagttagacc aaaatgtaac acttccagtc 107820
tttcactata aataatggga gttgtgtaaa ataaacctca atacctcagg aagaaaaaga 107880
agccaacacc aatagactgt tcaccaacta ttccatagtg atctcatatt atacagtgaa 107940
agctttgaaa actatcagtt tctttctata gaagttttct atctctttcc caatttagca 108000
ctaacagata aattaagaag caagtgaact gcaattcatt catggtcaat ggccatcccc 108060
atgggacaca gtgcccatta tgagcacagc ctccgcaact ctttcattag atctagacat 108120
gtatcgcagc ctaataaaat tactctgttg catgaattta catctcaaag tattaacaca 108180
acttttaaga atttttcaaa ggcaaccatt attttttat atgattgact ccatccacta 108240
aaccctctgc ctaagacgcc caagagaggt ttcccccttt atcccttcgt taatcaaacc 108300
cccaacctta tggttggaga tgaaggacct taccctagga tatcactcca gtcaaagata 108360
attgtcttaa ctttcatgaa acagaaatgg tattacctac aggatggaga aaggaggact 108420
tttccaccca aagtttatgt aatcatccac atccaggctg aaaaaacata agttcttctc 108480
tataagggca tgcttgtttc gaaacgtcac ctatgttaaa cccatttaag cctttctatt 108540
tacttctttt cttccacctt gttagccaca agataccaca aaaagtgctc tttaaaacct 108600
atctaatatt taattgtttt gttaaactag taaagaaagg agatacactc atcctacaac 108660
actcacttta ctacatgaaa gacttgctag ataatgccta ctggagaata acagttgtag 108720
agactggaaa caagataaag catatataac ttgccaattg cactttttct ggtttgttga 108780
tttttgaacc acgtcggcct ccacctttgc tagtgccatc agtagctgaa gccaccgaaa 108840
acaaattctc aagctccgta atatcaattt caggtgctct gtcatgtaca ttaataaaat 108900
cttatcagaa ctacccataa cagacagata acaaataaaa gttgcagtac ccaacacaaa 108960
ctaggttaag ctcaaagggc tcagaactac tatatctgta atctattaag cattcgaagt 109020
tgaaaccatg agaatgatag tgcttatgac aacctgttaa ggggtttcac gagacacgag 109080
aaatagcgaa caatttagct ctgactatta acttgaaatg acacacaaag ttctcattgt 109140
aatttttcat ccccaaaaat aaaatcttta tacctggaag tattttcctt gttttgcgta 109200
tcagcccata aactcccttg catagcccgt gtaactttcg accaatgtaa gggcttcaat 109260
gaagcttttt tcggaggaat tgaagtacct cctgtacctc gcccttttcc tagagcagtt 109320
gaacctacag aggctcttac acgtccggta gatggaggtg gtggcgctgg cacactaagg 109380
ccctttccac caggcggggg aggtggagtg ggtgtcaaac cccgcctagg gggtggtgga 109440
gcattaggag cctttggtgc tggtggaggt gctggtggag tggaaccttg cctaggaact 109500
cccaaaggag gtggaggagg tgcaggtggc cttgtagaat tgtttgacgg tggaggtggt 109560
ggcggtggag gtgccaacgg agtaggccta tttgatgaag aaggcggagg tggaggcggt 109620
ggtggtggag gtgccaacgg agttggccta tttgacgtag aggatggagg tggaggcggt 109680
ggtggtggag gtgccaacag agttggccta tttgacgtag aggatggagg tggaggtgga 109740
ggaggtggag gtggaggtgc caacgaagtt ggcctttttg acgtagaaga tggaggtgga 109800
ggtggaggcg gtggaggtgg aggtgccaac agagttggcc tatttgaagt agaggacgga 109860
ggtggaggtg gaggtggagg tggagcggga ggtggagggc ctttggaaag ggctgaaggg 109920
gtaagcgggg gaggtggaga aggcggggaa gttacacaaa gcaagggtga acacttcaat 109980
gacatgaaag gggaggggag gggtggagga ggagctgata aattacagtt agatggaccc 110040
cgaggaggag gaggtggagg tggaggtgga ggcaaggcac ttctagaagt agaaaacgta 110100
gggacagatg gtggatgtgg aggagcagaa gagcataaaa ggctctgatt aggaagtggt 110160
ggaggtggtg gaggtggcgg aggtcctcta gaaaagctat caggggaagt tgaagaagta 110220
ggttgtcttg gcggtgaatg ttctctatgg ctaccaattg aaggtggtgg tggtggtggt 110280
ggtggaggtg gaggtggagg tgatctatta gaacttgcaa gtggtggaag cggacgagta 110340
cgttggacag aagaagggac accaattata ggaggaggtg gaggtggtgg aggaggcgga 110400
ggaggtaatg agacctcctt gctaggagaa ccaaacagag agggtggtga agggggagat 110460
ggagctgatg attgagtgac ttttatacta gaaatcacag aggcaggtga cggaggtggt 110520
gaaggtagcg gagaagaaga ggaagtcctt gtatcgcaaa tttgaactcc ctttaaacgt 110580
tcaggagaaa tggcagtatc caattgacag ttactttcag aaagagactg aacaggacca 110640
agatctgact ttgaaagctt catttgaccc tcagaaatct tgggatcaga agttccatca 110700
gaagctgaat cctgttcatc taaaaagttg acatctgttg tattagcata actaatacta 110760
ctagctttct ctgagtccag aaaatccaaa ctgtcggcaa tgctcgatgc attattttct 110820
tcttcagaat caaatgggga tgaataccca ctcatcctac tttgcaaaat tgacaaatct 110880
ttcatatcat tcagcaccga tagctgttta aacaaccaca acgcagcatc atcaccagta 110940
tcaacccaat cagcaccact aaaaagttct tgtacccttg aaaaggcttc aataggaagt 111000
ccaccagtct cctcaccatt gagagctgca gtgggagctt ttagtggaga tatgctctca 111060
acatcaccaa ataaaacctg caaagcagaa agtataagtt agaggagaaa tatgaagagc 111120
aaaggtgatc caataaaaca aaactaatca gacagtttgt aaataagtat tcacctcagc 111180
tcgaaagcct tttggatagc gtgcctttga atcccataga atatccaggt tatcgcagtt 111240
taacatcaaa atgttagagc gaataaaagc agtgttaaac acaatacgga acatcatgac 111300
ttccctttca ggatccaggt ctaagtggac acactccaaa actacatctc cttgcaccaa 111360
acactgaata tcaatcttga tgacatcact gtccttctgc aaaacaataa caatcatgtt 111420
gccacagagc agaattgaag aagacaacaa acaagatgca gtgatagcaa tttttcacct 111480
ggcgataatg tcgaaggctt ctacctttct tcggcatgga gtacaacata tgagttgaca 111540
atccatcctt gctgagaagg ttccttccaa aaatgcgcac aattggccta cacccttttt 111600
gattgtcaaa tcttggaatg gcacgaagaa tgaggcaatc cagagaaaga gcttgttcag 111660
gaggaggcca ctcgggagat atatttcttc ttgatatata ttgcaggtaa cgaagctgag 111720
aagggaatgg gttcaaaggt gacaacaatt gcgataaacc tttaggtgcc tcacgataaa 111780
ccatctcgag agtttttctc tctccgcttt gtaactttct gaaaaccaag aaactggcga 111840
aaatgaaggc tagaaggggc caaccacctc tctcacagtg taacaaaatt acattgttat 111900
gattttgaag agagagccaa ctctcacaga tacatagaaa atgatgtatc aatgacaatg 111960
gcagtacagg acagccttca tattgtcttg ggtaatccat tacagtcaca tcatactcgc 112020
ataaaatctc agcaaactgg ctccttttct cgccttctct gaaattgaaa gcaagaaagg 112080
aggaatctgg aaattcttca tgtagttcat ttatgatttc gtgcaagtaa agctgataaa 112140
ttccctcagg cagtacttca gtcgaaaaac aagaatcaaa aactgcagat attcaacata 112200
agataaaaag atgttgagaa aactacaatg cacttccaat gttcaataaa aaacacatta 112260
taaagtcaaa gctagttcct ttaccatata ctctatcatc aagttccagc aacccatctg 112320
ggggccttct atagaaaaat ctactcaaca gcgacataat actgagccaa tatatcacct 112380
aaatttacct gacatcaaag aaattcaaac ccattttcat tcctttggtg tcccaatatc 112440
aaaagggtca gagaatcagc tcgtacaaat tcaagaaaat gtgaaattca taagaagaac 112500
tcaaaattaa tctcaaattc agaataccca caaagctaaa aagggattga actatatttc 112560
aggcgaaaaa attggaactt gacaccaaat aaactacaac aagactgaaa cacacacaaa 112620
actcacatgg aaaatatttg catataaaac accaaaaaag gaaatctttg aactgaagca 112680
aaccgacaga agccgttgag gaaggattcg agatgtgagg tgaagaaccg acagtgttgc 112740
cagtaaagtt ttcacctgcg ctttccgatt ttagtatgaa ttttttttt tttctgatta 112800
cggatttgaa ctctttggag ttcaaaattt tgggaacgaa aaaaaagggg ctgatttttt 112860
attttaacat atggttgttt tcaatttttg aaattacaga accaacccaa tacttgtatg 112920
gataactttt agttagtgtt ttattttcga aaactctacg atgaaggatc gatcggaaat 112980
aatttttatt ttctactcat aattaggaat aagattataa tgtgaaatat tcaatgatga 113040
ttaatgaata gtgttatatt taattgatta ttattgactt gaataataat aaaaatataa 113100
attacaaata tatataaatt aaatacgaat gagtataata taactttctt aaaacaattg 113160
agtgcgatgg cttaatggtc aagatgaata tattgtactg gatgatcatg tctttgaatc 113220
cccatttata tcagggtcaa atacataaag agatttctaa acttgttggg tttttttctt 113280
cacgtacttt aactacgtca tttttctatt gaatcattga accatccaaa aatttattcc 113340
tttaagaaca ttgttggttt attttgatcg gctattctat tgtaaatgcc tttaattggg 113400
ttcgaattgt aatgattttg attgaaggaa tgaagacaac ccgttttagt ctcatttgtt 113460
ttttaacgtc ttcaaatgac ttaattaaaa tacaattatt ctcgaacatt tttactatca 113520
attggactaa tgatttctga aacaacatat atatcctcta tcaatccccc tcacaaatct 113580
ggtttcacat cagacaacag tgtttattta aatggaacaa attatagggg tttaatgatt 113640
caataggaaa atgacgtagt taaagtacct gaggagaaaa aacacaagtt tagagatttg 113700
cttatgtatt tgaccttaaa tcagctatcc aacatgcact tttgagcttt ctatgggtgc 113760
gctaatactt gtgtgtcaac ttttttaaag atatatatga ataaatatat ataacatgat 113820
tttttttttg aaattaacag gtatacgtgc acctcattta tacatgttag gtctgtctct 113880
aaaatcagat ctacaaagtt acatcgggta tgtttttaat attattgtgg ttgtttgtaa 113940
taaatatttt aattagagtt gttcaaaatc aaatcgaaat tgataattcg aattggaaaa 114000
aaaagttatt gatttatcag tattgggtta ttgatttagc gatttagtta agggtctgat 114060
ttttttgtt atcgggttat cagtttgaag tttttctcc cgatagtaaa ttaaataatt 114120
atatttatac cattttatgt ttgactcgaa gtttgctttc ctacttttat ttttggttat 114180
tcaatgtatc tgcttttgag taagatgtaa cttgtgaact gatgtgcata gtttatttgg 114240
tttgtcacct tgtttctaag tgatttttaa tataaatttt tgtgtcaaat cttaaccagt 114300
taaactgata accaaatcga tagcgataaa aaatcgataa gccaatatgt taatagttct 114360
ataacgattt aacatctcta cacactatca accaataagc caatcaataa actttaaaac 114420
cgaatcgaac agaccgatac gcagagctaa ttctaatgac aataatcgat tgtggaatct 114480
atattaatgc atggctgcat tgaactctaa attgaagtat cttcttttct gcttaaatta 114540
cctccaaaag gtaccaatga taccaaaatt tccaggcttg gttgatgggc caaagtgacc 114600
atgtgatcgc ctttattggg cttttagccc agttaaactt agggcccaat gacgcatatt 114660
ctatcagcaa caagaagtat tgttggtgac tagagaattt tagaatgtaa ttaaactatt 114720
tttggccaac aaaaaatata aatgatatac aatatttaat ataaaactag aaaaagttaa 114780
cattattcct caatgagtat gattcgaaat gcatagacga ggctatatac aaaaatagag 114840
gaagattgga tcgcctattt gaatctggtt tggtgttaga aattcgtaga taaatcgagt 114900
tgaaaaaaac gttgtgacac gtgttttacg tatgagagcc aaatgatatg gactttgatc 114960
aacttttcaa gatgtatttt ttcgtcatat tgatattgag aaagattgca atttatagta 115020
ttgtcctcat tgttttagaa aaccaaaaga ttttaagttt gaagtataga attaatccaa 115080
tcaaatttag ttttgaaagt caattaaagt gactctcaaa aacgcaaatc atgataaatat 115140
tttgaaataa attagggtgt ttttttatt gttctatctc atttgtttga aatatagtat 115200
ttagaaatta cgcgaacatt ctaatcgtta ttcattgagt aatatacctg attataagac 115260
gattaatatt gagattgtga gacaaaagga agaaaatata aatttatagt actaaggaca 115320
agggcggacc cacaaggtgt caagtcgggt gctcgaaaca cccattaacc gttattgaaa 115380
tatgtatatc tatgttaaaa tcgatagcta tttgtataaa attaacatag agcacccaat 115440
gaataaatca tatagttggc ccaatggttc tagaatgggt acttaagact cttttaatgt 115500
tattgtacca aggttcgaat tccgccactg actaaggatc acgatggagt catggagatc 115560
attatttgga taatataaca agcaaatgca acttaaattc aaatttcttt tattcaatta 115620
caattaatta aattatgatt aaatcatttt ataagtggag atcattattt ggataatata 115680
acaagcaaat gcaacttaaa ttcaaatttc ttttattcaa ttacaattaa ttaaattatg 115740
attaaaaaat cattttataa gtaaaaatac ttctataaaa ggaaatttta tccttaaaat 115800
tcaaatatta aacttcaaat taacaacaca tgcaacctta tacaaaacaa atcaactagg 115860
atacctcccc caataattaa attggtggtc aataaaattg tactccataa ttatgaattg 115920
tagttggcaa taataaatat gcattgtatt gtcctcatcg actagtcaat ggaacattta 115980
tgaaaccaaa aaacatgaat caatgttctc tacttgcacc aaagttttta tgaatgagaa 116040
ataatattag atttgtccgt taaggatttc aaatgtttta aatattgtac ttggggtata 116100
aatgagcttt tttttatcag taaattttta tcgtatatct gatgattata gatctccatt 116160
ctcagaaaca tcacttgaaa atagttgtta ctccatccgc tcacccaatt ataacatcga 116220
tcttaataaa aatacataaa aatcatttag ttcaaatggt ttccctcact ttatattttt 116280
atcatttttt tctattacca attaattagt tttgttataa aatcgttgat ggtcaacaat 116340
tataactcta tcttgattgt catacgattg ttaagatgga gtttcagcga ggttaaaaat 116400
taactcgttg gtataattat gcattattta aattttattt gagatgattt tatagattaa 116460
tggtaattaa tttagtcttg aggagtaaaa taaaatcgtt ataggttttt gagtgttcct 116520
aacatcagaa tggtgacatc attatgaagt tataaagaca tataatataa tttaaactag 116580
gaaaaaagat aaatatcctt ttgaattatc gtaaatagta tgtaaatgct ctctgtcaat 116640
tttttgggac actgatgctc ctgtcgttca aaaactagaa ataatatata ctctttacac 116700
taacggacac acacgtgtca taatcttatt caccaattct acatttattg acggagaaga 116760
ttgcgccatg tgtttctatt tagtcttcct ttagagttaa cggcatataa actttagttt 116820
ttttttaca gcaggaacat caatgtccca aaaatatgac aaagaatatt tccatatcat 116880
ttacgatagt ttgagatata ttttcccttt ttccatttaa actaatatgc aaaatacgat 116940
cctgctcctc tttatttctc ttctctccat tttccccaag tttccatttg gattaatgac 117000
acatgtcatg ggttaaaata aatggttaaa atttaatttt tcaaagtaaa cctctaaaca 117060
tgatttagtt aatatatata ttatatatca agtatcaaaa tttttataat ttcacaatct 117120
tagcaaacat attattttgt ccatattatt tatgtaaaaa gtttcttcc tataattttt 117180
ttttttcgta ggatcttttt tattttttat tttatacaat attttaattg taatcttttg 117240
ttaaaggtat attggtccgt gattaataaa ttacctagag ataatcaaat cattttgaca 117300
aactaatttt aatttcataa taagattaag aatacggtga taccaagaca tacgatagat 117360
taattatagt tttcatactt ctattcagtt gcttattctt ctaattagat aaaaaaaaat 117420
ttatataaag ggaaaaaaaa gatcctacgt aaaaagaaat aataggaaga aaactttttt 117480
tacctatatt tatggacaaa ataatatgtt cctaagattg tgagattata ataattttga 117540
tgcttgatat ataatatatt tattaactaa atctgtcacg acccaaacgg gtcgcgagtg 117600
gcacccacat ttactctcct atgtgagcga accaaccaat ctaatcccaa catttcaacc 117660
ataataaaca gaaaataaag cgaaagactt aaaactcatt aacgaaatca attaataact 117720
tctaaaattt aatattcatc atccccaaaa tctggaagtc atcaccacaa gaacatctat 117780
cctcaaaata ctaaatctaa gaatgtctag aaaactaaaa taataaacag ctagtctatg 117840
ccgaaacttc aaggcatcaa gacacacgaa ggaagatccg tcaagctgct aaagcgttag 117900
ctcaccccga gatccgacgt gatgaagacc ggctagagtt acggttgagt tgaagacgat 117960
gatacgtttg tgcgactcca caaataacaa agaaaacaat tacaagtagg gtcaagataa 118020
aaaacagtaa tcgaaagtag tatcattgcc aactcaaaat agaaagcaat atatttcaga 118080
taatatcata aaatcaacta atattcttaa caggtgatag caacaagtat aaaactcatt 118140
tataacaaac caaccacatc catgaggact caagcctcca taccatactc tttagggaaa 118200
caagttcttt ggattgacta tattaacata tttcaagatt cattatcttt ctatctccgg 118260
tgtcggaacg tgacaccgat cctcatcata ctatctggtg ctctaacgtg acacccgatc 118320
catattctat cctgcgtggg aacgtggcac cgatcctcat tctatctcgg tgccgaatgt 118380
ggcaccgatc ctcattctat cccagtgccg aacgtgggca ctccgatcct cattctatca 118440
cggtgcggga acgtgacacc cgatcctcta ttactatccc ggtgctcaac gtgacacccg 118500
atcctctaat ctcattactt tagttcatca agccttcttt tataccaaga catcatcatt 118560
aacaaagtaa aatttaggat ttaagattca acagcctcat catgctagtt tcatcacaat 118620
tatatatata aactcatcat gctagtttca tcacagttat atatataaac tcatcatgca 118680
tacacacaat taagcatata gaagagttta caatactacc caaaacatat cattcgctat 118740
taagagttta ctatgaaata gcataaacca taacctacct ccaccgaaga atcgcgatcg 118800
acaagctatc ttcccaaagc tgcgttcttc ctctctctct ttgttctttc tatttttctt 118860
attcaaaccc ccttttcttt taccctaatt agcatataat taagtataaa agatgataaa 118920
ataccccact acttgtttcc aaggttatct cttttaaccc ccaagtaatt gaattattaa 118980

-continued cattaaacca ctaactttat aattataagc aggaatagtc caaaacgtcc cttaaaatat 119040
ttaacagaaa tccgacccat tcggtcacgc gttttagacg gcccgtcgtg ctgcgacggt 119100
caaatctctt tgcttccgta caaagttcgg gagactcaat tcattaaaaa gtccagcggc 119160
ggcccgttat gctcggagac ggtcgccccg ccacccgtcg tgacgttcga tcgatctcgg 119220
tacccaaatt tttaaattct aagtgtttta gaacgagacc cctcgacggt ccggtcgtgc 119280
ccatgacggt ccatcgtggg atccgtcgac tcaccagctt tttccggaaa taaaaatcac 119340
gctaaaaacg actaaacagg tcgttacaaa atcatggtta aaggtttact ttgaaaaatt 119400
aaatcttaac tatttatttt aacctataac atgtgtcatt aatccaaata gaaacttgaa 119460
aaaaatgaag agaaagagaa atggagagga gccgaatccc gcaaagtaga aatatatttg 119520
acccctgcta ttaactatta aaacgttctt gtttcatttt gaacttgcaa atatctgtgg 119580
tacactacaa atttaagggt tataatatct attaataaac ctaattagta agggctaatg 119640
agactttaaa cacaataggc aaatgacagg taagccctca gattttgatt ctcctatatc 119700
acacatgacg ttgtcagagg tcaaaactgt cattatatgt ccaaaatacg tgagtatgat 119760
tttttagcag caagaaacca aaaaaaaaaa aagagataca gattttggca atttatacct 119820
ttttgaattg aaatgattac acaccttttt cacattgtca gtttattttc tttttggggt 119880
ctaaaagttt tggtttttga aaaaaaaaat atccgttgat ttaattttgg agtaatttaa 119940
gggggatgtt tggttatgaa aatataaaaa tattcatttt atttaaaaaa aattaaagtt 120000
gaagtttgaa ttgtgttggg ttatattttt tgtaaataat atgtataatt ggttatgttt 120060
ttgggtgact aaaagtattt actttagaaa agaagatatt tatgtcaaga aaataagtgt 120120
tgcttaagag tagaaaaata ttattttgac aaaaaaaatg cacttaaaaa cactttgaag 120180
aaatgcaatt aaacactaat tgtcgtgtaa gaggtcttta aaaattaatt ggtcaatgca 120240
ttatgatcac aaaagtattt tttaaaaatt aaacctttac taaaataaat taattttaga 120300
aattcgacct aacaagtcat aaaaataaaa taaactttta cttatttaat gtttgaaggc 120360
cattaacaat tgaattaata ttgctttttc aataaagatt tgattttaac caacctcaat 120420
taataccaat taaagtttaa ttttgtaaat tggattgaag ttgcacaaat gagtatattt 120480
agttatgtac taacatcttc catattaatt ctcctaaatc tttaggtaca tatttttctt 120540
ttccatattt ttaacgattt tactttctaa gttttaaact ttaacttttt taaattaatt 120600
agttcaatct tcttcttctt cttttttttt tggagggaca taatttgatc gatctattaa 120660
tcataaaaca tgtctttttt tttgtccaat attatatgaa ttttatgaaa taaatttatt 120720
ttagaacttt ttaacgtatt ttgactttaa gctttattca atccgccttc actgacaaaa 120780
attccaaata aaaataaagt gctaaagtat aatttatata ctctctctgt tttataaaga 120840
atggtctaat ttgacttgat acgatatttc tcctatttta taaagaatga tctaatttga 120900
tttgatacga aattaaatat acaaccctta catgccacgt ggaaagttat tgtcagaaaa 120960
aaaaaattat tctttttgat atggactata aaaaaaaggt cattcctttt taaaacgagc 121020
agaataatat atatcccaaa actttattat tgagaaagca tctaaaattt gatatggcaa 121080
ttgcatgaat gtggagtaaa attattctaa tacaccagat atgatgccat gcagaaatga 121140
tgtggaaact atatatagca caattcccaa tgaaatttaa tgtactgtct cataactata 121200
tagtataggc tttcctctaa ctatacataa agttacccct aaaatatagg ctagctaccc 121260
ttctagcttt cccccaaatt ctaaattaga acaaaaaaat atttctacat ctttttacag 121320
tttttagtcc ctttcactct ttggggttat ttggaggtaa attatttata gtaatttaga 121380
attttatatg tataaattat aaaaacttat atttgtggca tctttggagg taaattatta 121440
atagtaattt agaattttat gcgtatgagt tataaaaact tatatcattc atataaggta 121500
gaagatataa taattaaatt ttatataata attatctgta ttactaatat ttgtataact 121560
ttaatcaatc attctttaat gagcaatttt cacatataac aaataaaaaa aatcatattt 121620
gtatgttata acaaagtttg cttaattaag gctccataaa gaacatagaa acatataatt 121680
cgctatacat atacggttga agcaaattgt ataaaacgaa gtgtataaaa caagaaagag 121740
aaagacatca agagaatcgt ataaaaataa attgtattat tataagtgta tagaacgatt 121800
atatacaatt tgaatttgta taaaatgaga aatagagaaa gacaaaagag acttgacagg 121860
gaatatacaa ttgaatcgaa ttgtataaaa cgagaaaaga gaaattagat acaatttgaa 121920
aattgtataa aacgagaaag agagaaagac aaaagaaact ggtcagatga gtatttttat 121980
tgtataatta taagtgtata ggacgaaaat atatgtactt gtatgtgtat atacaatttt 122040
ctcacgcttt atacaaacat aaacacaatt tatacattta gcttctgttt gtataagtga 122100
gaaaggcgag ggtggtgagc gagatttggg agagtggcga gcgagatctg gaagaggaga 122160
gagaggggaa caaaaatata tgtattatac aattttctct gctttaaaca attagaaata 122220
atttttatat acttgtgttt gtataaaaaa taaggaagcg agtgagagat tagaggaaag 122280
tggcgagcga gataattggg agagaggcgc ctggcaattt ttcgcaaata tttgcgatgg 122340
agcacaatta tatcaaactc taactacatt tattttagat tattagtttg ctattatata 122400
taattttctt ttttttaatt gtttagtact tgaaagttga gtaagtgttc taacccaaaa 122460
tgagttatat ttatacactg atactcctat ttaaagttta gtaatagtac ttatgtagac 122520
cattgtataa gtttttaact ggccaacaat ctatttcata caatatattt ggacttacaa 122580
acactataga acttatcttt aagtattaaa gataattttt tatcacataa gcaggagcct 122640
ctatttgatc tatttcgctt taatataacg tgcaatatcc tatttgattt tcttatttac 122700
tttaattata gactcgagat ttgtaaaact tcttattttg aggataacta gtgtatcaat 122760
atcactttcc tatttacctt atgtgacgcg acacataact tccatttaat gtactttctt 122820
ttagtcccgc tcatccaaaa atatttaaac tctttggtcg gtctccaaat ctcttatata 122880
tcattaattc aatagcatga ctcatcaata aaatattata tcatctacac ataacataca 122940
ttgtgatact tccactcgaa tatgtcatgt taattcatcg atcatcaaag caaataaaaa 123000
caaattgaga actaattcct agtgcatccc atctcgattg gtatcaaggt ctttttcttt 123060
aacagtcctt acttagatct tgactccatt atacatgcct ttaattactc taatatatat 123120
cgtaattata tttctagact ccaaacatct tcgtaaaacc tctctcataa tcaccatata 123180
aataaaagat aactcaaact tgacctatta agagttgatt ggttgaaatt ccatgttaaa 123240
gatctgaaaa aggccttata taaaaatggt cctttgtaca gtctgttgat tctgattcca 123300
aattgtttat gcctaaaaca aacatgatct aaatatttaa ttaaaaggtc tctaattcaa 123360
tcaagatcca ttttgtagtc aaaatatata ctattttggt ggaattttgg acataagaat 123420
taatgaaaaa tagtccatta tattttttc atagttaaac aacacacttt atactacatg 123480
cctatttttt gctagtaatt tcgcctaaga attaaaatta aaagtgctaa ttaattaaga 123540
cattaagctg taaaaatatt taaatatgca aaggctaatc attaatgcaa aaacaatagg 123600
ctccccaacc gcactttcat atataaatag caagaaggaa ataataagta aaatggataa 123660
aaatatgata acgtctagat acacaaagac tatcttattt gaaaaaattg tttatataat 123720
agcaacctat tagtttaaat taaatgttat aaccatagtt tgatttaact gtaactctta 123780
ttaaattctt gttgttcaca tcccgttcac cactctcact cgtctctcca ctttatagaa 123840
acacaaatgt atacattgcg tttgtgtttg tataaagcaa aaaaaattgt atatacaaaa 123900
ataatgcata tattttcgtt cgatacactt atgattatga aaatacaatt tttccttgcc 123960
caatttcttt tgtctttcta tctttttcgt tttataaaca caaattatac aattgattct 124020
tttgtatatg tataccgaaa catattatat aattttttttt ttgtatataa gtataacgaa 124080
atatccatag caaacataaa gtttgctata aagcgtaatt aatgtaaact atagttataa 124140
cttacaaata taatttttgt atttcttata tgtgaaagtt gctctttttt ttcaagtgtg 124200
tgaataaatt aatacttaaa gtatgtaatc acttttaatt gggaaaatgc ataagtatcc 124260
caacaaccta tgtccgaaat cacagagaca cacttatact atactaaggt cctattaccc 124320
tatgaacttg ttttataaat aactttatac ccttttttcgg ccttgatgcg ggagaggcat 124380
gagtgcaatt caatcttgtg gtgtattcgt ttgtagtgag tagggcctct ttctcgttga 124440
tctgacacta tcaaccacat aacttaaaaa aattgtcagc acactttggg cccacaagag 124500
agtgtcacgt aggccgtaaa gggatagaaa gttatttata aaataagttt acatgggtaa 124560
tatgacctta gtatattatg agtgtatctc taaaatttcg gacatatgtt gaaggggtac 124620
ttaagcattt ctccctttta attatatgca ttaacctcta ttagttataa aaaaaaaact 124680
tattttgaga ttgaagcata taatgaaatg caataacaca tattattcac atttttaaaa 124740
cgttcaacat aattatatat cgtggatctt gctttcgaaa taactggaat cggcatgcta 124800
gtccgaaatt ctcgtggaag cttcattaga ggccacactc gtcggttagg atgacaacaa 124860
gatccactta tggccgagga actgggtgtt caagaagcac taagctggtt gaaggacact 124920
ttacggcaaa caacccagat agttatagag atggacaatc tttttggtta aacaagagat 124980
aaaaaaggtg caaaaactac tcttactttt atgttattat tcatgattgt aaagcattcg 125040
tgtgtgactt tacttctatt tctttgtctt tcgataaaag atgagcaaac cagtgtaccc 125100
atcagttagc tcaaattttg ggttttatga ctaatgctat aaagcggata atagatctcc 125160
atctttaatt caagatgtac tcaattttaa tttgatcaat aattaattaa aatgtttgat 125220
taaaaaaaaa aagaatgttc atcatactaa acctactttg taatgacata tataactaac 125280
tattttgatg aataatcaaa ctactcaact ttctttaaag gttttgaaga acaaaaatgt 125340
catattggct atttacactt catttagcta ataagaaatt gattttcctt tcttataatt 125400
ttttttgtgt ttttctttct cacctccatt ttttctgact tagagctcgt tttgattgat 125460
ttaaaagaat agtttttaaa tcaaacttaa ataattttaa attaaaaaat aaaaagtaga 125520
aggagatcta cttttaattt taaacttatt ttaagtcatt tataatcttg tcaatcatat 125580
aaagtcaaaa ttctgactca aaaataagtt tgattaactc ttgagtcaat tcaaacaccc 125640
tcttagtttt aattgacatc tataacctct aattttaggt atgtacaaat aaatacttaa 125700
atttatataa aaattaaaca aattaatatt tgtgatatgt gacattgcat aagacaattt 125760
tatatcaacg tgatgtccta cctatattac gccacataaa ttacatatat attgatcttt 125820
caattttata tcgtttaaat tatacatata taccctatca aaaaagtatt atgcttgttg 125880
aatagttcta acttgtaaca tccactttcc tctttccact tcaatcccaa aaacatttct 125940
tacaaatttg caaaaaacaa tgaaaaggac ttaattagca aaagagacca caaaatgaaa 126000
gggtcacatg gggtgtgtta aaactcaagc ctaaaaagac tttgttttgt ttttgaatag 126060
atatatcact caaaaaccca aaaagcaaac cagtaaaagg tgaccccaaa aagcttcccc 126120

```
acacacacac tgaagacaac tttccagtaa tggcggcaca tgaagaacaa caccaccatc 126180
atcaacaaca agaacaagag aaccccattt cctctttatc cttaaaaccc aacaataaac 126240
acttggagaa gattttctcc tcatatttgg gtctaagttt cgctgtcttt cttgggtctt 126300
taccaagaaa tgcagtttct ttggttggga gacttcagaa ccgtaacaag gagctaactt 126360
ttcagcttat tgatacagag gagcagttaa agcagctact tttcaggaga aaagaggatt 126420
caaaggcaaa tgcaagagtt gtggaaatct ttgcaagtca tagacatgcc tggcagcaag 126480
aagagaagag gttgttacag cagatcgatg agtgtgatga agaaattgct gagttaagag 126540
ggagagctga gcagtttgag acaatggaaa gtgagttgag ggctaatatt gaggacttga 126600
aaagggagat tagtgaaaga gatgaaatgt tgaactttat gagtagaagg ggttgtgaga 126660
tggagaatag tactagtgga gatggtggga gtgatggtgt tggagattgt tatgctgaaa 126720
tgggtttgag gtttgggaaa gttgggatat ctgaagggat ggatttgggg gtagggatgg 126780
aagagtgtta cttggctaat gggattccta atgctgaaca aatgagtggt gtttatggac 126840
agagtaatgg gtttaactca gaatacttga attctgcttc taagttttgg gctgaaaaag 126900
ctagtccttg gcaggtatga tccattcatt atttcttttt gggaactttt ttgttcttta 126960
tagttgttgt tatttggggt tttatagtga gtggtgtcat aatgtggtaa aaataaacgc 127020
aaaagtcctt tccaggatct tcatatgtag gaagaacttg gactaaagtt tgtcgcttta 127080
atgtttgtct tatatatggt ttttcatggt gaaacttatg aataaagttg cttcttttat 127140
ttaaccatgg gattgtactt taagtactac cacctgatat tctttctttt agtgtttatc 127200
tgtttgttca tcttgaggct gtggaatttg tttttgtatg tgatatctga tgaaacaaat 127260
gatccagagc aattgaggat gaacgaaatt aagtaataaa atgtttggct tatagggttc 127320
ttggtgaagt acaggccttt atgatctttc ttcacatacc tgaaaatttc acaggaatat 127380
ccacttctaa ttgtttctga taaagctgaa atgaaggtgt ttctccagga gtagttcagc 127440
gccaaattca aattgaattg tataatgatt acattctgag atgcttatta atgaaatatg 127500
tagtttagtg tgtactcagt gacctcctac ttgtcttgtg atttgtcttt attgttgaga 127560
ctcttgtctc tattatctaa aattttgaat ggtttgatct tcttagtggc tgctgaaagt 127620
tcaaactacc caggatatgg ttttctgttt actgaaagat aatactcacc tcaactgttc 127680
atttttaccc tatactggtg ttatggacca ctgcttgaaa accaggtcac cgttttgtac 127740
ttttcttctt tcaccgtttt cgtcctatta gaggtttgca attcttgctt caagaatggt 127800
ccccttggc tgaatacttt gcatgaaggt tggtttcctg gttatgaagg aagctcaaaa 127860
aaatgtattc gggtaactct agaaatccga aatccgttta aaacggaccg ttttgttggc 127920
atagaccact gtgcctctaa aataccaact aatgacatcc aattatatat cccctttggt 127980
ttgggaagtt caattctggt taaaatggat ccgtatatca gcaaaggatg ggctgttatc 128040
agtcaacatc tagtccatct gttatatttc tgtttaagat tcatcaacct caatggaaag 128100
atgtcctctc cctttcttgt tgcaagctgt atcttgtcct tgtctgtctc tgtatcttat 128160
tttccaatta caatgttatc tttggtaatt cgttacacat ccttgaaata aagcaaatgc 128220
ctccatgaaa cttgaactcc ccgcggcctc taatccaggc actaatcttt cccgttcaaa 128280
aggatcactg gaacattttc ctatacttgg tggatgtgtc aaagtttgga ctaggtagag 128340
atcacacatt caatttatgg ctgtgttttt tgtcttttat catttttgtc tttttatatt 128400
atatagaaaa gaagatctgg atttcttac ccttggtaca gtcacccttt tcatttattt 128460
```

ggaaccagag ggaactggag catttcacta tgttgtcttc aactttaata gaaaggctaa 128520
agaaaacaca caaccttaaa aataaaccta aattgcctaa ctattagttg atctatgcct 128580
tgtgagctgg ttaaggatta gtcatattta caatggttag agcaaaaaga gaaataaaca 128640
tctagatcac aatgcttata ttctagtttc aagcttgaat ggtaggagaa atgaggttct 128700
tttgactctt attcagcttc ttccttctat gtgagatgtc ctacctatct tagtaaaacc 128760
agcttggtat ttaggatgct attgggtctt aagaaaatgt gttttcttca tgcaggatat 128820
gcagtatgat tctggcgatt cacttcacca tttaaagcat tttgtagcaa ggtaaacatt 128880
ctgtgattag ttagacagat gcttagatgt ttgcattttg atgttgaatc aactaactag 128940
ggtgagccct tttgctttct cagacgggag gccccttgga agatagatgg tgaatcaaca 129000
ggagtctcct ccaaactaaa gttacttgag caggagctac tgaatttgga aaaaattggg 129060
aagactgatt tatctaaggt accatcatca acgcggaagc aagtgaagag ataccaagct 129120
ctagctggca agattgatga tttatgcaga agaatggtaa ttactgcatc tctgcaagct 129180
tattggttat aactttagta tatggatttc aaagcttgtt acatgcatgc ttaggtttct 129240
ctaagaatgg acaatagtct tgattacatc tgctaactca aatatttaga tgttgggtta 129300
tactcttagc ttgcacgact aggccttaca attagctttt tacctaacac aaacatacat 129360
ctgataatga tctccctccc tcttagcagc aggccagtga tccttgcgaa tcaaacctga 129420
gtcctgagtt ccggacccaa agacagaccg agtttttgct tgaagcattt cgacttcagc 129480
agcgtgcatc tgaaactgca cagaagctga tggtactaca aactgacagt ggaaaaagtt 129540
attacgggga cgaatttgaa gggcaagccc aactagccac taaacgatcc tttgactcca 129600
tccggaacaa cttaaaagaa atccaacgga atttagagat atggcttgcc agaattattg 129660
gggatctgga gggaatcctt tctcgagatg gtgcttctcg tgtaagggat tattacatat 129720
ctagatatcc ttttgttcaa tagttatgtc ttaacatgct cagtaaaatc atgattgaaa 129780
aaatgatgta taggtccttc ctgttatgtt aacaagatag ctccagctga atgaacaata 129840
tgaggttgat aagtccattt atgcacataa atctgcttca cagaagcaaa ctattaatgc 129900
taactagtac tttaaagagt gaagattttt gacagaatta ttgctggatg tcactgttcc 129960
tgatctggat gcttgtcatt tactagtttt acttggtccc ggtctttctg gattaaaaag 130020
ttgaaaggat ggtgtggccc tttgcaactg gataaatgtc atgtctacac aaatctggca 130080
aacattaaat atttgtggac caagtttaca gccccatttg atttgaaatc agattgattt 130140
taagttgata tttgttttga tttggattct taagctgtat tgattattct taagcttagc 130200
aaatgagcaa atcatatttt catgaataag atatcaaaat attctaggaa gttgaattaa 130260
caagttatat agcttcatgt tacttttttt ataaataaat atttgtaatt atatgttatt 130320
ataaactttc aaatatgttc aataaaccaa acaacagtaa tactttcttt tgataaaagt 130380
tattcgcttg gtacaaacaa tttcttccgc tagattttct tttttaaatt ttaaaattat 130440
gggtcttttc ttgtaaaaat taggtttctt tttctcacct aacctagtcg tggacatgag 130500
ttcataagtt gaataatctc taactaaaag gatagtcaag gatgtgccac cgtcgaacaa 130560
gaaggatagt taaggacact ctcaagcaaa ggccagtagc atgtactcta aatttagtca 130620
aagttccaat acaagctttt tgagcgccac tgtgactttg ataggtggaa aaataattaa 130680
aatttatctt taatatataa tactcccttc attttaccac aatacctatt aattgatgta 130740
atggcctgag gttataactt ttaaccatct ctgttctatt tatgtcaaga agtgcaatca 130800
ggttttgaac caagtagcta atcactcaat ataaagaaac caaattcaaa ctttttttagg 130860 ggtttattat agaaggttca gacatactta tagcagtaat ttttttcct agccaggaaa 130920 aggcatacac ctgctgttac actaaaatca aacaagccac ataatccaat tccaataaca 130980
atttaacaac atagatagat gagccttatg ctgaagcagc accttcttcc agcaactgtt 131040
tcaccttggt gatgtagtcg ttcatggctt catcggtgga ttttcctgtc atagatgcat 131100
gcagtgcaat tagttgtgtt tctcatacaa ccaagagaaa ggaagtcaat ctgaacactg 131160
ttgttagatc acataccttc aacagccttc catgcatccc actttgctct gtctctcatg 131220
ttgaaaatgc caggacggcc tgcccataag aaagggcgta agaacaaagt gtagctagtt 131280
tgagacagca tgtacatatg cataagacat ttcaagcatt atactcactt gtgttgacac 131340
tgccaacggt ggcttgcttg taaagtccgt aaagaataag cttgttctca ttggtggtac 131400
tctcaggcaa tgtcttagct ttctcagcat gtgcttcaaa ttcctcctga aacccaaata 131460
gttcagtaaa aaggtgtggt agctgaagtt acaaagataa atttccaggt atactttctt 131520
agtgataaaa taaggatgag aatccaactt aatagttgag atcgaaacta tttgtgaatt 131580
aagagggaac tgaacttatg gaaatctaaa atacaaattg agtgttcctt cattgggtaa 131640
atgaaaagtt tgcagttcag gatatcaaat atgtacgaat tcattgatgg actttagcac 131700
aagtgtacgc ttagcctagc ggtgaaaagg gttcattcta tttagccaac ccgagttcaa 131760
ttctcgcttt attttatttt ataacttgaa tccgcttcgt gaaaatccta ggtccgccac 131820
tggttagtga aagagtattt gcaagaatgt tagacaagaa aagcacaaca atacattcct 131880
caacattgta agagattctg ctggccaaca ttttgctttg acaatgttaa gacgcaaatt 131940
ttagacacat gtgttaatca tacaattctc caacctttc ctcttctaga aatgcttcta 132000
tttacagatc acagtgaagc accaaaaaca tcctcagata atgtattatg acctcttcag 132060
tttgtttact ggtttgccct gtttgttacc ctacgattca accattacca ctcagtagcc 132120
tacatacttg tggtaacagg aatcctttta gtgcgaggcg attggccaac caacaatttt 132180
tgtagtcact taaaaatagg tcagactaaa ttacatccac tataggttat gaacagcaga 132240
gaaatttcaa agacaggctg aacacaaagt gcacatttcc ttcaactttt ccccttcccc 132300
aataaaagaa atatggaagg gtgatgatag gtttttgacc aggaaacaaa aactagtctt 132360
ggactaggca atacaggata ggaaagagaa agaagcgggc gctatctcat attcaatttt 132420
tgctagacta tttacacaga agttggccaa tgtagcacca tataaatttg agaaagagcc 132480
atttgttcac tactaacatt ttgatggccc taactgcaca tgaactaata gtaatctgat 132540
tctaacatct cgttccctgg gtttagtcat cgacttaagc ttcaaagtat acaccatata 132600
tatagccaat aatatcaaca atctcaaaaa ctaaaagaag aagacattca taagatgaaa 132660
tcttcaaaac attgttgaaa ttatggacta cttctgggcc agagacaata tatatgcctt 132720
ttgataaggc caaaaatgac atacacaaat ccggaccaaa gtactactca tctgccatta 132780
cattcgcact acttcttatc gaattcagtg cttacattgc tataattacc ataaatcttt 132840
caacaaggcc aaaaatgtac agcataattg aattcattat aagatctatt tataagatgg 132900
tatgccgcca ctcaaccaca gtatgaactg ctaaaaaaaa aataatctta aacatcaatt 132960
acaccaacag atcagatcaa tccaatcacc gagccttcac actaaataat aaccaaacaa 133020
tcctcacgta acacagcatc cacaaaatta cagcacaagc tgcacaatcg acaaagaaaa 133080
ctaacagatc cgcaaatacc aattgcacaa acaacacaaa acccagaatt gaaaacgaac 133140
attaatcaca gaaaaatact tttcactgtc aaaaaagatt aacactcgct tcaaacaaga 133200
taaatacata ctgaaaggca aaaaaaaaac agaaatctaa aggggtttta aagaatttac 133260
cttcaacgcc attgttgtgg aaatctgatc tggttagctt gataaaaacg agagaaaact 133320
ggagatgtga ttgtgatgga gattgaagaa gaagggtggg tatatatata tagtggagta 133380
tttagcatag gaattaacgt aaaattcgat tcgattatga taatctaaac aagttgcact 133440
tggatcactt actagtcata gtggacccaa aaattgagta tagattatgg acctatacta 133500
tgtgagctcc acaac 133515

<210> SEQ ID NO 2
<211> LENGTH: 15891
<212> TYPE: DNA
<213> ORGANISM: Solanum habrochaites
<220> FEATURE:
<223> OTHER INFORMATION: >Genomic fragment 2

<400> SEQUENCE: 2
tctgtggttt gatgctttca aatcacagca atcctctgta taattatggt ttatatttta 60
ggggttttca gtttacaaag tcattttatc cttccaatca ccaaaagtat tatcttggct 120
ctagtgacta gtaacaagtt agttttgtgt tatgtggaaa tttacaacag atcaccttca 180
tactgaggag ggagatgatc attttgtcgt ggctcggccc gtctgtcttt tagccaaatg 240
ctgcgggaga gagtgggatt ataacagtaa gtattttgtg ttttaatact gcttctatca 300
gctaatgttt catagaaatg acagtgtgaa tgaaattgca aattttgtgt ggtaaatagt 360
ttcaggctcc aatctagtga tcattttttc tgggtaatca gttaacaaga tctctttaag 420
cattcaaatt tatgtatggt aggtaagtgc acatcatgtt aggaccgaaa ataagcgggt 480
gtaaatgcgg aagctagcaa agcaaacctc gaaagatcac gagtaagaag ataacgagaa 540
atataccaaa agacacaaag atttaacgtg gttcggtcaa ttgacctacg tccacaaagg 600
agatgagcaa tccactataa atatgagagt acaaaatata gagagaaaca acctcaacca 660
attcactcgg aatacatggg aggttcacac aagtgataac gtatcaagct tgtgacccac 720
aaattctccc tctaaccaaa actctcaaaa ctctttaaga ctacattgtg aatgctgatt 780
aagttagaag gaacatgtct ctatttatag agtcctaaac tttttcatac tagaaaaaag 840
attagtcaat tcaaaacctt ttcctaaaag gaaaacctat ttatggtaag aaatcagggc 900
aaataaaacc caacacatca tggtttgaac cgtactacat aagaaaagtt ctagtattta 960
aattgagaag gatagagggg aggggcctat ccttaaatct gttaaagttt tacgtactag 1020
cccaactatt tgtgcgcgtg aagaaaagat gtgacagctc cactatagat ttcagcacta 1080
ccatttagtt tgttacaaca ttttgctgaa attgagttag gatcttcttg agtcgcagag 1140
taatatcttc catgcgaatt ctctcttcag gcaaatcatt tgtacattca agagctaatt 1200
ccatgattga tttgaagcat ctatctttag aagtaaaatt ttcttcgttc agtgaaaata 1260
gattaatgtc cactacatcc accaatcggt ctggtaatga ttggcatatc catcttttca 1320
aggtgaagtc tccaacgaat agatcatcca cagggctctt tcttgtaaaa gtctccatta 1380
acaatatacc aaagctataa acatctcccg aagttgatac tttgccttca gacccatact 1440
ctacaaaaaa aataaatcac gccatcatta atgaaaataa ttaacaacat ttaaaatcct 1500
caagtgaact tgataataac atttacctgg tgccatgtag ccgatagtac ccaaagtctt 1560
ggtatgtgct attagcgtct cagatgtaag aagtttggat atcccaaaat cactcacttt 1620
tgccaccata tcttcatcca aaagtatgtt acttggtttc aaatcacaat ggacgactac 1680
aaacaaatgt cctccatgta aatactccac agcagaagcc acatcaatca tcacctttag 1740

```
tctttgagtt atatccaaaa ctttgtcagt agagtgaagc caacattcga ggttttcatt   1800
aggcatgtac tctagcacca acactttata atcgaaattt gcacaactac ttatcacctt   1860
aacaaggttt ctgtgtcgaa tgctacctaa aacttgacat tccacctcga aacttctaaa   1920
tgcaagttgc agttctgtat tgaatacctt tatcgccaca accattccat ctgctagtgt   1980
ccctttatac accaaaccaa ggctccccct tccaatcaag tttgcttcat caaagttgtt   2040
tgtcccttga gaaatatcat agtacgaaat cctcttatgt acctgaccaa atgtatcaac   2100
tagaggaagt tccgtactcc tttttcggca tttcagaaac caaatgataa aaatggttgt   2160
gactacaatt cctgaggaaa ctgatgcaag aacagaagtt aggactctgt tctttctttt   2220
tctttcaaga cttgtcactc tgcattgcat cacatggaag cgtgatgatc cacataatgc   2280
agggttaccc atgaatgatt cagctgtaaa atttacgaat ggccctccat ctggaatttc   2340
acccatgagc ccattgaacg agacattgaa atgcatgaga tgttcaagat tcctcaagga   2400
cttggggatc atgcctgata gattgttgct agatagatcc aaatattcca acgaaaccaa   2460
atcttcaaat acttcaggta tggaaccatc taacatattc tttgacaatg aaaggctaac   2520
caagctttgt agttggccaa tcgtgctagg aatctgacca gagaactgat taccatgtaa   2580
atgtaatatc cgcaaactcc ttaaattccc catttctact gcaagagacc cattcagcaa   2640
attggaggcc aaagtgagaa ttgaaatatc tttgttcctc caaaaagttg atggaatatg   2700
ggaaattagt gcattggaat ctaagtagag ttctcttaaa gatgaaagat ttccaaaaca   2760
atttggtaat tcaccagtaa gttgattttt ccccaagata atttggtaca agttttccat   2820
gttacacaag ctagttggta taattccatc taaattgttt ttctctaggc taaatctttt   2880
caacttcctc aagttcccca aatctggagg aatagatcct ataagtttat tgtctcccaa   2940
gcttaaccac tccaggttcc taaagttact gatgttaggt ggtatttttc ctgtgatacc   3000
attttgaagg gcaatgaaat attcaaggga aaaggaccag tttcctgaac ctaaagatgt   3060
tggaagactt ccattaaatt ggttacctcc tatttgaacg gttttcatat acttgcaatt   3120
agataatgaa gtcaggaaac ttaactcgcc tgtagattga tcattcgtca attggtttat   3180
ttgcaagttg atgaattgta gctgttgtag ctttccaaga ttcataggta caggtccact   3240
aaacagattg cggccaaaat caagctggat aagcatggtg gaattcacaa tggaggtagg   3300
aatcagcccg gtgaactggt tatccccaag gtaaaggcct tcaaggtttg gaagagtatg   3360
gcctatgttt gagggaagtg ttcctgaaag ctcatttgct acaaatgaaa tcttttttag   3420
tccagaaatg ttgtacaaac gccttggaac ttcacccgat aatctgtttg gaccaagata   3480
cacttctttc aaatttacaa gatgttcaaa ctcctgagga attccaccat ataaactgtt   3540
gtcacctagg tctatcatct ctagatttga caaatttcca attgatggtg gaagaattcc   3600
caccaaattg ttccgtcgta gacttaatct tcgaattgct gataggttat cgatttcact   3660
tggtatatgt cctgtaaaat atatgtcgaa ttgtgtggtt actacactga aatgtccaat   3720
actgtataac agctttatag tcactaagtt actataaata acagaaactg ttagttgtat   3780
gccttttaaa tagttcagca atcctcacaa actgttttga tgtccttttg aagatgggac   3840
taaatggatc aacatggata attaggattc atatagcaga cacaaactag aattgagcca   3900
atgtagtagt tactgttgtt gtttgaaaat gaagaacaaa gagctatacc aacatttttt   3960
gctactaccc tttgaaatgc aaatactaat ttcttataaa tgagttgaag agcaagtttt   4020
taaatatcaa agatctctag tgctacaagg tgagaagtcc agcaataaag ttaggtggat   4080
```

-continued

```
tcagttaaac cagaacatta taaatacctg ttatgttatt ccatccaaga aatagatgtt   4140
gaagttttgt caagttccac atgtctctag gcaagtttcc tgtaatagga tattacgata   4200
agttatatgt acctctcacg gcctatgatt gtttaactaa aaaattgttg caatctttgt   4260
tgtcaatatg aaccaaaagt agcagagaaa gaagttggtt ccgttttttt ttacctgtga   4320
agtggttata tgacaaggac aaatatatta gctctttgca tttgtctaaa ttgcttggta   4380
gttggccaga gagttgattt cttgctattt gtaatccctc cagccgcgga agattatggc   4440
aaatgtcatt cggcaaagtc ccagatagtg cattataaat caaattgatg accttcaaag   4500
aagagacatt gaagatagac gaaggaacag atccaaagag atcattttca gaaagatcca   4560
acaactcgag ccttctcagt aatccaagac tttctggaat ttgacctgtg agattattca   4620
ttgacaagga caagtgcttc agcctcctca aatagccgag ttcatcaggg atttcaccgt   4680
tgatgctgtt gttgccaatg tccaagaaac taagaaagga gaggttccca atatctgtcg   4740
cgattgaacc tcttagtctg agaccattga ggtctagtga tgtcactctt tgatgccttt   4800
tactgcaaga tatgcctatc caattgcaaa cgtgagtccc ctttgtccag tttttcgaca   4860
acattccatt tggatctgaa gttatatgag ctttgaaagc taaaagagca gcctcatcag   4920
ttgaaatgtt cgatgcatta gtattcgaga ggtacgttaa caaaactagc aatcctataa   4980
tcatagccac ggaaaccgtt ttgtgcaact tctcttgcag ctatttgtgg gggaaattta   5040
taagtgcctg atttttttatt tttcaagtga cattaatata tatttctata attaaaggca   5100
ataaagaatc atgtattagc actggaatat atagaatcta gagttcaatg tcaatgatca   5160
acatatatac gtaatatgtt ttgagacatt tttttttaaa ttgaatgttg ctgaacttga   5220
ctgcaattca ttgctgaagg gaaatcattg gttgtgggat tctgtagtga tagtaaaata   5280
atttacttgg atttataagc cttgtatatt cattattcaa gaatattaaa gactaaaatc   5340
atgatataat gtcatcattc gaatgtatat agcctccgct gaatagatgt ttgacaaaag   5400
aacgtgaagt gttacggtca aattagtgaa tctaacgtgt aatgttggat ttacgtgaat   5460
tcaatagctt ttattcctat cttttatata tattaagtaa tttattaaaa atctaaaatt   5520
atcgtatatt actatcttgc agtctgtgtg agaatactat tttgataatc gtcaaataat   5580
tatctataaa tttcaaatct tgaatcacac ttatttaata ggaggaaatg gtaaaaagga   5640
agtgaggttg acaagatctc aagactcttt cttaattttg atgaaatgtt gtaaaaactt   5700
gaattagtag attgcatggc atcactatac acgtgtcagt ctagtgttta gagaaattta   5760
atcaaagaat ataagttata atatatatta tccatgagaa tcttgagaaa gatttctgt   5820
atctgtctga tgaaatagaa attggagttt cccaattcta tattacttgg cttattctaa   5880
cttctagtgc agaatctgca gatggtcaat attctttgaa tatataatag caaatttgat   5940
tattagtttc atttttaaac tattgatagt tttaaaaata tttattattt aactaattaa   6000
atttaaatat atcctcgatc ttgcaatatg agagaaatac atctctaaat tctttccttt   6060
tcaacatttc tttcgttttt ctaattaaaa gcctcatact tatacaagag tttgaaacca   6120
cttgatatgt cacgtgacaa aaaagaattg tatctaagtt tggctactca tgtagagaag   6180
tatttttaaa gcggtcaata tctcaaaaga gaaacaaata aattatgtat ctacaaatta   6240
taaaaaaagg agtctacctt tattgggaaa gtcatatgca attcatgtat gctttcctaa   6300
ttggggatac aaagtcaatc ttgttaaacc cctaaactat tacaatcatt ttaagaatta   6360
tatatatatg tactatttga gtgttgacaa aagccttaaa ttatcataaa actcatatta   6420
aaatatctct tagagtaata tgacatgtca tgtgaatatt atgtttgaca aactcaattt   6480
```

caaagagttc aaagtggtta tacacgtagg ttttagaaaa attctaaact cactgttttg 6540
tgactttcat acctaaaatt gttaggtgtt tatataacca cccctgaatt ataccatgaa 6600
attattgtgc caggtggcct aatttgaaat ttaatagggc tgaattaaga tttttgaagt 6660
caattaaaga aaatattttt ttaatttatc ctgaataagc ttgctatttg aggggtttga 6720
gaaatatcgg tagggcggta catgggctaa taaaattgat taaaaatata atatgatatt 6780
aaatttaaaa ttaaagagaa tccaaactca aaacaattag gttaatattt ctatttagct 6840
atttatcttt gttatcttga aaaaaactta ataaatatta taaagataat tttatttgtg 6900
gatttgatta acaagtagta acattaacat catgtaatat tgttttgtgg atatttttcg 6960
ataatatttt ttaaattata atttataatt taatttaata attataaaaa aataaaaaaa 7020
aagtgggcca cggcaagttc tgtagctctc acgtacttat gggttggacc gacccatttt 7080
ctgacccata caaaaaatga gctagcctag cttaacccat aaaatatcaa aacatgtatg 7140
gattagccca ggatgagata tgttagccca tattgacagc tctattccca catcaacaag 7200
gtatttaata tgtcaacttg aaaagaaaag atattccaaa attaatctgc ttatactcta 7260
tcaattccat atctcactta gtgaaatttc gcagaatata tcgttgaata tattgttgtt 7320
gtcgttgtcc tctcccatca ttctaaattt aaagaacatg caatgtaaga ggtaatttag 7380
aaaacttagt tcggccgtag aagaaggatc atctgtaaat ttattcctct gcaagttgat 7440
gctctgttgg aaatttatta ctacaagata gattggttaa tttgaccgta aaacagttga 7500
cattcttttg tcaaggatct attctgggga ggttatagat atacatttga ataatgacat 7560
tgtcaagtaa attatttaac tgtcaataca gaattccaca accaatggtt tatttccctt 7620
tagcaatgaa ttgcagtcaa gttcagctag caatatacga ttaaaagttg tttcaaatca 7680
ttggtattaa ttagataagt attgactcaa ttacaagtat acacacagta tatatagaat 7740
ggcgtttgaa aacgaaaaca taggcacaaa tagcagctaa agaagttgaa caaatccaaa 7800
tggttgcgaa gactattatt atagcatgcc tagttttgtt agcatgcctc tcagttacta 7860
atgcatcaaa cattacaact gatgaggctt ctcttttagc tttcaaagct catataactt 7920
cagatcccaa tgaaatgttg tcgaaaaact ggacaaaagg aactcacatt tgcaattgga 7980
taggcatatc ttgcagtaaa aagcatcaaa gagtgacatc attagtcctc aaaggtttaa 8040
ataaatgcac caaacttgaa gttctgtcct tgtcttataa caaattcact ggtaattaac 8100
taacttgtaa acttttcatt tactaatttc ttcttgaatt aatcatcatt tttgtgtgtg 8160
tctgtcattt tataattgat aggaaattta ccaagagaca tgtggaacat gtcaaaggtt 8220
caagaactgt ttattggatg gaataacttt acaggtacgt gattcttgta tgtattaaat 8280
cttgaatact cttcacgaag ttcctaattt cactagatat agtcaatttg tgcattgtct 8340
agtaacaaac aaagattaat atatgttgtg gagaacattt tcgaaagaca ctctatgtct 8400
gatctttagc atgataacca tgtacttatt ttcaaaatga atttgcagga aatataccaa 8460
atgaaatgaa cctaccatct atttgcagga aagttaacaa agcttgagca tctcaactat 8520
ctgaaagtct cttacaatga gttatcaggt gaaataccag atggagggcc ttttggtaat 8580
tttcacagct gaatcattca tcggcaacga agagttatgt ggaccgccta gattccaagt 8640
caaggtgtgt gaaatccaga acaacgtgac aagaagaaac aggaagaaaa cagtactaaa 8700
atttgttctt ggaccagttg cagctggagg tttagtcata ggggttttag gcatgatatg 8760
gttgttgaat tatcggagac gtaacaacca acttattcct ttaactgatt ggtatgatca 8820

-continued

```
gttatcacac aaaaggtttt cttactatga acttgttcga gggactaaca actttgacga   8880
atcaaatttg attggaaagg gaagccttgg tatggtttat aaggggacat ttacaaatgg   8940
gaccatagct gctgtaaagg ttttcaatgc acaactgcaa gatgcattca agaggtttga   9000
tttggagtgt aaggttttgc gtaacactcg aaataggaat cttgttaagg tgataagtag   9060
ttgtgcaaat cttgatttta aggcattggt gtttgagtac atgcctaatg gagatcttga   9120
ttattggctt tactcacaca acaatttctt ggatttaaac aagaggctga aaattatgtt   9180
tgatgtggct tgtgtcgtag agtatctaca ccaaggccat tcacttgtag tggtccattg   9240
cgacttgaac atacttttgg atgaagacat ggttgccaga gtaagtgatt ttggtatatc   9300
caaactcttg accgcgtatg atccagtggc attgacaaag actttaggca ccattggcta   9360
cacggcagca ggtactgatc aaacttttat ttactaatta ctttcttcaa cttgtattcg   9420
atatgcatat atgatgtatt tcattttaat ggcagagtag ggatagtgtc aactatgggg   9480
gatgtttaca gctacggcat tttattgatg gaaaccttca caagaaagaa accagtagat   9540
gatgagtttg ttggagacct tacattgaag agatgggtcg cggaatcata tcctcataga   9600
gtcattgtta tgaaataaaa acgaatacac gctgaacgtc acttatgagt catttatcta   9660
atatgatcca ttaacaattg attaatgtaa cgcaaggaag aagaaaacaa tttgcattgt   9720
tatgaatgaa tgtgtttgta ctacaatata tacagtactg acaagtccag caaactttct   9780
aaccaactta ttctaaccaa ctctactcat tattaattta gctcacttaa tcaagaaatt   9840
aaacttaaca actaactacc attactcatt caactgatca cggaacatca acacattttg   9900
ttgatttctt tcacacacac cctctgcttc gaaaacccct ctttttaaca tgtaagcgac   9960
aatatctttt ttttaggaga gtgttcaaca ttgagcataa aaataataaa atagagaaca  10020
aaaaagatga gtataaaata aataataata taagatcgat tttaccgatt gtcaattttg  10080
tgtatggact aaagaaataa cagcttcaca tatctaatat taaatgtaat actgaatttc  10140
acatatggtc agaggtgaat ccacctgcac ccgatatatt ctttttaaa aaaattatat  10200
gtatatatat agattgttga taagacggta atatatttaa ttgtgcactc ttataacgaa  10260
caaatgattt gacttgtcca ttggaaaaac gaaaagtgtc acataaattg agacatgggg  10320
agtaacattt ctttcttaaa tttttcgtgt gaagtcaaac taattcatat aaaatgagac  10380
ggaaggagta ctgtttaata ttaattgcat atggtagtaa atttgataga catggtcccg  10440
tgggagtgtg tgttatttcc attgaataat tgagtttgta attgttacaa gtccattcta  10500
atttccaaca ccttacttca tttcaaaaat atactctatg gctgaagctt tccttcaaat  10560
tatgttagag aatctgactt gtttcatcca agggaacttg gattgattct tggttttaag  10620
gatgagttca aaaagcttca aagcacgttt actacaatcc aagctgtggt acaagatgct  10680
cagttgaagc aattgaagga caaggcaatt gaaaattggt tgcagaaact caatggtgct  10740
gcatatgaag ctgatgacat cttggacgaa tgtaaaactg aggcaccaat tatacagaag  10800
aagaataaat atgggtgtta tcatccaaac gttatcactt tccgtcacaa gattgggaaa  10860
cggatgaaaa agattatgga gaaactagat gcaattgcag cggaacgaat taagtttcat  10920
ttggatgaaa ggactataga gagacaagtt gctatacgcc aaacaggtaa atatttttct  10980
aaataacagc tttatatcat caaattcatg tgtgttttgg ggattttgtc taagtagata  11040
agtggttcaa aatctattat ctaaatctgt ttggtgaagt ctttaacata tatataaatc  11100
catagcttac tcatatgccc caaagtctaa atgacaggat aaagccagag ttgttttaga  11160
ttttataaat taacaaagat aataatgtaa attcaaaata gtgcatttgt tttatatttg  11220
```

-continued

```
aaatatgtct gctgcttctg atcaagctga tcattgtctt ttgcaaaatt cttctttgtt  11280
ttttttgctg actcttaccg atcttggacc aggttttgtt ttaaatgaac cacaagttta  11340
tggaagagac aaagataagg atgagatagt gaaaatcctg ataaacaatg cccaaacact  11400
ttcagtcctc ccaatacttg gtatgggggg actaggaaag acgacccttg cccaaatggt  11460
cttcaatgat cagagagtaa ttgagcattt ccatcccaaa atatggattt gtgtctcgga  11520
agatttaatg aaaagaggtt gataaaggaa attgtagaat ctattgaaga aaagtcactt  11580
ggtgacatgg acttggctcc acttcaaaag aagcttcggg acttgttgaa tggaaaaaga  11640
tacttgcttg tcttggatga tgtttggaat gaagatcaag ataagtgggc taagttaaga  11700
caagtcttga aggttggagc aagtggtgct tctgttctaa ccactactcg tcttgaaaag  11760
gttggatcaa ttatggcaac attgcaacca tatgaattgt caaacttttc tcaagaagat  11820
tgttggttgt tgttcatgca acgtgcattt gggcactaag aagaaataaa tcttaatctt  11880
gtggctatcg gaaaggtgat tgtgagaaaa tgtggtggtg tgcctctagc agctaaaact  11940
cttggaggta ttttgcgctt caagagagaa gaaagacagt gggaacatgt gagagatagt  12000
gagatttgga aattgcctca agaagaaagt tctattctgc ctgccctgag acttagttac  12060
catcaccttc cacttgattt gagacaatgc ttttcatatt gtgcagtatt cccaaaggat  12120
accaaaatgg aaaaggaaaa tctaatctct ctgtggatgg cacatggttt tcttttatca  12180
aaaggaaact tggagctaga ggatgtaggt aatgaagtat ggaatgaatt atacttgagg  12240
tctttttcc aagagattga agttaaatat gatcgaactt atttcaagat gcatgatctc  12300
attcatgatt tggcaacatc tctattttca gcaagcacat caagcagcaa tatccgagaa  12360
ataaatgtag aaggttacct acatatgatg tcgattggtt tcgcaaaagt ggtgtcttct  12420
tactctcctc ctcacttgca aaagtttgtc tcattgaggg ttcttaatct aagttccatg  12480
ggacttaagc agttaccgtc ctccattgga gatctagtac atttaagata cttgaacctc  12540
tctctcaata acatgcgtac tcttccaaag cagttatgca agcttcaaaa tctgcagact  12600
cttaatgtag agtattgctg gtcactttgt tgtttgccaa aagaaacaag taaacttggt  12660
agtctccgaa atctcttact tgatggttgc gatggattgg attctatgcc accaaggata  12720
ggatctttga catgccttaa gactctaagt ttctttgtta ttggcgagag aaaagattct  12780
ctacttggtg aattacgaaa cctgaatttg tatgggtcag ttgaaatcac gcatcttgag  12840
agagtgaaga atgataggga tgcaaaagaa gccaatttat ctgcaaaaga aaatctgcat  12900
tctttaagca tgagatggaa aaaaccacat agatatgaat cagaagaagt tgaagtgctt  12960
gaatccctca aaccacaccc taatttgact tctttactaa tcactggctt cagaggattc  13020
cgtcttccaa agtggatgaa tcactcagtt ttgaaaaatg ttgtctctat tgcaattaga  13080
ggttgtgaaa actgctcatg cttaccaccg tttggtgatc tgccttgtct tgaaagtcta  13140
gagttaggag atgggtctgc ggaactgaag tatgttgaag attctggatt ccctacaaga  13200
agaaggtttc catctctgag aaaacttatt atagtcaatt ttgataatct gaaaggattg  13260
ttgaaagagg caggagaaga gcaattcccc gtgcttgaag agatgacaat tagctggtgt  13320
cctgtgcttg ttattccgac cctttcttct gtcaagaaat tggtagttta tcggaacatg  13380
tcagatgcaa taggtttgag gtccatatat aatcttaggg ctcttacttc cctcaacatt  13440
agccataact tgacagctac ttcgctccca gaagagatgt tcaaaagcct tgcaaatctc  13500
aaatacttgg aaatctcttt catcttcaat ctcaaagagc tgccaaacag cctggctagt  13560
```

```
ctcaatgctt tgaagcatct gaaaattgaa tattgtgacg cactcgagag tctccccgag  13620
gaaggggtga aaggtttaac ttcactcaca gaattatcca taacaaattg taagaggcta  13680
aaatgtttac cggagggatt gcagcaccta acaaatttat cagttaggga atgtccaaca  13740
ctggccaagc ggtgtgagaa gggaatagga caagactggt acaaaattgc tcacattcct  13800
catctgctta ttactaatga gatgtaattt tctgattttt cttttggaaa caaatcaact  13860
atttgtaacc aattcgtatt ggacttttga gccctgcatt tgttcgaata cgcctttcaa  13920
cctgtatatc agtgtataac aaatgtatac aatatgtata ctgctgctca aatctgcaga  13980
tttgattttc cagcaacaca tttgctgatt cttccgacct gtaaattaat ttccagcagc  14040
tcattttttt gtgttcaacc tgtacgccag ttgtgagggt ctaagacttg aggaggaggt  14100
ttgagccttt acggctcagc gaggaagtgc agggatacgg gcgaaatccg ttaggactca  14160
tggcgaatgc acgtgaaacg gatcaaaagg aaacataaag aaaaacagtc aacgatgaaa  14220
acaattctgc atttatacgc ataactaagg caatgtaaat caaattgaag aatgggcagc  14280
caagataaat gaaagcaaat aaagccacaa tgcatgtttt aaaatactat aaccctgcca  14340
tgctgcatag acacacattt atattcaaga ttcaagtcat aacaaaatat aatttgaaag  14400
tttaaagctc tggatatcag cttactacag ttcaatcttc ttacttaaaa aagatgctaa  14460
aaaaaaacaa aattcaactc ttccaggcaa ctaacaatat caaacctaca aactaacata  14520
tgagcaaaaa aaaatcattg aaataaaggc atacaaatac taaaatgaca accactagtt  14580
catgaaaaac aaaatggagc aggcaataaa taataaacaa gataatagat aaatatgtct  14640
tttaatttta ttttatttta tatttgtatc cttcaaattt gaatgtacac ataatttgat  14700
attttaactt gtatataatt gaacaagtac atagttaagt catatgtagc ataaatatat  14760
atatatatat atatatatat gaaacaccac ctatgacaca atttccatga agcatgtaca  14820
cttttatttg ttcatttcaa tactgagttt aagtatttta ctttgtttca tattatagtt  14880
gaacaccata aatataaaat aatatcaaat ttaaaaaata tatttatgta ttatgcttta  14940
aaaaatattt tttaaaaatc tagtaattgc cccaccataa aagagatgcc cattatacgc  15000
cgaaagaatg tttaaaatca aaagcaactg ttagttattg gattgaaaaa taaaaccaaa  15060
tactccaatt gagagacatg gcggccccat ggtggaataa ttattacaac acaccttcca  15120
taattaaagt ttgaccttac acctagagac aatcaaattt tggatttggg tcttatttta  15180
ctagttaaca tttcagataa tcacttaatt ttaaataatt tatttcgata gtcattcaac  15240
tttgaattat tctgttagaa agtcattcaa ttctatttta aagtcaaaag tcactaatat  15300
ttgagttgtt ggtttaaaag gtcattcaac tctctttata attcaaaagt aacataatta  15360
ttttttgttt cacttaaaag acatccgatc aacttaaata ttttttcata aaatcttatt  15420
tttatgttaa actattcttt ttaaaaataa taagatattt attttagaaa aagggaaaat  15480
atgttaaaaa gttagttatt ccaaaaaaga agaaagaagt tggaattgaa aagaaataat  15540
ataaaaaccg cagcacagtg cctttttttct tattactttt tatttaaaag atagttataa  15600
agaaatatta tacttcaaca aaatttaata aaataattaa aagcagctta taattttatt  15660
ttatttttgt attcagtcaa atttaataaa aaatttcatt ttaaaataat tgtctgactt  15720
tctaagtaaa attagttgag taatttttag gttataaaac aaaattgagt gactttcgaa  15780
gttaactcaa atctgagtga ctttctaagt gaattattcg aagttgagtg aatattaact  15840
ccttatacaa gttcgaggaa gatattgaaa aagattgtac atatggggtt c           15891
```

<210> SEQ ID NO 3
<211> LENGTH: 85327
<212> TYPE: DNA
<213> ORGANISM: Solanum habrochaites
<220> FEATURE:
<223> OTHER INFORMATION: >genomic fragment 3

<400> SEQUENCE: 3

```
gtaagctcct tcatgtcagc ttataaaagg cttcacacaa gtatatatag cgggtaaaat     60
tttattttgt gagaggtaga aatgttactc ggcagacaat acttgtatga catgcttaaa    120
gcttcatttt tttctctttc acctatttct atcttcttct tctctctttt tttctccgtg    180
cttcataaaa ttttatttta tttttcatca aaaacttgat acttaatata ttttattgaa    240
tgaaaattga tttaataatt ttatttttca aatgttaaaa tcaagacaaa tcaattaagt    300
tgattttttt cattacttta ttttttttcc ttgcgatttg ttttttgtgg acttctcgaa    360
aatatataat aatataaaat tatcctctga aaaaattatg cattacgaag aatttaatca    420
ttactaagaa atttgataaa aaattcccaa tgattttact atattcttac aaaaattaaa    480
gatttaaggc tgatatatta aagatgtctt gttaatattt tatttaaata aaataatcaa    540
ttaaattacg agttattttg aacatgaaaa aacactttca attttatcta aataaaaata    600
taaattaaat tacaaagtaa aaagaataat tattataaag agaaacacat gagtactcac    660
aaagagaaca aaaaaaatat ttataataat ttttttagct tcagagaagg ttatacgtat    720
aatcaaaatt attacggatc atttattaat aaaataataa aataaaaatt ctcctaaaaa    780
attaatgtat gatcttttta taagcaaaca caaaaattat ttaattacac tatattaaat    840
ttctttaatc tcactaaaaa actatttttt ctcgtttcat ttactttaag ttttccttaa    900
ataaataata taaaaataaa atagttaaac attgtggcta atttttttta aaaaaaacac    960
aaaagactac aaaggagaac aagagaatga gaaacaaaag tttacgggaa aagagtctga   1020
tataccccctt aactttgtca tttggagcta atatatccct cgttataaaa gtggctcata   1080
tatgccctta ccgttataca aacggctcat atataccccct gtcgttataa aatgactcac   1140
atataccctt aatttgtgga agttaaaaat tagttttaaa tttatattta atacttctaa   1200
tttttaaaaa aaattattta gaggtatata tgattcttct atcaaagttc aaggtatatt   1260
ttaatttttt tttcatacat aaactatttt tgacttcttt tattataatt atttgagttt   1320
cttattctta ttttattttt ttttctttca ttccttagtt taaagagaga gaaaaattaa   1380
actatttttt ttgtatgtat tgtaatttaa tttcgtattc aaagaaaaaa atttagtcat   1440
ctacaataag ttttacaaga atattagtga aaaaataaat aaatttgatt atcaaaataa   1500
taattataaa ttagtcattg aaaaaaaaag tcaaaaaaaa atgtttttga gaattaaatt   1560
tattcatatg agattatatt ttatagaaaa aataataaaa atttagatta aaattatatt   1620
ttttcatttc cgttagatta aagggatatc tcgagccatt tgtttacaag tagggtatat   1680
atatgctact ttcatgttag gtatatcagc tctaaataac aaaattgatg ggtatatcag   1740
acccttttct caagtttaaa ttaatgtgaa aaagttttaa gtgtgggtcc catgttgtac   1800
atttaaaatt ctcatacaac agacaaaagg ttagcttttc acaaaataaa atttttccca   1860
tgtgaaactc aaaataaaat aattgcgtac agacatattt atgcaacaca acattaattt   1920
atttatttac ccattcaata agtaaaggaa taattataaa gctttgtgct cttactttta   1980
gctgttcata tttcattcca acatcgatct tatagattta ttgctaattc acaacaattc   2040
cagcaatcta catggctgaa gctttccttc aaattttgtt gaaaaatttg acttctttca   2100
```

-continued

```
tacaagagga acttggattg tttttttggtt ttaagaacga gtttgaaaat cttaaaagca   2160
cgtttactac gatccaagct gtgcttgaag atgctcagga gaagcaactg aaggacaagc   2220
cactagaaaa ttggttgcag aaactcaata ttgctgcata tgaagttgat gacatcttgg   2280
atgaatgtca aactgaggca gcaagactca aagagactaa atatgggagt tatcatccaa   2340
aggctatcgc tttccgttac aagattggga aaaggatgaa agagataatg gagagactag   2400
atgcaattgc tgcagaacga agcaagtttc atttggaaaa aaggactaca gagagagaag   2460
ctgctagacg agaaacaggt gctcatcttt aattagttta tattcatttt tttgcgatta   2520
tcaagttcat gtgtgtttat ggacccaagg gactttttc taatctaatg tttgtctcaa   2580
gtctaaacag atttgtaatt ctaccactta tttatttagt gaagttctta aacatatata   2640
catggtgtaa gccagctcag ataaatccat agtcagttgt ttcggactga acttaacttg   2700
gatgtcaatt tttcaaagtc aatcatgttt tcaactcctc cccctgattc tcatctcttt   2760
gtagtgcaaa aatcttctct ctgtttttcg ctaaacatat tctcgtgtga acatatattg   2820
cttgaaacag gttttgtttt aactgaacca gaaccttatg gaagagacaa agaagaagat   2880
gagatagtga aaatcctgat aaacaatgcc caacaacttt cggtcctccc aatacttggt   2940
atggggggc taggaaaatc gactcttgcc cagatggtct tcaatgatca gagagtaact   3000
gaccatttcc atcccaaaat atggatttgt gtctcagaag attttgatga gaagaagttg   3060
ataaaggcaa ttgttgaatc tatcgaagga aacccacttg gtgaccacat ggatttggct   3120
ccacttcaaa agaagcttca ggacatgttg aatggaaaga gatactttct cgttttggat   3180
gatgtttgga atgaaaatca agaaaagtgg gataagataa aagcagtctt agaggttgga   3240
gcacgaggtg cttctgttct aaccaccact cgtcttaaaa ggttggatca attatgggaa   3300
ctttgcaacc atatgaattg tcaaatctgt ctcaagaaga ttgttggttg ttgttcatga   3360
aacgtgcatt tgagaaccaa gaaaaaaata aatcctaacc ttgtggctat cggaaaggag   3420
attgtcaaaa aaagtggtgg tgtgcctcta gccgccaaga ctcttggagg tcttttgcgc   3480
ttcgtggatc aagaaagaga atgggaacat gtgagagata atgagatttg gaatctgcct   3540
caagatgaaa gttctattct gcctgccctg agacttagtt atcatcatct tccagttgat   3600
ttgacacaaa gttttgcata ttgtgcagta ttcccaaagg acacggtaat ggaaaaagga   3660
aatctaatct ctctctggat ggcacacggt tttcttttat cgaaaggaaa cttggagcta   3720
gaggatgtag gtaatcaagt atggaatgaa ttatatttaa ggtctttttt ccaagagatt   3780
gaagttaaag atggtaaaac ttatttcaag atgcatgatc tcatccatga tttggcaaca   3840
tctctatttt cggcaagagc atcaagcaac aatatccgtg aaataaatgt aaaacggaac   3900
ccacatatga tgtcgattgg ttttgcaaaa gtggtgtctt cttactctcc ttctcacttg   3960
caaaagtttg tgtcgttgag ggtgcttaat ctaagtgaat taagacttaa gcatttaccg   4020
tcttccattg gagatctagt acatttaaga tacttgaacc tctaccgcaa taacatgcgt   4080
agtcttccaa agcagttatg caagcttcaa aatctacaga ctcttgatct acagtattgc   4140
gccttacttt cgtgtttgcc aaatcaaaca agtcaactta gcagtgtcag aaatctttta   4200
cttcatggtt gctataaatt gaattctatg ccaccaagga taggatcttt gacatgcctt   4260
aacactcttg gttgctttgc tgtgggaagg aagaaaagtt gtcaacttgg tgaattacga   4320
aacttgaatc tctatggctc aattcaaatc acacatcttg agagactgaa gaatgatagg   4380
gatgtaaaag aagccaattt atctgcaaaa gaaaatctgc attctttaag catgacttgg   4440
aaaggaccac atagatatga attagaagaa gttgaagtgc ttgaagccct caaaccacac   4500
```

tccaatgtga cttgcttaac aatccatggc ttcagaggaa tccgtttccc agagtggatg 4560
aatcactcag ttttgaaaaa tgttgtctct attgatatcc ggggttgcga aaactgctcg 4620
tgcttaccac cctttggtga gctgccttgt ctaaaaagtc ttaagttaca ggacgggtct 4680
gcggaaatgg agcatgttga ttctggattc cctacaagaa ggaggtttcc atctctgaga 4740
aatcttatta tagtcaattt tgataatctg aaaggattgc tgaaagaggc aggagaagag 4800
caattccccg tgcttgaaga gatggatatt tggtggttcc ctgtgtttgt tattccgacc 4860
ctttcttctg tcaagaaatt gttagttcat tggaacatgt cagatgcaat aggtttgagt 4920
tccatatcaa atctcagggc tcttacttca ctccacatta gaactaactt catagctact 4980
tcgctcccag aagagatgtt caaaagcctt gcaaatctca aatacttgaa aatctctttc 5040
ttctacaatc tcaaagagct gccaaacagc ctggctagtc tcaatgcttt gaagcatctg 5100
gagatgaatt gttgtcccaa actggagagt ctccccgagg aaggggtgaa aggtttaact 5160
tcactcacac agttatccat tacatactgt gagatgctaa aatgtttacc agagggattg 5220
cagcaactca caaatttatc aattaagaat tgtccaacac tggccaagag gtgtgagaag 5280
ggaataggac aagactggta caaaattgct cacattcctc atctgcttat tactaatgag 5340
atgtaatttt ctgattttct tttggaaaca aatcaactat ttgtaaaatc tatttgtatt 5400
atacttgatt tttcttggtt atgtaacaat aaatatttga aaattttcat ataaaaatag 5460
ttacatttct atatgtataa ttcgccagaa taatacatat atatgtataa tatacaatta 5520
tttaaccgat atacatatat aattcacctc tctcccactc tctgtcctct ctcactcgcc 5580
tctctcctcc ctctctcaat ttcgctttcc atatatacaa atacaattat ctaaaagata 5640
tatatatata tatgcaattc atctctctcc cactctttgc ttcacttgac aactatgaca 5700
tttaacattg gacaagcaca aattgacact taaaaactgg ttacagaaac tcaacgctgc 5760
tgcgtataaa gttgatgact tattgaatga atgagaatac gaggcagcaa gactaaagca 5820
gtctcgacta ggacggtatc atccaaaggc tatcaataca aactcagttg tttagaccac 5880
gaaaagactg tgaattcaat acaggagtag ttaacgatta ctctaattct atgtcacaga 5940
aagtaatttc ataagcgaga aaatcctcta gcatttttcc atttctcttt atggcgtgca 6000
aatatcgtta tctattttct gctgtctcct agctaattat cttgaatgta cgtaacactc 6060
tctatttatt tccaagagat tgaactaaaa tctggtaaaa cttatgatct ctgttttcag 6120
caaacacatc aagcagcaat atctgcgaaa ttaaacacat atgatgatgt cttcttactc 6180
accgagttat tagttatgct aaaatgttta cccgagggat tgcagcacct aacaaatctc 6240
acaatttttt tttattagtg aaagcatagt tatcaaaata aaaacaaaaa atgagcaata 6300
tttatacaac agacaaaaaa aagaatgatt tttcatattc tttgcttatg ttaccgattc 6360
ataacccata taaaaacaaa tttcaatcac ccattaaacc aaaaatgatt aaacaaaaaa 6420
aatcttctag atatctaact aatgaataat aacatattca gtgtagtccc acaagtggaa 6480
tctgggttaa ctatccaact aatcatagat caaaattgca gtgaaaggta ttttattaga 6540
ccacttccaa tctcaactat ttcaacacaa aacttatatt caatctttga tggataatag 6600
accatctatt tttaattccc ttttctcacc aacaaattga aatgtcagtg atgtttctga 6660
gcaacaaaaa gtactttaag atgatattct aaatgtgcac aatttcatgc tccaacaatc 6720
gaccaattag attaaaaaat atactcattg agtatttctt ctgtcacatg gtcaatacca 6780
tagaaaatga aaaatataat cacaatttaa caacataact attgagatgg aatatgtttc 6840

-continued

```
atctagttaa aaaaaattta cttgagaatg ttgtttgtga gcattacact aatagacgtc   6900
agatgatttt cggatggtgg tcaaatgaca cttgttactg gttcaagcag agtaatggga   6960
tgtgaaattg cccttcaatc gtagaaaatg gaatatataa agcaaagtta cacaatttaa   7020
tcgtactctt gaaacttatc tctctataat ccatgtttgc tataaacaat aatattgtct   7080
tacacatatt caacaattac atatcctatt taaactaata tacgaaatat attcaataaa   7140
aagtgcatgc agacgatttt tctacaataa agactccagg tttagagtgt ttagcgactc   7200
ctgataaaga caatgagatt atagtaaaca ggagaaacag agcagctctt cataaataaa   7260
gaggaggaaa aaatctaccg attgatgcac gtaaaagagt aaatgtgaga ctaatgacaa   7320
taacctgttg ttggagagat ttatatagat gagtatttga aaagtttacg atcaaatgaa   7380
cttgagcgtc agaaaagttg tcgcttgagc agtaactgtt atagtgatca atgaggcatt   7440
ttttggagaa ttaaattagg tctcaaacta tgagcaaatt taatttataa taaattaata   7500
cttattaaaa ctgtagggtt aaaacggtaa atcaagttta tgattaaact cttcccactt   7560
ataataatat aagattaaaa ataatcataa aatagaatgg tgcattggta tcaaacaaga   7620
aatatgtgaa actaattaag agaatatagt ctctaagggt atgaatatat cgatgaatgc   7680
ttgattgaaa aataataata aatgtatata agtctttaat gaaataacaa aggcacgaga   7740
taaatttatt agaaatataa atctacatat tctaggtatt acaaaaaaga tcctaaaata   7800
tgtagcaaac aaatgactta ttcttctata aagcacgtaa ccatcgaagt ttaatgttaa   7860
tacgataaga ttgccttgag aatgcattta cttgtgataa gtccacgggt ctacgtataa   7920
gtatagttta ttgtattctt ataaaataat agtaaaaata atagtctctt tttatttcaa   7980
atttaatttt taataaacag aaaataaatt aataaaataa gacaaaaaac aataataata   8040
ttatagacat gtttatgatg agtacgtata atttgaaggg gaaaactaca aattcaaact   8100
caagagaaaa taataaaggt ttggaataaa atatctaaga tacggaaaga ttaaaatgtg   8160
ttctctaact aaaatcttca tcttcatgaa taattaacat gaaaatagag gatccaccaa   8220
aaattaaata ggagaaggaa agagacttat tagaaaaatg atgaattata aaatctaaaa   8280
gcctatatgt gaaaataaga gaacaagaat attgcataaa aaaaaattat agctacgaaa   8340
aatactatgt gtgattttaa agataaaatc tattttattg ttacatgtat catatttatt   8400
gttgaaattt caccttttaa aaaatgaaaa acaagctaag aaaaaaaaag taaaaagagg   8460
aaaatgaaca aataaaagat taatagagaa aagggaaaaa taccaatgaa tatcctgatt   8520
gaaactgcat tatataaatc ttcggatcaa tccatttacc ttgaatttca agaacactgc   8580
aaattcgatc ataaattaat ctaaaaagag gcatgtttat gataaaaggg gggaaaacag   8640
tgttagaaga aaacaataaa gaaatagtgt tagaagtttg aaatcttcat gtttcaaaaa   8700
agaacaaatt aatcttcaat gtcaagtaaa atctcaagat ctctagtaaa gaaaatttat   8760
ttttatacta caaacaaatt aatggcattt taaacatata aagaaatatg aggatcaaca   8820
tattatagat taactacaag ttttcatgtc cttaaaagat aacttatcaa ccacaaacaa   8880
aagtaaattg aagggcaaga gatgaagaag tcttcagttt gttaacttaa ttggtgtttc   8940
tatcttccat gtcttttgaa atgtgtatga agatgaaatg tttcaagtac ttgaagatga   9000
aatatagttt cttacttgga tgcttaacaa tgttattact tcaaaaagaa cctgaaaaaa   9060
atcattattc acttggttgc ttaactattc tattacttca aaagatttat tactttcaat   9120
tggcttttca cttaccctat tcatggtgat taatatgtaa gtttcatgca atgtcttttc   9180
aattatccta attattgtaa ttgaaatgtg aatttatttt tcagataatt aaaatattat   9240
```

gtttttttc atataataat gttcaagaat aaattggtaa ttcaacttta agctaaaggg 9300
cttcccactt ataataatat gatatgatat gatgattatt agatgtaatt ttctgatttt 9360
tcttttggaa acaaatcaac tatttgtaac atctatttgt attatacttg atttttcttg 9420
ggtctgtaaa aataaatatt tgaatttttt catattaaga ttcataatta gtcttatagc 9480
ttaactgtaa gaaagaaatt acaaattaaa tttgacaaat aattaagcta cttaaataac 9540
ttaattgttc aatataaaat tttaaggatt gcctaaactt agaaaaaaaa aacaattaaa 9600
tttagttata tggttgcaat gtgtaatcaa atagtaataa atatgtggct gtttgtacag 9660
ctacaatatg acatgagata attaaaatat atgtgtcttt aagctctcct ctttttgttt 9720
gttttgagga aaatctgttg tattttgatg tgtataattg gttaattata cactctttta 9780
gaaacaaata gtgttgaatc tacaataaca tgtgaataca tagatttgat aaaatataaa 9840
atcgtaaata gattagacca tctttttat tgacagaggt gaaagacaaa gcaaccccac 9900
aagaaaagat aggtatgaaa ctagctagca gttttatgaa caattaatat aaaatataaa 9960
acacttttta ttttactcaa caattaattt ataagctatt tttattttaa aacacttaaa 10020
ataagttaat tcgaacatgt actataaatc aaaacaaata aggaaaaaaa ggaaaagcta 10080
aaggtgtgtt tggtatgaag gaaaatgttt tcctaaaaaa taaatagatt ttggatttat 10140
tttctcatgt ttgattggta agtagaaaat attttcctgt gtttgattta tgaatgaaat 10200
taatttttgg ggggtggggg tgggtggggg ctggtagggg tggatagggg gctggccggg 10260
tggaggaggg taggagttta aaaataaaaa tttgaagttg aaaatatttt aaaaagcaaa 10320
attaatttt ggggagggtg aggtttaggg gctggtcggt ggtgggtgga cgggggtcaa 10380
ggatcgagtg aaaaaataaa ttttaaaatt gaaaatattt ttattaatat tgatattttc 10440
ctaaattttt gaagggaagt cattttcctt aatttttagg aaaatgagtt gatttgaaaa 10500
atattttcta aaacttttat tccaaccaaa catgaaaaaa ttgaaaaata ttttccagaa 10560
aatgttttc ttcataccaa acacactcaa aaagagactc ttttaatcaa gtattattgc 10620
taaaaaaaaa agagacaaag aataataatt taccccataa atttcgcaaa tcaatctata 10680
aaagattgag ggtgagatat tgataagata aaacaatcaa aataatagat aaatatgtct 10740
tttagtttaa tttaatttta tatttatatt ccttaattta gaatggacac ataatttgat 10800
atcttaactt gtatataatt aaacaagtat gtatatatat atatatatat atatatatat 10860
atatatatat atatatatat atatatatat ataacaccac ctatgacaca atttccatga 10920
aggatgtgca cgtttatttt attgattcta tacaagttta agtatacgct tattcatact 10980
atagttgaat aatataaata taaaataata tcaaatttaa aagatatatt tatatattat 11040
cttaaacaaa tatgttttaa aaaaaaataa aatctagtaa ctaccccacc ataaaagtga 11100
tgcccttata cgccgaaaga acgtttaaaa tcaaaagcaa ctgttagtgt tattggattg 11160
aaaaataaaa ccgaatactc caattaagag acatggcggc cccatggtgg aataattatt 11220
acaacacacc ttccataatt aaagtttgac cttataccta atgacaatca aattttgagt 11280
tcggatccta tttcatgagt taatatctca tataatcact taattttaaa taattcattt 11340
agtatgttat tcaagtttaa attgttcact taaaaagtca ttcaactcta ttttataagt 11400
aaaaaatcac taatatttga gttgttcatt tagaaagtca ttcaactctc tttataattc 11460
aaaagtaact caattatttt tgtttcactt aaaaagtcac ccgatcccaa cttaaatatt 11520
ttttttcat aaaatcttat ttttatgtta aactattctt ttaaaaaaaa aataagatat 11580
ttattttaga aaaggggaaa acatgttaaa aagttagtta ttccaaaaaa gaagaaagaa 11640
gttggaattg aaaagaaata atataaaaaa aaaacgcagg acagtgcctt tttttcttat 11700
tactttttat ttaaaagata ggtataaaga aatattatac ttcaacaaaa tataataaat 11760
aattaaaata agcagcttat aattttattt tatttttgta ttcagccaaa tttaattaaa 11820
aaatcattta aaaataattg aatgacttct taagtaaaat tagttgagta atttttaagt 11880
tataaaataa aattgagtga ctttcaaagt gaactcaaag ctgagtaact ttctaagtga 11940
actattcgaa attgagtgaa catctgagat attaacacct tattttatac gtgaaacaat 12000
ttaaactata ttacaaaagt tggaggaaga tattgaagaa agattgtaca tatgttcgta 12060
agctccttta tgtcagctta taaaaggctt aacacaagta tatatagcgg gtaaaatttt 12120
attttgtgag aggtacaaat gttacttagc agacaatatt tgtatgacat tctctcagct 12180
tttgccaagt ggagtttggg tctcacttac agaaaatgtg cttaaagctt catttttttc 12240
tctttcacct atttctatct tcttcttctc tctttttttc tccgttcttc ataaatttta 12300
ttttattttc tgtcaacaaa catcgatact taatatattt tattgaatga aaattgattt 12360
aataattttt atttttcaaa tgttaaaatc aagacaaatc aattaagtcg atttttcatt 12420
actttttttt tccttgcgat ttgtttttttg tggacttctc gaaaatatat aataatataa 12480
aattatcctc tgaaaaaatt atgcattacg aagaatttaa tcattactaa gaaatatgat 12540
aaattatttc cttacaaaaa aattaaagat ttaaggctga tatattaaag atgtcttgtt 12600
aatatctgat ttaaataaaa taatcaatta aattacgagt tattttgaac ataaaaaaac 12660
actttcagta ttatctaaat aaaaatataa gttaaactac aaagtaaaaa aaaataatta 12720
ttataaagag aaacacatga gtactcacaa agagaacaaa aaaaatattt ataatgattt 12780
ttttagcttt agataaggtt atacatataa ccaaaattat tacggaccat ttgttaatga 12840
aataataaaa tataaagatt ctcctaataa attaatgtat gatctttttt aaacaaacac 12900
aaaaattagt taattacact atatttaatt tctttaatct cactaaaaaa actatttttt 12960
ctcatcacat ttactttaaa ttttccttaa ataaataata taaaaataaa atagttaaac 13020
attgtggcta attttttttt ttttttacaa aaaaacacaa aagactacaa aggagaacaa 13080
gagaatgaga aacgaaagtt taaagggaaa aaagtctgat atacttctca actttttcat 13140
ttggagctga tatatttctc gttataaaag tgactcatat atgcccttat cgttatacaa 13200
acgactcata tatctgagtc atttgtttac aagtaaggta tcactttctt aaaaaagcaa 13260
tgatatcatc tctaaaacga caaagattga ggggtatatc gatccttttt caaagtttaa 13320
atgaatgaga aaaagtttta agtgtgggtc ccatgttgta catttaaaat tctcataaac 13380
tgacagaagg ttagcttttc acaaagtaaa atttttccca tgtgaaactc aaaataaaat 13440
aattgcgtac agacatgttt atgcaacaca acattaattt atttatttac ccattcaata 13500
agtgaaggaa taattataat gctttgtgct cttactttta gctgttcata tttcattcca 13560
acatcgatct tatagattta ttgttaattc acaacacttc cagcaatcta catggctgat 13620
gctttccttc aaattttgtt gacttctttc atacaagagg aacttggatt gaaaatctaa 13680
aaagcacgtt tactacgatc caagctgtgc ttgaagatgc tcaggagaag caactgaagg 13740
acaagccaat agaaaattgg ttgcacaaac tcaatgttgc tgcatatgaa gttgatgaca 13800
tcttagatga atgtcaaact ggaattttta accaaattaa gtcattatat aaaataattt 13860
accaaagtaa aatatttttc taaaagttta caaaactaat ataaacgtat ttcatggtaa 13920
cgttttaggg tatattttat tttttaaaaa ctaatgactt taggttgata tcgttctttg 13980

```
taagtaacgt tttactccta aaacgttatt ttcaataaca ttttactctt aaaacgttac  14040
tcatagtaac gttttactcc taaaacgtta ttttcaataa cattttactc ctaaaacgtt  14100
actatgagta acgttttagg agtaaaacgt tactgtgagt aacgtatatc aatctgacgc  14160
catcaacttt taaaaaataa aatatatcct aaaacgttac tgtggaatac gtttatacta  14220
gttttgtaaa attttagaaa aacatattat tttggtgaat gactttatat aatgacttag  14280
tttggttaaa acctcgtcaa actgaggcag caagactcaa tcagactaaa tatgggagtt  14340
atcatcctaa ggctatcact ttccgttaca agattgggaa aaggatgaaa gagataatga  14400
agaaactaga tgcaattgct gcagaacgaa gcaagtttca tttggaaaaa aggactacag  14460
agagagaagc ttctagacga gaaacaggtg ctcatcttaa atatattagt attaattaca  14520
acaatttaat tagtttatat tcattttttt gctattatca agttcatgtg tgtttatgga  14580
cccaagggac ttttttctaa tctaatgttt gtctcaagtc taaacagatt tgtaattcta  14640
ccacttattt atttactgaa gttcttaaac atatatacat ggtgtaagcc agctcagata  14700
aatccatagt cagttgtttc ggactgaatt taacttggat gtcaattttt caaagtcaat  14760
catgttttca actcctcccc ctgattctca tctctttgta gtgcaaaaat cttctctctg  14820
tttttcgcta aacatattct cgtgtgaaca tatattgctt gaaacaggtt ttgttttaac  14880
tgaaccagaa ccttatggaa gagacaaaga ggaagatgag atagtgaaaa tcttgataaa  14940
caatgcccaa caactttcgg tcctcccaat acttggtatg ggagggctag gaaattcgac  15000
gcttgcccag atggtcttca ataatcagag agtaactgac catttcaatc ccaaaatatg  15060
gatttgtgtc tcagaagatt ttgatgagaa gaagttgata aaggcaattg ttgaatctat  15120
cgaaggaaag tcagttggtg aaaacatgga tttggctcca cttcaaaaga aggcattgtg  15180
tcgatttgag ataatacgag aaaaatatac atgcgaaaaa caagacaaca gatttcgtgg  15240
ttcaccaata aattggctcg tccacgggaa gagggcgggt tttattatgg aggcaaaaac  15300
caattctgag aatagggttt gccatagcgt ctatatatag tgtaaactaa gcccctaaca  15360
ggcttgggcc caaaatataa attgaatgat aattaagggc ccaattcaag gcattcaaca  15420
aatctccacc ttgacttgaa ttctccaagc agattcttgg gcgcactatg atagtgccag  15480
gcctcccccc tcttcctcgg gttgcccttg agtataatta cttgacacga tgttgagcaa  15540
gtcaaacgag tgttgaaact tgctcacgtg gagccaagct ttgtgaacat atcagcggga  15600
ttatcaacag ttctactttc ttcaccttga ttctcttctc acttctcggg aaaatgatac  15660
ctccgtcaat atgcttggtt ctctcatgat ggacttgatc cttggctaga caaattgcgc  15720
tcaaaagctg tcaatacaca cgtgctttga gtcatgatcg agaccaagat cactaaccag  15780
ccccttcaa ccaaatccct tcttttgcag cctctgtcaa ggccatgtac tccgcttccg  15840
tagtagacaa agtcccatgt aggttgcaaa gttgccttca atgacgcgga tcctcaaggg  15900
taaacacttg agtcatccga tcttcttgtg tcaacatctc caaagatagt ctgaatcaga  15960
atagccaata accaagcact gagtatcacc tccataaatg ggaccagcgt cggatgtacc  16020
tctaaggcac cgaaaaattc tcttctgact gccaatgttc tctccacgtt gtcccatgaa  16080
tgctcactac actaatttgc atgtactaaa tctggcctta tacagaccat agcatacatc  16140
aaacttcctc agcactggca taagggactc gtgacatata ctccttctct tcttctgact  16200
gtggagccga acatggcgag tgggatggat aaaggcgtgg ggtatcaatg ggcttagatg  16260
aagacatgcc aaacctagcc aagaccttga atgtaacctt ctctgtgaca agaaaagttt  16320
```

```
ccttctctct ctgtctctaa tgatctccat ccctaaaatc ttcggctccc ggatccttca  16380
tctcaaactc agactaagta aacccttgac ttctgagatg tcatacttct tctttgcagc  16440
tatcaatata tcatctacat aaagcactag atagatgaat gaatcatcct tgagcctatt  16500
gtagtagaca caacaatcat atgagctccg agtatagccc aacttcacca tatagctgtc  16560
aaacctttta taccacatcc ttggagactg cttaagtcca tataaggact tcttcaactt  16620
caggacgtga ttttccttct ggaacttgga aaccatcctt tgagtcatgt atatctcttc  16680
ctccaactct ccatgtagaa acgctgtctt cacatcaagt tattcaagct ccattctgat  16740
gtgtaactat cgctagtaac actcggatgg aagtatgtct gaccactggt gagaagatct  16800
cattgtagtc cactccctct ctttggttga aacctctggc aacaaccctg gctttatact  16860
tgactccttc tgctggtgat atcccttcct tcttcttgaa aacccatttg caagtaataa  16920
tctttctccc cgaaggctgt atgaccagat cccatgtctg attcttgtgt agggactcca  16980
tctcatctcc catagcggca aaccattttt cagaatcaga acttaaaatg gcttctttgt  17040
aagtagacgg ctcagatgta tctacctctt cagcaacctg cagtgcataa cccaccatgt  17100
cctcaaaacc atacctcgta ggtggccgaa ctccaaccct ccttggccga tcttgagcta  17160
aactctgatg gatatctgat ggcatagatt ctggaatatc agtttctgtc tgtggctctt  17220
gatcctcctc ttcaggttct ttcaaatcgc tctcgttctg aatgacttga aactccacct  17280
gtttatcaag actcccagtt tctgacgtag ttgtaggctt cacaatggtt ctaagcagag  17340
aactttcatc aaagacaacg ttcctgctca taataaccct cttttctgga gccggattac  17400
gaaacctttc actccatctc atgccccaaa tactcctttt tggctcttgg tttctaactt  17460
accttcactg acgtgatagt aagccgtaca accaaaagct ttcagatttg aataatcggc  17520
agcttttcga ccacatctcc ataggtgttt tgcactgtgg ctgtatgtgg tcccttgatt  17580
atcagtagca aagctgtact aaccgcttct tgagaatctt ctatccccag cattgaaagc  17640
atgcaccttg ctctctccag aagtgtttga ttcatccgct cggctacacc gttctcttgt  17700
ggtgtatttc taagcacatg cgatgtcggg caatccttca tccttacgaa ttgatcaaat  17760
tcagaccaac agaattccag cccattatca gttcgcaacc tcttgatctt cttccctgtt  17820
tgattttcca tcaaaatttt ccactccttg aacttctgga aagcttcact tttatgcttc  17880
atcatgtaca cccaagtcat ccttgagtag tcatcaatca tggacacaaa aaatgggcga  17940
cctcccaaag actcaacacg gcatggaccc caacaatcag aatggatata atcaagtgtg  18000
ccttttgttc tttgaatggc ctttggaaac ttgttgcgat gtagttttcc aaagacacaa  18060
tgttcacaaa actctaggct cttaacctta tgaccagcaa gaagatcctc tttttgatga  18120
atttgcatcc ctctttcacc catatgacca agtctattgc cataacttag tcatatcctt  18180
ctggtgaaat tctgacgatg caacatgggc tgaacctgta accggaacct tgtagaaaat  18240
ataaaagtac cacatgacac ctttcaagaa tcaatttgaa cctttccaga ccccaagact  18300
ccatcttttc ccgaccattt gaatcccttg ctgtcaaaag actgagagat atcagatttt  18360
cgtcatcaat ggaacgtgct gaccctcgtt caatgtgcca aaactaaatc gtcgtgtcct  18420
tatcttgatc agcctgtccc aaccaccttg cggtgaaact gttggccatc gagatcttgc  18480
ctcaaatcta ccactcataa gtcgtgaacc actctcccta ggacagatgt gataggatgc  18540
cccagaatcg agaacccaca tatctgaatg atgagtgtgc tcatcgtcaa ctagggcaat  18600
atcttcttga attggtgtct tcttgactag caacagcaga gaccactgat tgttttcgat  18660
tgcttcttct tcttggacaa tcaaatttca atgtcccttc tccttgcagt aattacaaac  18720
```

```
atcatccctt tgcaccttcg acatcggctt atttttcttt ccgccgtttt ccttcccttt  18780
ccgctcttgg tcagcaggcc cggaaggtat aatgtcgtac ttgtgccgtt agccttatgc  18840
cgtaattccc tgctatgaag ggccgatctg acttcttcca gtgacacagt atctttccca  18900
acaatgaacg attgaacaaa attctcaaac gacattggga gagatactaa caatcaggcg  18960
acatcttcat cctcgatctt cacatcgata ttcgcaattc taataacaaa gtattcaatt  19020
gctctaagtg ttccctgagt tgtaccttga ccattcgtaa accgaatagg cgttgtttga  19080
agcagcttgt tggttagaga ttttgtcatg tacaaactct ccgacttcaa ccgagaccag  19140
acggtctctt catccgagac ctctgcgtga tgacgtcatc cgcgagacac aaagatgatc  19200
gtcagtgcgc ctttcctccg gaatctccat ctcgggagta acgacggcgt tcttgtcttt  19260
cgacaacggc gcccgtaaaa ccttgttgtt tcaacaaagc ccgcatcttg atcgccataa  19320
accaaactgg ctattcctcc accgtgaatt tgtcgatttt cacgttcaaa gcgtacatct  19380
caattctcaa gaacacccga ttaaccgaga ggctcgatac caatttgttg tgcggaattt  19440
gagataatac gagaaaatat aaacgcgaaa aacaagacaa cagatttacg tggttcacca  19500
ataaattggc tacgtccacg ggaagaggga acattttatt atggaaggca aaaaccgtaa  19560
ttacgaatag ggtttgccat aagcgtctat atataactaa actaagccct taatgcttgg  19620
gccaaaatat agaattgaca gataattaag ggcccaattc aaggcattca atgaagcttc  19680
aagatatgtt gaatggaaag agatactttc tcgttttgga tgatgtttgg aatgaaaatc  19740
aagaaaagtg ggataagata aaagcagtct tagaggttgg agcacgaggt gcttctgttc  19800
taaccaccac tcgtcttaaa agggttggat caattatgga cactttgcaa ccatatgaat  19860
tgtcaaatct gtctcaagaa gattgttggt tgttgtgcat ttgagaacca agaaaaaata  19920
aatcctaacc ttatggctat cggaaaggag attgtcaaaa aaagtggtgg tgtgcctcta  19980
gccgccaaga ctcttggagg tcttttgcgc ttcgtggatc aagaaagaga atgggaacat  20040
gtgagagata atgagatttg gaatctgcct caagatgaaa gttctattct gcctgtcctg  20100
agacatagtt atcatcatct tccagttaat ttaacacaaa gttttgcata ttgtgcagta  20160
ttcccaaagg acaaggtaat ggaaaaagga aatttaatat ctctctggat ggcacacggt  20220
tttcttttat cgaaaggaaa cttggagctg gaggatgtag gtaatcaagt atggaatgaa  20280
ttatacttga ggtctttttt ccaagagatt gaagttaaag atggtaaaac ttatttcaag  20340
atgcatgatc tcatccatga tttggcaaca tctctatttt cggcaagagc atcaagcagc  20400
aatatccgag aaataaacgt agaaggttac ccacatatga tgtcgattgg tttcggaaaa  20460
gtggtgtctt cttactctcc ttctcacttg caaaagtttg tgtcgttgag ggtgcttaat  20520
ctaagtgaat taagacttaa gcgtttacca tctttggaga tctagtacat ttaagatacc  20580
tggatttgtc ttacaatagt aaaatgcgca gtcttccaaa gcagttatgc aagcttcaaa  20640
atctgcagac tcttgatcta aagtattgct ggtcactatg ttgtttgcca aaagaaacaa  20700
gtaaacttgg tagtctccga aatcttttac ttgatgattg cgatggattg aattctatgc  20760
cagcaagatt aggatctttg acatgcctta agactctaag tagatttgca gtggggagga  20820
gaaaaagttg tcaacttggt gaattctgaa acctgaatct gtatgggtca attgaaatca  20880
cgcatcttga gagagtgaag aatgataggg atgcaaaaga agccaattta tctgcaaaag  20940
aaaatctgca ttctttaagc atgagttgga atatcaacga accgcgtaga tatgaatcag  21000
aagaagttga agtgcttgaa gccctcaaac cacactccaa tgtgacttgt ttaacaatca  21060
```

aaggcttcag aggaatccgt ctcccagagt ggatgaatca ctcagttttg aaaaatgttg 21120
tctctattac aattggaggt tgtgaaaact tctcatgctt accactgttt ggtggtctgc 21180
cttgtctaga aagtctagag ttatggaatg ggtctgcgga attggagtat gttgaagatt 21240
ctggattccc tacaagaaga aggtttccat ctctgagaaa acttattata gtgaattttg 21300
ataatctgaa aggattgctg aaagaggcag gagaagagca attccccgtg cttgaagaga 21360
tgaaaattag ctgttgtcct gtttttgtta ttcagaccct ttcttctgtg aagaaattga 21420
atgcttattg gcacaagtca gatgcaacag gtttgagttc catatcaaat cttagggctc 21480
ttacttccct caacattagc cataactcca cagctacttt gctcccagaa gagatgttca 21540
aaagccttgc aactctcaaa tacttgaaaa tctcttactt cgataatctc aaagatctgc 21600
caaacagcct ggctagtctc aatgctttga agcatctgga gattaattgt tgttatgtac 21660
tagagagtct ccccgaggaa ggggtgaaag gtttaacttc actcacacag ttatccattg 21720
catactgtga gatgctaaaa tgtttatcag agggattgca gcaactcaca aatttatcaa 21780
ttacgaattg tccaacactg gccaagcgat gtgagaaggg aataggacaa gactgataca 21840
aaattgctca cattcctcat ctgctgatta catagtgtca tactaaatta aatgattctt 21900
atagcaatat tattggttca accaacaaaa ctaaatctct aattatatta cttaattgct 21960
tttagtttgc tacaattatc actcatgact aacattatgt atcaattacg tggtttgtct 22020
tcaattttgt ataattagtc atgtttttat atgtataatt cgctagaata atacagatat 22080
atgtataata tacaattatt taactgatat acatatataa ttcacctctc ttccactctc 22140
tgtcctctct cacttgcctc tgtcctctgc caatcgacga gatgagccta cgaaagattt 22200
caagttcaga ctatgatgac tgacatcctc acttacgcaa cgaaatggag ttgatggagt 22260
agccagtgcc cttgagtcat tctcttcggt atcgccttct ctcatcgtta atggcgccgc 22320
aaggcactcg actagcaagt tagaccttag ttagggcgaa agatttcttg gatggttcat 22380
ttcagtctga agtcgggtca agtcatggaa ttgatgtgaa gttctctcaa tttcgctttc 22440
catatataca aatatatatg tataacatac aattatctaa atgatatata tatatatata 22500
tatatatata tatataagca atttatctct ctcccactct ttgtttcacc tgacaactat 22560
gacaactatg tttgttaggg ctggaaggtc taacttcact caccgagtta tttgttgaac 22620
atatgctaaa atgtttaccc gaggaattgc accacctaac aaacctcaca atttttttt 22680
tataagtgaa agcatagtta aactctcaaa tgtagatgat aattaagctc ttgaagatta 22740
ttgctgaatt aagtgaattc gtcaagctat atttgtaaaa ttcttatggc caaacaagta 22800
atattgcaac aaattgtaga aggattatta tactcttaac actaactaaa agattcttcc 22860
aattctcaaa gcaatttata ttcctttcca accaaagagg ttttccaaat ttgctttcta 22920
gcaaaaaaca attttctgca cgataggaat agatctcata tatactccct ccgtttcatt 22980
ttatgtgaag tagtttaact gagtacggaa tacaaaaata aaagaaagac atttaaaatt 23040
tatggtctaa aatgaaggga aaaaggtcga tatctcctca actttgtcat tttagaaatg 23100
atataccttg ttatgaaagt ggctcatata taccccctact tgtaaacaaa tggctcacat 23160
ataccttttt cctctaacgg gaaatgaaaa ataataattt tcaatctaaa tttttttattt 23220
tttttctaaa aaatataagt ccatatgagt aaatttaatt ctcgtcaaac aattttttttt 23280
tttttacttt tttttttgttt caatgactaa tttataatta ttagtttgat aatcaaattt 23340
atttatgttt cactaatatt cttgtaaaac ttattgtaga tgaaaaaaaa aaaatttgaa 23400
tacgaaatta aattacaata aacacaaaaa aatagtttat ttttttttt ctttaaacta 23460 aggaatgata gaaaaaaata aaataagaat aagaaactca aataattata ataaaagaag 23520
ttaaaaataa tttatgtatg aaaaaaaaat taaatatact ttgaactttt attgaagaat 23580
catatatacc actaaataat ttttttaaaa ttttttaagt aataaatata aatttaaaac 23640
taattattta aaattttgtt aaatgaaggg tatatttgaa caattttgta acggcagggg 23700
tatatgtgag ccgtttgtat aacggtaagg gtatatacga gccactttta taacgagagt 23760
atatcagatt caaatgacaa agttgagggg tatatcaaac ccttttcccc taaaatgaat 23820
aataaaaaat tgtgtgagta taaatcattt cattaagagt aaatggacaa tttaaaatta 23880
aattgttact taatatagta acgtatcttt tttgtttttg agtctgcttt aaaaagaaaa 23940
taaaccatat aaattggaac atagggagta tctacttaca aagtaaaagt tgtgtgtaga 24000
agattttggc atacaaatca aatcatatat catatcatat atcatcatat catatatcac 24060
atcatatcat atattagtaa aagcatgaat aaaaaaagtt gaaagttgaa ttacggtttt 24120
attccttcta ttaattaact tgttataaaa tatttaaata tttgatttta caagtttaat 24180
taaaatgtta aatgactttt agacttccta cgattaattt ctaattaaat atctaattta 24240
ttaatattta tcatttataa tctatatgta tataataatt ataatttttt aaaataaaag 24300
tctaattata attttaatga ctttttagac ttcctaacac taattcctaa ttaaatatct 24360
aatttattaa tatttttatc atctataatg ttataataag catctttaga aggtttctct 24420
gaaatactct ttaaaagaat gcttggacta tgccatccta aggttgaaac cagtaggcaa 24480
aagaaggtcg ttatggggag taaacaaagt tgaggcgctg ttagggtaac caattaaaga 24540
agaaagctgt agtagtgact aggcgagatg attattaaat cattattatt acataataag 24600
taagtataat ttattaagag gtcggaagga ataaaacttt tagcaaaaat gaataagatg 24660
actacctacc taattgatga tgatgatgaa tataagatat tattacttta tatattaaaa 24720
aatcttaata ctgatcaagt tagcagtctc aaaaatcttt ttttacttca tggttgccat 24780
aaattgaatt ctatgccacc aagtatagga tctttgacat gccttaagac tctaggtcac 24840
tttgttgtgg gaaggaagaa aggttctcaa cttgatgaac tacgaaacct aaatctctat 24900
ggatcaattt caatcacaca actagagaga gtaaagaatg atagggatgc aaaagaagcc 24960
aatttatctg caaaagctaa tctgcattct ttaagcatga gttggaatat caacgaaccg 25020
cgtagatatg aatcagaaga agttgaagtg cttgaagccc tcaaaccaca ctccaatgtg 25080
acttgtttaa caatcaaagg cttcagagga atccgtctcc cagagtggat gaatcactca 25140
gttttgaaaa atgttgtctc tattacaatt ggaggttgtg aaaacttctc atgcttacca 25200
ctgtttggtg gtctgccttg tctagaaagt ctagagttat ggaatgggtc tgcggaattg 25260
gagtatgttg aagattctgg attccctaca agaagaaggt ttccatctct gagaaaactt 25320
attatagtga attttgataa tctgaaagga ttgctgaaag aggcaggaga agagcaattc 25380
cccgtgcttg aagagatgaa aattagctgt tgtcctgttt ttgttattca gacccttttct 25440
tctgtgaaga aattgaatgc ttattggcac aagtcagatg caacaggttt gagttccata 25500
tcaaatctta gggctcttac ttccctcaac attagccata actccacagc tactttgctc 25560
ccagaagaga tgttcaaaag ccttgcaaat ctcaaatact tggaaatctc tttcttcgat 25620
aatctcaaag agctgccaaa cagcctggct agtctcaatg ctttgaagca tctgaagatt 25680
agttgttgtc ccaaactgga gactctcccc gaggaagggg tgaaaggttt aacttcactc 25740
acactgttat ccattacata ctgtgagatg ctaaaatgtt taccagtggg actgcagaca 25800

```
ctcacaaatt tatcaattaa gaaatgtcca acactggcca agcgatgtga gaagggaata  25860
ggacaagact ggtacaaaat tgctcacatt cctcatctgc tgattactga ttagatgtaa  25920
ttttctgatt tttcttttgg aaacaaatca actatttgta acatctattt gtatgatact  25980
tgatttttct tggttatgta acaataaata tttgaaattt ttcatattaa agattcagaa  26040
tgagttttat agctaactct atattttcac agtttaataa cgtaaaaatg tgatatttat  26100
atcaaattat tacttatgtt gtcatttatc aacatgttgg agatgatttt gacagtttat  26160
taaagaattt ctaagttttt attgtttgca caagtaacaa gccataaatt aagtttcgag  26220
ataaaagtga tttgtgtatc atggcttaat tagtcggaat ttcaagtttt tttctcaagt  26280
tatatatatg acaatttgta aaaaatagat agtattgatt ttgatttaat tcaagcattt  26340
ttaaaaatat aaacattata atatgggaga tacacacgct aaacgcgtac ccagaaacta  26400
gtatataaag aatcatgacc gaaaaataaa atgaagttct gtcaacaact atctcgacat  26460
ctttgctgat atatatatat atctaactag tgtacttatt cggacttgac atggtataaa  26520
aagatattaa atatattttt aaataattaa taaatgatat aataaaaaga aagaaataca  26580
aattcagtta tgattctgat aaaagggaaa ctaattttct gatttttctt ttggaaacaa  26640
atcaactatt tgtattatac ttgttaatgt tgcaattatt agtgaacagt tgtattttgg  26700
attatcactt acagcagatg tctaaaatgt gaataagata atacttagaa taatttatgc  26760
aatatacttt tgtttaaata caagaaattt aaataaagat tgctaaagat tattattttg  26820
aatgaaagat tttgattttg ttactttgtc gcctatgtaa catagtactg ttgcaaacat  26880
atacatatgt gttcattttt ccccttgtgt ttcattttat tttctacaac tcataaatac  26940
taaaaagaaa acgttaggaa tgagttttaa ctagatttaa attttaacaa aaacaacgtg  27000
attatatttc actaaattga cttaaatata tttatactta aaaaaaaatt attaatttat  27060
aatattaatg ggaccatata tttatataaa aattttctat aaatatatta tcttatatct  27120
cctctaaatt catttcacga gaattaaaac catcctaacg gatgacgttg ccaaaaagaa  27180
tagaaatttt ctttgaaagc gtgttaagtt ttttttaaaa aaaagtaatg gtctcacttt  27240
gtatatatga agaaaaaaaa aacccacccc tttcttcttc ttcttcaaac ccccaccccc  27300
gctttttcaa aacccaccag ccccctttac ctgcttgtct tttcttcctc atattcccga  27360
cgtcacccta tccccaaccc accccatcct ctttctcatt tttcgaactc tacattcaaa  27420
gcacataaat aaaaagaatc acatttaaga ttcatataat ttttttactc tttacttttg  27480
agatttgatt tttcttaaaa agttatgatt tttttgaaaa taaagaatag ggcataaaag  27540
aagatgaggt tttgtcaacc aatctataat gttaatggct gggaatggtg attgaagcaa  27600
tggatagaga aagatttttt tttaaaaaaa aaagagaaga aaaatcacta caatcagtaa  27660
ccgcaattgc agtaggctta catcatggag tatcccaatg agtctcttca ctgttcaatc  27720
ggccatcggt aaccgcatta caatgggctt tgggtcaccc acccaatttc ttataaatag  27780
aaagagacat gagatttatg attgcaccta gatcacatag tgatttggca aagtgtaata  27840
atacgaatgg tacatgaaat agtgaaagcg ccaggatctt ccttcttctg cacaagagtt  27900
cttgtgacaa tagcactaca atgctgcatt cagttatcat cctcaaaact taccgatctc  27960
ttctttgtaa ctatatcctt catgaacttg gcataaccgg accatttgct ccaaagcttc  28020
tatcaaaggg acattgatgg aaagttgctt caacatagtg ataaaatgtt ggtatttacc  28080
attctcacta ttcttcacca atctaaaagt ggtggtggtc taggaatggg gaccactttc  28140
tagggtatct ttgctttttt cgccgctttg tccaccaatt caccactagt ttccaccacc  28200
```

tcttcatctt ttctcatctc atcttctacc acagacgaca taggtgaatc aatagtttgc 28260
atacctcctc aagtagtgac tgtcatgcaa tgtccatcat ttttaggatt tgaatggaat 28320
tactatgaaa agtgacagtt gtcgcgggtt ctgatagtga acaattggac catttataat 28380
tcaagatgct taatcgagac cgcatgtgca tccacctttt tcccgatatt agccaaatca 28440
cctctcaatt tcttggcgtg ctcatcacta gcatcaaacc ttctcatcat ctttagcaac 28500
atatcttcaa cttgcgccgt actacctcca ccatctcaag gagcaacttt ctgattttga 28560
ggtggaacat agggcacact tcaatcattt ctattaccat agttaccccg gttgaagttg 28620
ttatctcggt tgtagtttct tctcgaactt actggccctc ttgttgtaat tcccattctg 28680
cattttcaat ttaaaattgt tgataaaaaa gacaaaaaca taaaaattga tatgaaagag 28740
ctttggttaa gtaacaatct aattatcata gtgtcatatt caattcaatg attcttatag 28800
caatattgtt ggttcaacag tttaacttta ctcgctgagt tttctattta tgatgttaaa 28860
atgtttaccg aagggttatt atacttgttt ttaatgttgt aactattagg ggtagattat 28920
cactttatga atgaatattt tggcacattg gaaaaacacc aaatatagcg cgcaaaagct 28980
aaacaaggaa attttcatat attggatata gtctttgtca tttccaaagg tctccaacat 29040
agagatagta attgagagaa aacttctatt gctattaaat agaatctgca attaaaaaaa 29100
aaataaatta ttattatatt ttatattata agtgggaaga tgcttagtct aaaggtggat 29160
taagaaaacg ccttcaactt ttttaattat cattattata ttatattata aataataatt 29220
aattattttt ctataagtgt gaaactatta aagttgaata accttttaat tctacaagaa 29280
ctcaccatta agttgaatga ctttttaact cttcaagaaa tcactaataa gtctttttac 29340
acgtcgtctt ataatgataa tattgtacat ttgaatttgg tttagagagc ataaatccct 29400
tattatacta tgtgttttca agcatttctt tacatttaga ttttttttat tttttgctat 29460
aattcaagtt atattcttaa attgatattt aagtgtttga tttctcacat gaaaatatac 29520
agttaaaatt ttgttttatg aactcatgat gtaatttttt ctcaggtata attttaatgt 29580
gattcttttg cagacaattg actaaaattt ttagtagaaa ttgcaccaat acaaataagg 29640
tatgcggcat gtctctccaa caattttaca ttttttgcat gattattttt taataaattt 29700
gatatacata cgattattgt atttttaact agattttaat aacttaatgc atgttttttt 29760
ttataataga gcctccttga taactttaca attacttatt gaaatttatt tttcttcaat 29820
ctcctagctt ccgagataaa atgggtaact aatatttctc cctcaacaac atggagcaaa 29880
aaaaatcgag aaaatctatg aagaagacat attctaacaa atggagtaat ttaatttaat 29940
ttaaaggagt acttaatagt caaatatgaa tagtaaagta agagaaaaaa aaataaaaaa 30000
attagaatat gacaagtatg aaagacaacc atgaacaaat tattggagtt ttttgttcat 30060
gctacaaaga acaataaagt tactatgtca tttgaatgta atatgtagac aacatatata 30120
cttgttacaa gtatatatgg taattcaaat tttggtacaa attgagcagg tgtgttatgt 30180
gtgtattgtt cctttcttag aaaagtaaca aactaatata ttgtagattt cgacctaata 30240
acataaaaat gtaaattatt tatcacatta aattttgttg tccaaatttg acaagttatt 30300
ggaatatcta attatttgac atttacattt tacaataaag aagtcatttt tataggttga 30360
ttgtccattt atttcgttta tattttttc gttaaatcat ttttgaaaat tttcaaactg 30420
tgattttaat atattttttt agtttaatgt aattttaata taactcctac aatatataat 30480
atttttgtgg gactgacatg caaaacacgt gtcttggact agtctttcac ataaagacag 30540

```
acaactaaga agattgtatc gcggataaac gctactggaa tagccctatt atgaagagtg  30600
tttgtcaaac agccaaatga ctgtagtttt ttcttttcca gaaatatgac tgaaggacta  30660
tatcttggat cgatcagagt gcatgaatca ctcagttttg gaaaataaag ttttgcttga  30720
taaacacaaa tttatctatt cacaccacaa gcaatggtaa gtcatcataa aaaaaaagag  30780
agagagagaa atttgttgtt agatcgagaa agattttgat aattgacgaa tagacgaaca  30840
aatgaaagaa acaggttgca tgtacatgtt cctttcaaac caaatccgac tgggattgtc  30900
aaccatgcga attagaagtt ataaagtaat ggaagggttg ctttttcgac ccgaacgaag  30960
agtgcaaaag gtttcctttc ataaagaaat cctaagcaaa gtgggaagtg taaacgaagt  31020
aggtagcata agcgagtagg aagtataacg acgtgaataa atttcaaatc tgaatggagt  31080
agatgatcag atatgtaaaa caagtacaag atgaaaaagg ttttgaagag tccaaagttt  31140
ataaataggg caatattttc tttggagaaa attgtgcact taaacagaga gttacaagca  31200
aaatacaatc aaatagaggg agtttatatt tgagtgaatt ctgattacga actgcagcca  31260
acacaagaaa acaagaattg aagaactcat tcattggctt atgttttata gttcttaagt  31320
caagtttttt tgtattgagt ttttatcgag ttgtatattt aaccctttct aaatccagtg  31380
aagtataaac tggagtagaa atagagtctt taagttaaag acttggaaac ataaaccttg  31440
ggggattttg ttggagtcta ggaattagaa tcagttctag tattgcaaga gttggaatcc  31500
gaattcataa cttgaagtgg gatcgacgat ctagttggtt gttggtaggg ccgactcaac  31560
aagattgagg gcctaaagtc aaaccttaaa gagggctcca atattttttt aattcttttt  31620
aaaaaaaaaa aaaaaaaaac taataatcat gtatatatta tttaaaatct attttctagc  31680
ttttctagat gtgaagtcat taattactat tttctaatgg atttgtttta ataattcttt  31740
ttcaattgat aatatagcta atacattcaa tctcattgtt gatattacat atataagatt  31800
ttatcaattt aaattttaaa aaattctttc ggccgaaaca atagttctgg attgttaact  31860
ttattcgtta agcaatatat gcattaggat tagaatcaag tctttttatt agattgcgta  31920
tttccattaa atcattatct tctacttgta ttatttctct taataataat aactaaagcg  31980
agcatgtata cttactatga atatcaacaa caacaaaagt tcaagaaaaa ttacaaaata  32040
agttagtata ataaaacttg gcttgcgaat ttgataaatt gatataacaa tactgaaata  32100
gtgtttcatt tcttcaatat aatgactgtt tgtttaaaca agacactcaa aaacaaattt  32160
tatttttttt aacatgtaag cgacaataac tttttttag gagagtgttc aacattgagc  32220
ataaaagtaa taaaatagag aataaaaaag atgagtataa gataaatat aatataagat  32280
cgattttacc tattgtcaat tttgtgtatc gactaaagaa ataacagctt cacatatgaa  32340
tttgtatttt aggctgctgt aagtactaaa agatagttat tcaaccagta gaagagatga  32400
aggtgggggg cagctgttgg caatcaataa gggcatattg agccaatttt tttcttctct  32460
gaaaaacttt ggcagagaaa ttaaggctaa cgaaaagtct ttgtgcagtt gtttcccaaa  32520
actttgtgaa ttgtatttca aaaaatacat tatttaatac tccaacaact ttgtgattcc  32580
actctagact accatcacat atctaatatt aattataata gtgaatttca catatggcca  32640
gaggcgaacc cacctgcacc caatatattt ttaaaaaaaa ttcatatgta gattgttgat  32700
aagacgctat aatatattta attgtgcact cttataatga acaaatgatt tgacttgttc  32760
attgaaaaaa caaaaagtgt cacataaatt gagacatgaa aaataatatt tctttttaa  32820
atttttcgtg tgaagtcaaa ctaattcata tataaagcga aagcggaagg agtactgttt  32880
aatattaatt gcatatggta gtaaatttga tagacatggt cccgtggggt gtgtgttatt  32940
```

tccattgaat aattgagttt gtaattgtta caagtccatt ctaatttcca acaccttact 33000
tcatttcaaa aatatagatt cattgcttac tcaccacata ctcgatggct gaagctttcc 33060
ttcaaattct gttagaaaat ttaacatctt tcatacaagg ggaacttgga ttgtttttg 33120
gttttaagga cgaatttgaa aatctgaaaa gctcgtttac tacgatccaa gctgtgcttg 33180
aagatgctca ggagaagcaa ctgaaggaca agccactaga aaattggttg cagaaactca 33240
atgttgctgc atatgaagtt gatgacatct tggatgaata tcaaactgag gcagcaagac 33300
tcaatcagac taaatatggg agttatcatc caaaggctat cgctttccgc tacaagattg 33360
ggaaaaggat gaaagagata atgaagaaac tagatgcaat tgctgcagaa cgaagcaagt 33420
ttcatttgga aaaaaggact acagagagag aagctgctag acgacaaaca ggtgctcatc 33480
ttaaatatat tagtcttagt tacaacaatt taattagttt atattcattt tttggcgatt 33540
atcaagttca tctgtgttta tggactgaac ttaacttgga tgtcaatttt tcaaagtcaa 33600
tcatgttttc aactcccccc tgattcttat ctctttgtag tgcaaaaatc ttctctctgt 33660
ttttcgctaa acatattctc gtgtgaacat atgttgcttg aaacaggttt tgttttaact 33720
gaaccagaac tttatggaag agacaaagag gaagatgaga tagtgaaaat cctgataaac 33780
aatgcccaac aactttcggt cctcccaata cttggtatgg gggggctagg aaaatcgacg 33840
cttgcccaga tggtcttcaa tgatcagaga gtaactgacc atttccatcc caaaacgtgg 33900
atttgtgtct cagaaggttt tgatgagaag aagttgataa aggcaattgt tgaatctatc 33960
gaagaaaacc cacttggtga cgacatggat ttggctccac ttcaaaagaa gcttcaggat 34020
aggttgaatg gaaagagata ctttctcgtt ttggatgatg tttggaatga aaatcaagaa 34080
aagtgggata agataaaagc agtcttagag gttggagcac gaggtgcttc tgttctaacc 34140
accactcgtc ttaaaagggt tggatcaatt atgggaactt tgcaaccata tgaattgtca 34200
aatctgtctc aagaagattg ttggttgttg ttcatgaaac gtgcatttga gaaccaagaa 34260
aaaataaatc ctaaccttgt ggctatcgga aaggagattg tcaaaaaaag tggtggtgtg 34320
cctctagccg ccaaaactct tggaggtctt ttgcgcttcg tggatcaaga aagagaatgg 34380
gaacatgtga gagataatga gatttggaat ctgcctcaag atgaaagttt tattctgcct 34440
gccctgagac ttagttatca tcatcttcca gttgatttaa cacaaagttt tgcatattgt 34500
gcagtattcc caaaggatac ggtaatggaa aaaggaaatc taatctgtct ctggatggca 34560
cacggttttc ttttatcgaa aggaaactta gagctggagg atgtaggtaa tcaagtatgg 34620
aatgaattat acttgaggtc ttttttccaa gagattgaag ttaaagatgg taaaacttat 34680
ttcaagatgc atgatctcat ccatgatttg gcaacatctc tatttttggc aagagcatca 34740
agcagcaata tccgagaaat aaacgtagaa ggttacccac atatgatgtc gattggtttc 34800
gcaaaagtgg tgtcttctta ctctccttct cacttgcaaa agtttgtgtc gttgagggtg 34860
cttaatctaa gtgaattaag acttaagcgt ttaccatctt ccattggaga tctagtacat 34920
ttaagatact tgaacctctc tcgcaataac atgcgtagtc ttccaaagca gttatgcaag 34980
cttcaaaatc tacagactct tgatctacag tattgctggt cactttgttg tttgccaaat 35040
caaacaagtc aagttagcag tctcagaaat cttttacttc atggttgcca taaattgaat 35100
tctatgccac caaggatagg atctttgaca tgccttaaga ctcttggttg ctttgctgtg 35160
ggaaggaaga aaagttgtca acttggtgaa ttacgaaacc tgaatctgta tggctcaatt 35220
caaatcacac atcttgagag agtgaagaat gatagggatg taaaagaagc caatttatct 35280

-continued

```
gcaaaagaaa atctgcattc tttaatcatg gaatgggacg acgatgaacg tccacataga  35340
tatgaatcag aagaagttga agtgcttgaa gctctcaaac cacactccaa tgtgacttgt  35400
ttaaaaatct atagattcag aggaatccgt ctcccagagt ggatgaatca ctcagttttg  35460
aaaaatgttg tctctattag aattggaggt tgtgaaaact gctcatgctt accaccgttt  35520
ggtgatttgc cttgtctaga aagtctagag ttatggagtg ggtctgcgga agtggagtat  35580
gttgaacatt ctggattccc aacaagaaga aggtttccat ctctgagaaa acttattata  35640
gacaattttg ataatctgaa aggattgctg aaagaggcag gagaagagca attccccgtg  35700
cttgaagagt tgacaattag ttgttgtcct gtgtttgtta ttccgaccct ttcttctgtc  35760
aagaaattgg tagtttatgg gaacatgtca gatgcaacag tttttaggtc catatataat  35820
cttagggctc ttacttccct caacattagc cttaactcca tagctacttc gctcccagaa  35880
gagatgttca aaagccttgc aaatctcaaa tacttggcaa tctctttctt cgacaatctc  35940
aaagagctgc caaacagcct ggctagtctc aatgctttga agcatctgaa aattgaatct  36000
tgttatgcac tcgagagtct ccccgaggaa gcggtgaaag gtttaacttc actcacacag  36060
ttatccatag aatactgtga gatgctaaaa tgtttaccgg aggaattgca gcaactcaca  36120
aatttatcaa ttacgaattg tccaacactg gccaagcgat gtgagaaggg aataggacaa  36180
gactggtaca aaattgctca cattcctcat ctgctgatta catagtgtca tactaaatta  36240
aataattctt atagcaatat tattggttca accaacaaaa ctaaatctct agttatatta  36300
tttacttgct catcatagct atagtttgct ataatcatca ctcgcgatta acattatgca  36360
tcaattacgc gggctgactt cgattttgta taattagtca cgtttttatg tgtataattc  36420
gccagaatat acggatatat gtataatata taattattta accgatatac atatataatt  36480
cacctctctc ccactctatg tcatctctca ctcgcctctc tcctccctct cttaattttg  36540
cttttcatat atacaaatac atatgtgtaa tatacaatta tctaaacgat atatatatat  36600
gcaattcatc tctctcccgc tcttttgctt cacctgacaa ctatgacatt taactttgga  36660
tatgcacatt taaaaactgg ttacagaaac tcaatgttgc tgcgtataaa gttgatgact  36720
tattggatga acgtgaatac gaggcagcaa gactaaagca gtctcgatta ggacgttatc  36780
atccaaaggc tatcaaatac gaactcagtt gtttagacca caaaaagact gtgaattcaa  36840
tacaggagta gttaacgatt tagaagagat ctactcttaa cgctaactaa aagattattc  36900
caattctcaa agaaaattta tattcctttc caaccaaaga ggttttccaa atttgctttc  36960
tagtaatttt tttttttttc tgcacgatag gaatagatct catatactcc ctccgtccca  37020
ttttatgtga agtagtttaa ctcgtacgga atacaaaaat gaaagaaaga catttaaaat  37080
ttatggtcta aatgaataat aaaaaatcgt gtgactataa atcatttcat taagagaaaa  37140
tagacaattt aaaattaaat tgttacttag tatagtaacg tgtctttttt tttttaaact  37200
gtctaaaaaa gaaaataaat tatataaatt ggaacatagg gagtatctac ttacaaagta  37260
aaagttatgt gtagaagatt ttggcataca aatcatatca tatatcatca tatcatatat  37320
cacatcatat catcatatat tattataagc atgaagttca aaacttaaaa gttgaattac  37380
cattttagcc ttatactaaa ttaaaatatt ataaaataat taattaatta aatattaaat  37440
atgcttaaat tgttaattaa gttgattcac ttattgttaa aataaatagg agaatgaata  37500
gttgtaaaaa taattaatta taaagttatt acaaaaactt attagagaaa cgtttcattt  37560
ctctatcgat cgattttagg tgtaattttg tcataatgtg tattaatacc acacctccac  37620
tatctcatca ttaatatcca caccttcata atcttccaca ctctcaagaa gttgatggca  37680
```

```
taattatgag acttttgatt ttactcaatg atgtcctata aattgcggta tttgacacaa  37740
caatctatac actttgaaga tatttaggta cagtttggaa gaaattaaaa aaaatgtcta  37800
tatttctatt gtttttatcc tttagtatat atttaaatca ctttttaaac tgctcataac  37860
accgattcat taattttcct tatcttcatt tgttgtttat aggaaggaaa tgtgtacaaa  37920
ttgttagatc ttctaatgga gtttacaacg agagaaggga tgttcaagtc ttccggaggt  37980
tgaaatcaat tttaatttca agtattatat tcatgctttt agatgtttat atatatatat  38040
atatatatat atatatatat atatatatat atatattcaa atgagtcaac atagactaat  38100
atgagactta aaggtcggaa aattggagta tcacaattag tagtaaaaca aagtaagaaa  38160
tctcaattag atatatttta ttatttttta agaaataata cactcatggg tataagtgtg  38220
aagctccaaa atgcaaaaag ttgaattact attgtatccc tataatagtt aattattttt  38280
aaatattagt tcatatgata ttattaaatt atacttcttt gaaattaata acataataaa  38340
aaccaaattc atctttgaag tgcaaattta tcgtccttca ttattgataa tttgaatgca  38400
ctaaaaacta tttaatatcc cggaaggtgg aagagtgaaa gtattcataa ttaatttcta  38460
gataaaattt tactagataa aaaagtatac atgcattgga attaataatt taaaaataaa  38520
gaaataatga tttagccttt taagttacct actttttatta tgctctttaa accattgtta  38580
ttatttttta aaaaaaaaac tcatattaag gtgttagctt gattagtcta aagatatcaa  38640
aatgtcattt cttggatcac ttaatttgta acgtttttat cttctattag cgtgattctc  38700
cattttccta tattatatat tatactttct catgtaatca tgttatctat atttattttt  38760
ttatataagt ttgttatgct caatgtttta tttatcttta tttgaactca tctaaattgt  38820
tgaatatttc aactactaat aaattttttta aatttgactt tttttttatg aaaatacaat  38880
taagaaatga cgctaatatt tcatagtgat gatgcagtaa gtgaagcaac acagattgaa  38940
ctgtttcaag tggtatcaat tttcaggtaa taaatcattg ttccttatat gcaattaatt  39000
atttttgtgt aagttgatat gttcttaata aaattttggt ttgattttta aataaaaatt  39060
attttataga agttgagacg gtacacttaa ttggattatc caaaaaaaga atcttttaca  39120
caaggacaag aagaaagact tctagcttta tcactgcatt catgacaatc aatggaatat  39180
cctacaagac aaaaagttga tgtgattctg tacaagtgaa tccaactcac taacaaaaaa  39240
attaaagaaa gaaaaaaatg aacatgaaga gaataaaaat gaagatgaag agaatcaatg  39300
gtgtcttata agttgatgaa ccactgtaac ttcattattt tttaaattta cgaggaaatg  39360
aattattgac gaaatttatg aaatgtacat atataccttt gggtcggtaa caaatgtgat  39420
tgaaagtagt attttttcat gcataatagc taattcttga tatatatatt gtttaaattt  39480
attatttgta ctacaaacat tgtatgatat attttaggat aagcgtaacg catgcgacgt  39540
ggaaactagt atattagtaa aagcatgaat aaaaaaagttg aaagttgaat tacgatttta  39600
ttccttctat aattaacttg ttataaaata tttaaatatt tgattgtaca agtttaatta  39660
aaatgttaaa tgacttttag acttcataag attaatttat aattaaatat ctattttatt  39720
aatatttatc atttataatc tatatgtata taataattat atttttttt aaataaaagt  39780
ctaattaaaa tattaatgac ttttagactt cctaacacta atttctaatt aaatatctaa  39840
tttattaata tttttatcat ctattatctc tctctatata ataattttac aaaaattaac  39900
aaaaaaagtc tctacgtaaa tttttatact ttttttttta ttctcataaa tttttcctaa  39960
ataacaaaat ttaataattt gaaggatgca aatctgcaaa atggagacac acacatttga  40020
```

-continued

```
taatgtcctc ttaattatca ttaaagaatg actctaacta gcttcacaaa tttaaattca  40080
ttgatactta attactcgga gaaaagtaga tgaagactct taattttgat agtatatgga  40140
aggagtcaat aaagtttcgt agatttatgc aataattttg tacttatttt ttcatctaca  40200
tatacatagt cttatgagaa tgatgtctac attgtatttt ttcttaaatc tgtttctttt  40260
gtcttttatc cccaattaga cttcttaatt taattttata caaatgtttt attgtcataa  40320
gtctttatac ttattttgta attgtagcat tttattgttc attacaattt gcatatatat  40380
atttccatga aatattagta attctatcat atctataaaa attcacatga aatacacgtg  40440
caaagcacgt gttcagaaac tagttaggaa aacaacacaa atatacatct gaactatcgt  40500
aaatgatata cagataccat catcatactt ttgggacatt ggtgtccatg tcgtcaaaaa  40560
aatagagcaa atatattaat ggacatcacg tgtcagaatc atatcaattg atccaacatt  40620
tattaaatgt ttgatcgaag aatagattgt gtcacatgtc cctatttagt catctgttaa  40680
aatgaatgac atatgggttg ggccgaccat tttctgaccc acacaaaaaa tgggctagcc  40740
cggtttaacc cgtaaaatat caaaacatgt atggattagc ccggataagg tgtgttagcc  40800
atattgacag ctttatcccc acatcaagaa ggtatttata tgtcaacttg aaaagaaaaa  40860
attttccaaa tatgatctgc ttatactcta tcaattccat atctcactta gtgaaatttc  40920
actgaatata ttgttgttgt tggtgtcctc tcccatcatt ataaatttaa agaacatgca  40980
atgtaagacg taatttagaa aacttggttc gcccgtagaa gaaggatcat ctgtaaattt  41040
attcctctgc aagttgatgc tttgaatctg ttggtacatt tcctctaaac atgttagatt  41100
ggattgaatc ttaagtcatc atgtgttact atctgaaaga ccaatattta aatttattgc  41160
tcacaagtaa aaattagaac taaaaatata caaacatgaa gttcaacata tattataact  41220
taattcataa aagaaaaatt atttgcatgc ataatatttg tttattcatt tcttagtgta  41280
catattttaa ctttatcagc gtagtaattt ggtttgattt gtttgtttgt tataatgtaa  41340
ttacaagtgt acttagcttg tttgattaca caagtgtaat catataatta tactgaattt  41400
taaagataaa agttaattat ttgaaacaaa aaaattatat taggcaaata agagccttta  41460
taaatgatat tcaattgaat atttaagata tatagtgtct tttaaaaaat atgttattta  41520
ataaacatat gttcttaatt aatattataa aaaaagcaaa tgatttatat atttcaatgt  41580
agtattttta aagtaaatta atcataaaaa ttaaaaatgc atgaacatca tgaaatgctt  41640
gtttcacaaa aaaattaata ttataaatat aatgtcataa aatcatagaa aaataattga  41700
caaaagaact aatttatcaa gtctaactta aaaagaatag gttgcaatgg aatatcaagt  41760
caatactcct aaaacaaatg aaattgaaaa tataatataa gttctaaatt taaaataaaa  41820
aatttaacat aatactttta tgtcaaattt caacataata tgattaaaag aaaaggaaaa  41880
tttaagtccg taactttgtt caacaataaa ttctacttta attcaaaaat tagaatacta  41940
acaaaattat actaataatt tttttagata ttatgaagaa ttgcatgaaa tcacatgaag  42000
taaaagttaa aaataagaag gaaatgaaat ataaataata aaggaaaact ttcatatata  42060
gccacttaaa aataattaat tactctccat agctatagtt tgataattac aatttgtagc  42120
tacatgttat gtggaggaga gagaggcgag cgtcacttgg agagagaggc gagagagaga  42180
gggggaaaag agtgggagaa aggtgaattg tatatgtata ttggctagat aattgtatat  42240
tatacatatg taattgtata tatggcaaga gagattgaga gagggaggag agaggcgagt  42300
gagactgtga gagagagaga gaggcgagcg agatcaagag agggaggaga gaggtgagcg  42360
agagagggca gagagtgaga gggatgtgaa ttgtatatgt atataatttt atataactgt  42420
```

atattataca tatacatttg tataaatggc aagcgagatt gggagaggga tgagagagac 42480
gagcgagaga gggcagagag tgggagagag gtgaattgta tatgtatata ggctaaaaaa 42540
ttgtatatta tacatattta tttgtatatc ctggcaaatt atacatatat aaacatgata 42600
attatacaaa catgaagtca acccacgtaa ttaatgtata atgttagtcg cgagtggtaa 42660
ttataacaaa ctatagttat gatgcataat taaaataata taagtttgtt tattcgcata 42720
atttttcctt ttttaaattc ctccttctat tcaacttgca ttttttgtca aatataatca 42780
tcgttaaaaa ttatttgatg ttgaattaac aaacatccat ctttattata tcacatgttg 42840
tgacatgcac caaaacgata aaaacgacac cttcaaaatg attttttttta aaataagcct 42900 agttaattga tgtttaacat ataaataatc aactaataag gttaaaggct tacacataca 42960
aactaaaaat tagatcaaat gcactaaaaa taaataatat gaggaaaatc tgttttaggg 43020
attatagtgt cccccaacga ccaagtctta tttttaatgg agcatcattg attggtctat 43080
tgacaaagaa aatttggaaa ttaatgattt tgttttatcc tctggaaatt tattatgtta 43140
tcacaactat ttgttaattt gaactgcata aaagtttttg ttcgaacttc atatatgaaa 43200
attctaaaca agaattggaa acttgaaatg aatccaacat ttaaatcaat agataattat 43260
tgattgaatt tcttaatacg tatatataca aaagatctga ataaaagcta ttgaatacat 43320
tacatgttat attggttaat ttgaccgtaa aacagttgac attcttttgt caagcatcta 43380
ttctggggag gttatatata tatacatttg aataatgacg ttatactata gcctaaaact 43440
acataaaaaa tgtcaagtaa attatttaac tgtcaataca gaattccaca accaatagtt 43500
tatttccctt tagcaatgaa ttgcagtcaa gttcagctag caatatacaa ttaaaagatg 43560
tttcaaatca ttggtattaa ttagataagt attgactcaa ttacaagtat acacacagta 43620
tatatagatg gcgtttgaaa acgaaaacat aggcacaaat agcagctaaa gaagttgaac 43680
aaatcaaaat ggttgcgaag actattatta tagcatgcct agttttgtta acatgcctct 43740
cagttactaa tgcatcgaac attacaactg atgaggcaca aatgactata tctagtgaaa 43800
ttaacatgca gatgaatagg catatcttgc agtaaaaagc atcaaagagt gacatcatta 43860
gtcctcaata gctttggatt tagaggttca atcgcgacag atattgggaa tctctccttc 43920
cttaactttt tggacattgg aaacaacagt ttccatggcc aaatacctga tgaaataggg 43980
cgtttgaggc gtttaaaata catgtatttg cagatgaata atctcgctgg tcaaatccca 44040
gaaagccttg gatttctcac aaggcttcaa gttcttcatc tttctgaaaa tcgtctattt 44100
ggaaatgttc cagcttccat tttcagcgtg tcttctttaa aggacattga tttgtctcag 44160
aattacgagt taactgggag tttaccaaat gagatatgca ctaatcttcc agtgttggaa 44220
tatatatccc tgcaagataa tcaatttgta ggtgaacttc ctaaaggttt aaataaatgc 44280
tccaaacttg aagttctgtc cttgtcttat aacaaattca ctggtaatta actaacttgt 44340
aaacttttca tttactaatt tcttcttgaa ttaatcatca tttttgtgtg tgtctgtgat 44400
tttataattg ataggaaact taccaagaga catgtggaac atgtcaaagg ttcaagaact 44460
ttttattgga tggaataact taacaggtac gtgattctgt atgtattaaa tcttgaatac 44520
tcttcacgaa gttcctaatt tcactagata tagccaattt gtgcattgtc tagtaataaa 44580
caaagattaa tatattttgt ggagaacatt ttcgaaagac actctatgta tgatctttag 44640
catgataacc atatacttat tttcaaaatg aatttgcagg aaatatacca aatgaaatga 44700
acctaccatc tatttgcagg aaagttaaca aagcttgagc atcttgttgg gttatgggtc 44760
tttttccctt cctatttgga taactaaaag cccaatttgg accaatccat ttttgcctat 44820
aagcccattc ttatgaggca aatataaact gattttaggg tctgattttc agaacatata 44880
gagagttctt cagcagccaa aaagagagaa agagagattt tcgcaggcaa aattcagatc 44940
taatagacaa cttcaaattg cgattcccgc ttcttttctt atccgattga gttgattttt 45000
ggacagcata ttgtcttcat ctcaatcttt gattagaaac tgacagagtt ggatttggtg 45060
gcctgcgact ttcagttttg cttttgtcgt gagcgaagct gcaaaattgg tgattttgct 45120
cctttaattt tctagatttg gtgcaatctt attttgttgt tgctcgttgt ttggcacttg 45180
ttttgtggcc aattttggag aacaatattg taactcttgg tgattatagt ggagcttttg 45240
gtccgtggtt tttactcttc acatgaaggg ttttcaacgt aaatcttggt gtcttatgtg 45300
attggtttca cattgtcttg ttatatttgt ttggttgaat tggaatcgcc ttactatcat 45360
attgcttgtg gttgtttgtc ttctcttggt tcaaatcgaa aaagggaaag tatagacttg 45420
gatattcttc cgttatctgt cgtcagcatt cttggtagtg tcttgtcttt cccaacaaag 45480
tggtatcaga gcattgggta ttgttgattg tcgttttgaa tgatggagac aaatatgagc 45540
aaaatggtgt ttttaaatgg tagtaactat catatttgga aaggcaagat gaaagatctt 45600
ctatttgtca agaagatgca tttacctgtg tttgtttcta ataagcctaa gtctttgaat 45660
gatgaagaat gggaatttga gcatcatgca ggtttggcta tattatacaa tgggttgaag 45720
ataatgttat tagaaatcag tattgtgaat gagacatgcc aaaagtttgt ggacaagtcg 45780
agacacttta tgcttcaaga ttgtgtaaca actgctccta ttgaacaatt aatgaatatc 45840
gtataaagag ggcactccta tttctgatca tattaatgat tttagggggt tcttgaccgg 45900
ctgtccgaaa tgggtgtaaa gtttgatgat gagatacagg gactttggct tcttaatacc 45960
gccagatctt gggaaactct tcagtttctt tgaccaatct gctcccaaag ggtgttgtaa 46020
ccatcggaat atactaaaag tagtgtcttg aatgaagaaa taagaagaag atctgacctc 46080
atcttcagac ttctacactc cgatgttttt ccactgaaga tagggggaga aacaagtcgg 46140
taggaggaat gatagaggta aaagtgtatg tcaaagtcta agtctaacac aagaatatta 46200
catgtgacta ttgccacaag aatgggcata tcatgaaata ttgttacaag cctgagagat 46260
atgagacaac aaaaaagaga aggcgataat gaaaatcgtg ttgttgttgt tgctaatgat 46320
cttctttctt tttttcttga tgcaaatgcc attaatcttg ttcgtgatga gtctagctgg 46380
tttgtggatt cgggtgctac ttctcatgtc atgccaaaga aggaattcta tttcttatac 46440
tccggggtaa ttttgaaacg ttgaaatggg caataatcat gaagttgaag ttattggcat 46500
tgggacagtt tgtttggaaa ataacaatgg ttcaaaacta gttctcaata atgtcaagca 46560
tactccggat gttcgcttga atttgattta cgtaggatat cttgatgatg aggttatgtt 46620
aaacacattt ggtgttggct agtggaagct tactagaggt ttgatggttg tggcccgtgg 46680
tgacaagttg tctaactttg tatgtatttg gggctccgtt tcgagagact caagaatttg 46740
gtagagaatg atacttatcg aagttatggc atgtaaaatt tgagtcatat gagcgagaag 46800
aggattgata gtttggctaa gaaaaatttg ctttctggag tgaaacaagc aaagttgaag 46860
aaatgtgttc attgcttagc cggtaaacat aaagagtttc ttttgaaatc atccgccttc 46920
aagaaagctt gatttgcttg gagttggtac attcccgatt ttgtggtcct tttaaggtaa 46980
gatcccatag tggtgcaatt ttactttgtg actttttatt gatgatcatt ctcgcaaact 47040
cggggtattt cctttgaagt ccaaggatca agtacttgat gtgttcaaga gttttcaggc 47100
cttggttgaa agacaaacag gaagacattg aaatgcatcc gctcgaataa tggtggtgag 47160

-continued

```
tatattggtc ctttttgata gatattgaag agagcggggt attaggcacg aaaactcctc  47220
caaaactcgc ggttaaatgg tttagcaagg aggatgggca gaactctagt tgagaggctt  47280
agatgtatgc tctcggatgc taatttgcca ttcctttagg cggaagcact taatctgccg  47340
cttatgttat cgatttatct cctttgttgc tttagataga tggtgatgtc acagcggagt  47400
ttgggtggta agaatgtttc ttatgatcat cttagagtct ttgggtgtaa agcctttgta  47460
catgtttcta aggatgaaag gtcaaagttg gatgttaaaa ctaggcgagg tatcttcatt  47520
ggttatagtc aagatgaatt tggctatcgt ttctatgatc tgttgagaag aaacttgtta  47580
gaagccatga tgttgagttc tttgaagacc aaacaattga agattttgac aaaagtgaca  47640
aggctgattt tcgagtagtg agagcttagt tgatgttgat ccggttcctt tgactattgc  47700
cgaagaaaat cttcttaatg aagaaaatca agttgataat gaagatggtg atcatgttct  47760
aatgaccggc atgatgttgt ttatgctccc aagaagatga tgtggttgtc caacaaccaa  47820
ttatagatgc tccggagagt tctctcgcac gatctagtag agaattcctt catctcgtga  47880
ttctcctaat gagtatgtac ttgacttacg gggagaaccc agagtcttga tgaggccatg  47940
gaaagtgaag aaaaagaaag gtggtttgat gctatggaag atgagattaa atccttgcat  48000
gataatcata cctttgattt gttgttacct aaactgaaaa actttttgaa aaaaggtggg  48060
ttttttcggg tgaaacatga agatggtaat ccggttccac cagacaaagc tagattagtt  48120
gtcaagggat ttaatcagaa aagggagttg attttgatga aatattctct ccgattgtga  48180
agatatcatc cattcggtgt ggttctaggt cagctgcaag tctagattta gaggttgagc  48240
aaatggatgt taaaaaccgc tttcctccat ggtgacttag actaagaaat ttatatggag  48300
caaccggaag gttttgaagt caaggtaaaa gagaattatg tttgcaaatt aaagaagagc  48360
ttgtatggtt tgaaacaagc tcccgtgcaa aggggtacag tgaagtttgg ttttttatga  48420
gtcaaagggg cttcaagaag acttcttaac cattgtgttt tgtgcaaagt tctctgatgg  48480
tgacttttat tgttgcggtt gctttatgtt gatgacacgc ttgttgtcgg gtcataatac  48540
ttgcagtagg atcaagttga agcaaggagt cgaggcaagt ctttttgcat gaaagactta  48600
gaccaaagaa ggcagattct tggcatgcag attgcccgtg atagaaaaag ccaagaaatt  48660
ggtattatca caagagaaag tacattttta aagtacttca agcagattca aagatggaca  48720
aagctaaggt tgtcaagaca ccttagctat gccttcaaat tgaaagcatg gaaatgctgt  48780
cctttctagc gatgatggaa aggaagatat gaagaaagtt ccttatgctt caaattggta  48840
gtttgatgta tgcgatggtt tgtacaagac cgatattgct cacgctgttg agttgttaag  48900
cgggtttctt tctaatccag gaagagaaca ttggaatctt tgtgaagtgg gttatgagat  48960
atctcatggc acttctagtc cgagtttgtt tttggcaggg aagcctattt ttttgattta  49020
tcttgattag gacatggttg gtgatgttga tactcgcaag tctacttggt gcttggttac  49080
ttttagggga gtattgtctt ggcaatctag attgcaaaat gtgttactct atctctacta  49140
tggaaggctt attcttttcg tgaagcttgt aaagaattgc tttggatgaa gagattatta  49200
agaacttggt ttgtgctcaa agaggtatgt actttattgt gaccggtcaa agtgctatac  49260
atcttggcaa gaattctacg ttccatggtc ggttaaacac attgatgtga gataccattt  49320
gattcgagat gtattggatt ctaagttgct tgagcttgaa aaagattcat acaaatgaca  49380
atggttccga tatgatgact aaagctttgc caagaggaag tttgaagatt gttgcatggt  49440
cgtggggacg ggcggtcctc cacatagtcg tgagggagaa ttgttgggtt atgggtcttt  49500
```

-continued

```
tttccttcta tgtggataaa taaaagccca atttggacca acctattttt gcctataagc  49560
ccattcttat gaggcaaata taaactgatt ttagggtctg attttcagaa catatagaga  49620
gttcttcagc agccaaaaag agagaaagag agattttcgc aggcaaaatt caaatctaat  49680
agccaacttc aaattgcgat tcccgcttcg tttcttatcc gattgagttg atttttggac  49740
agcatattgt attcatctca atatttgatt aggaactgac agagttggat ttggtggcct  49800
gcagcttcag ttttattgtg aggaattagc tgcaaaattg gtgattttgc tcctttaatt  49860
ttctagattt ggtgcaatct tattttgttt tgttgctcat tgtttggcac ttgttttggc  49920
caatttttgga gaacaatatt gtaactcttg gtgattatag tggagctttt ggtcccgtgg  49980
ttttactctt cacatcgaag ggttttccac gtaaatcgtg gtgtcttgtg tgattggttt  50040
catattgtct cgttatattt gtttggttga attacctgct gccttagtat catattgctt  50100
gtggttgttt gtcttctctt ggttcaaatc gaaaaaggga aagtatagac ttgggtattc  50160
ttccgctgtt atcctgtcag gcattcttgg tagtgccttg tctttcccaa cacatctcaa  50220
ctatctgaat gtctcttaca atgagttatc aggtgaaata ccagatggag ggccttttgg  50280
taattttcac agctgaatca ttcatcggca atgaagagtt atgtggaccg cctagattcc  50340
aagtcaagat ttgtgaaatc cgaacaacgt gacaagaaga aacaggaaaa aacaagacta  50400
aaatttgttc ttggaccagt gcagctggag gtttagtcat ggggttttag gcatgatatg  50460
gttgttgaat tatcggagac gtaacaacca acttattcct ttaactgatt agtatgatcg  50520
gttatcacac aaaaagtttt cttactatga acttgtttga gggactaaca actttgactt  50580
taatcaaatt tgattggaaa gggaagcctt ggtatggttt ataaggggac atttacaaat  50640
gggactatag ccaactgtaa aggttttcaa tgctggcgca agatgcattc aagaggtttg  50700
atttggagtg taaggttttg cgtaacaccg aaataggaat cttgttgggt gataagtagt  50760
tgttcaaatc ttgattttaa ggcattggtg tttgagtaca tgcctaatgg agatcttaat  50820
tattggcttt actcacacaa caatttcttg gatttaaaca aaatttgaaa attatgtttg  50880
atgtggcttt gtgtcagaga gtatctacac caaggccatt caaaacatag tggtccatca  50940
tgacttgaac atacttttgg atgaagacat ggttgccgag taagtgattt tggtatattc  51000
aaactcttga ccgccagatg atccaaaggg cattgacaaa gactttaggc accattatcc  51060
tggcactgtg cccgatcaaa tttttattta ctaattactt tcttcaactt gtattcgata  51120
tgcatatatg atgtatttca ttttaatggt agagtacggg tcagaaggga tagtgtcaac  51180
tatgggggat gtttacagct acggcatttt atttatggaa accttcataa gaaagaaatg  51240
atagatgatg agtttgttgg agaccttaca ttgaagagat gggtcatgga atcatatcct  51300
catagagtca ttgttatgaa ataaaaacga atacaagttg aacgtcaatt atgagtcatt  51360
tatctaatat gatccattaa caattgatta atgtaacgca ggaagaagaa aacaatttgc  51420
attgttatga atgaatgtgt ttgtactaca atatatacaa agatcgacaa gtctagcaaa  51480
ctttctaacc aacttattct aaccaactct actcattatt catttagctc acttaatcaa  51540
gaaattagac ctaacaacta actaccatta actcattcaa ctgattgttg ggttataggt  51600
ctttttccct tcctatgtgg ataaataaaa gcccaatttg gaccaaccca tttttgccca  51660
taggcccatt cttatgaggc aaatataagc ctatttaggg tcttattttc agacaaaaca  51720
gatcagtttt tcagcagcca aaaagagaga aagagagatt ttcgcaggca aaaatttaga  51780
tctaatagct aacttcaaat tgcgattttc acttcgtttc ttatccgatt gagctgattt  51840
ttggacagca tattgtcttc atctaaatat ttgactagga actgacagag ttggatttgg  51900
```

tggcctgtag cttcagtttt gctgtcgtga acagtagctg cgaaattggt gattttgctc 51960
cctttaattc tctagatttg gtgcaatctt attttgttgt tgctcattgt ttggcacttg 52020
ttttgtggcc aattttggag aacaatattg taactctttg gtgattatag tggagctgtt 52080
ggtccgtggt ttttactctt cacatcaaga gttttccacg aaatcttggt gtctttgtga 52140
ttggtttcac attgtcttgt tatatttgtt tggttaaatt acttgccgcc ttactatcat 52200
attgcttgtg gttgtttgtc ttctcttggt tcaaatcgaa aagagaagta tagacttgga 52260
tattcttcat ttgttatccc gtcgagcatc atttgttatt gccttgtctt ttcccaacaa 52320
agtggtatgt caggagcatt ggttattgtt gattgtcgtt ttgaatgatg gaggcaaata 52380
tgagcaaaat ggtgtgttta aatggtagta actatcatat ttggaaaggc aagatgaaag 52440
atctttattt gtcgaagatg aatttacatg tttgcttcta ataagcctaa gtctttgaat 52500
gatgaagaat tggaatttga gcatcctggg tttcggctat attagacaat gggttgaaga 52560
taatgttaga aatcatattg tgaatgaaac acatgccaaa gtttgtggga caagctcgag 52620
acactttatc ttgaagacgg caacaaacaa gttgttctat tgaaacaatt aatgaatatc 52680
ggtataaaga gggcactcta tttctacgat catattaatg attttcaggg tgttcttgac 52740
cagcctgtcc ggaatgggtg taaagtttga tgatgagatc acaggggact ttggcttctt 52800
aatactcatc cggactcttg ggaaacttct tctagtttct ttgactaatt gctcccggtg 52860
gtgttgtaac catggaatat actaagagtg gtgtcttgaa tgaagaaaat gagaagaaga 52920
tcttgcctca tcttcttaaa cttcactccg atgttttggt tcttgaagat ggggagaaac 52980
aagtcagtag atcgaatgat agaggtaaaa gtagaagcaa gtcaaagtct aaatacaaga 53040
atattacttg tgactattgc cacaagaatg ggcatatcat gaaatattgt tacaagcaca 53100
agagatatga gacaacaaaa caagagaagg cgataatgaa aatcgtggtt gctgttgttg 53160
ctaatgatga tcttcttttt tcttgtgatg caaatgccat taatcttgtt catgatgagt 53220
ctatttggtt tgtggattcg gtgctacttc tcatgtcacg ccaaagaagg aattattttc 53280
ttcttatact ccgggtaatt ttgaaacgtt gaaaatgggc aataatcatg aagttgaagt 53340
tattggcatt gggacgtttt gtttggaaag taacaatggt tcaaaactag ttctcaataa 53400
tgtcaagcac acccaaatgt tcgcttgaat ttgatttccg tgggatatct tgacgatgag 53460
ggttatgtta atacacttgg tgttggcggt ggaagctcac tagaggtttg atggttgtgg 53520
cccgtggtga caagttgtct aacttgtatg tatttagggg ctccatatcc ggagactcca 53580
agaatttggt ggagaatgat acttcatcga gttatggcat gaaggtcgag tcatagagaa 53640
ggggattgat agtttggcta agaaaaattt tctttctgga ttgaaacaag caaagttgaa 53700
gaaatgtgtt cattgcttag cgggtaaata gaaaagagtt ttttttagt catccgcctt 53760
caagaaagct tgatttcttt ggagttggta cattccgatt ttgtgtggtc ctttaaggta 53820
agatctcatg gtggtgcact ttactttgtg acttttattg atgatcattc tcgcaaactc 53880
taggtatttc ctttgaagtc caatgatcaa gtacttgatg tgttcaagag ttttcgtgcc 53940
ttggtttaaa gacaagcagt ggaagacatt gaaatgcatc cattaagata atggtggtga 54000
gtatattggt ccttttgata gatatttgca gagcggggta ttaggcatga aaaacctcca 54060
aagactccct cggttaaatg gtttagaagc agaggatgag cgagaactct agttgagagg 54120
gttagatgta tgcttttaga tgttgtcgtc gattcctttt gggcggaagc acttaacatc 54180
gctgcttatg ttatcaattt atctccgttg ctttagatgg tgatgtcctc gatgtagttt 54240

-continued ggatcgtaag aatgttttta catcatcttg tagtctttgg gtgtaaagcc tttgtacatg 54300
ttcctaagga tgaaaggtca aagttggatg ttaaaactag gcaaagatat cttcattgga 54360
tatggtcaag atgaatttgg ctatcgcttt ctatgatccc gttgagaaga aaacttgtta 54420
gaagtcgtgg atgttatgtt cttttgaaga ccaaacaatt gaagattttg acaaactgac 54480
aaggctgatt ttgagagtag tgagagctta gttgatgttg atccggttcc tttgactatc 54540
aacttgggaa gaaaattttc ataatgatga aaatcaagtt gataatgaag atggtgatca 54600
tgttcagtaa tgacctatga cgatgacgct ttttgatgct cgatgcagaa gatgacgggt 54660
tgtccaacaa ccaattatag attctccgag agttctctca gacgcatcta gtagagagag 54720
atttcttcat ctcgttattc tcccaatgag tatgtactct tggtgacggg gagaacccga 54780
gagtcttatg aagccatgga aagtgaagaa aaagaaaggt ggtttgatgc tatggaagat 54840
gagattaaat ccttgcatga taatcatacc tttgatttgg ttaagttacc taaaagcgta 54900
aaaagctttg aaaaaaaagg gtttttttg ttgaaacatg aagatggtaa tcaagttcca 54960
cggtataaaa gtagttgtca agggatttaa tcggaaaagg gagttgattt tgatgagata 55020
ttctctccgg gttgtgaaga tgtcatccat tcgtgtggtt ctaggcttgg tacgcaagtc 55080
tagatttaag ttgagcaaat ggatgttaaa ccgcttccca tggtgactta gatgaagaaa 55140
tttatatgga gcaaccggaa ggttttgaag tcaagggtaa agagaattat gtttgcaaat 55200
tgaagaagag cttgtacggg tttggaaaca agctcccaaa gcaaattggt acagaagttt 55260
tggttcttta tgctggggaa aggcttcaag aagacttctt cagaccattg tgtttttgtg 55320
caaaagttct ctgatggtga ctttattatt gtgttgcttt tatgttgatg acatgcttgt 55380
tgttgggtca taatacttgc ggggattcag aagttgaagc aagagttgag taagtctttc 55440
tttatgaaag acttaggacc aaagaagaca gattcttggc atgcagattg tccgtgtgat 55500
agaaaggcta aaaattggta ttatcacaag agaagtacat tcagaaagta cttccacagt 55560
attcaagatg gacaaagcta aaggttgtca gtgacacact tttagctatg cacttcaaat 55620
tgagcactag cttaggtgtc cttctagtga cagatgagaa ggaagatatg aagaaagttc 55680
ttatgcctag ctgggttggt agtttgatgt cacgatggtt ttgtacaaga ccggatgttg 55740
ctccatattt ggggttatta accgttttct tttctaatcg ggaagagaga acattggaat 55800
ctttgtagtg ggttatgaga tatctttgtg gcacttctag taaagtttgt gttttagtgc 55860
agaagcctat tctttgtggt tatccggatt cggacatggc tggtgatgtt gatactacgc 55920
aagtctactt gatgcttaat tctttttgt ggggagctgt gtcttggcaa tctaggttgc 55980
aaaatgtgtt gctctatcta ctctctgctg gaggcttatt ctttatcgtt gaagcttgta 56040
aaattacttt ggatgaaaga ttaacacggg aacttggttg tgctcaagag aggtatgtgc 56100
tttattgtgg tcaaaagtgc tatacatctt ggcaagaatt ccacgttcaa tagtcggtct 56160
aaacacgttg atgtgagata ccattggatt cgagatgtgt tggattctaa gttgcttgag 56220
cttgaaaaga ttcatacaaa tgacaatggt tacgatatga tgactaaagc tttgccaaga 56280
gggaagtttc aagattgttg catggtgctt gggatggcgg gcctccacat agtcgtgagg 56340
ggggagaatt gttgggttat aggtcttttt tccttcctat gtgataataa aaagcccaat 56400
ttgaccaacc catttttgct catagcccat tcttatgagg caaatataag ccttatttag 56460
gatcttattt cggaaaatga cagttagttt tttggtgagc caaaatagag aaagagagat 56520
tttcgcaggc aaaaattcag atctaataac caactttaaa ttgtgattcc cgcttcgttt 56580
cttatccgat tgagctgatt tttggtcaga atattgtctt catctcaatc tttgactagg 56640
aaccgacaga gttggatttg gtggttcggt aacttcagtt ttctttgcga atgagcgatg 56700
gctaaattgg tgattttgct cctttaattc tctagatttg gtgcaatctt tttgttgttg 56760
tcgttgtttg acacttgttt tgtggccaat tttggagaac aatattgtaa ctcttggtga 56820
ttactggtgg gagcttttgg tcctgtggtt ttttactctt cacatcgggc cgattttccg 56880
taaatcttga tgtcttgtgt gattggtttc acattgtctt gttatatttg tttggttgaa 56940
ttcttgctgc cttactatca tattgcttgt ggttgtttct tctcttggtt caaatcaaaa 57000
ggaagtatac ttgggtattc ttccatcgtt atcctgtcga ggcattctta tttgtgcctt 57060
gtctttccta acactgatca cggaacatca acacattttg ttgatttctt tcacacacac 57120
ctcctcaaaa aaccctcttt tttaacatgt aagcgacaat atcttttta ggagagtgtt 57180
caacattgag cataaaaata ataaaataga gaacaaaaaa agatgagtat aaaataataa 57240
ataataatat aagatcgatt ttaccgattg tcaattttgt gtatgaacta aagaaataac 57300
agcttcacat atgaatttgt attttaggct gctgtaagta ctaaaaatag ttattcaacc 57360
agtagaagag atgaaggtgg gggccagctg ttggcaatca ataagggaaa gaaaagacaa 57420
ggaatattga gccaattttt tttcttctgt ggaaaacttt ggcagagaaa ttaaggctaa 57480
cgaaaagtct ttgtgcaatg accccatggg catgtgcagt tgtttcccac aactttgtga 57540
attatattcc aaaaaataca aattcattat ttaatactcc aacaactttt tgattccact 57600
ctagactacc atcacatatc taatattaaa tgtaatactg aatttcacat atggtcagag 57660
gcgaatccat cagcacctga tatattcttt ttttaaaaaa attatatcta tatatacaga 57720
ttgttgataa gacggtaata tatttaattg tgcactctta taacgaacaa atgatttgac 57780
ttgtccattg gaaaaacaaa aagtgtcaca taaattgaga catggcgaat aatatttctt 57840
tcctaaattt ttcgtgtgaa gtcaaattaa ttcatataaa attagacgaa aggagtaatg 57900
tttaatagta attgcatatg gtagtaaatt tgatagacgt ggtcccgtgg gagtgtgtgt 57960
tatttccatt gaataattga gtttgtaatt gttacaagtc cattctaatt tccaacacct 58020
tacttcattt caaaaatata ctctatggct gaagctttcc ttcaaattat gttagagaat 58080
ctgacttgtt tcatccaagg ggaacttgga ttgattcttg gttttaagga tgagttcgaa 58140
aagcttcaaa gcacgtttac tacaatccaa gctgtggtac aagatgctca gttgaagcaa 58200
ttgaaggaca aggcaattga aaattggttg cagaaactca atggtgctgc atatgaagct 58260
gatgacatct tggacgaatg taaaactgag gcaccaatta tacagaagaa gaataaatat 58320
gggtgttatc atccaaacgt tatcactttc cgtcgcaaga ttgggaaaag gatgaaaaag 58380
attatggaga aactagatgc aattgcagcg gaacgaatta agtttcattt ggatgaaagg 58440
actatagaga gacaagttgc tacacgccaa acaggtaaat atttttctaa ataacagctt 58500
tatatcatca aattcatgtg tgttttgggg attttgtcta agtagataag tggttcaaaa 58560
tctattatct aaatctgttt ggtgaagtct ttaacatata tataaatcca tagcttactc 58620
atatgcccca aagtctaaat gacaggataa agccagagtt gttttagatc ttataaatta 58680
acaatgataa taatgtgaat tcaaaatagt gcatttgttt tatatttgaa atatgtctgc 58740
tgcttctgat caagctgatc attgtctttt gcaaaattct tctttgtttt ttttgctgac 58800
tcttaccgat cttggaccag gttttgtttt aaatgaacca caagtttatg gaagagacaa 58860
agataaggat gagatagtga aaatcctgat aaacaatgcc caaacacttt cagtcctccc 58920
aatacttggt atggggggac taggaaagac gacccttgcc caaatggtct tcaatgatca 58980

-continued

```
gagagtaatt gaacatttcc atcccaaaat atggatttgt gtctcggaag attttaatga  59040
aaagaggttg ataaagaaaa ttgtagaatc tattgaagaa aagtcacttg gtgacatgga  59100
cttggctcca cttcaaaaga agcttcagga cttgctgaat ggaaaaaaat atttgcttgt  59160
cttagatgat gtttggaatg aagatcaaga taagtgggct aagttaagac aagtcttgaa  59220
ggctggagca agtggtgctt atgttctaac cactacccgt cttgaaaagg ttggatcaat  59280
catggggaca ttgcaaccat atgaattgtc aaatttgtct caagaagatt gttggttgtt  59340
gttcatgcaa tgtgcatttg ggcaccaaga agaaatgaat cttaatctag tggctatcgg  59400
aaaggtgatt gtgaaaaaat gtggtggtgt gcctctagca gctaaaactc ttggaggtat  59460
tttgcgcttc aagagagaag aaagacagtg ggaacatgtg agagatagtg agatttggaa  59520
tttacctcaa gatgaaagtt ctattctgcc tgccctgaga cttagttacc atcaccttcc  59580
acttgatttg agacaatgct tttcatattg tgcagtattc ccaaaggata ccaaaatgga  59640
aaaggaaaat ctaatctctc tctggatggc acatggtttt cttttatcaa aaggaaactt  59700
ggagctagag gatgtaggta atgaagtatg gaatgaatta tacttgaggt ctttttccca  59760
agagattgaa gttcaatatg atcgaactta tttcaagatg catgatctca ttcatgattt  59820
ggcaacatct ctattttcag caagcacatc aagcagcaat atccgagaaa taaatgtaga  59880
aggttaccta catatgatgt cgattggttt tataaaagtg gtgtcttctt actctcctcc  59940
tcacttgcaa aagtttgtct cattgagggt tcttaatcta agttccatgg gacttaagca  60000
gttaccgtcc tccattggag atctagtaca tttaagatac ttgaacctct ctctcaataa  60060
catgcgtact cttccaaagc agttatgcaa gcttcaaaat ctgcagactc ttaatgtaga  60120
gtattgctgg tcactttgtt gttttccaaa agaaacaagt aaacttggta gtctccgaaa  60180
tctcttactt gatggttgcg atggattgga ttctatgcca ccaaggatag gatctttgac  60240
atgccttaag actctaagtt tatttgttat tattagagaa aagattctct acttggtgaa  60300
ttacttaaac ctgaatctgt atgggtcaat tgaaatcacg atcttgagag agtgaagaat  60360
gatagggatg caaaagaagc caatttatct gcaaaaaaga aaatctgcat tctttaagca  60420
tgagatggga aggaccacat agatatgaat cagaagaagt tgaagtgctt gaatccctca  60480
aaccacactc caatgtgact tgtttaacaa tcactggctt cagaggaatc cgtctcccag  60540
agtggatgaa tcactcagtt ttgaaaaatg ttgtctctat tgcaattaga ggttgtgaaa  60600
actgctcatg cttaccaccg tttggtgatc tgccttgtct agaaagtcta gagttacgga  60660
gtgggtctgc ggaagtggag tatgttgaag attctggatt cccaacaaga agaaggtttc  60720
catctatgag aaaacttact atagaaaatt ttgataatct gaaaggattg ctgaaagagg  60780
caggagaaga gcaattcccc gtgcttgaag agttgacaat tagatgttgt cctgtgtttg  60840
ttattccgac cctttcttct gtcaagaaat tggtagttca tgggaacaag tcagatgcaa  60900
tagttttgag gtccatatat aatcttaggg ctcttacttc cctcaacatt agccataact  60960
tcacagctac ttcgctccca gaagagatgt tcaaaagcct tgcaaatctc aaatacttgg  61020
aaatcgcttt catctccaat ctcaaagagc tgccaaacag cctggctagt ctcaatgctt  61080
tgaagcatct gtttattaat tgttgttttg cactagagag tctccccgag gaagcggtga  61140
aaggtttaac ttcactcaca cagttatcca taacatactg taagaggcta aaatgtttac  61200
cagagggatt gcagcaacta acaaatttat cagttaggta ttgtccaaca ctggccaagc  61260
gatgtgagaa gggaatagga caagactggt acaaaattgc tcacattcct catctgctga  61320
ttactgatta gatgtaattt tctgattttt cttttggaaa caaatcaact atttataaca  61380
```

tctatttgta ttatacttga tttttcttga ttatgtaaca ataaatattt gaaatttttc 61440
atattaaaga ttcagaatga gttttacagc taactctata ttctcacagt ttaataacgt 61500
aaatatgata tttatatcaa attattactt atgttgtgat ttgatttatc aacatgttgg 61560
agatgatttt gacagtttat taaagaattt ctaagttttt attgtttgca caagtaacaa 61620
gccataaatt aagtttcgag ataaaagtaa tttgtgtatc atggcttaat tagtcggaat 61680
ttcaagtttt ttctcaagtt atatatatgg caatttgtaa aaaatagata gtattcattt 61740
tgatttaatt caagtatttt taaaaatata tacaaataat atgggggata cacacgctaa 61800
acgcgtaccc aaaaattagt atataaagaa taatgacgaa aaaataaaat gaagttctat 61860
caccaactat ctctacatct tttgctgata tatatatata tatatatata tatatatata 61920
tatatatata tatatatata tatatatata tatatatata tatatatata tatatatata 61980
tatatatata tatatatata tatatatata tatatatatc taactagtgt acttattcgg 62040
acttgacatg gtataaaaag atattaaata tattttaaat aattaataaa tgatataata 62100
aaaagagaaa tacaaaataa gttatgattc tgataaaagg aaacttacat aaatgtgtta 62160
taataaaaaa atatttacca tttatagcta taatttttttt tttcactcga tcacttttaa 62220
ttaatttata atacaagttt aatatatatt acaaagaaca atttattatt cacatacaat 62280
acaagtttta atgatggatt ttatcacaca ttttaataca cttataatat aatgttacta 62340
ttttttacca aacaaacaca atatatttca aaaacaatta taattcaaat atattgcata 62400
aataattcac ttttaataaa tattacagat ttatcacaat attgctataa atgataataa 62460
acaaaagtat cgctaaaatc agtaattatt ttttaacata tattaattca tgtaattttt 62520
cttattatct attcagaaaa attgcttaaa aaatctcatt tgacattttc aatttaaaat 62580
tgttgataaa aaagacaaaa acataaaaat tgatatgaaa gagctttggt taagtagcaa 62640
tctaattaca tagtggcata ctaaattaaa tgattcttat agcaatatta ttggttcaac 62700
caacaaaact aaatctctag ttatattact taattgctca tcatagctat agtttgttat 62760
aatcatcact cgcggttaac attatgcatc aattacgtgg gctgacttcg attttgtata 62820
attagtcatg tttttatatg tactagattc tgagaacatg ccttgcacgt ttgtccttta 62880
ttattattaa ctttttatat actaaaaagt taagtaatta aaaagatgct taaataaaca 62940
ataatagttt aaccatttat cttttattcg ctaaataata actaatataa tatgaagaac 63000
attaaataga tgataatatc taccttagta attggttctt aaaaagcata ttaaaaaattt 63060
aattctcaaa gtgtttttac ataaatagtg gagaatgact cttcacattg agcttttaat 63120
tttaaaaaat tatgtgtatg agaaataatt aacattcaat aattaggtag aataatatca 63180
cattatcata aataaaataa tatctctaag tcaaaagtag acattctagt ttggaaaata 63240
attactacta actatttatg ggtccagctc caatcaataa tctatagatg ggagtttgac 63300
aatttttcag ctatagttaa aattttacat caacaataaa taacttatta tcacagtaga 63360
tagacgtttg atgcataaaa gttataaatg ctaaaagatt ttgtcaatgt agtacatatg 63420
caaacttatg ataaaaacac ttggtatatt acgaaacaca cttgaagcca ttaccatgat 63480
taacatatca attattttta tcattatatc acatatacgt cttcttttta accttaaaag 63540
tattgtacac atgatttatg aagagaaaag aatagtactc ctttttttcat gtaacgacct 63600
gtttagtcgt tttgagcagc agaatttatt tctggaaaaa ctgtctgagt caacggaacc 63660
cacgacggac cgtcatgggc acgacggacc gtcgatggtg tctcattcca aaacacttag 63720

```
aattttgaaa tttgggtctg aaatcgactc tccaacttcg tgcttgagat ggccggggcg  63780
aacaagtaag tggagccgca cggctgcacc gtcacaaatc ttccatgggg aagtgatccg  63840
aatgtgtgga tttggcgggg agatgccgtc cacgatccac gacgggacgt cactgttgcg  63900
cgtaatcccg gtgggtcgga tttctgttaa gtgatttaag gggcgttttg gactattcct  63960
gctttaatta taaagttagt gggttaatgt taataagttt aattacttgg gggttaaaag  64020
aggtaacctt gagttaatta gtgggttatt attgacatct ttatacttaa ttatattcta  64080
attagggtaa aagaaagagg gtttgaataa gaaacaatag aaagaacaat gagagggaaa  64140
gagaaacgag aaagagagaa acgaacgaag aggaaaacac aagctttggg aaaattgctt  64200
tcttgatcaa aattcttcgg tggaggtagg ttattgtttt tatactattc gtagtaaact  64260
cttaatagcg aatgatatgt gttgggttgt attgtaaagt cttctatatg cttaattgta  64320
tgcttgtata aatgtgatta tataattgtg ataaaataag caagataaag ctattgaatc  64380
ccaaatcttg aaaacccctt gttaatgatg atgccttggt ataaaagaag gcttgatgaa  64440
ctaaagtaat gatattgatg atgtcttggt ataaaagaag gcttgatgaa ctaaagtaat  64500
ggggttgatg atgccttggt ataaaagaag gattgatgaa ttaatagaat gagattagtg  64560
gagcgggtgt cacgaaccga cacatagtat taggggggacc gggtgtcacg aaccgacacg  64620
tagtattagg gggaccgagt gtcacgaacc gacacataga attaggggat cgggtgtcac  64680
gaaccgacac gtagaattag gggatcgggt gtcacgaacc cacatgtata attggggatc  64740
gggtgtccga accgacacgt gggaattagg agatcggtgt cacgtgcgga caaatagtag  64800
taggggcggg tgtcacatac caaaccaaga ggaataaaga taatgaatct tgaaagatgt  64860
taatatactc aatctaatga acctaatccc aaataggtat ggtattgagg cttgagtctc  64920
atgtgaactt ggcggtgctt attaatgatt atagtacttg ttgttgttac acatattgag  64980
tattgtagtt gatttatgat attatcagta tatcttttgt tttctatttt gagttggccg  65040
atgataccta cctcgatgcc cgtgttttat cttgacccta cttgtatttg ttttctttgt  65100
tatttgtgga gtgtagcaag cgtaccgtcg tcttcaactc attgccaact ctgtgatctt  65160
cattacaccg gattttaggg tgagctaatg cttctagctt ggactggatc ttcttcctca  65220
tgtcttgatg ccttgaagtt ccggcatgga ctagattttg tttattttag cttctttaga  65280
atactcttag tttagtaatt tgatcataga tgttcttgtg gtgatgacgg gatttttgggg  65340
aatactagtt gttgaatttt agaagttatt gaattggttt tattaatgag tttaagtctt  65400
catattactt ctgttgatat tatattgaaa tgttggggtt tagattggtt ggttcgctaa  65460
cataggatgg taagtgtggg tgcgttggct cggttttggg tcgtgacaaa cttggtatcg  65520
agcattaggt tcgttggtct catcacacaa gagaaccagt ctagtagagt cttaaggagc  65580
gtaggggggg ccttttactt ttctttgaga ggctataaga ctttaggaaa ttttcctttc  65640
ttttcttttt ctttattact tggatccaat tggtatctag gtgatacaaa ttggtaatcg  65700
accatcttca ctctattttt cgcaaatggt tagaacaaaa gcgacgacta acaacagcac  65760
cgatagcgcg ggcggagcga ggtgcgtccc gggcgtgctg gggagtacat ggctgggaag  65820
gcggctgaca gaggccgtgg tgaaattagg tggggagacg tctacagggg acaaacaccg  65880
ccccatagta ctgggcggtg actcactcca cccggtaggt ggtaagagag ggtgaggaag  65940
gaggcccggc aagtgcgagg agatgaggaa ctaccgctga cctacccgga gatgataaat  66000
caggttctgc ttaccttagt aggttgctct gatcaaggtc aaacacctcg atgtttctgc  66060
tgcttctctc gggttttgga aatacgacgg gcaaaatctg tttcacgcat ggatatgcca  66120
```

```
ttggaagcga aactatttcc tcgtttgact acggggccta tgatgacaag cggtgacaaa  66180
gatgaaccaa gaagggattg aaattgaaac ctccgtcttc aagggtgcta accgggatgc  66240
ctacgatttt ccgtcgattg tcatgagtta ccaagataaa atgggcatag tggaacgatt  66300
cggtgttgag tttttggact tatcagtttc aaaggaacgc caaatgcgcg gcggtcacat  66360
gttgagtgtc aaccaacgga ggaaccacct atgacttggc cattctctag cttatttatg  66420
gaagtatatc ccctgacctt gagggatagg aggagatgag ttttttggct tagagcaagt  66480
agaacgacgg tcacttcata tgaaggctaa gtttcgtgca ttatctaggt atgtcacttt  66540
gcgcccgggt tcacaagaag cggattcaaa ccgttttgtg aaaggggttg aggtcagttt  66600
tcagcccttt tgtagcggtg gcaaaatgaa atccttccag aaagtggtag acttctgtga  66660
tagaggtgga ggagtaaagt aggatgactt caccatggca tcgacatcaa aaaggtttga  66720
aaagggagag gtttaatggt tcttacacta cagggcgaga gttcgaggat tttcggtggg  66780
ccgttgtctg ctcaggaggc tgtggtgggg tccgctaccg gaccgtgaca tttctgcggg  66840
agtagggtca ttccagacct caatcattct cacaaatact atactgggct ccagagaatg  66900
ttatggatgt gggaggctgg accataatgg gaagttatga cgaggtccca tgggccaggc  66960
cagctaggtg gggtggtggt aggagaggca gttgataagg aggccagtgg ccaggtaatg  67020
ggtgagtcct gaaggcagcc aggagtgagg acaagtgaac tacaacctta ccacatggtg  67080
agggcagccg aggcagcagg caaattagta ggggctacgg ctgtgcagcc tcgcagtctg  67140
gcggggacat cagatgttgt tatcaccggt aatcttttgg tttgtgattg catggctacg  67200
tcattatcgg atcctgatcc acatttcata tgtatcttcc tatttgttac tggtgtaatt  67260
tacattgtga attgcttgac atgctatttg tgtttctact ccgttggtga gtcatgatag  67320
ttgaaaaggt atataggtct tgtccgtgac ttttgtgggg agcacactca tgtagatttg  67380
gttattttag aaatggttga tttctgatgt aattacgggt atgacttgct ttccaaattt  67440
tgcaatctta gattgtaatg ctaaaagcgt aacgttggcc aagccaggga catccagatt  67500
agtaatggga gtgtgactac acttccgctc cagataaata tcatatcctt tttcgtgcta  67560
agagaatggt tagtaaaggg tgtttagcct tcttggcacc tcagtgatga tactaagtac  67620
cttcgagtga gcctggggtt tcggtagttc gtgagtttta gacgtgttcc ctcgcacctt  67680
ctccggtatg ccaccgacga ggatattgac ttttgcattg atttgggccg agtactcatt  67740
cccatttccc cccttatag aatggctcaa acgagttaag gagttaaaag cccaacttca  67800
aaaactgtta ggggaagagc tttattaggc cgagtgcatc cccttagggt gctttgtttt  67860
tgtttgtgaa gaagaagatg ggagtcttcg gatgtgcata gattactggc aactaaataa  67920
agtaactgtt aagaacaggt accctcttcc ctcgcattga tgacttgacc gatcgatttc  67980
taaggtgcta tgtcttctct aagattgact tgagatggtt atcatcaatt gaaaatccag  68040
gcgtgagata tgccaaggcc cttttcgaag acggtatggg cattatgaat tcttggtaat  68100
gtcctttgga ctaacaaaat gcccctgcta ctttctgcga gcttgatgag catttttttaa  68160
gccatatcta tggatctctt tagatcgtat ttattgatga tatcttgata tactcaagag  68220
aaagaaggaa catgaggagc atttgagagt tgtgttggaa atgttgagga gaaaaagctt  68280
tatgccaaat tctccaagta tgagttttgg ctagattgat tgtccttctt gaggcaacgt  68340
agtttctaag ggaggagtga tgtagatcct tctaagatca agtagttaga agaattgggt  68400
aagacctact aatatgtcgt aaataagaag ctttgttggt ttaaccattc taccgtcgat  68460
```

-continued

```
ttgtcaaggg attctcttcc attgcttccc aattcgaact taactaagca gaatgttcca  68520
tttgtatggt cggatgaatg tgaggaaatc tttcgtaaac tcaagacctt gtttgacttc  68580
accgcaccta tccttacctt tccaaagaga gagggtaaga acttcattgt gtattgtgat  68640
gcatcatatt ctggttcgca aaaaaaaaaa aaaaagtgct aatgcaagag aagaacgtaa  68700
ttgtgtatgc ttcgaggcaa ttaaaggtgc atgaacgtaa ttatccaacc cacgtatttg  68760
gagttggtca tggatagtgt ttgcattaaa caatggagac actatctata tggggggtta  68820
agtgaagtct atcacggatc atcgtagcct acagtatgtc tttaccggaa agatttgaat  68880
ttgagacgga gggaggtgga tggaactaat gcgaaggatt atgatgttta ccatcttgta  68940
tcacccagaa aggctaatct tgtggcggta taggtagaaa aagcaggagc atggtagttt  69000
agctcacttg caagcttcta ggcgcccatt ggcctagaga ggtgagacta cggctaataa  69060
ctttatgaga ttggaagtaa aaaatgagaa gggagtgatt ttttggcggt gtggaggcgt  69120
agatattctt ttcttgacaa gatcaaagga aaaacagttt ttaatgatga gaaattgatc  69180
cgaattaggg atatggtgtt atgagggaga gtctaaaaaa gcaacaatcg atgaggaagg  69240
tgttttgaga atcaagggaa gggtgatgtg taccctgcgt tgatgacttg atcaacacta  69300
ttatgagagg ctcatagttc aaggtatttt atacacctgg tgcaaccaag atgtatcgtg  69360
acctaaagca acacttttgg tggagtagaa tggtagcgac attgttgatt ttgttgccaa  69420
atgtccaaat tgtcaacaag taaagtatga acaccggagg caggaggaac actttcagag  69480
aatgcccatt ctgaatggaa atgggagaaa ttgcaatgga tttcgtggtt ggtcttccaa  69540
agacaatggg taaatgactc tatttgggtg attgttgata ggttaactaa gtctgctcat  69600
ttcattcgtc aaggtgactt acaatgctga gaaattagcc aaactttaca tccagtagat  69660
tgttaggttc atggagttcc actctccatc atatcggata aattaccagt ttactttaag  69720
ttttggagaa cattgcatgc ggaattaggt actaggttga accttagtgc gcatttcacc  69780
cctcgagacg atggagatga tcggcgagcg attcaagtgt tggaggatat gccgtgcatg  69840
tgtgatagaa tttggtggcc atgggatagc ttcttaccct tagcggagtt ttcatacaat  69900
aatagctatc actcaagtat tgacatggcc ccatttgaag cattgtatgg taggagatat  69960
aggtctccca ttgggtggtt tgatgcattt gaggttagac cttgggggtc ttgacctttt  70020
gaggttatta gaggcggtga aatctattca gaaaagcttt taagcggtaa agtaggcaaa  70080
aataatgtcc ggatcgaagg ttagagactt aaggtttatg gagggtgagc aagtcttctt  70140
tgaaggtttt cgccaaagaa aggggtgatg cggtttggta aagaggtaag ctaagcccaa  70200
ggtatattgg accatttgaa gtacttagcg aataggggag gtggcttatg aattagcctt  70260
gcctcggggt tgtcagagtg catccggtat ttcatgtgtc tatgttgaaa agttaccatg  70320
gggatggaaa cacatcatcg ttgggattga tctggctttg atgagaattt gtcccataag  70380
tatgagcctt tgtgccattc tagatagaga aattcgcaag ttaagatcaa gtgagattgc  70440
atccatcaaa gttcaatgga agaatcgacc cgattgaaga ggccacttgg ggagaaggaa  70500
gtcgatgtgc aaagaaagat acccacaacc tacttacgta ttcgtgtact cccgcttttt  70560
tttttggcgt gatcgttcga ggacgaacga tgggtaaatt ggtatctatt gtaacgactg  70620
cttagtcgct tttgagtatt gattttattt ccccgaaaaa ctgaagtcat cggaacccac  70680
gacggaccgt cacgggcaca cgacggaccg agggtgtctc attccaaaac acttagaatt  70740
ctggaatttg ggtaccgaat cgactctctc gaacttcgta acgatggcga cggaccgtcg  70800
tgagcggcgg accgtcacac atcttccata ggaattgagt ctacgaactt ctgtgtgacg  70860
```

-continued

```
gcggcggaga cggaccgtcg cagtacccgt cactgcaatc ccgtaatccc agctggccgg  70920
tcacattaag tgatttaagg ggcgttttgg actattccct ttaattataa agttagtggg  70980
ttaatgttaa taagtctaat tactgagggt taaaaagagg taaccttgag ttaatttggg  71040
ttattattga catctttata cttaattata ttctaattag ggtaaaagaa agagggtttg  71100
aataagaaac aatagaaaag agcgagagga agagaatgag aaagagagaa aacaagcgag  71160
cgaaaaaaca caagatttga aattgctttt tgcttgatca aaattcttga ttggaggtag  71220
gttattgttt ttatactatt attagtaaac tcttaatagc gaatgatatg tgttgggttg  71280
tattgtaaag tcttctatat gcttaattgt atgcttgtat gaatgtgatt atataattgt  71340
gataaaataa gcaagataaa gctattgaat cccaaatctt gaaaacccct tgttaatgat  71400
gatgccttgg tataaaagaa ggcttgatga actaaagtaa tgagattgat gatgccttgg  71460
tataaaaaaa gggttgatga tgccttggta taaaagaagg attgatgaat taatagaatg  71520
agattagtgg agcgggtgtc acgaaccgac acgtagtatt agggggaccg ggtgtcacga  71580
accgacacgt agtattaggg ggaccgggtg tcatgaaccg acacatagaa ttaggggatc  71640
gggtgtcacg aaccgacacg tggaattgg ggggatcggg tgtcacgaac cggccacgta  71700
taattggggg atcgggtgtc accgaaccga gccgcgtaga attaggggat cggagtgtca  71760
cgcatcgacc acatagtagt aggggagcgg gtgtcgtcgc accgacacaa gaggaataaa  71820
gataatgaat cttgaaagat gttaatatac tcaatctaat gaacctaatc ccaaatgagt  71880
atggtattga ggcttgagtc cgcatgtgtg aacttggcgg tacttattaa tgattatagt  71940
acttgttgtt gttacatgtt gagtattgta gttgatttat gatattatct gatatatata  72000
ctattttcta ttttgagttg gccgatgata cctactcagt acccgtgttt tgtactgacc  72060
cctacttgta tttgtttcct ttgttatttg tggagtgtag caaacgtacc gtcgtcttca  72120
actcaaccgc aactctagcc agtcttcatt acaccggatt ttagggtgag ctaatgcttc  72180
tagcttggac tggatcttct tcctcatgtc ttgatgcctt gaagttccgg catggactag  72240
attttgttta ttttagcttc ttagaatact cttagtttag taatttgatc atagatgttc  72300
ttgtggtgat gacttccaga ttttggggaa tattagttgt tgaattttag aagctattga  72360
attggttttt attaatgagt ttatgtcttc cgcattactt ctgttgatat tatattgaaa  72420
tgttaaggtt tagattggtt ggttcgctca cataggaggg taagtgtggg tgccagtcgc  72480
ggctcggttt tgggtcgtga catttcataa cattactctt tgaataatta atataaattg  72540
agcaatataa acttttcaaa atgacttatt ctagatatat gatcaatttg aggaatgaat  72600
gttccaacaa acatataata gactaataag atcaataaat tatacatata aacgaaaagt  72660
ttaaataaaa atacaacctc aaaatcacat atatactaca tagaatatga ttcattcttt  72720
atctccaatt aggtgggtca tttttatttt agttcatata tatatgtgtg tgtgtgtgtg  72780
tgtgcgtgtg tgtgtgtgtg tggcgtcttg gcgtcttggc gtgtcttggt gtgttaatgt  72840
gcgtgtgcgt gtgtgtgtgt gtgtatgaat ttcatcagta attaagatac atagtagaac  72900
atgaattgta tattactatt ttcttcatgt aggatacaaa atattctaat aaaaaaatct  72960
aagaaagtac atcaacatat ataaaaagga aatatataat acttaggacg gacaaaagga  73020
gcggataaaa acaaaaaata attactacac atacaaaatg atttgcaaag ttcatttttg  73080
catgataatc tctcatcctc ttcttgtcat atacatgaag atcatgctag ataatttata  73140
gaagtagcta tgatgacctt tgaatagata attaatttgc attaaattag ttcaatggtt  73200
```

-continued

```
ttagtccata tcaaatttgt ttaatggaaa aaattttcaa atactcctga ttttcacaat  73260
agagtaatta attattaatg tgaatttgat acatgcatca atctaaatga gttatttatc  73320
aaaaataaaa tgaaatagag tagactaaaa ataataaaat agctaatgaa ttctaaaact  73380
tttaaataac aaaaattaaa gaaagaaata gttctagttt ataagaatag tggaacttcc  73440
tcaataacta acaaaaacat aaacaaatct atatcttttt tattgcatat gttatgaaca  73500
attacattca tcaacaatta tccatcaata attatacatt agaataacaa agcatatgca  73560
tcaacaaaaa gtaattgtgt tgaacaatgt gtcaagtgta attacatcca ccaataatta  73620
ttcataaaca attatacatc ggaataacta agtgtgcatt aatataaagt gattttgaag  73680
ataatttttt ggtatttata gttacaagtt tggaattgta aaagtcattt aaaaattaat  73740
gatatacata acgtttatga gaattagatt gtttaaagtt gagcatatgt aaagtttctt  73800
actaaaatct aaatgtgtca tattaagatg tatggtaatt caaaggacat ttttgttctt  73860
taatgttaat tgatattttg aatataattt atcatctttt tgttatgaaa tacttcatct  73920
cttgaactct attttagaat aaaagacaaa ttaaacattt ctttaattat ttctacctag  73980
aaacataatg gattaatacc atataagtat tatttaagta atattttatt aattatttct  74040
ttaataatat ttaaattagt aaaagggtag aatcataatc ctattttaaa gttaagatct  74100
tctcacttat aataaaataa taataattta cggactagcc ccgcttgttt acctatatta  74160
gtcaatacat ttttaaaaaa aagtataaat attattaata atattgtttt atgtttaaaa  74220
attaaaagga gtatatactc cttaaaatga gtaaaagaat ctatgagatt ttttatccaa  74280
atactttttt tttctagata gaataaatga aataataagt tctaaattta atcaataaaa  74340
acataaagtt gcagaatata aaaatattta gcaatactgt ttttcttctt caacgctacc  74400
tcgtctttcg ttattagggg tatttattta caaacatgaa atcacaccat gattttattt  74460
tcatacaagt agtaaatcat ttataaattc taaaaaaaca cattaaatat aatgcatgct  74520
aatttttgt agatttaatt atgagaaaaa actaattaca tcaattattc aattctctta  74580
tccaataacc tagagtgttc actacatgat aatcaacttg ttataacaaa cataatcttt  74640
aaaagaagat ttgtacatca gacatgtaaa tgaaaaattt tcttttcttt tttcactgcc  74700
attattcaag aaaaagtagt caatttacct tccttcaacc gaaaaattga atgtaacaaa  74760
taatgaacta agtaaaaata tgcaacattg aaatgaaaaa taatacttac caaacaacaa  74820
ataaatgtcc atgacgcctt taaccttctt gaagaatgca tcgaatgcac tgaaatgatt  74880
aaattctaat tcagatacta tattctccaa gatttaccgt caataaatta acaaaacaac  74940
atacatattt tttctcacac aagtaggttt gttttacctc atgaacgttg agcagactat  75000
ttgtccaaat gaaaaactct ctagaattat ttatcacctg tttgcgttga aaacataaat  75060
tttcgatgaa aagaataaaa caaaacatgt aatattagtt ctatctatat acatatatgc  75120
ctaaaattta ttgatcaaaa gaaacatgaa aattttgaag aagaattttt gagataaatc  75180
aattcacatg ctattgtcat gagaagacat caaaataatg tattttgttg gaaaaatcat  75240
gtatataatt ttatcaatgg aactcttcaa attctttaac ttaaaattaa ataaaagatg  75300
ttttgaaatg tttgaacttc atttgtttga atgactattt atctttcatt atatctttat  75360
tactttaaag tttattatct aattatttat taaaaatact tttacatttt aaaaaaataga  75420
aaaaatttaa gtgaatggta aaatggtaat ttaactttga ggttaggagc ttcccactta  75480
taataatata tgatgataat tcgccagaat aatacagata tatgtataat atacaattat  75540
ttaaccgata tcatatctga ttcctctctt ccactctctc tcctctctca cccgcctctc  75600
```

```
tcctcccact ctcaattttc ctttccatat atacaaatac atatgtataa tatacaatta  75660
tctaaacgat atatatatat atatgcaatt catctctctc tcactctttg cttcacttga  75720
caactatgac acttaacttt ggatatgcac aaattgacat ttaaaaactg gttacagaga  75780
aacttaatgc tgttgcgtat aaagttgatg acttattgga tgaacttgaa tatgaggcag  75840
caagactctg tttttcagca aacacatcaa gcagcaatat ctgagaaatt aaacacatat  75900
gatgatgtct tcttactcac cgagttatta gttatgctaa aatgtttacc cgagggattg  75960
cagcacctaa caaatctcac aatttttttt gataagtgaa agcatagtta aactctcaaa  76020
tgtagatgat aattaagctc ttgaagatta tcgctgaatt aagtgaattc gttattagtt  76080
tcaaaatgtt tagcctcctt gggacctgac gaatgattta aatttcaaac acaaggtcaa  76140
gctatatttg taaaattctt atggccaaac aagtcatact gcaacaaatt gtaaaaggat  76200
tattatactc caaaagtaaa gatttagaag agatctactc ttaacactaa ctaaaagatt  76260
attccaattc tcaaagcaaa tttatattcc tttccaacca aagaggtttt ccaaatttgc  76320
tttctagtaa tttttttttt ctgcacgata ggaatagatc tcatatactc cctccgttcc  76380
atattatgtg gtgtagttta attcaatacg gaatataaaa atgaaagaaa gacttttaaa  76440
atttatagtc taaaatgaat aataaaaaat tgtatgacta taaatcattt cattaagagt  76500
aaatgtacaa tttaaaataa aattgttact taatatagta acgtgtcttt tttttggaa  76560
actgcctaaa aaaaaaaaaa tagtcatata aattgaacac agggagtatc tacttacaaa  76620
gtaaaagttg tgtgtagaag attttggcat ataaatcata tcatatatca tcatatcata  76680
tattagtaaa agcatgaatt aaaaaaagtc aaaaagttaa attacgattt tatcccttct  76740
attaattaac ttgttataaa atatttaaat atttgattgt acaagtttaa ttaaaatgtt  76800
aaatgaattt taaacttcct aatattaatt tctaattaaa tatctaattt attaatattt  76860
atcatttata atccatatgt atataataat tataattttt taataaaagt ctaatcaaaa  76920
tattaatgac ttttagactt cctaacacta attcctaatt aaatatctaa tttattaata  76980
tttttatcat ctataatctc tctatatata ataattttac aaaaattaat aaaaagtctc  77040
tacgtaaatt tttatacttt tcttattctc ataactttta ccctaaataa caaaatttaa  77100
taattttaag ggtgcaaatc ttcaaaatgg agacacacac attgataatg tcctcttaat  77160
tattattaaa gaatgactct agcttcacaa atttaaattc attaatgctt aattacttag  77220
agaaaagtag atgaagactc ttaattttga tagtatatgg aaggattgtg tactaatttt  77280
gtacttattt tttcatctac atatacatag tcttataaaa atgatgtcta cattgtattt  77340
tttcttaatc tgtttctttt tgtctttttc ccccaattag acttcttaat ttagttttct  77400
acaaatgttt tattgtcgta agtctcttta cttattttgt aattgtagca ttttattatt  77460
cattataatt tgcatatatg tatttccatg aaatattagt aattctatca tatctataaa  77520
aattcacatg aaatacacgt gctcagaaac tagtaaggaa aacaacacaa atatacatcc  77580
gaactatcgt aaaaatgata tgcagatacc atcctcatac ttttgggaca ttgctgtcca  77640
ttacgtcaaa aaaatatagc atatatatta acggacatca cgtgtcataa tcatatcaat  77700
tgatccaaca tttaataaat attcgatcga cgaatagatt gtgtcacatg tccctattta  77760
gtcatatgtt aaagtgaatg acatatatgc tctagttttg aaactttctt gtaaaattta  77820
agtatatgcc ctaaattttt aacaatattt tgctacattt tacgtttttt ccattcacgt  77880
attttcttat ttactaaaca agtttctatc gtcctcagag tatttcctta attagcacta  77940
```

-continued aatgttgtga tgtttttctt caactaagtt tcattgaagg attgagatta aacctatttc 78000
ggtatccacg atctttgaat gaatcgccaa actctatcta tgaatttaat agcaaaagct 78060
cagattttgt tccaaattga gatataatat ttctataaag aaatttaaat taatgatgtg 78120
atataatgat aatgaattca gtttttacat tagaaagact ctatttttct ctcttacttc 78180
acaacaatgc aagaattctt aaagacctaa aaatggggta ggggtggggg aagggggcca 78240
acaacaacaa gattctaaat tcttgaatat ttttaactaa aaaattaatt cttttcccaa 78300
tggattcaaa ttgaaaagga aaactacaac tttgtgatta tcgcgctttc aaaatgttga 78360
atagattgtc ttcaggtgtg agaagaatga gagtgagatg gagaaccata cgaataaaga 78420
aattctcaag tacgattcca atggaaggaa ttgaactacc tattttgatc ggagataaca 78480
agtcattcga tagagagatt ttgaaactgc atatgtttcc taaatgaaag ttatatatta 78540
gctagatagg gatatagatg ggttgaattc tcaaaatcta agaataattt tggatatgtc 78600
taaagtgatt ggaaagtgaa tatatttagg acaaattaca tgattcgata tacttcacta 78660
ttatatatat tatttttaca tatactttta aaacactagt ttctggacac gtgcattgaa 78720
cgtgtatctc aaatatatga aatagatatt tttgaaattg taagacaatt ctaaaatatg 78780
gttgtgatgt ttagttatgt atgagagcaa tttaataaaa tatgtatgag actttttttaa 78840 tttgtttccc atttggtgtt ccgctagcta attcaaattc atgtgtgaca ttccactttg 78900
aggatacttc ctataaagtc tttccatcat caagaattga attcaaaaga ttgaatttag 78960
aacgaacgaa tatttatcaa tcaatcaact tatttgatga aaacatatat gaatttcagt 79020
ttgcacatat tataaaaggg caaacttcat atttcaaggg tactacctat aaggtctttc 79080
cattatcaag aattgaattc aaaagattga atttagaacg aacgaatatt tatcaatcaa 79140
ccaacatatt cgatgaaata tatatgaatt tcggtctgca catattttaa aagggcaaac 79200
ttcaaaattt atcgtatatg ccccaaattt ttaacaatat tttgctagtt tttagttttt 79260
tccattcacg cattttctta tttactaaac aagttcctat cgtcctcagg gtattttctt 79320
aattcagcac taaatgttgc gatgtttctc ttcaacaaag ttttcattga aggactgaga 79380
ttaaacctat ttgggtatcc atgatctttg aatgaatcgc caaactccat ctaagaattt 79440
aatagcaaaa gctcagattt tgttcaaaat tgagatataa catttctata tagaaattta 79500
aatcaatgat gtgatataat gataaatatg aattcagttt ttacattaga aggattcttt 79560
ttttctctct tatttcacaa caatgctaga attcataaaa acctaaaaat gggaatatta 79620
tcatattata attaaaagta aaactctatt ttagaaatag tggactaaac atctaaacta 79680
ataattcaat ggcctacgtt gatgtaagtt acgttatttt agcaaaatta agaagaaatt 79740
ccttcatttg agggtagaat cataaaaata aaaaatagaa aaatacatat gaaatatctt 79800
accgcaatca tgtgccctct ttgtattttt cattactatt gtctctcccc ccaacttgat 79860
caattacttt ttttaggaaa aataatccac gatgaatgta ttcgtcaatt ttcactgatt 79920
atgtgaacac aaattattaa gttctctctt gaatgaaaac aaaaaaaaaa gaaattattt 79980
aaagaatcaa aaaaaattaa acgtaaatcc ccttgcacta tttagagaaa ttttctatgt 80040
gaagcatatt tcacaattaa ttgcacattt ctctgttctc ttcttctctt cttgaataaa 80100
aagtcaatac ctaaattccc atgataagag tatcaaagaa acatattact ggattaggga 80160
tgaatcattt atgaaattgt gaagtgattt tagatactca cagaaaaaaa atcaccaaga 80220
atttataagg agtggatgat tgtgatttat gatcgaaaaa agatgaaggt taaaattgtt 80280
gtgactatta atacgaaata tgtcttcttt aacaaataaa agtttattta attttaaatg 80340
atacaaataa tattgaagta tgtacatgat gaaaatcgta agaagaaata caagtatgat 80400
tgatgaataa gttgctataa tttattcacc gattctttct tatgtagtac ctcgagtttg 80460
gttgaatttc gaacttgatc aatagttgca aacaacactt gagatatttt aagaagaaga 80520
aatataaaaa tgtgaagaaa cacttcaatt tatagctaac aaattgtgtt atgaatatgt 80580
gttaattgtg tctttttagt aaagctacaa cccttcgaaa aaggcattgc tcatgagaaa 80640
gtcacaatac tgagaaaaag ttacaactta tcaaaaaaga cacaatgctt tcgaaaactc 80700
aaaacctttt gaaaaaatca caacccttct gaaaagtcac aactcaccga aaatgtcaca 80760
actgtcaatt tcaacccttc aaaaagttac aattcatagc aaaaattcac aaaccgttta 80820
atgaaaaaaa actatctata tttaatataa tataagtaaa taaaataaaa ataaattaat 80880
tgtgtatttt tttttaattg gggatattat agtaatttaa cattcatttt gggagttcat 80940
gctttttagg tagtgctagt ttcgagcacg tgttttgcac gtgtgatcca tgtgaatttt 81000
atagatatgt tagaatgact aaaaattaat ggcaatatat atgtaaattg taatgaaaaa 81060
taaaatgtaa caattacaaa tctagtataa agacttacgg caataaaaca ttcatagaaa 81120
actaaattaa gaagtctata gagagaaaaa aagacaaaaa gaaacagatt taagaaaaat 81180
acaatgtaga cattattctt ataagactga taaatatata gctgaaagaa taagtataaa 81240
attagtacat ataactctct gagttcttca actcctttca tatcctatca aaattcaaga 81300
gtcttcttca tctactttaa caatagaata aaattaatag cctaataatc ttggtagggg 81360
tttcatgaga taaaaagttg aattttatag atagagtaga aggaatatca aaagatatct 81420
ttaagtttaa gtttagatat ttggaagtta tgaatatgaa aagattagag ttatgaatgt 81480
tgagagtaaa aaagttgaat aagtaattat aaaataataa taaataagta aataaatatga 81540
aaaagaaaat taaaggtagc aaaccatgta gaaagaacaa ctaaagttct tatcacgtaa 81600
ttaattttaa tttaaatttg ttaagctaga gtcattcttt aataataatc aagaggacat 81660
tatcaatgtg tgtctccatt ttgcagattt gcacctttta aattactaaa tttcgttatt 81720
tatcataaag aataatactt tatccacata aattatatta ttcatgagag gggttaagga 81780
aagttatgag aagaggaaaa gtatagcaat ttaggtatag actttttaat tttatttttt 81840
ttttataatt attatataca tatagattat atgataatta ttaataaatt agatatttaa 81900
ttaggaatta atcttagaaa gtctaaaagt cattaagatt ttaattaaat aaacaatcaa 81960
atatttaaat attttataac atttaattta tagaagagat aaaaccgtaa ttcaactttc 82020
aacttttttt gttcttgctt ttagtaatac tagcaattat aacaaactca tcagcatcaa 82080
ctcgacctgt atatttcata atcaataatg tcttgtaaat attcatcgat gtgtcgaaac 82140
aaagcccccc acgtataata caatcatctt ctaattaatt gagctcaagc actttgatga 82200
aaaatcgaat ggcaggattc cacaagtaaa tatgcttgtt tataccaatc agtataaaac 82260
tatgactgtt aggttgtgga gcctgattaa tatttgatgt attatttatt ctctgtaact 82320
aaatatactc tgaattatta atatataccc caccgccgtg gaagtttacc cacgggggtg 82380
ttaccacgaa atattggttt ctctctttct agatctctct agatctctca tctctctcaa 82440
aagtttttgt gttcttcatt catcaagtgt gtgtggattc gatcctaaca acgacaagaa 82500
cctaaaatca tacaagttgg gggaaaagct cattatcatg acttagagga taggtgagtt 82560
cttccacaat gagttgttgg tttatttatt gaaagcaagg gttagagttc tacgttgcat 82620
tgacaattgc tcctccttct cgacgttgat ttgagagatg aataaaattt ggacttgaaa 82680
ttcaagaatg tcatgatcgt gaaacacact tgaatcgtaa tagagatttc acagataaaa 82740
ttgaaagaat tatcataatg gtttcattgg gtagatacac catcttgaca agtagtagat 82800
tttctgggta attttaattc tcgtatttct gatatagaca tatgctcaca aattgacgtg 82860
aaaccgcatg cgaaatttag gaacttatgc aggtgtttgg gcgcagtttt gactgtctat 82920
tgttgttccc taattaaata tacaccttct ctgtttcaac tttccaacag ttttgtgcta 82980
aagtatttgt tgttgcattt atttattcaa acttaatttg ttccaaaata tcatcagagt 83040
acaaactaaa ggattcaaca tgccttgagt acattttata ctgtcaatgg caatgctaca 83100
gcaattaagc accagtacat gaagcaaccg tttattggtt gagatttgag tgtcagtgtc 83160
attccttttc cattctttgt ttttggtagt aactatgata ttgccattgt ttataacttc 83220
aatgatctgc tgatattgtg gagcatgcaa aactaaaagc tatcgagtaa aagtgatcat 83280
aatgtgctag ttcatataag accatctaaa agctatcaat taaaacttat cgcagtgtgc 83340
taggaagtta agggtgtaca tatatttgca attggcagca aaacagagca aaagcaaagc 83400
attaagatca gaaaaagtag attaacctta acaaatcgag ctcgcctatt gtcccctaca 83460
gcaaagttaa acacctgcag tgtttaaaaa ccacaaacaa catttaacaa aagtgaatga 83520
ttaaaagtaa aaaaagaaaa aatcgagaaa gataaaaaag aacagaagac ggcataaact 83580
acaatatatg ttttccatca caggttattc atatcatccc ccataaaact ttctacttga 83640
gcactaccaa gaaactattg aggatgtggg accttgggat ggttagtcaa aatgagcttc 83700
tattatatcc ttctgtgtcc ttctattaaa gctctcctct tcttgtttat tttgtggagt 83760
cccaatttg gcgtggccaa ttccatgatg ccaaattggt aacaaatact tgaaagagtg 83820
atgactcaag agagatggtg aagaaagtag acatagttca acgaattgaa gtcatattcg 83880
agaacaatat tatccagata gttcaatgaa gtcatttatt caaaattcat aagcaaatat 83940
taatgtggaa aagttctatt catttccaaa ttgaacaaaa gaagcaaaca atagataagg 84000
tctccaacat ggagataata attgagagta aaaacttcta ttgctattaa atagaatctg 84060
caattaaaaa aaaaattaca tagatacaat atggaacttc aatatgtaca acttggaaac 84120
cctttcaatg cttgaggtct cagtttttac cacattcaga tacaaaaatg tagtaacaat 84180
ggcaattgtg cgcgattcta aaatggcaaa aaaataatgc caacttaact atggaaatta 84240
tgtacagata taactaacta taaaacttaa atcgtacagt ggcatatcaa cagagccttc 84300
ttaggctctg ctgctatcat caaaaaaagc ttttgactga ttctggcagt tcatggagta 84360
gtataagctt cggacgattt gaactgattc acacagcatg taactgattt aaaaattcag 84420
ttttactcta tcagagtcac caactccttt cttcccagaa gaactagcag ccgcttgttc 84480
cttcaaagct tccttctcca gtttcttctt ttcagcatca gctgcttgtt cattctcatc 84540
acgtgatttt ttaaacatct tcatgaacac caccaaaatt tgtgtcactg catccagaaa 84600
gtaaggaaat gaaaactgac aaagttcgtc acaaacattg tccggttaaa gagttggtga 84660
ggaaaaatct gttgaagcaa ttctcacacc agttaaaaca agatctcaag gacaaacgca 84720
attcgagaaa tctagccgat ggctatatgc actcaacaaa agctacaaag gccataaatg 84780
ttgcatccca taatcttcac ataaagatag acaactaaaa agcatcactg ataaacgcta 84840
ctggaatatc tatattacca agactgtttg aacgactgta gttttttctt ttccagatga 84900
ctgataagtg ataatacagc aagaaaataa cgtatgtatc tctaaccttg ctcaaagggg 84960
catcgagctg gatcttcgcc aaaatacagg gatagggagt ctgcactcct tccctgcaga 85020
tttacaggat agaaaaacaa tcaataaact tggcatggct tatacatcca ggaggcttta 85080

-continued

```
aaatatgaca taatggatgc aagaaactca ccacttcaat ataaagagta gtgagagact  85140

tgacttcagc ctcagcagta tcaaggaaat tctttaacac ctgagaagga atgcacgagt  85200

cacaaaccgc atatttcaga tgtttataac aaaattatat gtacaccaaa tcacagacat  85260

cgcaatcaag tttgactgca tcaccagact ccactctaaa accatgtcca acacaaacca  85320

aattggg                                                            85327
```

```
<210> SEQ ID NO 4
<211> LENGTH: 33516
<212> TYPE: DNA
<213> ORGANISM: Solanum habrochaites
<220> FEATURE:
<223> OTHER INFORMATION: >Genomic fragment 4

<400> SEQUENCE: 4

caacttggaa accctttcaa tgcttgaggt ctcagttttt accacattca gatacaaaaa     60

tgtagtaaca atggcaattg tgcgcgattc taaaatggca aaaaaataat gccaacttaa    120

ctatggaaat tatgtacaga tataactaac tataaaactt aaatcgtaca gtggcatatc    180

aacagagcct tcttaggctc tgctgctatc atcaaaaaaa gcttttgact gattctggca    240

gttcatggag tagtataagc ttcggacgat ttgaactgat tcacacagca tgtaactgat    300

ttaaaaattc agttttactc tatcagagtc accaactcct ttcttcccag aagaactagc    360

agccgcttgt tccttcaaag cttccttctc cagtttcttc ttttcagcat cagctgcttg    420

ttcattctca tcacgtgatt ttttaaacat cttcatgaac accaccaaaa tttgtgtcac    480

tgcatccaga aagtaaggaa atgaaaactg acaaagttcg tcacaaacat tgtccggtta    540

aagagttggt gaggaaaaat ctgttgaagc aattctcaca ccagttaaaa caagatctca    600

aggacaaacg caattcgaga aatctagccg atggctatat gcactcaaca aaagctacaa    660

aggccataaa tgttgcatcc cataatcttc acataaagat agacaactaa aaagcatcac    720

tgataaacgc tactggaata tctatattac caagactgtt tgaacgactg tagtttttc     780

ttttccagat gactgataag tgataataca gcaagaaaat aacgtatgta tctctaacct    840

tgctcaaagg ggcatcgagc tggatcttcg ccaaaataca gggataggga gtctgcactc    900

cttccctgca gatttacagg atagaaaaac aatcaataaa cttggcatgg cttatacatc    960

caggaggctt taaaatatga cataatggat gcaagaaact caccacttca atataaagag   1020

tagtgagaga cttgacttca gcctcagcag tatcaaggaa attctttaac acctgagaag   1080

gaatgcacga gtcacaaacc gcatatttca gatgtttata acaaaattat atgtacacca   1140

aatcacagac atcgcaatca agtttgactg catcaccaga ctccactcta aaaccatgtc   1200

caacacaaac caaattggga gttttcccag cgcaagcctt tttcacttga ccttgttaag   1260

aacacaaatg tcatccatcc attggggaca cctatcactc ttctaaaaca gtggtacact   1320

gcttccttac tttgttttct caaactatct agaataaagc tttttgatag taaataggga   1380

tccttgtaat gtataatgaa ggaaacctgg ggaaagagga atccgcacaa cgccgttcat   1440

ttcatatctg gcgtaagaaa atctcgagaa tttgataata catttagggg tcgtttggta   1500

gagcgtatta agaaaaatca tggatgcatt agccttgttt attgctagta ccatgtttgg   1560

tactcttttc taaactatgt acaactagtg ttgcattagt tatacactat cgtttattaa   1620

agtagattat gatatgacct tcaaagttaa aatttaaaac taaaaagaaa cattatcttg   1680

gaagtacaag taactcattt ggtttgtagg aataattcac atgttaccat tctcttttct   1740
```

```
caccttctga aatcctgaag atattgtacc atcattgtcg gatgcagtaa gttcttgttc   1800
aactttctca agacctttac tcactgcttg catttcttca gccaaagact tcagttgaat   1860
ctaaccatat aatatgatgt aaacaaacat ttcagttcac caaaatacca gtagtactgc   1920
aaaggaagac cataataaat agcaagggta ccttagaagc agcttccaag tgaagaagat   1980
ccttgtcaaa atcaagcaac tctggcattt tctcagcaag gagctgacaa aaaaacgaat   2040
ttacacattt ggcatcacat tgagaagtgc aaacatatat atgccgaaga gtaaagacta   2100
aggctggtca agccagctat agttgatagc taaaggctat caactaaagt tcactgatgg   2160
ttgggcaaaa gaacagcata aacgtagaat actgaaagta gaaaataaat acaaaaacat   2220
atagttttct acagaactca accttctata ttacaggaac ctcatgggtg caccaaaaag   2280
caataaggga caagaggcta ttccttaact gtgcaaatta ctctacactt tcaaaagctc   2340
tcctaattct cactctccac aaaacccaca taagtgcaaa agcatacctt tcacgccttg   2400
tgtctcctcc ttcatcttcc gccatttcag ttgagcaaca ttacttatac agtgacgggc   2460
atcacccaaa tttaccaaac gaacaccaca tttcccacca taaccgagaa gttatcgcac   2520
aatctagaag acgattcgcg tcttcacctg acccccttac acataaaaca ccgcccaaca   2580
taagtagttc tcctcttcat tcttttatca tccatcaaga tcacccctct tgttcctaac   2640
caagtgaaaa aacctacctt tctcagtacc ttagggatcc atatcaaaat atatggaagg   2700
ctatctttct tctcattgat caaaaatttg tccaaagaaa aggactttag caaatttatt   2760
cttaggcggc caaaatgaaa cttagattac aatgaaacct taacaaagac aagaattcaa   2820
tgaaacctaa acaaagacaa ggaccagaca atagagtcta gctaaaaaga atctgggctt   2880
gctttttcaa ttcaaatctg tgagcgagga ttcctctttc tcttctccac aaaaatttga   2940
agtggtttat aacttacgga gtatccgata atctcttgca atcttgtata agcctgtgca   3000
gatgaaataa cttgaacatt tccaggagtc aatcgatttg caccagtcga ccagtgggag   3060
cgataatttt aagatataaa catcatataa ccttcctttt agcctattcc cacttgagcg   3120
tacttcacag ctgatacgct cataatactt gacgccccga aataatgaac agggatagat   3180
atggagatac aatttaagaa aatgaacctt aggcacttca atataagaga agagagaagt   3240
agaacaaaat aaagaacaat gcaactggaa aaatgttgaa aataaagtga acgatataag   3300
atggattagt tttcagattt tcatctttaa gagctgctga ctctcaaaaa tctgctacac   3360
cgccttgccg ccgccttctt gtttgagtgc tcaacagaag cacctatacg cacttggact   3420
ttccttaggg tgatttaata gatttttgt gtattttatt tccaattgtt tcatttggca   3480
agatactcta agcttgaaat ttttaatttc tatttagata gtcttgtatg cctaatttca   3540
tgtttgatct tctatttcat tttagagtat tggagttgat actggatcta gctatcaccg   3600
acctactgtc gtactagcgt caagtgcagc acttagccaa taatccccaa taataggggc   3660
tacacttaga caaagtatga atcaagaagt tgtaagtgtt agatgcatgt gtggcattta   3720
gctatgttta acctcttttg ctggagtaat ctctcctttg taaatgatat ggatcaatca   3780
acccaccaat agttctagta attcctgaac tactaagtgt actaccaagc attctaaagc   3840
ctcatgcatc ttccttgatt gtgtagaaca tgccatactt atgtggtgag ccttgcttgt   3900
gcactatggc tcccacttgt gcatcaccat gcctcgtgca tgctacatca tcagaccatg   3960
ctcttgtgct aacactatca ccataccagc ccagccatgc ctccatgaaa cagttcctaa   4020
ttttctttgc gttactacta agacaacgaa tcgtttgatc ttgaaattcc ttgcctcctc   4080
tctgttagcc tggtccatgg ctttgttgca cttgcgcatc atgccacact tatgtttgtg   4140
```

-continued

```
aaccgtgctt gtacactatg gcttccacta gtgcttcttc accatgcctc atgcatgctt   4200
catcttagta gcatcctctt gtgccaaaac aaccacgcct accagccatg cctaacatgg   4260
aactgttccc caatttcttt aactttctaa ttaaaactta aacaaagaat catttggttt   4320
ttgagtgttg aaaccttgaa agcgctcgcc tcctctaaag tagcccctt catggtttta    4380
gatgggttat gacatagacc tcaaatacac ttggcacttt ttcaatccaa tcatgagcta   4440
ctcaacaatt attactgagc caaaactaat ctgattcaac ttacgcttaa gtcacctcca   4500
actcttccca attcagagct aattgatcaa tactaattac ataaaggtaa aaacagaaag   4560
gcatcataat gcagtaattc taccttgcac agataatgca tcaaggtcat tttgttgttt   4620
ctcgcacgag tgtcagaaag cttaagaaga ctgtccaact tgaaccctac agcagatcct   4680
gtaacgtaat tacaaaacaa agatgttagt cacgatgcct ccacccaaca actgattatt   4740
ttcttataga gatatagatc ttagaaaact gtacctcgtg ctgtaccctg attcagtgca   4800
ttacccaatg ttagaatggt ctgcattatc tgacgtaatt tggcagattc tttcacctac   4860
ttgaccagga aattcagtta gagcctagtt aaatcagaat gtgccaaatc aaacttcata   4920
aggtattaaa aatacctctc tagtagcatc attgattgta ctcaggttac ttctcaagtc   4980
cttcacctga acaattcaac atattatagt caacagaaaa ttaatggcag aatccataga   5040
cattagatca ctaagaagta caagagaaaa tacctgatta gagaaagtga tagtaaatga   5100
aaacactcgt aacttggact caactcgtgg gaccttcatc agctccagga aaaactgaaa   5160
cgggtattac ttatccggtt aattacttat aacttaaagg ataggaaaac ttgtacttcc   5220
ccacatatat ggtcaaaatg gagaagacct gctcacactt tccaagcatc cccttgtccc   5280
cattatagtt ctggaaaata gaacataacc agtaagatca aattgtgaaa tcaagaataa   5340
caattaaata tcaaattgca agtatagact gtcaagaaac taacataact aagttcacaa   5400
agagaggggg aaatcaagca gaaacaagta tggatctaca tacacaaaag actaagatat   5460
atgcctatgt ttatacacat ccacacccac cgggaaagga agttcccagg aaaaggtatc   5520
tgcatgatta gacattgaaa cagacacatg agcatgcacg cacagcatag atgcaagtac   5580
atactgtata agcatgaaac cgccaaatgg gtcattgact tatgggcatc aacctacaca   5640
gctacttgca acaaatggca catcaacaaa actataggct cctgctgttc ctacgactca   5700
cttaactatt cttacgttaa gtacaattgc agaatgtgaa ggttccgact cttgtttcca   5760
aatactatgg gcaaaaaact tcaatatgga gtattttctc taaacgggaa aagttaaaag   5820
aagaatcaaa gcaaacttca gaacatacct ctaatattac ttgtgaactc aaaataaatg   5880
actagacaca cattataagc atattattgt aacttaaact ttgccatgat aggcaagcac   5940
agtaggatga gaaagagatt ataccctcag tgtctccatt tcttcttttg ttgggcaaaa   6000
ttttatcaga ttttcaacct gatcaatgtc cagagctgat gaatccaaag ccaaaatagc   6060
attctgtatg acatgcatac aaatataatt tgtaagaaat ccgcggtaaa ttttcctttg   6120
taaacagaaa ttttatttgc atttgcataa tactggccgc gagttcaaat agcggacccc   6180
aacttgtctg gaactgaggc gcaactgttg ttataatatt agtaaaaaga aatccatggc   6240
aaatatttca ttcatttcaa tgtacctcca ttaaaactca aaataaggaa aaaagaactt   6300
ccaaagaaac catgcatgag catcctaaag aaatgctcgt cagtcattac acttattgaa   6360
cacatgcatg aatcagcata ttgatactgt gcattatgaa acatgatttt gaccaaaggc   6420
caaaggatag aatattttat acaatttcta tcatgattcc tttgaatttc aaaggaaaaa   6480
```

```
tatccataag agttcaattt tgaactcttc aagttcggtg aaattacatg atcttttcaa   6540
cacaataaaa ttatcaaaaa tataaaaaat aagaaagtct tttggataaa tagttctaca   6600
gctacttcca tagaaagctc cttttctcct tgtacaaaat aaaggtttct ttatccattt   6660
cattgaactc cggctaaaaa atatttctaa taacgatagt gtctgatcct acttgtgctc   6720
gtatcttgac taatttatag ggtacttgac acctcctatc aacataggta tggggaacta   6780
tgccctccaa aatgcaatca gatgaggaaa accaccaagt cttagttttg gtcgctacta   6840
gaaaaaccac ttggccacac tctaaagtgc tcattgaact ccaccaatat gagaaaagca   6900
taactaactt gaaactgaat tacaaggaga actgttatag gttaatggct aacataaaaa   6960
tagtcaaact accaaactcc tctgtgtatg acctaaatgt tatgtgtagt taaccgattt   7020
atacgttctt cattcctttg ttgagaaaaa atatagatag ttaatcaata tattgtactt   7080
ctattaagca gaaacgaaga tacttcaatt tagagttcag tacataatat aatctttttg   7140
atctagtaaa aagattatag catgaagagt tcaatacata caagatacaa caatcttttc   7200
cttttttttg ttgttgagaa tggactttta gtcaaaccca ttaagctgat tcaataattt   7260
tgcagatcta tttgattcat cagatacata cttctatagt tttagcaaat gtacaaaggg   7320
attaaaaaaa actaaaatac taaattgtaa tcttttggaa aataaagtca aacaacatat   7380
gcattcaatt gcatatgtaa tttgttactt gatttcaatt gataaacaca tcaggattcg   7440
ttaattttaa tggctgttta gtttgtgtta ctttttaaat tattagcagc tcaatttcca   7500
aatatctgat tgtcctaaag cccaagtaaa gatcacataa tctaatagtt tcatctgata   7560
aacaataata gattattatc aaaagaccca cctgttggct agaagacata aattagtgcg   7620
caatagataa aagtatcgaa gctcatagta gaaacgagaa gacacaaaaa gaactcacaa   7680
gcatatcagg caggggaatc ttgatttttg taagcatgat ttcacaattg tatgccctgc   7740
gcaaatcaat ctggcaaaag catatgttaa gaaatcatcc cggtctttta acagttagac   7800
caaaatgtaa cacttccagt ctttcactat aaataatggg agttgtgtaa aataaacctc   7860
aatacctcag gaagaaaaag aagccaacac caatagactg ttcaccaact attccatagt   7920
gatctcatat tatacagtga aagctttgaa aactatcagt ttctttctat agaagttttc   7980
tatctctttc ccaatttagc actaacagat aaattaagaa gcaagtgaac tgcaattcat   8040
tcatggtcaa tggccatccc catgggacac agtgcccatt atgagcacag cctccgcaac   8100
tctttcatta gatctagaca tgtatcgcag cctaataaaa ttactctgtt gcatgaattt   8160
acatctcaaa gtattaacac aactttttaag aatttttcaa aggcaaccat tattttttta   8220
tatgattgac tccatccact aaaccctctg cctaagacgc ccaagagagg tttcccctt    8280
tatcccttcg ttaatcaaac ccccaacctt atggttggag atgaaggacc ttaccctagg   8340
atatcactcc agtcaaagat aattgtctta actttcatga aacagaaatg gtattaccta   8400
caggatggag aaaggaggac ttttccaccc aaagtttatg taatcatcca catccaggct   8460
gaaaaaacat aagttcttct ctataagggc atgcttgttt cgaaacgtca cctatgttaa   8520
acccatttaa gcctttctat ttacttcttt tcttccacct tgttagccac aagataccac   8580
aaaaagtgct ctttaaaacc tatctaatat ttaattgttt tgttaaacta gtaaagaaag   8640
gagatacact catcctacaa cactcacttt actacatgaa agacttgcta gataatgcct   8700
actggagaat aacagttgta gagactggaa acaagataaa gcatatataa cttgccaatt   8760
gcactttttc tggtttgttg atttttgaac cacgtcggcc tccacctttg ctagtgccat   8820
cagtagctga agccaccgaa aacaaattct caagctccgt aatatcaatt tcaggtgctc   8880
```

```
tgtcatgtac attaataaaa tcttatcaga actacccata acagacagat aacaaataaa   8940

agttgcagta cccaacacaa actaggttaa gctcaaaggg ctcagaacta ctatatctgt   9000

aatctattaa gcattcgaag ttgaaaccat gagaatgata gtgcttatga caacctgtta   9060

aggggtttca cgagacacga gaaatagcga acaatttagc tctgactatt aacttgaaat   9120

gacacacaaa gttctcattg taatttttca tccccaaaaa taaaatcttt atacctggaa   9180

gtattttcct tgttttgcgt atcagcccat aaactccctt gcatagcccg tgtaactttc   9240

gaccaatgta agggcttcaa tgaagctttt ttcggaggaa ttgaagtacc tcctgtacct   9300

cgcccttttc ctagagcagt tgaacctaca gaggctctta cacgtccggt agatggaggt   9360

ggtggcgctg gcacactaag gccctttcca ccaggcgggg gaggtggagt gggtgtcaaa   9420

ccccgcctag gggggtggtgg agcattagga gcctttggtg ctggtggagg tgctggtgga   9480

gtggaacctt gcctaggaac tcccaaagga ggtggaggag gtgcaggtgg ccttgtagaa   9540

ttgtttgacg gtggaggtgg tggcggtgga ggtgccaacg gagtaggcct atttgatgaa   9600

gaaggcggag gtggaggcgg tggtggtgga ggtgccaacg gagttggcct atttgacgta   9660

gaggatggag gtggaggcgg tggtggtgga ggtgccaaca gagttggcct atttgacgta   9720

gaggatggag gtggaggtgg aggaggtgga ggtggaggtg ccaacgaagt tggccttttt   9780

gacgtagaag atggaggtgg aggtggaggc ggtggaggtg gaggtgccaa cagagttggc   9840

ctatttgaag tagaggacgg aggtggaggt ggaggtggag gtggagcggg aggtggaggg   9900

cctttggaaa gggctgaagg ggtaagcggg ggaggtggag aaggcgggga agttacacaa   9960

agcaagggtg aacacttcaa tgacatgaaa ggggagggga ggggtggagg aggagctgat  10020

aaattacagt tagatggacc ccgaggagga ggaggtggag gtggaggtgg aggcaaggca  10080

cttctagaag tagaaaacgt agggacagat ggtggatgtg gaggagcaga agagcataaa  10140

aggctctgat taggaagtgg tggaggtggt ggaggtggcg gaggtcctct agaaaagcta  10200

tcaggggaag ttgaagaagt aggttgtctt ggcggtgaat gttctctatg gctaccaatt  10260

gaaggtggtg gtggtggtgg tggtggaggt ggaggtggag gtgatctatt agaacttgca  10320

agtggtggaa gcggacgagt acgttggaca gaagaaggga caccaattat aggaggaggt  10380

ggaggtggtg gaggaggcgg aggaggtaat gagacctcct tgctaggaga accaaacaga  10440

gagggtggtg aagggggaga tggagctgat gattgagtga cttttatact agaaatcaca  10500

gaggcaggtg acggaggtgg tgaaggtagc ggagaagaag aggaagtcct tgtatcgcaa  10560

atttgaactc cctttaaacg ttcaggagaa atggcagtat ccaattgaca gttactttca  10620

gaaagagact gaacaggacc aagatctgac tttgaaagct tcatttgacc ctcagaaatc  10680

ttgggatcag aagttccatc agaagctgaa tcctgttcat ctaaaaagtt gacatctgtt  10740

gtattagcat aactaatact actagctttc tctgagtcca gaaaatccaa actgtcggca  10800

atgctcgatg cattattttc ttcttcagaa tcaaatgggg atgaataccc actcatccta  10860

ctttgcaaaa ttgacaaatc tttcatatca ttcagcaccg atagctgttt aaacaaccac  10920

aacgcagcat catcaccagt atcaacccaa tcagcaccac taaaaagttc ttgtaccctt  10980

gaaaaggctt caataggaag tccaccagtc tcctcaccat tgagagctgc agtgggagct  11040

tttagtggag atatgctctc aacatcacca aataaaacct gcaaagcaga aagtataagt  11100

tagaggagaa atatgaagag caaaggtgat ccaataaaac aaaactaatc agacagtttg  11160

taaataagta ttcacctcag ctcgaaagcc ttttggatag cgtgcctttg aatcccatag  11220
```

aatatccagg ttatcgcagt ttaacatcaa aatgttagag cgaataaaag cagtgttaaa 11280
cacaatacgg aacatcatga cttccctttc aggatccagg tctaagtgga cacactccaa 11340
aactacatct ccttgcacca aacactgaat atcaatcttg atgacatcac tgtccttctg 11400
caaaacaata acaatcatgt tgccacagag cagaattgaa gaagacaaca aacaagatgc 11460
agtgatagca atttttcacc tggcgataat gtcgaaggct tctacctttc ttcggcatgg 11520
agtacaacat atgagttgac aatccatcct tgctgagaag gttccttcca aaaatgcgca 11580
caattggcct acaccctttt tgattgtcaa atcttggaat ggcacgaaga atgaggcaat 11640
ccagagaaag agcttgttca ggaggaggcc actcgggaga tatatttctt cttgatatat 11700
attgcaggta acgaagctga gaagggaatg ggttcaaagg tgacaacaat tgcgataaac 11760
ctttaggtgc ctcacgataa accatctcga gagtttttct ctctccgctt tgtaactttc 11820
tgaaaaccaa gaaactggcg aaaatgaagg ctagaagggg ccaaccacct ctctcacagt 11880
gtaacaaaat tacattgtta tgattttgaa gagagagcca actctcacag atacatagaa 11940
aatgatgtat caatgacaat ggcagtacag gacagccttc atattgtctt gggtaatcca 12000
ttacagtcac atcatactcg cataaaatct cagcaaactg gctccttttc tcgccttctc 12060
tgaaattgaa agcaagaaag gaggaatctg gaaattcttc atgtagttca tttatgattt 12120
cgtgcaagta aagctgataa attccctcag gcagtacttc agtcgaaaaa caagaatcaa 12180
aaactgcaga tattcaacat aagataaaaa gatgttgaga aaactacaat gcacttccaa 12240
tgttcaataa aaaacacatt ataaagtcaa agctagttcc tttaccatat actctatcat 12300
caagttccag caacccatct gggggccttc tatagaaaaa tctactcaac agcgacataa 12360
tactgagcca atatatcacc taaatttacc tgacatcaaa gaaattcaaa cccatttca 12420
ttcctttggt gtcccaatat caaaagggtc agagaatcag ctcgtacaaa ttcaagaaaa 12480
tgtgaaattc ataagaagaa ctcaaaatta atctcaaatt cagaataccc acaaagctaa 12540
aaagggattg aactatattt caggcgaaaa aattggaact tgacaccaaa taaactacaa 12600
caagactgaa acacacacaa aactcacatg gaaaatattt gcatataaaa caccaaaaaa 12660
ggaaatcttt gaactgaagc aaaccgacag aagccgttga ggaaggattc gagatgtgag 12720
gtgaagaacc gacagtgttg ccagtaaagt tttcacctgc gctttccgat tttagtatga 12780
attttttttt ttttctgatt acggatttga actctttgga gttcaaaatt ttgggaacga 12840
aaaaaaaggg gctgattttt tattttaaca tatggttgtt ttcaattttt gaaattacag 12900
aaccaaccca atacttgtat ggataacttt tagttagtgt tttattttcg aaaactctac 12960
gatgaaggat cgatcggaaa taatttttat tttctactca taattaggaa taagattata 13020
atgtgaaata ttcaatgatg attaatgaat agtgttatat ttaattgatt attattgact 13080
tgaataataa taaaaatata aattacaaat atatataaat taaatacgaa tgagtataat 13140
ataactttct taaaacaatt gagtgcgatg gcttaatggt caagatgaat atattgtact 13200
ggatgatcat gtctttgaat ccccatttat atcagggtca aatacataaa gagatttcta 13260
aacttgttgg gttttttttct tcacgtactt taactacgtc atttttctat tgaatcattg 13320
aaccatccaa aaatttattc ctttaagaac attgttggtt tattttgatc ggctattcta 13380
ttgtaaatgc ctttaattgg gttcgaattg taatgatttt gattgaagga atgaagacaa 13440
cccgttttag tctcatttgt tttttaacgt cttcaaatga cttaattaaa atacaattat 13500
tctcgaacat ttttactatc aattggacta atgatttctg aaacaacata tatatcctct 13560
atcaatcccc ctcacaaatc tggtttcaca tcagacaaca gtgtttattt aaatggaaca 13620

```
aattataggg gtttaatgat tcaataggaa aatgacgtag ttaaagtacc tgaggagaaa  13680
aaacacaagt ttagagattt gcttatgtat ttgaccttaa atcagctatc caacatgcac  13740
ttttgagctt tctatgggtg cgctaatact tgtgtgtcaa cttttttaaa gatatatatg  13800
aataaatata tataacatga tttttttttt gaaattaaca ggtatacgtg cacctcattt  13860
atacatgtta ggtctgtctc taaaatcaga tctacaaagt tacatcgggt atgtttttaa  13920
tattattgtg gttgtttgta ataaatattt taattagagt tgttcaaaat caaatcgaaa  13980
ttgataattc gaattggaaa aaaaagttat tgatttatca gtattgggtt attgatttag  14040
cgatttagtt aagggtctga ttttttttgt tatcgggtta tcagtttgaa gtttttttctc  14100
ccgatagtaa attaaataat tatatttata ccattttatg tttgactcga agtttgcttt  14160
cctactttta tttttggtta ttcaatgtat ctgcttttga gtaagatgta acttgtgaac  14220
tgatgtgcat agtttatttg gtttgtcacc ttgtttctaa gtgattttta atataaattt  14280
ttgtgtcaaa tcttaaccag ttaaactgat aaccaaatcg atagcgataa aaaatcgata  14340
agccaatatg ttaatagttc tataacgatt taacatctct acacactatc aaccaataag  14400
ccaatcaata aactttaaaa ccgaatcgaa cagaccgata cgcagagcta attctaatga  14460
caataatcga ttgtggaatc tatattaatg catggctgca ttgaactcta aattgaagta  14520
tcttcttttc tgcttaaatt acctccaaaa ggtaccaatg ataccaaaat ttccaggctt  14580
ggttgatggg ccaaagtgac catgtgatcg cctttattgg gcttttagcc cagttaaact  14640
tagggcccaa tgacgcatat tctatcagca acaagaagta ttgttggtga ctagagaatt  14700
ttagaatgta attaaactat ttttggccaa caaaaaatat aaatgatata caatatttaa  14760
tataaaacta gaaaaagtta acattattcc tcaatgagta tgattcgaaa tgcatagacg  14820
aggctatata caaaaataga ggaagattgg atcgcctatt tgaatctggt ttggtgttag  14880
aaattcgtag ataaatcgag ttgaaaaaaa cgttgtgaca cgtgttttac gtatgagagc  14940
caaatgatat ggactttgat caacttttca agatgtattt tttcgtcata ttgatattga  15000
gaaagattgc aatttatagt attgtcctca ttgttttaga aaaccaaaag attttaagtt  15060
tgaagtatag aattaatcca atcaaattta gttttgaaag tcaattaaag tgactctcaa  15120
aaacgcaaat catgataata ttttgaaata aattagggtg tttttttttat tgttctatct  15180
catttgtttg aaatatagta tttagaaatt acgcgaacat tctaatcgtt attcattgag  15240
taatatacct gattataaga cgattaatat tgagattgtg agacaaaagg aagaaaatat  15300
aaatttatag tactaaggac aagggcggac ccacaaggtg tcaagtcggg tgctcgaaac  15360
acccattaac cgttattgaa atatgtatat ctatgttaaa atcgatagct atttgtataa  15420
aattaacata gagcacccaa tgaataaatc atatagttgg cccaatggtt ctagaatggg  15480
tacttaagac tcttttaatg ttattgtacc aaggttcgaa ttccgccact gactaaggat  15540
cacgatggag tcatggagat cattatttgg ataatataac aagcaaatgc aacttaaatt  15600
caaatttctt ttattcaatt acaattaatt aaattatgat taaatcattt tataagtgga  15660
gatcattatt tggataatat aacaagcaaa tgcaacttaa attcaaattt cttttattca  15720
attacaatta attaaattat gattaaaaaa tcattttata agtaaaaata cttctataaa  15780
aggaaatttt atccttaaaa ttcaaatatt aaacttcaaa ttaacaacac atgcaacctt  15840
atacaaaaca aatcaactag gatacctccc ccaataatta aattggtggt caataaaatt  15900
gtactccata attatgaatt gtagttggca ataataaata tgcattgtat tgtcctcatc  15960
```

gactagtcaa tggaacattt atgaaaccaa aaaacatgaa tcaatgttct ctacttgcac 16020
caaagttttt atgaatgaga aataatatta gatttgtccg ttaaggattt caaatgtttt 16080
aaatattgta cttggggtat aaatgagctt ttttttatca gtaaattttt atcgtatatc 16140
tgatgattat agatctccat tctcagaaac atcacttgaa aatagttgtt actccatccg 16200
ctcacccaat tataacatcg atcttaataa aaatacataa aaatcattta gttcaaatgg 16260
tttccctcac tttatatttt tatcattttt ttctattacc aattaattag ttttgttata 16320
aaatcgttga tggtcaacaa ttataactct atcttgattg tcatacgatt gttaagatgg 16380
agtttcagcg aggttaaaaa ttaactcgtt ggtataatta tgcattattt aaattttatt 16440
tgagatgatt ttatagatta atggtaatta atttagtctt gaggagtaaa ataaaatcgt 16500
tataggtttt tgagtgttcc taacatcaga atggtgacat cattatgaag ttataaagac 16560
atataatata atttaaacta ggaaaaaaga taaatatcct tttgaattat cgtaaatagt 16620
atgtaaatgc tctctgtcaa ttttttggga cactgatgct cctgtcgttc aaaaactaga 16680
aataatatat actctttaca ctaacggaca cacacgtgtc ataatcttat tcaccaattc 16740
tacatttatt gacggagaag attgcgccat gtgtttctat ttagtcttcc tttagagtta 16800
acggcatata aactttagtt ttttttttac agcaggaaca tcaatgtccc aaaaatatga 16860
caaagaatat ttccatatca tttacgatag tttgagatat attttccctt tttccattta 16920
aactaatatg caaaatacga tcctgctcct ctttatttct cttctctcca ttttccccaa 16980
gtttccattt ggattaatga cacatgtcat gggttaaaat aaatggttaa aatttaattt 17040
ttcaaagtaa acctctaaac atgatttagt taatatatat attatatatc aagtatcaaa 17100
atttttataa tttcacaatc ttagcaaaca tattattttg tccatattat ttatgtaaaa 17160
agttttcttc ctataatttt tttttttcgt aggatctttt ttattttttta ttttatacaa 17220 tattttaatt gtaatctttt gttaaaggta tattggtccg tgattaataa attacctaga 17280
gataatcaaa tcattttgac aaactaattt taatttcata ataagattaa gaatacggtg 17340
ataccaagac atacgataga ttaattatag ttttcatact tctattcagt tgcttattct 17400
tctaattaga taaaaaaaaa tttatataaa gggaaaaaaa agatcctacg taaaaagaaa 17460
taataggaag aaaacttttt ttacctatat ttatggacaa aataatatgt tcctaagatt 17520
gtgagattat aataatttg atgcttgata tataatatat ttattaacta aatctgtcac 17580
gacccaaacg ggtcgcgagt ggcacccaca tttactctcc tatgtgagcg aaccaaccaa 17640
tctaatccca acatttcaac cataataaac agaaaataaa gcgaaagact taaaactcat 17700
taacgaaatc aattaataac ttctaaaatt taatattcat catccccaaa atctggaagt 17760
catcaccaca agaacatcta tcctcaaaat actaaatcta agaatgtcta gaaaactaaa 17820
ataataaaca gctagtctat gccgaaactt caaggcatca agacacacga aggaagatcc 17880
gtcaagctgc taaagcgtta gctcaccccg agatccgacg tgatgaagac cggctagagt 17940
tacggttgag ttgaagacga tgatacgttt gtgcgactcc acaaataaca aagaaaacaa 18000
ttacaagtag ggtcaagata aaaaacagta atcgaaagta gtatcattgc caactcaaaa 18060
tagaaagcaa tatatttcag ataatatcat aaaatcaact aatattctta acaggtgata 18120
gcaacaagta taaaactcat ttataacaaa ccaaccacat ccatgaggac tcaagcctcc 18180
ataccatact ctttagggaa acaagttctt tggattgact atattaacat atttcaagat 18240
tcattatctt tctatctccg gtgtcggaac gtgacaccga tcctcatcat actatctggt 18300
gctctaacgt gacacccgat ccatattcta tcctgcgtgg gaacgtggca ccgatcctca 18360
ttctatctcg gtgccgaatg tggcaccgat cctcattcta tcccagtgcc gaacgtgggc 18420
actccgatcc tcattctatc acggtgcggg aacgtgacac ccgatcctct attactatcc 18480
cggtgctcaa cgtgacaccc gatcctctaa tctcattact ttagttcatc aagccttctt 18540
ttataccaag acatcatcat taacaaagta aaatttagga tttaagattc aacagcctca 18600
tcatgctagt ttcatcacaa ttatatatat aaactcatca tgctagtttc atcacagtta 18660
tatatataaa ctcatcatgc atacacacaa ttaagcatat agaagagttt acaatactac 18720
ccaaaacata tcattcgcta ttaagagttt actatgaaat agcataaacc ataacctacc 18780
tccaccgaag aatcgcgatc gacaagctat cttcccaaag ctgcgttctt cctctctctc 18840
tttgttcttt ctatttttct tattcaaacc cccttttctt ttaccctaat tagcatataa 18900
ttaagtataa aagatgataa aataccccac tacttgtttc caaggttatc tcttttaacc 18960
cccaagtaat tgaattatta acattaaacc actaacttta taattataag caggaatagt 19020
ccaaaacgtc ccttaaaata tttaacagaa atccgaccca ttcggtcacg cgttttagac 19080
ggcccgtcgt gctgcgacgg tcaaatctct ttgcttccgt acaaagttcg ggagactcaa 19140
ttcattaaaa agtccagcgg cggcccgtta tgctcggaga cggtcgcccc gccacccgtc 19200
gtgacgttcg atcgatctcg gtacccaaat ttttaaattc taagtgtttt agaacgagac 19260
ccctcgacgg tccggtcgtg cccatgacgg tccatcgtgg gatccgtcga ctcaccagct 19320
ttttccggaa ataaaaatca cgctaaaaac gactaaacag gtcgttacaa aatcatggtt 19380
aaaggtttac tttgaaaaat taaatcttaa ctatttattt taacctataa catgtgtcat 19440
taatccaaat agaaacttga aaaaaatgaa gagaaagaga aatggagagg agccgaatcc 19500
cgcaaagtag aaatatattt gacccctgct attaactatt aaaacgttct tgtttcattt 19560
tgaacttgca aatatctgtg gtacactaca aatttaaggg ttataatatc tattaataaa 19620
cctaattagt aagggctaat gagactttaa acacaatagg caaatgacag gtaagccctc 19680
agattttgat tctcctatat cacacatgac gttgtcagag gtcaaaactg tcattatatg 19740
tccaaaatac gtgagtatga ttttttagca gcaagaaacc aaaaaaaaaa aaagagatac 19800
agattttggc aatttatacc tttttgaatt gaaatgatta cacacctttt tcacattgtc 19860
agtttatttt ctttttgggg tctaaaagtt ttggtttttg aaaaaaaaaa tatccgttga 19920
tttaattttg gagtaattta agggggatgt ttggttatga aaatataaaa atattcattt 19980
tatttaaaaa aaattaaagt tgaagtttga attgtgttgg gttatatttt ttgtaaataa 20040
tatgtataat tggttatgtt tttgggtgac taaaagtatt tactttagaa aagaagatat 20100
ttatgtcaag aaaataagtg ttgcttaaga gtagaaaaat attattttga caaaaaaaat 20160
gcacttaaaa acactttgaa gaaatgcaat taaacactaa ttgtcgtgta agaggtcttt 20220
aaaaattaat tggtcaatgc attatgatca caaaagtatt tttaaaaaat taaaccttta 20280
ctaaaataaa ttaattttag aaattcgacc taacaagtca taaaaataaa ataaactttt 20340
acttatttaa tgtttgaagg ccattaacaa ttgaattaat attgcttttt caataaagat 20400
ttgattttaa ccaacctcaa ttaataccaa ttaaagttta attttgtaaa ttggattgaa 20460
gttgcacaaa tgagtatatt tagttatgta ctaacatctt ccatattaat tctcctaaat 20520
ctttaggtac atatttttct tttccatatt tttaacgatt ttactttcta agttttaaac 20580
tttaactttt ttaaattaat tagttcaatc ttcttcttct tcttttttttt ttggagggac 20640
ataatttgat cgatctatta atcataaaac atgtcttttt ttttgtccaa tattatatga 20700

```
attttatgaa ataaatttat tttagaactt tttaacgtat tttgacttta agctttattc  20760
aatccgcctt cactgacaaa aattccaaat aaaaataaag tgctaaagta taatttatat  20820
actctctctg ttttataaag aatggtctaa tttgacttga tacgatattt ctcctatttt  20880
ataaagaatg atctaatttg atttgatacg aaattaaata tacaaccctt acatgccacg  20940
tggaaagtta ttgtcagaaa aaaaaaatta ttctttttga tatggactat aaaaaaaagg  21000
tcattccttt ttaaaacgag cagaataata tatatcccaa aactttatta ttgagaaagc  21060
atctaaaatt tgatatggca attgcatgaa tgtggagtaa aattattcta atacaccaga  21120
tatgatgcca tgcagaaatg atgtggaaac tatatatagc acaattccca atgaaattta  21180
atgtactgtc tcataactat atagtatagg ctttcctcta actatacata aagttacccc  21240
taaaatatag gctagctacc cttctagctt tcccccaaat tctaaattag aacaaaaaaa  21300
tatttctaca tctttttaca gtttttagtc cctttcactc tttggggtta tttggaggta  21360
aattatttat agtaatttag aattttatat gtataaatta taaaaactta tatttgtggc  21420
atctttggag gtaaattatt aatagtaatt tagaatttta tgcgtatgag ttataaaaac  21480
ttatatcatt catataaggt agaagatata ataattaaat tttatataat aattatctgt  21540
attactaata tttgtataac tttaatcaat cattctttaa tgagcaattt tcacatataa  21600
caaataaaaa aaatcatatt tgtatgttat aacaaagttt gcttaattaa ggctccataa  21660
agaacataga aacatataat tcgctataca tatacggttg aagcaaattg tataaaacga  21720
agtgtataaa acaagaaaga gaaagacatc aagagaatcg tataaaaata aattgtatta  21780
ttataagtgt atagaacgat tatatacaat ttgaatttgt ataaaatgag aaatagagaa  21840
agacaaaaga gacttgacag ggaatataca attgaatcga attgtataaa acgagaaaag  21900
agaaattaga tacaatttga aaattgtata aaacgagaaa gagagaaaga caaaagaaac  21960
tggtcagatg agtattttta ttgtataatt ataagtgtat aggacgaaaa tatatgtact  22020
tgtatgtgta tatacaattt tctcacgctt tatacaaaca taaacacaat ttatacattt  22080
agcttctgtt tgtataagtg agaaaggcga gggtggtgag cgagatttgg gagagtggcg  22140
agcgagatct ggaagaggag agagagggga acaaaaatat atgtattata caattttctc  22200
tgctttaaac aattagaaat aatttttata tacttgtgtt tgtataaaaa ataaggaagc  22260
gagtgagaga ttagaggaaa gtggcgagcg agataattgg gagagaggcg cctggcaatt  22320
tttcgcaaat atttgcgatg gagcacaatt atatcaaact ctaactacat ttattttaga  22380
ttattagttt gctattatat ataattttct ttttttaat tgtttagtac ttgaaagttg  22440
agtaagtgtt ctaacccaaa atgagttata tttatacact gatactccta tttaaagttt  22500
agtaatagta cttatgtaga ccattgtata agtttttaac tggccaacaa tctatttcat  22560
acaatatatt tggacttaca aacactatag aacttatctt taagtattaa agataatttt  22620
ttatcacata agcaggagcc tctatttgat ctatttcgct ttaatataac gtgcaatatc  22680
ctatttgatt ttcttattta ctttaattat agactcgaga tttgtaaaac ttcttatttt  22740
gaggataact agtgtatcaa tatcactttc ctatttacct tatgtgacgc gacacataac  22800
ttccatttaa tgtactttct tttagtcccg ctcatccaaa aatatttaaa ctctttggtc  22860
ggtctccaaa tctcttatat atcattaatt caatagcatg actcatcaat aaaatattat  22920
atcatctaca cataacatac attgtgatac ttccactcga atatgtcatg ttaattcatc  22980
gatcatcaaa gcaaataaaa acaaattgag aactaattcc tagtgcatcc catctcgatt  23040
ggtatcaagg tctttttctt taacagtcct tacttagatc ttgactccat tatacatgcc  23100
```

-continued

```
tttaattact ctaatatata tcgtaattat atttctagac tccaaacatc ttcgtaaaac  23160
ctctctcata atcaccatat aaataaaaga taactcaaac ttgacctatt aagagttgat  23220
tggttgaaat tccatgttaa agatctgaaa aaggccttat ataaaaatgg tcctttgtac  23280
agtctgttga ttctgattcc aaattgttta tgcctaaaac aaacatgatc taaatattta  23340
attaaaaggt ctctaattca atcaagatcc attttgtagt caaaatatat actattttgg  23400
tggaattttg gacataagaa ttaatgaaaa atagtccatt atattttttt catagttaaa  23460
caacacactt tatactacat gcctattttt tgctagtaat ttcgcctaag aattaaaatt  23520
aaaagtgcta attaattaag acattaagct gtaaaaatat ttaaatatgc aaaggctaat  23580
cattaatgca aaaacaatag gctccccaac cgcactttca tatataaata gcaagaagga  23640
aataataagt aaaatggata aaaatatgat aacgtctaga tacacaaaga ctatcttatt  23700
tgaaaaaatt gtttatataa tagcaaccta ttagtttaaa ttaaatgtta taaccatagt  23760
ttgatttaac tgtaactctt attaaattct tgttgttcac atcccgttca ccactctcac  23820
tcgtctctcc actttataga aacacaaatg tatacattgc gtttgtgttt gtataaagca  23880
aaaaaaattg tatatacaaa aataatgcat atattttcgt tcgatacact tatgattatg  23940
aaaatacaat ttttccttgc ccaatttctt ttgtctttct atctttttcg ttttataaac  24000
acaaattata caattgattc ttttgtatat gtataccgaa acatattata taattttttt  24060
tttgtatata agtataacga aatatccata gcaaacataa agtttgctat aaagcgtaat  24120
taatgtaaac tatagttata acttacaaat ataattttttg tatttcttat atgtgaaagt  24180
tgctcttttt tttcaagtgt gtgaataaat taatacttaa agtatgtaat cacttttaat  24240
tgggaaaatg cataagtatc ccaacaacct atgtccgaaa tcacagagac acacttatac  24300
tatactaagg tcctattacc ctatgaactt gttttataaa taactttata cccttttttcg  24360
gccttgatgc gggagaggca tgagtgcaat tcaatcttgt ggtgtattcg tttgtagtga  24420
gtagggcctc tttctcgttg atctgacact atcaaccaca taacttaaaa aaattgtcag  24480
cacactttgg gcccacaaga gagtgtcacg taggccgtaa agggatagaa agttatttat  24540
aaaataagtt tacatgggta atatgacctt agtatattat gagtgtatct ctaaaatttc  24600
ggacatatgt tgaaggggta cttaagcatt tctccctttt aattatatgc attaacctct  24660
attagttata aaaaaaaaac ttattttgag attgaagcat ataatgaaat gcaataacac  24720
atattattca catttttaaa acgttcaaca taattatata tcgtggatct tgctttcgaa  24780
ataactggaa tcggcatgct agtccgaaat tctcgtggaa gcttcattag aggccacact  24840
cgtcggttag gatgacaaca agatccactt atggccgagg aactgggtgt tcaagaagca  24900
ctaagctggt tgaaggacac tttacggcaa acaacccaga tagttataga gatggacaat  24960
ctttttggtt aaacaagaga taaaaaaggt gcaaaaacta ctcttacttt tatgttatta  25020
ttcatgattg taaagcattc gtgtgtgact ttacttctat ttctttgtct ttcgataaaa  25080
gatgagcaaa ccagtgtacc catcagttag ctcaaatttt gggttttatg actaatgcta  25140
taaagcggat aatagatctc catctttaat tcaagatgta ctcaatttta atttgatcaa  25200
taattaatta aaatgtttga ttaaaaaaaa aaagaatgtt catcatacta aacctacttt  25260
gtaatgacat atataactaa ctattttgat gaataatcaa actactcaac tttctttaaa  25320
ggttttgaag aacaaaaatg tcatattggc tatttacact tcatttagct aataagaaat  25380
tgattttcct ttcttataat tttttttgtg tttttctttc tcacctccat tttttctgac  25440
```

ttagagctcg ttttgattga tttaaaagaa tagtttttaa atcaaactta aataatttta 25500
aattaaaaaa taaaaagtag aaggagatct acttttaatt ttaaacttat tttaagtcat 25560
ttataatctt gtcaatcata taaagtcaaa attctgactc aaaaataagt ttgattaact 25620
cttgagtcaa ttcaaacacc ctcttagttt taattgacat ctataacctc taattttagg 25680
tatgtacaaa taaatactta aatttatata aaaattaaac aaattaatat ttgtgatatg 25740
tgacattgca taagacaatt ttatatcaac gtgatgtcct acctatatta cgccacataa 25800
attacatata tattgatctt tcaattttat atcgtttaaa ttatacatat ataccctatc 25860
aaaaaagtat tatgcttgtt gaatagttct aacttgtaac atccactttc ctctttccac 25920
ttcaatccca aaaacatttc ttacaaattt gcaaaaaaca atgaaaagga cttaattagc 25980
aaaagagacc acaaaatgaa agggtcacat ggggtgtgtt aaaactcaag cctaaaaaga 26040
ctttgttttg tttttgaata gatatatcac tcaaaaaccc aaaaagcaaa ccagtaaaag 26100
gtgaccccaa aaagcttccc cacacacaca ctgaagacaa ctttccagta atggcggcac 26160
atgaagaaca acaccaccat catcaacaac aagaacaaga gaaccccatt tcctctttat 26220
ccttaaaacc caacaataaa cacttggaga agattttctc ctcatatttg ggtctaagtt 26280
tcgctgtctt tcttgggtct ttaccaagaa atgcagtttc tttggttggg agacttcaga 26340
accgtaacaa ggagctaact tttcagctta ttgatacaga ggagcagtta aagcagctac 26400
ttttcaggag aaaagaggat tcaaaggcaa atgcaagagt tgtggaaatc tttgcaagtc 26460
atagacatgc ctggcagcaa gaagagaaga ggttgttaca gcagatcgat gagtgtgatg 26520
aagaaattgc tgagttaaga gggagagctg agcagtttga gacaatggaa agtgagttga 26580
gggctaatat tgaggacttg aaaagggaga ttagtgaaag agatgaaatg ttgaacttta 26640
tgagtagaag gggttgtgag atggagaata gtactagtgg agatggtggg agtgatggtg 26700
ttggagattg ttatgctgaa atgggtttga ggtttgggaa agttgggata tctgaaggga 26760
tggatttggg ggtagggatg gaagagtgtt acttggctaa tgggattcct aatgctgaac 26820
aaatgagtgg tgtttatgga cagagtaatg ggtttaactc agaatacttg aattctgctt 26880
ctaagttttg ggctgaaaaa gctagtcctt ggcaggtatg atccattcat tatttctttt 26940
tgggaacttt tttgttcttt atagttgttg ttatttgggg ttttatagtg agtggtgtca 27000
taatgtggta aaaataaacg caaaagtcct ttccaggatc ttcatatgta ggaagaactt 27060
ggactaaagt ttgtcgcttt aatgtttgtc ttatatatgg tttttcatgg tgaaacttat 27120
gaataaagtt gcttctttta tttaaccatg ggattgtact ttaagtacta ccacctgata 27180
ttctttcttt tagtgtttat ctgtttgttc atcttgaggc tgtggaattt gtttttgtat 27240
gtgatatctg atgaaacaaa tgatccagag caattgagga tgaacgaaat taagtaataa 27300
aatgtttggc ttatagggtt cttggtgaag tacaggcctt tatgatcttt cttcacatac 27360
ctgaaaattt cacaggaata tccacttcta attgtttctg ataaagctga aatgaaggtg 27420
tttctccagg agtagttcag cgccaaattc aaattgaatt gtataatgat tacattctga 27480
gatgcttatt aatgaaatat gtagtttagt gtgtactcag tgacctccta cttgtcttgt 27540
gatttgtctt tattgttgag actcttgtct ctattatcta aaattttgaa tggtttgatc 27600
ttcttagtgg ctgctgaaag ttcaaactac ccaggatatg gttttctgtt tactgaaaga 27660
taatactcac ctcaactgtt catttttacc ctatactggt gttatggacc actgcttgaa 27720
aaccaggtca ccgttttgta cttttcttct ttcaccgttt tcgtcctatt agaggtttgc 27780
aattcttgct tcaagaatgg tcccctttgg ctgaatactt tgcatgaagg ttggtttcct 27840
ggttatgaag gaagctcaaa aaaatgtatt cgggtaactc tagaaatccg aaatccgttt 27900
aaaacggacc gttttgttgg catagaccac tgtgcctcta aaataccaac taatgacatc 27960
caattatata tcccctttgg tttgggaagt tcaattctgg ttaaaatgga tccgtatatc 28020
agcaaaggat gggctgttat cagtcaacat ctagtccatc tgttatattt ctgtttaaga 28080
ttcatcaacc tcaatggaaa gatgtcctct ccctttcttg ttgcaagctg tatcttgtcc 28140
ttgtctgtct ctgtatctta ttttccaatt acaatgttat ctttggtaat tcgttacaca 28200
tccttgaaat aaagcaaatg cctccatgaa acttgaactc cccgcggcct ctaatccagg 28260
cactaatctt tcccgttcaa aaggatcact ggaacatttt cctatacttg gtggatgtgt 28320
caaagtttgg actaggtaga gatcacacat tcaatttatg gctgtgtttt ttgtctttta 28380
tcatttttgt ctttttatat tatatagaaa agaagatctg gattttctta cccttggtac 28440
agtcaccctt ttcatttatt tggaaccaga gggaactgga gcatttcact atgttgtctt 28500
caactttaat agaaaggcta aagaaaacac acaaccttaa aaataaacct aaattgccta 28560
actattagtt gatctatgcc ttgtgagctg gttaaggatt agtcatattt acaatggtta 28620
gagcaaaaag agaaataaac atctagatca caatgcttat attctagttt caagcttgaa 28680
tggtaggaga aatgaggttc ttttgactct tattcagctt cttccttcta tgtgagatgt 28740
cctacctatc ttagtaaaac cagcttggta tttaggatgc tattgggtct taagaaaatg 28800
tgttttcttc atgcaggata tgcagtatga ttctggcgat tcacttcacc atttaaagca 28860
ttttgtagca aggtaaacat tctgtgatta gttagacaga tgcttagatg tttgcatttt 28920
gatgttgaat caactaacta gggtgagccc ttttgctttc tcagacggga ggccccttgg 28980
aagatagatg gtgaatcaac aggagtctcc tccaaactaa agttacttga gcaggagcta 29040
ctgaatttgg aaaaaattgg gaagactgat ttatctaagg taccatcatc aacgcggaag 29100
caagtgaaga gataccaagc tctagctggc aagattgatg atttatgcag aagaatggta 29160
attactgcat ctctgcaagc ttattggtta taactttagt atatggattt caaagcttgt 29220
tacatgcatg cttaggtttc tctaagaatg gacaatagtc ttgattacat ctgctaactc 29280
aaatatttag atgttgggtt atactcttag cttgcacgac taggccttac aattagcttt 29340
ttacctaaca caaacataca tctgataatg atctccctcc ctcttagcag caggccagtg 29400
atccttgcga atcaaacctg agtcctgagt tccggaccca aagacagacc gagtttttgc 29460
ttgaagcatt tcgacttcag cagcgtgcat ctgaaactgc acagaagctg atggtactac 29520
aaactgacag tggaaaaagt tattacgggg acgaatttga agggcaagcc caactagcca 29580
ctaaacgatc ctttgactcc atccggaaca acttaaaaga aatccaacgg aatttagaga 29640
tatggcttgc cagaattatt ggggatctgg agggaatcct ttctcgagat ggtgcttctc 29700
gtgtaaggga ttattacata tctagatatc cttttgttca atagttatgt cttaacatgc 29760
tcagtaaaat catgattgaa aaaatgatgt ataggtcctt cctgttatgt taacaagata 29820
gctccagctg aatgaacaat atgaggttga taagtccatt tatgcacata aatctgcttc 29880
acagaagcaa actattaatg ctaactagta ctttaaagag tgaagatttt tgacagaatt 29940
attgctggat gtcactgttc ctgatctgga tgcttgtcat ttactagttt tacttggtcc 30000
cggtctttct ggattaaaaa gttgaaagga tggtgtggcc ctttgcaact ggataaatgt 30060
catgtctaca caaatctggc aaacattaaa tatttgtgga ccaagtttac agccccattt 30120
gatttgaaat cagattgatt ttaagttgat atttgttttg atttggattc ttaagctgta 30180

```
ttgattattc ttaagcttag caaatgagca aatcatattt tcatgaataa gatatcaaaa  30240
tattctagga agttgaatta acaagttata tagcttcatg ttactttttt tataaataaa  30300
tatttgtaat tatatgttat tataaacttt caaatatgtt caataaacca aacaacagta  30360
atactttctt ttgataaaag ttattcgctt ggtacaaaca atttcttccg ctagattttc  30420
ttttttaaat tttaaaatta tgggtctttt cttgtaaaaa ttaggtttct ttttctcacc  30480
taacctagtc gtggacatga gttcataagt tgaataatct ctaactaaaa ggatagtcaa  30540
ggatgtgcca ccgtcgaaca agaaggatag ttaaggacac tctcaagcaa aggccagtag  30600
catgtactct aaatttagtc aaagttccaa tacaagcttt ttgagcgcca ctgtgacttt  30660
gataggtgga aaaataatta aaatttatct ttaatatata atactccctt cattttacca  30720
caatacctat taattgatgt aatggcctga ggttataact tttaaccatc tctgttctat  30780
ttatgtcaag aagtgcaatc aggttttgaa ccaagtagct aatcactcaa tataaagaaa  30840
ccaaattcaa actttttttag gggtttatta tagaaggttc agacatactt atagcagtaa  30900
tttttttcc tagccaggaa aaggcataca cctgctgtta cactaaaatc aaacaagcca  30960
cataatccaa ttccaataac aatttaacaa catagataga tgagccttat gctgaagcag  31020
caccttcttc cagcaactgt ttcaccttgg tgatgtagtc gttcatggct tcatcggtgg  31080
attttcctgt catagatgca tgcagtgcaa ttagttgtgt ttctcataca accaagagaa  31140
aggaagtcaa tctgaacact gttgttagat cacatacctt caacagcctt ccatgcatcc  31200
cactttgctc tgtctctcat gttgaaaatg ccaggacggc ctgcccataa gaaagggcgt  31260
aagaacaaag tgtagctagt ttgagacagc atgtacatat gcataagaca tttcaagcat  31320
tatactcact tgtgttgaca ctgccaacgg tggcttgctt gtaaagtccg taaagaataa  31380
gcttgttctc attggtggta ctctcaggca atgtcttagc tttctcagca tgtgcttcaa  31440
attcctcctg aaacccaaat agttcagtaa aaaggtgtgg tagctgaagt tacaaagata  31500
aatttccagg tatactttct tagtgataaa ataaggatga gaatccaact taatagttga  31560
gatcgaaact atttgtgaat taagagggaa ctgaacttat ggaaatctaa aatacaaatt  31620
gagtgttcct tcattgggta aatgaaaagt ttgcagttca ggatatcaaa tatgtacgaa  31680
ttcattgatg gactttagca caagtgtacg cttagcctag cggtgaaaag ggttcattct  31740
atttagccaa cccgagttca attctcgctt tattttattt tataacttga atccgcttcg  31800
tgaaaatcct aggtccgcca ctggttagtg aaagagtatt tgcaagaatg ttagacaaga  31860
aaagcacaac aatacattcc tcaacattgt aagagattct gctggccaac attttgcttt  31920
gacaatgtta agacgcaaat tttagacaca tgtgttaatc atacaattct ccaacctttt  31980
cctcttctag aaatgcttct atttacagat cacagtgaag caccaaaaac atcctcagat  32040
aatgtattat gacctcttca gtttgtttac tggtttgccc tgtttgttac cctacgattc  32100
aaccattacc actcagtagc ctacatactt gtggtaacag gaatcctttt agtgcgaggc  32160
gattggccaa ccaacaattt ttgtagtcac ttaaaaatag gtcagactaa attacatcca  32220
ctataggtta tgaacagcag agaaatttca aagacaggct gaacacaaag tgcacatttc  32280
cttcaacttt tccccttccc caataaaaga aatatggaag ggtgatgata ggtttttgac  32340
caggaaacaa aaactagtct tggactaggc aatacaggat aggaaagaga aagaagcggg  32400
cgctatctca tattcaattt ttgctagact atttacacag aagttggcca atgtagcacc  32460
atataaattt gagaaagagc catttgttca ctactaacat tttgatggcc ctaactgcac  32520
atgaactaat agtaatctga ttctaacatc tcgttccctg ggtttagtca tcgacttaag  32580
```

cttcaaagta tacaccatat atatagccaa taatatcaac aatctcaaaa actaaaagaa 32640
gaagacattc ataagatgaa atcttcaaaa cattgttgaa attatggact acttctgggc 32700
cagagacaat atatatgcct tttgataagg ccaaaaatga catacacaaa tccggaccaa 32760
agtactactc atctgccatt acattcgcac tacttcttat cgaattcagt gcttacattg 32820
ctataattac cataaatctt tcaacaaggc caaaaatgta cagcataatt gaattcatta 32880
taagatctat ttataagatg gtatgccgcc actcaaccac agtatgaact gctaaaaaaa 32940
aaataatctt aaacatcaat tacaccaaca gatcagatca atccaatcac cgagccttca 33000
cactaaataa taaccaaaca atcctcacgt aacacagcat ccacaaaatt acagcacaag 33060
ctgcacaatc gacaaagaaa actaacagat ccgcaaatac caattgcaca aacaacacaa 33120
aacccagaat tgaaaacgaa cattaatcac agaaaaatac ttttcactgt caaaaaagat 33180
taacactcgc ttcaaacaag ataaatacat actgaaaggc aaaaaaaaaa cagaaatcta 33240
aaggggtttt aaagaattta ccttcaacgc cattgttgtg gaaatctgat ctggttagct 33300
tgataaaaac gagagaaaac tggagatgtg attgtgatgg agattgaaga agaagggtgg 33360
gtatatatat atagtggagt atttagcata ggaattaacg taaaattcga ttcgattatg 33420
ataatctaaa caagttgcac ttggatcact tactagtcat agtggaccca aaaattgagt 33480
atagattatg gacctatact atgtgagctc cacaac 33516

<210> SEQ ID NO 5
<211> LENGTH: 4900
<212> TYPE: DNA
<213> ORGANISM: Solanum habrochaites
<220> FEATURE:
<223> OTHER INFORMATION: >Genomic fragment 5

<400> SEQUENCE: 5
cctacgtcca caaaggagat gagcaatcca ctataaatat gagagtacaa aatatagaga 60
gaaacaacct caaccaattc actcggaata catgggaggt tcacacaagt gataacgtat 120
caagcttgtg acccacaaat tctccctcta accaaaactc tcaaaactct ttaagactac 180
attgtgaatg ctgattaagt tagaaggaac atgtctctat ttatagagtc ctaaactttt 240
tcatactaga aaaaagatta gtcaattcaa aaccttttcc taaaaggaaa acctatttat 300
ggtaagaaat cagggcaaat aaaacccaac acatcatggt ttgaaccgta ctacataaga 360
aaagttctag tatttaaatt gagaaggata gaggggaggg gcctatcctt aaatctgtta 420
aagttttacg tactagccca actatttgtg cgcgtgaaga aaagatgtga cagctccact 480
atagatttca gcactaccat ttagtttgtt acaacatttt gctgaaattg agttaggatc 540
ttcttgagtc gcagagtaat atcttccatg cgaattctct cttcaggcaa atcatttgta 600
cattcaagag ctaattccat gattgatttg aagcatctat ctttagaagt aaaattttct 660
tcgttcagtg aaaatagatt aatgtccact acatccacca atcggtctgg taatgattgg 720
catatccatc ttttcaaggt gaagtctcca acgaatagat catccacagg gctctttctt 780
gtaaaagtct ccattaacaa tataccaaag ctataaacat ctcccgaagt tgatactttg 840
ccttcagacc catactctac aaaaaaaata aatcacgcca tcattaatga aaataattaa 900
caacatttaa aatcctcaag tgaacttgat aataacattt acctggtgcc atgtagccga 960
tagtacccaa agtcttggta tgtgctatta gcgtctcaga tgtaagaagt ttggatatcc 1020
caaaatcact cacttttgcc accatatctt catccaaaag tatgttactt ggtttcaaat 1080

-continued

```
cacaatggac gactacaaac aaatgtcctc catgtaaata ctccacagca gaagccacat   1140
caatcatcac ctttagtctt tgagttatat ccaaaacttt gtcagtagag tgaagccaac   1200
attcgaggtt ttcattaggc atgtactcta gcaccaacac tttataatcg aaatttgcac   1260
aactacttat caccttaaca aggtttctgt gtcgaatgct acctaaaact tgacattcca   1320
cctcgaaact tctaaatgca agttgcagtt ctgtattgaa tacctttatc gccacaacca   1380
ttccatctgc tagtgtccct ttatacacca aaccaaggct ccccccttcca atcaagtttg   1440
cttcatcaaa gttgtttgtc ccttgagaaa tatcatagta cgaaatcctc ttatgtacct   1500
gaccaaatgt atcaactaga ggaagttccg tactcctttt tcggcatttc agaaaccaaa   1560
tgataaaaat ggttgtgact acaattcctg aggaaactga tgcaagaaca gaagttagga   1620
ctctgttctt tctttttctt tcaagacttg tcactctgca ttgcatcaca tggaagcgtg   1680
atgatccaca taatgcaggg ttacccatga atgattcagc tgtaaaattt acgaatggcc   1740
ctccatctgg aatttcaccc atgagcccat tgaacgagac attgaaatgc atgagatgtt   1800
caagattcct caaggacttg gggatcatgc ctgatagatt gttgctagat agatccaaat   1860
attccaacga aaccaaatct tcaaatactt caggtatgga accatctaac atattctttg   1920
acaatgaaag gctaaccaag ctttgtagtt ggccaatcgt gctaggaatc tgaccagaga   1980
actgattacc atgtaaatgt aatatccgca aactccttaa attccccatt tctactgcaa   2040
gagacccatt cagcaaattg gaggccaaag tgagaattga aatatctttg ttcctccaaa   2100
aagttgatgg aatatgggaa attagtgcat tggaatctaa gtagagttct cttaaagatg   2160
aaagatttcc aaaacaattt ggtaattcac cagtaagttg atttttcccc aagataattt   2220
ggtacaagtt ttccatgtta cacaagctag ttggtataat tccatctaaa ttgtttttct   2280
ctaggctaaa tcttttcaac ttcctcaagt tccccaaatc tggaggaata gatcctataa   2340
gtttattgtc tcccaagctt aaccactcca ggttcctaaa gttactgatg ttaggtggta   2400
tttttcctgt gataccattt tgaagggcaa tgaaatattc aagggaaaag gaccagtttc   2460
ctgaacctaa agatgttgga agacttccat taaattggtt acctcctatt tgaacggttt   2520
tcatatactt gcaattagat aatgaagtca ggaaacttaa ctcgcctgta gattgatcat   2580
tcgtcaattg gtttatttgc aagttgatga attgtagctg ttgtagcttt ccaagattca   2640
taggtacagg tccactaaac agattgcggc caaaatcaag ctggataagc atggtggaat   2700
tcacaatgga ggtaggaatc agcccggtga actggttatc cccaaggtaa aggccttcaa   2760
ggtttggaag agtatggcct atgtttgagg gaagtgttcc tgaaagctca tttgctacaa   2820
atgaaatctt ttttagtcca gaaatgttgt acaaacgcct tggaacttca cccgataatc   2880
tgtttggacc aagatacact tctttcaaat ttacaagatg ttcaaactcc tgaggaattc   2940
caccatataa actgttgtca cctaggtcta tcatctctag atttgacaaa tttccaattg   3000
atggtggaag aattcccacc aaattgttcc gtcgtagact taatcttcga attgctgata   3060
ggttatcgat ttcacttggt atatgtcctg taaaatatat gtcgaattgt gtggttacta   3120
cactgaaatg tccaatactg tataacagct ttatagtcac taagttacta taaataacag   3180
aaactgttag ttgtatgcct tttaaatagt tcagcaatcc tcacaaactg ttttgatgtc   3240
cttttgaaga tgggactaaa tggatcaaca tggataatta ggattcatat agcagacaca   3300
aactagaatt gagccaatgt agtagttact gttgttgttt gaaaatgaag aacaaagagc   3360
tataccaaca ttttttgcta ctaccctttg aaatgcaaat actaatttct tataaatgag   3420
ttgaagagca agtttttaaa tatcaaagat ctctagtgct acaaggtgag aagtccagca   3480
```

ataaagttag gtggattcag ttaaaccaga acattataaa tacctgttat gttattccat 3540
ccaagaaata gatgttgaag ttttgtcaag ttccacatgt ctctaggcaa gtttcctgta 3600
ataggatatt acgataagtt atatgtacct ctcacggcct atgattgttt aactaaaaaa 3660
ttgttgcaat ctttgttgtc aatatgaacc aaaagtagca gagaaagaag ttggttccgt 3720 tttttttac ctgtgaagtg gttatatgac aaggacaaat atattagctc tttgcatttg 3780
tctaaattgc ttggtagttg gccagagagt tgatttcttg ctatttgtaa tccctccagc 3840
cgcggaagat tatggcaaat gtcattcggc aaagtcccag atagtgcatt ataaatcaaa 3900
ttgatgacct tcaaagaaga gacattgaag atagacgaag gaacagatcc aaagagatca 3960
ttttcagaaa gatccaacaa ctcgagcctt ctcagtaatc caagactttc tggaatttga 4020
cctgtgagat tattcattga caaggacaag tgcttcagcc tcctcaaata gccgagttca 4080
tcagggattt caccgttgat gctgttgttg ccaatgtcca agaaactaag aaaggagagg 4140
ttcccaatat ctgtcgcgat tgaacctctt agtctgagac cattgaggtc tagtgatgtc 4200
actctttgat gccttttact gcaagatatg cctatccaat tgcaaacgtg agtccccttt 4260
gtccagtttt tcgacaacat tccatttgga tctgaagtta tatgagcttt gaaagctaaa 4320
agagcagcct catcagttga aatgttcgat gcattagtat tcgagaggta cgttaacaaa 4380
actagcaatc ctataatcat agccacggaa accgttttgt gcaacttctc ttgcagctat 4440
ttgtggggga aatttataag tgcctgattt tttatttttc aagtgacatt aatatatatt 4500
tctataatta aaggcaataa agaatcatgt attagcactg gaatatatag aatctagagt 4560
tcaatgtcaa tgatcaacat atatacgtaa tatgttttga gacatttttt tttaaattga 4620
atgttgctga acttgactgc aattcattgc tgaagggaaa tcattggttg tgggattctg 4680
tagtgatagt aaaataattt acttggattt ataagccttg tatattcatt attcaagaat 4740
attaaagact aaaatcatga tataatgtca tcattcgaat gtatatagcc tccgctgaat 4800
agatgtttga caaaagaacg tgaagtgtta cggtcaaatt agtgaatcta acgtgtaatg 4860
ttggatttac gtgaattcaa tagcttttat tcctatcttt 4900

<210> SEQ ID NO 6
<211> LENGTH: 2684
<212> TYPE: DNA
<213> ORGANISM: Solanum habrochaites
<220> FEATURE:
<223> OTHER INFORMATION: >Genomic fragment 6

<400> SEQUENCE: 6
gttgatgctc tgttggaaat ttattactac aagatagatt ggttaatttg accgtaaaac 60
agttgacatt cttttgtcaa ggatctattc tggggaggtt atagatatac atttgaataa 120
tgacattgtc aagtaaatta tttaactgtc aatacagaat tccacaacca atggtttatt 180
tccctttagc aatgaattgc agtcaagttc agctagcaat atacgattaa aagttgtttc 240
aaatcattgg tattaattag ataagtattg actcaattac aagtatacac acagtatata 300
tagaatggcg tttgaaaacg aaaacatagg cacaaatagc agctaaagaa gttgaacaaa 360
tccaaatggt tgcgaagact attattatag catgcctagt tttgttagca tgcctctcag 420
ttactaatgc atcaaacatt acaactgatg aggcttctct tttagctttc aaagctcata 480
taacttcaga tcccaatgaa atgttgtcga aaaactggac aaaaggaact cacatttgca 540
attggatagg catatcttgc agtaaaaagc atcaaagagt gacatcatta gtcctcaaag 600

-continued

```
gtttaaataa atgcaccaaa cttgaagttc tgtccttgtc ttataacaaa ttcactggta    660
attaactaac ttgtaaactt ttcatttact aatttcttct tgaattaatc atcatttttg    720
tgtgtgtctg tcattttata attgatagga aatttaccaa gagacatgtg gaacatgtca    780
aaggttcaag aactgtttat tggatggaat aactttacag gtacgtgatt cttgtatgta    840
ttaaatcttg aatactcttc acgaagttcc taatttcact agatatagtc aatttgtgca    900
ttgtctagta acaaacaaag attaatatat gttgtggaga acattttcga aagacactct    960
atgtctgatc tttagcatga taaccatgta cttattttca aaatgaattt gcaggaaata   1020
taccaaatga aatgaaccta ccatctattt gcaggaaagt taacaaagct tgagcatctc   1080
aactatctga aagtctctta caatgagtta tcaggtgaaa taccagatgg agggcctttt   1140
ggtaattttc acagctgaat cattcatcgg caacgaagag ttatgtggac cgcctagatt   1200
ccaagtcaag gtgtgtgaaa tccagaacaa cgtgacaaga agaaacagga agaaaacagt   1260
actaaaattt gttcttggac cagttgcagc tggaggttta gtcatagggg ttttaggcat   1320
gatatggttg ttgaattatc ggagacgtaa caaccaactt attcctttaa ctgattggta   1380
tgatcagtta tcacacaaaa ggttttctta ctatgaactt gttcgaggga ctaacaactt   1440
tgacgaatca aatttgattg gaaagggaag ccttggtatg gtttataagg ggacatttac   1500
aaatgggacc atagctgctg taaaggtttt caatgcacaa ctgcaagatg cattcaagag   1560
gtttgatttg gagtgtaagg ttttgcgtaa cactcgaaat aggaatcttg ttaaggtgat   1620
aagtagttgt gcaaatcttg attttaaggc attggtgttt gagtacatgc ctaatggaga   1680
tcttgattat tggctttact cacacaacaa tttcttggat ttaaacaaga ggctgaaaat   1740
tatgtttgat gtggcttgtg tcgtagagta tctacaccaa ggccattcac ttgtagtggt   1800
ccattgcgac ttgaacatac ttttggatga agacatggtt gccagagtaa gtgattttgg   1860
tatatccaaa ctcttgaccg cgtatgatcc agtggcattg acaaagactt taggcaccat   1920
tggctacacg gcagcaggta ctgatcaaac ttttatttac taattacttt cttcaacttg   1980
tattcgatat gcatatatga tgtatttcat tttaatggca gagtagggat agtgtcaact   2040
atgggggatg tttacagcta cggcatttta ttgatggaaa ccttcacaag aaagaaacca   2100
gtagatgatg agtttgttgg agaccttaca ttgaagagat gggtcgcgga atcatatcct   2160
catagagtca ttgttatgaa ataaaaacga atacacgctg aacgtcactt atgagtcatt   2220
tatctaatat gatccattaa caattgatta atgtaacgca aggaagaaga aaacaatttg   2280
cattgttatg aatgaatgtg tttgtactac aatatataca gtactgacaa gtccagcaaa   2340
ctttctaacc aacttattct aaccaactct actcattatt aatttagctc acttaatcaa   2400
gaaattaaac ttaacaacta actaccatta ctcattcaac tgatcacgga acatcaacac   2460
attttgttga tttctttcac acacaccctc tgcttcgaaa acccctcttt ttaacatgta   2520
agcgacaata tctttttttt aggagagtgt tcaacattga gcataaaaat aataaaatag   2580
agaacaaaaa agatgagtat aaaataaata ataatataag atcgatttta ccgattgtca   2640
attttgtgta tggactaaag aaataacagc ttcacatatc taat                    2684
```

<210> SEQ ID NO 7
<211> LENGTH: 4297
<212> TYPE: DNA
<213> ORGANISM: Solanum habrochaites
<220> FEATURE:
<223> OTHER INFORMATION: >Genomic fragment 7

<400> SEQUENCE: 7

```
ataaataata atataagatc gattttaccg attgtcaatt ttgtgtatgg actaaagaaa     60
taacagcttc acatatctaa tattaaatgt aatactgaat ttcacatatg gtcagaggtg    120
aatccacctg cacccgatat attctttttt aaaaaaatta tatgtatata tatagattgt    180
tgataagacg gtaatatatt taattgtgca ctcttataac gaacaaatga tttgacttgt    240
ccattggaaa aacgaaaagt gtcacataaa ttgagacatg gggagtaaca tttctttctt    300
aaatttttcg tgtgaagtca aactaattca tataaaatga gacggaagga gtactgttta    360
atattaattg catatggtag taaatttgat agacatggtc ccgtgggagt gtgtgttatt    420
tccattgaat aattgagttt gtaattgtta caagtccatt ctaatttcca acaccttact    480
tcatttcaaa aatatactct atggctgaag ctttccttca aattatgtta gagaatctga    540
cttgtttcat ccaagggaac ttggattgat tcttggtttt aaggatgagt tcaaaaagct    600
tcaaagcacg tttactacaa tccaagctgt ggtacaagat gctcagttga agcaattgaa    660
ggacaaggca attgaaaatt ggttgcagaa actcaatggt gctgcatatg aagctgatga    720
catcttggac gaatgtaaaa ctgaggcacc aattatacag aagaagaata aatatgggtg    780
ttatcatcca aacgttatca ctttccgtca caagattggg aaacggatga aaaagattat    840
ggagaaacta gatgcaattg cagcggaacg aattaagttt catttggatg aaaggactat    900
agagagacaa gttgctatac gccaaacagg taaatatttt tctaaataac agctttatat    960
catcaaattc atgtgtgttt tggggatttt gtctaagtag ataagtggtt caaaatctat   1020
tatctaaatc tgtttggtga agtctttaac atatatataa atccatagct tactcatatg   1080
ccccaaagtc taaatgacag gataaagcca gagttgtttt agattttata aattaacaaa   1140
gataataatg taaattcaaa atagtgcatt tgttttatat ttgaaatatg tctgctgctt   1200
ctgatcaagc tgatcattgt cttttgcaaa attcttcttt gtttttttg ctgactctta   1260
ccgatcttgg accaggtttt gttttaaatg aaccacaagt ttatggaaga gacaaagata   1320
aggatgagat agtgaaaatc ctgataaaca atgcccaaac actttcagtc ctcccaatac   1380
ttggtatggg gggactagga aagacgaccc ttgcccaaat ggtcttcaat gatcagagag   1440
taattgagca tttccatccc aaaatatgga tttgtgtctc ggaagattta atgaaaagag   1500
gttgataaag gaaattgtag aatctattga agaaaagtca cttggtgaca tggacttggc   1560
tccacttcaa aagaagcttc gggacttgtt gaatggaaaa agatacttgc ttgtcttgga   1620
tgatgtttgg aatgaagatc aagataagtg ggctaagtta agacaagtct tgaaggttgg   1680
agcaagtggt gcttctgttc taaccactac tcgtcttgaa aaggttggat caattatggc   1740
aacattgcaa ccatatgaat tgtcaaactt ttctcaagaa gattgttggt tgttgttcat   1800
gcaacgtgca tttgggcact aagaagaaat aaatcttaat cttgtggcta tcggaaaggt   1860
gattgtgaga aaatgtggtg gtgtgcctct agcagctaaa actcttggag gtattttgcg   1920
cttcaagaga gaagaaagac agtgggaaca tgtgagagat agtgagattt ggaaattgcc   1980
tcaagaagaa agttctattc tgcctgccct gagacttagt taccatcacc ttccacttga   2040
tttgagacaa tgcttttcat attgtgcagt attcccaaag gataccaaaa tggaaaagga   2100
aaatctaatc tctctgtgga tggcacatgg ttttctttta tcaaaaggaa acttggagct   2160
agaggatgta ggtaatgaag tatggaatga attatacttg aggtcttttt tccaagagat   2220
tgaagttaaa tatgatcgaa cttatttcaa gatgcatgat ctcattcatg atttggcaac   2280
atctctattt tcagcaagca catcaagcag caatatccga gaaataaatg tagaaggtta   2340
```

```
cctacatatg atgtcgattg gtttcgcaaa agtggtgtct tcttactctc ctcctcactt   2400

gcaaaagttt gtctcattga gggttcttaa tctaagttcc atgggactta agcagttacc   2460

gtcctccatt ggagatctag tacatttaag atacttgaac ctctctctca ataacatgcg   2520

tactcttcca aagcagttat gcaagcttca aaatctgcag actcttaatg tagagtattg   2580

ctggtcactt tgttgtttgc caaaagaaac aagtaaactt ggtagtctcc gaaatctctt   2640

acttgatggt tgcgatggat tggattctat gccaccaagg ataggatctt tgacatgcct   2700

taagactcta agtttctttg ttattggcga gagaaaagat tctctacttg gtgaattacg   2760

aaacctgaat ttgtatgggt cagttgaaat cacgcatctt gagagagtga agaatgatag   2820

ggatgcaaaa gaagccaatt tatctgcaaa agaaaatctg cattctttaa gcatgagatg   2880

gaaaaaacca catagatatg aatcagaaga agttgaagtg cttgaatccc tcaaaccaca   2940

ccctaatttg acttctttac taatcactgg cttcagagga ttccgtcttc caaagtggat   3000

gaatcactca gttttgaaaa atgttgtctc tattgcaatt agaggttgtg aaaactgctc   3060

atgcttacca ccgtttggtg atctgccttg tcttgaaagt ctagagttag gagatgggtc   3120

tgcggaactg aagtatgttg aagattctgg attccctaca agaagaaggt ttccatctct   3180

gagaaaactt attatagtca attttgataa tctgaaagga ttgttgaaag aggcaggaga   3240

agagcaattc cccgtgcttg aagagatgac aattagctgg tgtcctgtgc ttgttattcc   3300

gaccctttct tctgtcaaga aattggtagt ttatcggaac atgtcagatg caataggttt   3360

gaggtccata tataatctta gggctcttac ttccctcaac attagccata acttgacagc   3420

tacttcgctc ccagaagaga tgttcaaaag ccttgcaaat ctcaaatact tggaaatctc   3480

tttcatcttc aatctcaaag agctgccaaa cagcctggct agtctcaatg ctttgaagca   3540

tctgaaaatt gaatattgtg acgcactcga gagtctcccc gaggaagggg tgaaaggttt   3600

aacttcactc acagaattat ccataacaaa ttgtaagagg ctaaaatgtt taccggaggg   3660

attgcagcac ctaacaaatt tatcagttag ggaatgtcca acactggcca agcggtgtga   3720

gaagggaata ggacaagact ggtacaaaat tgctcacatt cctcatctgc ttattactaa   3780

tgagatgtaa ttttctgatt tttcttttgg aaacaaatca actatttgta accaattcgt   3840

attggacttt tgagccctgc atttgttcga atacgccttt caacctgtat atcagtgtat   3900

aacaaatgta tacaatatgt atactgctgc tcaaatctgc agatttgatt ttccagcaac   3960

acatttgctg attcttccga cctgtaaatt aatttccagc agctcatttt tttgtgttca   4020

acctgtacgc cagttgtgag ggtctaagac ttgaggagga ggtttgagcc tttacggctc   4080

agcgaggaag tgcagggata cgggcgaaat ccgttaggac tcatggcgaa tgcacgtgaa   4140

acggatcaaa aggaaacata aagaaaaaca gtcaacgatg aaaacaattc tgcatttata   4200

cgcataacta aggcaatgta aatcaaattg aagaatgggc agccaagata aatgaaagca   4260

aataaagcca caatgcatgt tttaaaatac tataacc                            4297
```

<210> SEQ ID NO 8
<211> LENGTH: 4357
<212> TYPE: DNA
<213> ORGANISM: Solanum habrochaites
<220> FEATURE:
<223> OTHER INFORMATION: >Genomic fragment 8

<400> SEQUENCE: 8

```
aattaaattt attcatatga gattatattt tatagaaaaa ataataaaaa tttagattaa     60

aattatattt tttcatttcc gttagattaa agggatatct cgagccattt gtttacaagt    120
```

```
agggtatata tatgctactt tcatgttagg tatatcagct ctaaataaca aaattgatgg    180
gtatatcaga cccttttctc aagtttaaat taatgtgaaa aagttttaag tgtgggtccc    240
atgttgtaca tttaaaattc tcatacaaca gacaaaaggt tagcttttca caaaataaaa    300
tttttcccat gtgaaactca aaataaaata attgcgtaca gacatattta tgcaacacaa    360
cattaattta tttatttacc cattcaataa gtaaaggaat aattataaag ctttgtgctc    420
ttacttttag ctgttcatat ttcattccaa catcgatctt atagatttat tgctaattca    480
caacaattcc agcaatctac atggctgaag ctttccttca aattttgttg aaaaatttga    540
cttctttcat acaagaggaa cttggattgt tttttggttt taagaacgag tttgaaaatc    600
ttaaaagcac gtttactacg atccaagctg tgcttgaaga tgctcaggag aagcaactga    660
aggacaagcc actagaaaat tggttgcaga aactcaatat tgctgcatat gaagttgatg    720
acatcttgga tgaatgtcaa actgaggcag caagactcaa agagactaaa tatgggagtt    780
atcatccaaa ggctatcgct ttccgttaca agattgggaa aaggatgaaa gagataatgg    840
agagactaga tgcaattgct gcagaacgaa gcaagtttca tttggaaaaa aggactacag    900
agagagaagc tgctagacga gaaacaggtg ctcatcttta attagtttat attcattttt    960
ttgcgattat caagttcatg tgtgtttatg gacccaaggg actttttttct aatctaatgt   1020
ttgtctcaag tctaaacaga tttgtaattc taccacttat ttatttagtg aagttcttaa   1080
acatatatac atggtgtaag ccagctcaga taaatccata gtcagttgtt tcggactgaa   1140
cttaacttgg atgtcaattt ttcaaagtca atcatgtttt caactcctcc ccctgattct   1200
catctctttg tagtgcaaaa atcttctctc tgtttttcgc taaacatatt ctcgtgtgaa   1260
catatattgc ttgaaacagg ttttgtttta actgaaccag aaccttatgg aagagacaaa   1320
gaagaagatg agatagtgaa aatcctgata aacaatgccc aacaactttc ggtcctccca   1380
atacttggta tggggggggct aggaaaatcg actcttgccc agatggtctt caatgatcag   1440
agagtaactg accatttcca tcccaaaata tggatttgtg tctcagaaga ttttgatgag   1500
aagaagttga taaaggcaat tgttgaatct atcgaaggaa acccacttgg tgaccacatg   1560
gatttggctc cacttcaaaa gaagcttcag gacatgttga atggaaagag atactttctc   1620
gttttggatg atgtttggaa tgaaaatcaa gaaaagtggg ataagataaa agcagtctta   1680
gaggttggag cacgaggtgc ttctgttcta accaccactc gtcttaaaag gttggatcaa   1740
ttatgggaac tttgcaacca tatgaattgt caaatctgtc tcaagaagat tgttggttgt   1800
tgttcatgaa acgtgcattt gagaaccaag aaaaaaataa atcctaacct tgtggctatc   1860
ggaaaggaga ttgtcaaaaa aagtggtggt gtgcctctag ccgccaagac tcttggaggt   1920
cttttgcgct tcgtggatca agaaagagaa tgggaacatg tgagagataa tgagatttgg   1980
aatctgcctc aagatgaaag ttctattctg cctgccctga gacttagtta tcatcatctt   2040
ccagttgatt tgacacaaag ttttgcatat tgtgcagtat tcccaaagga cacggtaatg   2100
gaaaaaggaa atctaatctc tctctggatg gcacacggtt ttcttttatc gaaaggaaac   2160
ttggagctag aggatgtagg taatcaagta tggaatgaat tatatttaag gtcttttttc   2220
caagagattg aagttaaaga tggtaaaact tatttcaaga tgcatgatct catccatgat   2280
ttggcaacat ctctattttc ggcaagagca tcaagcaaca atatccgtga aataaatgta   2340
aaacggaacc cacatatgat gtcgattggt tttgcaaaag tggtgtcttc ttactctcct   2400
tctcacttgc aaaagtttgt gtcgttgagg gtgcttaatc taagtgaatt aagacttaag   2460
```

-continued

```
catttaccgt cttccattgg agatctagta catttaagat acttgaacct ctaccgcaat   2520
aacatgcgta gtcttccaaa gcagttatgc aagcttcaaa atctacagac tcttgatcta   2580
cagtattgcg ccttactttc gtgtttgcca aatcaaacaa gtcaacttag cagtgtcaga   2640
aatcttttac ttcatggttg ctataaattg aattctatgc caccaaggat aggatctttg   2700
acatgcctta acactcttgg ttgctttgct gtgggaagga agaaaagttg tcaacttggt   2760
gaattacgaa acttgaatct ctatggctca attcaaatca cacatcttga gagactgaag   2820
aatgataggg atgtaaaaga agccaattta tctgcaaaag aaaatctgca ttctttaagc   2880
atgacttgga aaggaccaca tagatatgaa ttagaagaag ttgaagtgct tgaagccctc   2940
aaaccacact ccaatgtgac ttgcttaaca atccatggct tcagaggaat ccgtttccca   3000
gagtggatga atcactcagt tttgaaaaat gttgtctcta ttgatatccg ggttgcgaa   3060
aactgctcgt gcttaccacc ctttggtgag ctgccttgtc taaaaagtct taagttacag   3120
gacgggtctg cggaaatgga gcatgttgat tctggattcc ctacaagaag gaggtttcca   3180
tctctgagaa atcttattat agtcaatttt gataatctga aaggattgct gaaagaggca   3240
ggagaagagc aattccccgt gcttgaagag atggatattt ggtggttccc tgtgtttgtt   3300
attccgaccc tttcttctgt caagaaattg ttagttcatt ggaacatgtc agatgcaata   3360
ggtttgagtt ccatatcaaa tctcagggct cttacttcac tccacattag aactaacttc   3420
atagctactt cgctcccaga agagatgttc aaaagccttg caaatctcaa atacttgaaa   3480
atctctttct tctacaatct caaagagctg ccaaacagcc tggctagtct caatgctttg   3540
aagcatctgg agatgaattg ttgtcccaaa ctggagagtc tccccgagga aggggtgaaa   3600
ggtttaactt cactcacaca gttatccatt acatactgtg agatgctaaa atgtttacca   3660
gagggattgc agcaactcac aaatttatca attaagaatt gtccaacact ggccaagagg   3720
tgtgagaagg gaataggaca agactggtac aaaattgctc acattcctca tctgcttatt   3780
actaatgaga tgtaattttc tgattttctt ttggaaacaa atcaactatt tgtaaaatct   3840
atttgtatta tacttgattt ttcttggtta tgtaacaata aatatttgaa aattttcata   3900
taaaaatagt tacatttcta tatgtataat tcgccagaat aatacatata tatgtataat   3960
atacaattat ttaaccgata tacatatata attcacctct ctcccactct ctgtcctctc   4020
tcactcgcct ctctcctccc tctctcaatt tcgctttcca tatatacaaa tacaattatc   4080
taaaagatat atatatatat atgcaattca tctctctccc actctttgct tcacttgaca   4140
actatgacat ttaacattgg acaagcacaa attgacactt aaaaactggt tacagaaact   4200
caacgctgct gcgtataaag ttgatgactt attgaatgaa tgagaatacg aggcagcaag   4260
actaaagcag tctcgactag gacggtatca tccaaaggct atcaatacaa actcagttgt   4320
ttagaccacg aaaagactgt gaattcaata caggagt                            4357
```

<210> SEQ ID NO 9
<211> LENGTH: 2561
<212> TYPE: DNA
<213> ORGANISM: Solanum habrochaites
<220> FEATURE:
<223> OTHER INFORMATION: >Genomic fragment 9

<400> SEQUENCE: 9

```
aagtctgata tacttctcaa ctttttcatt tggagctgat atatttctcg ttataaaagt     60
gactcatata tgcccttatc gttatacaaa cgactcatat atctgagtca tttgtttaca    120
agtaaggtat cactttctta aaaaagcaat gatatcatct ctaaaacgac aaagattgag    180
```

-continued

```
gggtatatcg atccttttc aaagtttaaa tgaatgagaa aaagttttaa gtgtgggtcc    240
catgttgtac atttaaaatt ctcataaact gacagaaggt tagcttttca caaagtaaaa    300
tttttcccat gtgaaactca aaataaaata attgcgtaca gacatgttta tgcaacacaa    360
cattaattta tttatttacc cattcaataa gtgaaggaat aattataatg ctttgtgctc    420
ttacttttag ctgttcatat ttcattccaa catcgatctt atagatttat tgttaattca    480
caacacttcc agcaatctac atggctgatg ctttccttca aattttgttg acttctttca    540
tacaagagga acttggattg aaaatctaaa aagcacgttt actacgatcc aagctgtgct    600
tgaagatgct caggagaagc aactgaagga caagccaata gaaaattggt tgcacaaact    660
caatgttgct gcatatgaag ttgatgacat cttagatgaa tgtcaaactg gaatttttaa    720
ccaaattaag tcattatata aaataattta ccaaagtaaa atatttttct aaaagtttac    780
aaaactaata taaacgtatt tcatggtaac gttttagggt atattttatt ttttaaaaac    840
taatgacttt aggttgatat cgttctttgt aagtaacgtt ttactcctaa aacgttattt    900
tcaataacat tttactctta aaacgttact catagtaacg ttttactcct aaaacgttat    960
tttcaataac attttactcc taaaacgtta ctatgagtaa cgttttagga gtaaaacgtt   1020
actgtgagta acgtatatca atctgacgcc atcaactttt aaaaaataaa atatatccta   1080
aaacgttact gtggaatacg tttatactag ttttgtaaaa ttttagaaaa acatattatt   1140
ttggtgaatg actttatata atgacttagt ttggttaaaa cctcgtcaaa ctgaggcagc   1200
aagactcaat cagactaaat atgggagtta tcatcctaag gctatcactt tccgttacaa   1260
gattgggaaa aggatgaaag agataatgaa gaaactagat gcaattgctg cagaacgaag   1320
caagtttcat ttggaaaaaa ggactacaga gagagaagct tctagacgag aaacaggtgc   1380
tcatcttaaa tatattagta ttaattacaa caatttaatt agtttatatt catttttttg   1440
ctattatcaa gttcatgtgt gtttatggac ccaagggact tttttctaat ctaatgtttg   1500
tctcaagtct aaacagattt gtaattctac cacttattta tttactgaag ttcttaaaca   1560
tatatacatg gtgtaagcca gctcagataa atccatagtc agttgtttcg gactgaattt   1620
aacttggatg tcaatttttc aaagtcaatc atgttttcaa ctcctccccc tgattctcat   1680
ctctttgtag tgcaaaaatc ttctctctgt ttttcgctaa acatattctc gtgtgaacat   1740
atattgcttg aaacaggttt tgttttaact gaaccagaac cttatggaag agacaaagag   1800
gaagatgaga tagtgaaaat cttgataaac aatgcccaac aactttcggt cctcccaata   1860
cttggtatgg gagggctagg aaattcgacg cttgcccaga tggtcttcaa taatcagaga   1920
gtaactgacc atttcaatcc caaaatatgg atttgtgtct cagaagattt tgatgagaag   1980
aagttgataa aggcaattgt tgaatctatc gaaggaaagt cagttggtga aaacatggat   2040
ttggctccac ttcaaaagaa ggcattgtgt cgatttgaga taatacgaga aaaatataca   2100
tgcgaaaaac aagacaacag atttcgtggt tcaccaataa attggctcgt ccacgggaag   2160
agggcgggtt ttattatgga ggcaaaaacc aattctgaga atagggtttg ccatagcgtc   2220
tatatatagt gtaaactaag cccctaacag gcttgggccc aaaatataaa ttgaatgata   2280
attaagggcc caattcaagg cattcaacaa atctccacct tgacttgaat tctccaagca   2340
gattcttggg cgcactatga tagtgccagg cctcccccct cttcctcggg ttgcccttga   2400
gtataattac ttgacacgat gttgagcaag tcaaacgagt gttgaaactt gctcacgtgg   2460
agccaagctt tgtgaacata tcagcgggat tatcaacagt tctactttct tcaccttgat   2520
```

```
tctcttctca cttctcggga aaatgatacc tccgtcaata t                 2561


<210> SEQ ID NO 10
<211> LENGTH: 3203
<212> TYPE: DNA
<213> ORGANISM: Solanum habrochaites
<220> FEATURE:
<223> OTHER INFORMATION: > Genomic fragment 10

<400> SEQUENCE: 10

acgtcatccg cgagacacaa agatgatcgt cagtgcgcct ttcctccgga atctccatct     60

cgggagtaac gacggcgttc ttgtctttcg acaacggcgc ccgtaaaacc ttgttgtttc    120

aacaaagccc gcatcttgat cgccataaac caaactggct attcctccac cgtgaatttg    180

tcgattttca cgttcaaagc gtacatctca attctcaaga acacccgatt aaccgagagg    240

ctcgatacca atttgttgtg cggaatttga gataatacga gaaaatataa acgcgaaaaa    300

caagacaaca gatttacgtg gttcaccaat aaattggcta cgtccacggg aagagggaac    360

attttattat ggaaggcaaa aaccgtaatt acgaataggg tttgccataa gcgtctatat    420

ataactaaac taagccctta atgcttgggc caaaatatag aattgacaga taattaaggg    480

cccaattcaa ggcattcaat gaagcttcaa gatatgttga atggaaagag atactttctc    540

gttttggatg atgtttggaa tgaaaatcaa gaaaagtggg ataagataaa agcagtctta    600

gaggttggag cacgaggtgc ttctgttcta accaccactc gtcttaaaag ggttggatca    660

attatggaca ctttgcaacc atatgaattg tcaaatctgt ctcaagaaga ttgttggttg    720

ttgtgcattt gagaaccaag aaaaaataaa tcctaacctt atggctatcg gaaaggagat    780

tgtcaaaaaa agtggtggtg tgcctctagc cgccaagact cttggaggtc ttttgcgctt    840

cgtggatcaa gaaagagaat gggaacatgt gagagataat gagatttgga atctgcctca    900

agatgaaagt tctattctgc ctgtcctgag acatagttat catcatcttc cagttaattt    960

aacacaaagt tttgcatatt gtgcagtatt cccaaaggac aaggtaatgg aaaaaggaaa   1020

tttaatatct ctctggatgg cacacggttt tcttttatcg aaaggaaact tggagctgga   1080

ggatgtaggt aatcaagtat ggaatgaatt atacttgagg tctttttttcc aagagattga  1140

agttaaagat ggtaaaactt atttcaagat gcatgatctc atccatgatt tggcaacatc   1200

tctattttcg gcaagagcat caagcagcaa tatccgagaa ataaacgtag aaggttaccc   1260

acatatgatg tcgattggtt tcggaaaagt ggtgtcttct tactctcctt ctcacttgca   1320

aaagtttgtg tcgttgaggg tgcttaatct aagtgaatta agacttaagc gtttaccatc   1380

tttggagatc tagtacattt aagatacctg gatttgtctt acaatagtaa aatgcgcagt   1440

cttccaaagc agttatgcaa gcttcaaaat ctgcagactc ttgatctaaa gtattgctgg   1500

tcactatgtt gtttgccaaa agaaacaagt aaacttggta gtctccgaaa tcttttactt   1560

gatgattgcg atggattgaa ttctatgcca gcaagattag gatctttgac atgccttaag   1620

actctaagta gatttgcagt ggggaggaga aaaagttgtc aacttggtga attctgaaac   1680

ctgaatctgt atgggtcaat tgaaatcacg catcttgaga gagtgaagaa tgatagggat   1740

gcaaaagaag ccaatttatc tgcaaaagaa aatctgcatt ctttaagcat gagttggaat   1800

atcaacgaac cgcgtagata tgaatcagaa gaagttgaag tgcttgaagc cctcaaacca   1860

cactccaatg tgacttgttt aacaatcaaa ggcttcagag gaatccgtct cccagagtgg   1920

atgaatcact cagttttgaa aaatgttgtc tctattacaa ttggaggttg tgaaaacttc   1980

tcatgcttac cactgtttgg tggtctgcct tgtctagaaa gtctagagtt atggaatggg   2040
```

tctgcggaat tggagtatgt tgaagattct ggattcccta caagaagaag gtttccatct 2100
ctgagaaaac ttattatagt gaattttgat aatctgaaag gattgctgaa agaggcagga 2160
gaagagcaat tccccgtgct tgaagagatg aaaattagct gttgtcctgt ttttgttatt 2220
cagacccttt cttctgtgaa gaaattgaat gcttattggc acaagtcaga tgcaacaggt 2280
ttgagttcca tatcaaatct tagggctctt acttccctca acattagcca taactccaca 2340
gctactttgc tcccagaaga gatgttcaaa agccttgcaa ctctcaaata cttgaaaatc 2400
tcttacttcg ataatctcaa agatctgcca aacagcctgg ctagtctcaa tgctttgaag 2460
catctggaga ttaattgttg ttatgtacta gagagtctcc ccgaggaagg ggtgaaaggt 2520
ttaacttcac tcacacagtt atccattgca tactgtgaga tgctaaaatg tttatcagag 2580
ggattgcagc aactcacaaa tttatcaatt acgaattgtc caacactggc caagcgatgt 2640
gagaagggaa taggacaaga ctgatacaaa attgctcaca ttcctcatct gctgattaca 2700
tagtgtcata ctaaattaaa tgattcttat agcaatatta ttggttcaac caacaaaact 2760
aaatctctaa ttatattact taattgcttt tagtttgcta caattatcac tcatgactaa 2820
cattatgtat caattacgtg gtttgtcttc aattttgtat aattagtcat gtttttatat 2880
gtataattcg ctagaataat acagatatat gtataatata caattattta actgatatac 2940
atatataatt cacctctctt ccactctctg tcctctctca cttgcctctg tcctctgcca 3000
atcgacgaga tgagcctacg aaagatttca agttcagact atgatgactg acatcctcac 3060
ttacgcaacg aaatggagtt gatggagtag ccagtgccct tgagtcattc tcttcggtat 3120
cgccttctct catcgttaat ggcgccgcaa ggcactcgac tagcaagtta gaccttagtt 3180
agggcgaaag atttcttgga tgg 3203

<210> SEQ ID NO 11
<211> LENGTH: 4181
<212> TYPE: DNA
<213> ORGANISM: Solanum habrochaites
<220> FEATURE:
<223> OTHER INFORMATION: >Genomic fragment 11

<400> SEQUENCE: 11
atacattatt taatactcca acaactttgt gattccactc tagactacca tcacatatct 60
aatattaatt ataatagtga atttcacata tggccagagg cgaacccacc tgcacccaat 120
atatttttaa aaaaaattca tatgtagatt gttgataaga cgctataata tatttaattg 180
tgcactctta taatgaacaa atgatttgac ttgttcattg aaaaaacaaa aagtgtcaca 240
taaattgaga catgaaaaat aatatttctt ttttaaattt ttcgtgtgaa gtcaaactaa 300
ttcatatata aagcgaaagc ggaaggagta ctgtttaata ttaattgcat atggtagtaa 360
atttgataga catggtcccg tggggtgtgt gttatttcca ttgaataatt gagtttgtaa 420
ttgttacaag tccattctaa tttccaacac cttacttcat ttcaaaaata tagattcatt 480
gcttactcac cacatactcg atggctgaag ctttccttca aattctgtta gaaaatttaa 540
catctttcat acaaggggaa cttggattgt tttttggttt taaggacgaa tttgaaaatc 600
tgaaaagctc gtttactacg atccaagctg tgcttgaaga tgctcaggag aagcaactga 660
aggacaagcc actagaaaat tggttgcaga aactcaatgt tgctgcatat gaagttgatg 720
acatcttgga tgaatatcaa actgaggcag caagactcaa tcagactaaa tatgggagtt 780
atcatccaaa ggctatcgct ttccgctaca agattgggaa aaggatgaaa gagataatga 840

-continued

```
agaaactaga tgcaattgct gcagaacgaa gcaagtttca tttggaaaaa aggactacag    900
agagagaagc tgctagacga caaacaggtg ctcatcttaa atatattagt cttagttaca    960
acaatttaat tagtttatat tcattttttg gcgattatca agttcatctg tgtttatgga   1020
ctgaacttaa cttggatgtc aatttttcaa agtcaatcat gttttcaact ccccccctgat   1080
tcttatctct ttgtagtgca aaaatcttct ctctgttttt cgctaaacat attctcgtgt   1140
gaacatatgt tgcttgaaac aggttttgtt ttaactgaac cagaacttta tggaagagac   1200
aaagaggaag atgagatagt gaaaatcctg ataaacaatg cccaacaact ttcggtcctc   1260
ccaatacttg gtatgggggg gctaggaaaa tcgacgcttg cccagatggt cttcaatgat   1320
cagagagtaa ctgaccattt ccatcccaaa acgtggattt gtgtctcaga aggttttgat   1380
gagaagaagt tgataaaggc aattgttgaa tctatcgaag aaaacccact tggtgacgac   1440
atggatttgg ctccacttca aaagaagctt caggataggt tgaatggaaa gagatacttt   1500
ctcgttttgg atgatgtttg gaatgaaaat caagaaaagt gggataagat aaaagcagtc   1560
ttagaggttg gagcacgagg tgcttctgtt ctaaccacca ctcgtcttaa aagggttgga   1620
tcaattatgg gaactttgca accatatgaa ttgtcaaatc tgtctcaaga agattgttgg   1680
ttgttgttca tgaaacgtgc atttgagaac caagaaaaaa taaatcctaa ccttgtggct   1740
atcggaaagg agattgtcaa aaaaagtggt ggtgtgcctc tagccgccaa aactcttgga   1800
ggtcttttgc gcttcgtgga tcaagaaaga gaatgggaac atgtgagaga taatgagatt   1860
tggaatctgc ctcaagatga aagttttatt ctgcctgccc tgagacttag ttatcatcat   1920
cttccagttg atttaacaca aagttttgca tattgtgcag tattcccaaa ggatacggta   1980
atggaaaaag gaaatctaat ctgtctctgg atggcacacg gtttctttt atcgaaagga   2040
aacttagagc tggaggatgt aggtaatcaa gtatggaatg aattatactt gaggtctttt   2100
ttccaagaga ttgaagttaa agatggtaaa acttatttca agatgcatga tctcatccat   2160
gatttggcaa catctctatt tttggcaaga gcatcaagca gcaatatccg agaaataaac   2220
gtagaaggtt acccacatat gatgtcgatt ggtttcgcaa aagtggtgtc ttcttactct   2280
ccttctcact tgcaaaagtt tgtgtcgttg agggtgctta atctaagtga attaagactt   2340
aagcgtttac catcttccat tggagatcta gtacatttaa gatacttgaa cctctctcgc   2400
aataacatgc gtagtcttcc aaagcagtta tgcaagcttc aaaatctaca gactcttgat   2460
ctacagtatt gctggtcact ttgttgtttg ccaaatcaaa caagtcaagt tagcagtctc   2520
agaaatcttt tacttcatgg ttgccataaa ttgaattcta tgccaccaag gataggatct   2580
ttgacatgcc ttaagactct tggttgcttt gctgtgggaa ggaagaaaag ttgtcaactt   2640
ggtgaattac gaaacctgaa tctgtatggc tcaattcaaa tcacacatct tgagagagtg   2700
aagaatgata gggatgtaaa agaagccaat ttatctgcaa aagaaaatct gcattcttta   2760
atcatggaat gggacgacga tgaacgtcca catagatatg aatcagaaga agttgaagtg   2820
cttgaagctc tcaaaccaca ctccaatgtg acttgtttaa aaatctatag attcagagga   2880
atccgtctcc cagagtggat gaatcactca gttttgaaaa atgttgtctc tattagaatt   2940
ggaggttgtg aaaactgctc atgcttacca ccgtttggtg atttgccttg tctagaaagt   3000
ctagagttat ggagtgggtc tgcggaagtg gagtatgttg aacattctgg attcccaaca   3060
agaagaaggt ttccatctct gagaaaactt attatagaca attttgataa tctgaaagga   3120
ttgctgaaag aggcaggaga agagcaattc cccgtgcttg aagagttgac aattagttgt   3180
tgtcctgtgt ttgttattcc gaccctttct tctgtcaaga aattggtagt ttatgggaac   3240
```

atgtcagatg caacagtttt taggtccata tataatctta gggctcttac ttccctcaac 3300
attagcctta actccatagc tacttcgctc ccagaagaga tgttcaaaag ccttgcaaat 3360
ctcaaatact tggcaatctc tttcttcgac aatctcaaag agctgccaaa cagcctggct 3420
agtctcaatg ctttgaagca tctgaaaatt gaatcttgtt atgcactcga gagtctcccc 3480
gaggaagcgg tgaaaggttt aacttcactc acacagttat ccatagaata ctgtgagatg 3540
ctaaaatgtt taccggagga attgcagcaa ctcacaaatt tatcaattac gaattgtcca 3600
acactggcca agcgatgtga gaagggaata ggacaagact ggtacaaaat tgctcacatt 3660
cctcatctgc tgattacata gtgtcatact aaattaaata attcttatag caatattatt 3720
ggttcaacca acaaaactaa atctctagtt atattattta cttgctcatc atagctatag 3780
tttgctataa tcatcactcg cgattaacat tatgcatcaa ttacgcgggc tgacttcgat 3840
tttgtataat tagtcacgtt tttatgtgta taattcgcca gaatatacgg atatatgtat 3900
aatatataat tatttaaccg atatacatat ataattcacc tctctcccac tctatgtcat 3960
ctctcactcg cctctctcct ccctctctta attttgcttt tcatatatac aaatacatat 4020
gtgtaatata caattatcta aacgatatat atatatgcaa ttcatctctc tcccgctctt 4080
ttgcttcacc tgacaactat gacatttaac tttggatatg cacatttaaa aactggttac 4140
agaaactcaa tgttgctgcg tataaagttg atgacttatt g 4181

<210> SEQ ID NO 12
<211> LENGTH: 1479
<212> TYPE: DNA
<213> ORGANISM: Solanum habrochaites
<220> FEATURE:
<223> OTHER INFORMATION: >Genomic fragment 12

<400> SEQUENCE: 12
acattacaac tgatgaggca caaatgacta tatctagtga aattaacatg cagatgaata 60
ggcatatctt gcagtaaaaa gcatcaaaga gtgacatcat tagtcctcaa tagctttgga 120
tttagaggtt caatcgcgac agatattggg aatctctcct tccttaactt tttggacatt 180
ggaaacaaca gtttccatgg ccaaatacct gatgaaatag ggcgtttgag gcgtttaaaa 240
tacatgtatt tgcagatgaa taatctcgct ggtcaaatcc cagaaagcct tggatttctc 300
acaaggcttc aagttcttca tctttctgaa aatcgtctat ttggaaatgt tccagcttcc 360
attttcagcg tgtcttcttt aaaggacatt gatttgtctc agaattacga gttaactggg 420
agtttaccaa atgagatatg cactaatctt ccagtgttgg aatatatatc cctgcaagat 480
aatcaatttg taggtgaact tcctaaaggt ttaaataaat gctccaaact tgaagttctg 540
tccttgtctt ataacaaatt cactggtaat taactaactt gtaaactttt catttactaa 600
tttcttcttg aattaatcat catttttgtg tgtgtctgtg attttataat tgataggaaa 660
cttaccaaga gacatgtgga acatgtcaaa ggttcaagaa ctttttattg gatggaataa 720
cttaacaggt acgtgattct gtatgtatta aatcttgaat actcttcacg aagttcctaa 780
tttcactaga tatagccaat ttgtgcattg tctagtaata aacaaagatt aatatatttt 840
gtggagaaca ttttcgaaag acactctatg tatgatcttt agcatgataa ccatatactt 900
attttcaaaa tgaatttgca ggaaatatac caaatgaaat gaacctacca tctatttgca 960
ggaaagttaa caaagcttga gcatcttgtt gggttatggg tctttttccc ttcctatttg 1020
gataactaaa agcccaattt ggaccaatcc atttttgcct ataagcccat tcttatgagg 1080
caaatataaa ctgattttag ggtctgattt tcagaacata tagagagttc ttcagcagcc 1140
aaaaagagag aaagagagat tttcgcaggc aaaattcaga tctaatagac aacttcaaat 1200
tgcgattccc gcttcttttc ttatccgatt gagttgattt ttggacagca tattgtcttc 1260
atctcaatct ttgattagaa actgacagag ttggatttgg tggcctgcga ctttcagttt 1320
tgcttttgtc gtgagcgaag ctgcaaaatt ggtgattttg ctcctttaat tttctagatt 1380
tggtgcaatc ttattttgtt gttgctcgtt gtttggcact tgttttgtgg ccaattttgg 1440
agaacaatat tgtaactctt ggtgattata gtggagctt 1479

<210> SEQ ID NO 13
<211> LENGTH: 2084
<212> TYPE: DNA
<213> ORGANISM: Solanum habrochaites
<220> FEATURE:
<223> OTHER INFORMATION: >Genomic fragment 13

<400> SEQUENCE: 13
agcatattgt attcatctca atatttgatt aggaactgac agagttggat ttggtggcct 60
gcagcttcag ttttattgtg aggaattagc tgcaaaattg gtgattttgc tcctttaatt 120
ttctagattt ggtgcaatct tattttgttt tgttgctcat tgtttggcac ttgttttggc 180
caattttgga gaacaatatt gtaactcttg gtgattatag tggagctttt ggtcccgtgg 240
ttttactctt cacatcgaag ggttttccac gtaaatcgtg gtgtcttgtg tgattggttt 300
catattgtct cgttatattt gtttggttga attacctgct gccttagtat catattgctt 360
gtggttgttt gtcttctctt ggttcaaatc gaaaaaggga aagtatagac ttgggtattc 420
ttccgctgtt atcctgtcag gcattcttgg tagtgccttg tctttcccaa cacatctcaa 480
ctatctgaat gtctcttaca atgagttatc aggtgaaata ccagatggag ggccttttgg 540
taattttcac agctgaatca ttcatcggca atgaagagtt atgtggaccg cctagattcc 600
aagtcaagat ttgtgaaatc cgaacaacgt gacaagaaga aacaggaaaa aacaagacta 660
aaatttgttc ttggaccagt gcagctggag gtttagtcat ggggttttag gcatgatatg 720
gttgttgaat tatcggagac gtaacaacca acttattcct ttaactgatt agtatgatcg 780
gttatcacac aaaaagtttt cttactatga acttgtttga gggactaaca actttgactt 840
taatcaaatt tgattggaaa gggaagcctt ggtatggttt ataaggggac atttacaaat 900
gggactatag ccaactgtaa aggttttcaa tgctggcgca agatgcattc aagaggtttg 960
atttggagtg taaggttttg cgtaacaccg aaataggaat cttgttgggt gataagtagt 1020
tgttcaaatc ttgattttaa ggcattggtg tttgagtaca tgcctaatgg agatcttaat 1080
tattggcttt actcacacaa caatttcttg gatttaaaca aaatttgaaa attatgtttg 1140
atgtggcttt gtgtcagaga gtatctacac caaggccatt caaaacatag tggtccatca 1200
tgacttgaac atacttttgg atgaagacat ggttgccgag taagtgattt tggtatattc 1260
aaactcttga ccgccagatg atccaaaggg cattgacaaa gactttaggc accattatcc 1320
tggcactgtg cccgatcaaa tttttattta ctaattactt tcttcaactt gtattcgata 1380
tgcatatatg atgtatttca ttttaatggt agagtacggg tcagaaggga tagtgtcaac 1440
tatgggggat gtttacagct acggcatttt atttatggaa accttcataa gaaagaaatg 1500
atagatgatg agtttgttgg agaccttaca ttgaagagat gggtcatgga atcatatcct 1560
catagagtca ttgttatgaa ataaaaacga atacaagttg aacgtcaatt atgagtcatt 1620
tatctaatat gatccattaa caattgatta atgtaacgca ggaagaagaa aacaatttgc 1680
attgttatga atgaatgtgt ttgtactaca atatatacaa agatcgacaa gtctagcaaa 1740
ctttctaacc aacttattct aaccaactct actcattatt catttagctc acttaatcaa 1800
gaaattagac ctaacaacta actaccatta actcattcaa ctgattgttg ggttataggt 1860
ctttttccct tcctatgtgg ataaataaaa gcccaatttg gaccaaccca tttttgccca 1920
taggcccatt cttatgaggc aaatataagc ctatttaggg tcttattttc agacaaaaca 1980
gatcagtttt tcagcagcca aaaagagaga aagagagatt ttcgcaggca aaaatttaga 2040
tctaatagct aacttcaaat tgcgattttc acttcgtttc ttat 2084

<210> SEQ ID NO 14
<211> LENGTH: 4300
<212> TYPE: DNA
<213> ORGANISM: Solanum habrochaites
<220> FEATURE:
<223> OTHER INFORMATION: >Genomic fragment 14

<400> SEQUENCE: 14
tattccaaaa aatacaaatt cattatttaa tactccaaca actttttgat tccactctag 60
actaccatca catatctaat attaaatgta atactgaatt tcacatatgg tcagaggcga 120
atccatcagc acctgatata ttcttttttt aaaaaaatta tatctatata tacagattgt 180
tgataagacg gtaatatatt taattgtgca ctcttataac gaacaaatga tttgacttgt 240
ccattggaaa aacaaaaagt gtcacataaa ttgagacatg gcgaataata tttctttcct 300
aaatttttcg tgtgaagtca aattaattca tataaaatta gacgaaagga gtaatgttta 360
atagtaattg catatggtag taaatttgat agacgtggtc ccgtgggagt gtgtgttatt 420
tccattgaat aattgagttt gtaattgtta caagtccatt ctaatttcca acaccttact 480
tcatttcaaa aatatactct atggctgaag ctttccttca aattatgtta gagaatctga 540
cttgtttcat ccaaggggaa cttggattga ttcttggttt taaggatgag ttcgaaaagc 600
ttcaaagcac gtttactaca atccaagctg tggtacaaga tgctcagttg aagcaattga 660
aggacaaggc aattgaaaat tggttgcaga aactcaatgg tgctgcatat gaagctgatg 720
acatcttgga cgaatgtaaa actgaggcac caattataca gaagaagaat aaatatgggt 780
gttatcatcc aaacgttatc actttccgtc gcaagattgg gaaaaggatg aaaaagatta 840
tggagaaact agatgcaatt gcagcggaac gaattaagtt tcatttggat gaaaggacta 900
tagagagaca agttgctaca cgccaaacag gtaaatattt ttctaaataa cagctttata 960
tcatcaaatt catgtgtgtt ttggggattt tgtctaagta gataagtggt tcaaaatcta 1020
ttatctaaat ctgtttggtg aagtctttaa catatatata aatccatagc ttactcatat 1080
gccccaaagt ctaaatgaca ggataaagcc agagttgttt tagatcttat aaattaacaa 1140
tgataataat gtgaattcaa aatagtgcat ttgttttata tttgaaatat gtctgctgct 1200
tctgatcaag ctgatcattg tcttttgcaa aattcttctt tgtttttttt gctgactctt 1260
accgatcttg gaccaggttt tgttttaaat gaaccacaag tttatggaag agacaaagat 1320
aaggatgaga tagtgaaaat cctgataaac aatgcccaaa cactttcagt cctcccaata 1380
cttggtatgg ggggactagg aaagacgacc cttgcccaaa tggtcttcaa tgatcagaga 1440
gtaattgaac atttccatcc caaaatatgg atttgtgtct cggaagattt taatgaaaag 1500
aggttgataa agaaaattgt agaatctatt gaagaaaagt cacttggtga catggacttg 1560
gctccacttc aaaagaagct tcaggacttg ctgaatggaa aaaaatattt gcttgtctta 1620

-continued

```
gatgatgttt ggaatgaaga tcaagataag tgggctaagt taagacaagt cttgaaggct   1680
ggagcaagtg gtgcttatgt tctaaccact acccgtcttg aaaaggttgg atcaatcatg   1740
gggacattgc aaccatatga attgtcaaat ttgtctcaag aagattgttg gttgttgttc   1800
atgcaatgtg catttgggca ccaagaagaa atgaatctta atctagtggc tatcggaaag   1860
gtgattgtga aaaaatgtgg tggtgtgcct ctagcagcta aactcttgg aggtattttg   1920
cgcttcaaga gagaagaaag acagtgggaa catgtgagag atagtgagat ttggaattta   1980
cctcaagatg aaagttctat tctgcctgcc ctgagactta gttaccatca ccttccactt   2040
gatttgagac aatgcttttc atattgtgca gtattcccaa aggataccaa aatggaaaag   2100
gaaaatctaa tctctctctg gatggcacat ggttttcttt tatcaaaagg aaacttggag   2160
ctagaggatg taggtaatga agtatggaat gaattatact tgaggtcttt tttccaagag   2220
attgaagttc aatatgatcg aacttatttc aagatgcatg atctcattca tgatttggca   2280
acatctctat tttcagcaag cacatcaagc agcaatatcc gagaaataaa tgtagaaggt   2340
tacctacata tgatgtcgat tggttttata aaagtggtgt cttcttactc tcctcctcac   2400
ttgcaaaagt ttgtctcatt gagggttctt aatctaagtt ccatgggact taagcagtta   2460
ccgtcctcca ttggagatct agtacattta agatacttga acctctctct caataacatg   2520
cgtactcttc caaagcagtt atgcaagctt caaaatctgc agactcttaa tgtagagtat   2580
tgctggtcac tttgttgttt tccaaaagaa acaagtaaac ttggtagtct ccgaaatctc   2640
ttacttgatg gttgcgatgg attggattct atgccaccaa ggataggatc tttgacatgc   2700
cttaagactc taagtttatt tgttattatt agagaaaaga ttctctactt ggtgaattac   2760
ttaaacctga atctgtatgg gtcaattgaa atcacgatct tgagagagtg aagaatgata   2820
gggatgcaaa agaagccaat ttatctgcaa aaaagaaaat ctgcattctt taagcatgag   2880
atgggaagga ccacatagat atgaatcaga agaagttgaa gtgcttgaat ccctcaaacc   2940
acactccaat gtgacttgtt taacaatcac tggcttcaga ggaatccgtc tcccagagtg   3000
gatgaatcac tcagttttga aaaatgttgt ctctattgca attagaggtt gtgaaaactg   3060
ctcatgctta ccaccgtttg gtgatctgcc ttgtctagaa agtctagagt tacggagtgg   3120
gtctgcggaa gtggagtatg ttgaagattc tggattccca acaagaagaa ggtttccatc   3180
tatgagaaaa cttactatag aaaattttga taatctgaaa ggattgctga aagaggcagg   3240
agaagagcaa ttccccgtgc ttgaagagtt gacaattaga tgttgtcctg tgtttgttat   3300
tccgaccctt tcttctgtca agaaattggt agttcatggg aacaagtcag atgcaatagt   3360
tttgaggtcc atatataatc ttagggctct tacttccctc aacattagcc ataacttcac   3420
agctacttcg ctcccagaag agatgttcaa aagccttgca aatctcaaat acttggaaat   3480
cgctttcatc tccaatctca aagagctgcc aaacagcctg gctagtctca atgctttgaa   3540
gcatctgttt attaattgtt gttttgcact agagagtctc cccgaggaag cggtgaaagg   3600
tttaacttca ctcacacagt tatccataac atactgtaag aggctaaaat gtttaccaga   3660
gggattgcag caactaacaa atttatcagt taggtattgt ccaacactgg ccaagcgatg   3720
tgagaaggga ataggacaag actggtacaa aattgctcac attcctcatc tgctgattac   3780
tgattagatg taattttctg atttttcttt tggaaacaaa tcaactattt ataacatcta   3840
tttgtattat acttgatttt tcttgattat gtaacaataa atatttgaaa tttttcatat   3900
taaagattca gaatgagttt tacagctaac tctatattct cacagtttaa taacgtaaat   3960
atgatattta tatcaaatta ttacttatgt tgtgatttga tttatcaaca tgttggagat   4020
```

gattttgaca gtttattaaa gaatttctaa gtttttattg tttgcacaag taacaagcca 4080
taaattaagt ttcgagataa aagtaatttg tgtatcatgg cttaattagt cggaatttca 4140
agttttttct caagttatat atatggcaat ttgtaaaaaa tagatagtat tcattttgat 4200
ttaattcaag tatttttaaa aatatataca aataatatgg gggatacaca cgctaaacgc 4260
gtacccaaaa attagtatat aaagaataat gacgaaaaaa 4300

<210> SEQ ID NO 15
<211> LENGTH: 9902
<212> TYPE: DNA
<213> ORGANISM: Solanum habrochaites
<220> FEATURE:
<223> OTHER INFORMATION: >Genomic fragment 15

<400> SEQUENCE: 15
aagaaactat tgaggatgtg ggaccttggg atggttagtc aaaatgagct tctattatat 60
ccttctgtgt ccttctatta aagctctcct cttcttgttt attttgtgga gtcccaattt 120
tggcgtggcc aattccatga tgccaaattg gtaacaaata cttgaaagag tgatgactca 180
agagagatgg tgaagaaagt agacatagtt caacgaattg aagtcatatt cgagaacaat 240
attatccaga tagttcaatg aagtcattta ttcaaaattc ataagcaaat attaatgtgg 300
aaaagttcta ttcatttcca aattgaacaa aagaagcaaa caatagataa ggtctccaac 360
atggagataa taattgagag taaaaacttc tattgctatt aaatagaatc tgcaattaaa 420
aaaaaaatta catagataca atatggaact tcaatatgta caacttggaa accctttcaa 480
tgcttgaggt ctcagttttt accacattca gatacaaaaa tgtagtaaca atggcaattg 540
tgcgcgattc taaaatggca aaaaaataat gccaacttaa ctatggaaat tatgtacaga 600
tataactaac tataaaactt aaatcgtaca gtggcatatc aacagagcct tcttaggctc 660
tgctgctatc atcaaaaaaa gcttttgact gattctggca gttcatggag tagtataagc 720
ttcggacgat ttgaactgat tcacacagca tgtaactgat ttaaaaattc agttttactc 780
tatcagagtc accaactcct ttcttcccag aagaactagc agccgcttgt tccttcaaag 840
cttccttctc cagtttcttc ttttcagcat cagctgcttg ttcattctca tcacgtgatt 900
ttttaaacat cttcatgaac accaccaaaa tttgtgtcac tgcatccaga aagtaaggaa 960
atgaaaactg acaaagttcg tcacaaacat tgtccggtta aagagttggt gaggaaaaat 1020
ctgttgaagc aattctcaca ccagttaaaa caagatctca aggacaaacg caattcgaga 1080
aatctagccg atggctatat gcactcaaca aaagctacaa aggccataaa tgttgcatcc 1140
cataatcttc acataaagat agacaactaa aaagcatcac tgataaacgc tactggaata 1200
tctatattac caagactgtt tgaacgactg tagttttttc ttttccagat gactgataag 1260
tgataataca gcaagaaaat aacgtatgta tctctaacct tgctcaaagg ggcatcgagc 1320
tggatcttcg ccaaaataca gggataggga gtctgcactc cttccctgca gatttacagg 1380
atagaaaaac aatcaataaa cttggcatgg cttatacatc caggaggctt taaaatatga 1440
cataatggat gcaagaaact caccacttca atataaagag tagtgagaga cttgacttca 1500
gcctcagcag tatcaaggaa attctttaac acctgagaag gaatgcacga gtcacaaacc 1560
gcatatttca gatgtttata acaaaattat atgtacacca aatcacagac atcgcaatca 1620
agtttgactg catcaccaga ctccactcta aaaccatgtc caacacaaac caaattggga 1680
gttttcccag cgcaagcctt tttcacttga ccttgttaag aacacaaatg tcatccatcc 1740

-continued

```
attggggaca cctatcactc ttctaaaaca gtggtacact gcttccttac tttgttttct   1800
caaactatct agaataaagc tttttgatag taaataggga tccttgtaat gtataatgaa   1860
ggaaacctgg ggaaagagga atccgcacaa cgccgttcat ttcatatctg gcgtaagaaa   1920
atctcgagaa tttgataata catttagggg tcgtttggta gagcgtatta agaaaaatca   1980
tggatgcatt agccttgttt attgctagta ccatgtttgg tactcttttc taaactatgt   2040
acaactagtg ttgcattagt tatacactat cgtttattaa agtagattat gatatgacct   2100
tcaaagttaa aatttaaaac taaaaagaaa cattatcttg gaagtacaag taactcattt   2160
ggtttgtagg aataattcac atgttaccat tctcttttct caccttctga aatcctgaag   2220
atattgtacc atcattgtcg gatgcagtaa gttcttgttc aactttctca agacctttac   2280
tcactgcttg catttcttca gccaaagact tcagttgaat ctaaccatat aatatgatgt   2340
aaacaaacat ttcagttcac caaaatacca gtagtactgc aaaggaagac cataataaat   2400
agcaagggta ccttagaagc agcttccaag tgaagaagat ccttgtcaaa atcaagcaac   2460
tctggcattt tctcagcaag gagctgacaa aaaaacgaat ttacacattt ggcatcacat   2520
tgagaagtgc aaacatatat atgccgaaga gtaaagacta aggctggtca agccagctat   2580
agttgatagc taaaggctat caactaaagt tcactgatgg ttgggcaaaa gaacagcata   2640
aacgtagaat actgaaagta gaaaataaat acaaaaacat atagttttct acagaactca   2700
accttctata ttacaggaac ctcatgggtg caccaaaaag caataaggga caagaggcta   2760
ttccttaact gtgcaaatta ctctacactt tcaaaagctc tcctaattct cactctccac   2820
aaaacccaca taagtgcaaa agcatacctt tcacgccttg tgtctcctcc ttcatcttcc   2880
gccatttcag ttgagcaaca ttacttatac agtgacgggc atcacccaaa tttaccaaac   2940
gaacaccaca tttcccacca taaccgagaa gttatcgcac aatctagaag acgattcgcg   3000
tcttcacctg acccccttac acataaaaca ccgcccaaca taagtagttc tcctcttcat   3060
tcttttatca tccatcaaga tcacccctct tgttcctaac caagtgaaaa aacctacctt   3120
tctcagtacc ttagggatcc atatcaaaat atatggaagg ctatctttct tctcattgat   3180
caaaaatttg tccaaagaaa aggactttag caaatttatt cttaggcggc caaaatgaaa   3240
cttagattac aatgaaacct taacaaagac aagaattcaa tgaaacctaa acaaagacaa   3300
ggaccagaca atagagtcta gctaaaaaga atctgggctt gctttttcaa ttcaaatctg   3360
tgagcgagga ttcctctttc tcttctccac aaaaatttga agtggtttat aacttacgga   3420
gtatccgata atctcttgca atcttgtata agcctgtgca gatgaaataa cttgaacatt   3480
tccaggagtc aatcgatttg caccagtcga ccagtgggag cgataatttt aagatataaa   3540
catcatataa ccttcctttt agcctattcc cacttgagcg tacttcacag ctgatacgct   3600
cataatactt gacgccccga aataatgaac agggatagat atggagatac aatttaagaa   3660
aatgaacctt aggcacttca atataagaga agagagaagt agaacaaaat aaagaacaat   3720
gcaactggaa aaatgttgaa aataaagtga acgatataag atggattagt tttcagattt   3780
tcatctttaa gagctgctga ctctcaaaaa tctgctacac cgccttgccg ccgccttctt   3840
gtttgagtgc tcaacagaag cacctatacg cacttggact ttccttaggg tgatttaata   3900
gatttttgt gtattttatt tccaattgtt tcatttggca agatactcta agcttgaaat   3960
ttttaatttc tatttagata gtcttgtatg cctaatttca tgtttgatct tctatttcat   4020
tttagagtat tggagttgat actggatcta gctatcaccg acctactgtc gtactagcgt   4080
caagtgcagc acttagccaa taatccccaa taatagggc tacacttaga caaagtatga   4140
```

atcaagaagt tgtaagtgtt agatgcatgt gtggcattta gctatgttta acctcttttg 4200
ctggagtaat ctctcctttg taaatgatat ggatcaatca acccaccaat agttctagta 4260
attcctgaac tactaagtgt actaccaagc attctaaagc ctcatgcatc ttccttgatt 4320
gtgtagaaca tgccatactt atgtggtgag ccttgcttgt gcactatggc tcccacttgt 4380
gcatcaccat gcctcgtgca tgctacatca tcagaccatg ctcttgtgct aacactatca 4440
ccataccagc ccagccatgc ctccatgaaa cagttcctaa ttttctttgc gttactacta 4500
agacaacgaa tcgtttgatc ttgaaattcc ttgcctcctc tctgttagcc tggtccatgg 4560
ctttgttgca cttgcgcatc atgccacact tatgtttgtg aaccgtgctt gtacactatg 4620
gcttccacta gtgcttcttc accatgcctc atgcatgctt catcttagta gcatcctctt 4680
gtgccaaaac aaccacgcct accagccatg cctaacatgg aactgttccc caatttcttt 4740
aactttctaa ttaaaactta aacaaagaat catttggttt ttgagtgttg aaaccttgaa 4800
agcgctcgcc tcctctaaag tagccccctt catggtttta gatgggttat gacatagacc 4860
tcaaatacac ttggcacttt ttcaatccaa tcatgagcta ctcaacaatt attactgagc 4920
caaaactaat ctgattcaac ttacgcttaa gtcacctcca actcttccca attcagagct 4980
aattgatcaa tactaattac ataaaggtaa aaacagaaag gcatcataat gcagtaattc 5040
taccttgcac agataatgca tcaaggtcat tttgttgttt ctcgcacgag tgtcagaaag 5100
cttaagaaga ctgtccaact tgaaccctac agcagatcct gtaacgtaat tacaaaacaa 5160
agatgttagt cacgatgcct ccacccaaca actgattatt ttcttataga gatatagatc 5220
ttagaaaact gtacctcgtg ctgtaccctg attcagtgca ttacccaatg ttagaatggt 5280
ctgcattatc tgacgtaatt tggcagattc tttcacctac ttgaccagga aattcagtta 5340
gagcctagtt aaatcagaat gtgccaaatc aaacttcata aggtattaaa aatacctctc 5400
tagtagcatc attgattgta ctcaggttac ttctcaagtc cttcacctga acaattcaac 5460
atattatagt caacagaaaa ttaatggcag aatccataga cattagatca ctaagaagta 5520
caagagaaaa tacctgatta gagaaagtga tagtaaatga aaacactcgt aacttggact 5580
caactcgtgg gaccttcatc agctccagga aaaactgaaa cgggtattac ttatccggtt 5640
aattacttat aacttaaagg ataggaaaac ttgtacttcc ccacatatat ggtcaaaatg 5700
gagaagacct gctcacactt tccaagcatc cccttgtccc cattatagtt ctggaaaata 5760
gaacataacc agtaagatca aattgtgaaa tcaagaataa caattaaata tcaaattgca 5820
agtatagact gtcaagaaac taacataact aagttcacaa agagaggggg aaatcaagca 5880
gaaacaagta tggatctaca tacacaaaag actaagatat atgcctatgt ttatacacat 5940
ccacacccac cgggaaagga agttcccagg aaaaggtatc tgcatgatta gacattgaaa 6000
cagacacatg agcatgcacg cacagcatag atgcaagtac atactgtata agcatgaaac 6060
cgccaaatgg gtcattgact tatgggcatc aacctacaca gctacttgca acaaatggca 6120
catcaacaaa actataggct cctgctgttc ctacgactca cttaactatt cttacgttaa 6180
gtacaattgc agaatgtgaa ggttccgact cttgtttcca aatactatgg gcaaaaaact 6240
tcaatatgga gtattttctc taaacgggaa aagttaaaag aagaatcaaa gcaaacttca 6300
gaacatacct ctaatattac ttgtgaactc aaaataaatg actagacaca cattataagc 6360
atattattgt aacttaaact ttgccatgat aggcaagcac agtaggatga gaaagagatt 6420
ataccctcag tgtctccatt tcttcttttg ttgggcaaaa ttttatcaga ttttcaacct 6480
gatcaatgtc cagagctgat gaatccaaag ccaaaatagc attctgtatg acatgcatac 6540
aaatataatt tgtaagaaat ccgcggtaaa ttttcctttg taaacagaaa ttttatttgc 6600
atttgcataa tactggccgc gagttcaaat agcggacccc aacttgtctg gaactgaggc 6660
gcaactgttg ttataatatt agtaaaaaga aatccatggc aaatatttca ttcatttcaa 6720
tgtacctcca ttaaaactca aaataaggaa aaaagaactt ccaaagaaac catgcatgag 6780
catcctaaag aaatgctcgt cagtcattac acttattgaa cacatgcatg aatcagcata 6840
ttgatactgt gcattatgaa acatgatttt gaccaaaggc caaaggatag aatattttat 6900
acaatttcta tcatgattcc tttgaatttc aaaggaaaaa tatccataag agttcaattt 6960
tgaactcttc aagttcggtg aaattacatg atcttttcaa cacaataaaa ttatcaaaaa 7020
tataaaaaat aagaaagtct tttggataaa tagttctaca gctacttcca tagaaagctc 7080
cttttctcct tgtacaaaat aaaggtttct ttatccattt cattgaactc cggctaaaaa 7140
atatttctaa taacgatagt gtctgatcct acttgtgctc gtatcttgac taatttatag 7200
ggtacttgac acctcctatc aacataggta tggggaacta tgccctccaa aatgcaatca 7260
gatgaggaaa accaccaagt cttagttttg gtcgctacta gaaaaaccac ttggccacac 7320
tctaaagtgc tcattgaact ccaccaatat gagaaaagca taactaactt gaaactgaat 7380
tacaaggaga actgttatag gttaatggct aacataaaaa tagtcaaact accaaactcc 7440
tctgtgtatg acctaaatgt tatgtgtagt taaccgattt atacgttctt cattcctttg 7500
ttgagaaaaa atatagatag ttaatcaata tattgtactt ctattaagca gaaacgaaga 7560
tacttcaatt tagagttcag tacataatat aatctttttg atctagtaaa aagattatag 7620
catgaagagt tcaatacata caagatacaa caatcttttc cttttttttg ttgttgagaa 7680
tggactttta gtcaaaccca ttaagctgat tcaataattt tgcagatcta tttgattcat 7740
cagatacata cttctatagt tttagcaaat gtacaaaggg attaaaaaaa actaaaatac 7800
taaattgtaa tcttttggaa aataaagtca aacaacatat gcattcaatt gcatatgtaa 7860
tttgttactt gatttcaatt gataaacaca tcaggattcg ttaattttaa tggctgttta 7920
gtttgtgtta ctttttaaat tattagcagc tcaatttcca aatatctgat tgtcctaaag 7980
cccaagtaaa gatcacataa tctaatagtt tcatctgata aacaataata gattattatc 8040
aaaagaccca cctgttggct agaagacata aattagtgcg caatagataa aagtatcgaa 8100
gctcatagta gaaacgagaa gacacaaaaa gaactcacaa gcatatcagg caggggaatc 8160
ttgatttttg taagcatgat ttcacaattg tatgccctgc gcaaatcaat ctggcaaaag 8220
catatgttaa gaaatcatcc cggtctttta acagttagac caaaatgtaa cacttccagt 8280
ctttcactat aaataatggg agttgtgtaa aataaacctc aatacctcag gaagaaaaag 8340
aagccaacac caatagactg ttcaccaact attccatagt gatctcatat tatacagtga 8400
aagctttgaa aactatcagt ttctttctat agaagttttc tatctctttc ccaatttagc 8460
actaacagat aaattaagaa gcaagtgaac tgcaattcat tcatggtcaa tggccatccc 8520
catgggacac agtgcccatt atgagcacag cctccgcaac tctttcatta gatctagaca 8580
tgtatcgcag cctaataaaa ttactctgtt gcatgaattt acatctcaaa gtattaacac 8640
aacttttaag aatttttcaa aggcaaccat tattttttta tatgattgac tccatccact 8700
aaaccctctg cctaagacgc ccaagagagg tttccccctt tatcccttcg ttaatcaaac 8760
ccccaacctt atggttggag atgaaggacc ttaccctagg atatcactcc agtcaaagat 8820
aattgtctta actttcatga aacagaaatg gtattaccta caggatggag aaaggaggac 8880
ttttccaccc aaagtttatg taatcatcca catccaggct gaaaaaacat aagttcttct 8940
ctataagggc atgcttgttt cgaaacgtca cctatgttaa acccatttaa gcctttctat 9000
ttacttcttt tcttccacct tgttagccac aagataccac aaaaagtgct ctttaaaacc 9060
tatctaatat ttaattgttt tgttaaacta gtaaagaaag gagatacact catcctacaa 9120
cactcacttt actacatgaa agacttgcta gataatgcct actggagaat aacagttgta 9180
gagactggaa acaagataaa gcatatataa cttgccaatt gcactttttc tggtttgttg 9240
atttttgaac cacgtcggcc tccacctttg ctagtgccat cagtagctga agccaccgaa 9300
aacaaattct caagctccgt aatatcaatt tcaggtgctc tgtcatgtac attaataaaa 9360
tcttatcaga actacccata acagacagat aacaaataaa agttgcagta cccaacacaa 9420
actaggttaa gctcaaaggg ctcagaacta ctatatctgt aatctattaa gcattcgaag 9480
ttgaaaccat gagaatgata gtgcttatga caacctgtta aggggtttca cgagacacga 9540
gaaatagcga acaatttagc tctgactatt aacttgaaat gacacacaaa gttctcattg 9600
taatttttca tccccaaaaa taaaatcttt atacctggaa gtattttcct tgttttgcgt 9660
atcagcccat aaactccctt gcatagcccg tgtaactttc gaccaatgta agggcttcaa 9720
tgaagctttt ttcggaggaa ttgaagtacc tcctgtacct cgcccttttc ctagagcagt 9780
tgaacctaca gaggctctta cacgtccggt agatggaggt ggtggcgctg gcacactaag 9840
gccctttcca ccaggcgggg gaggtggagt gggtgtcaaa ccccgcctag ggggtggtgg 9900
ag 9902

<210> SEQ ID NO 16
<211> LENGTH: 2863
<212> TYPE: DNA
<213> ORGANISM: Solanum habrochaites
<220> FEATURE:
<223> OTHER INFORMATION: >Genomic fragment 16

<400> SEQUENCE: 16
ggggaggggt ggaggaggag ctgataaatt acagttagat ggaccccgag gaggaggagg 60
tggaggtgga ggtggaggca aggcacttct agaagtagaa aacgtaggga cagatggtgg 120
atgtggagga gcagaagagc ataaaaggct ctgattagga agtggtggag gtggtggagg 180
tggcggaggt cctctagaaa agctatcagg ggaagttgaa gaagtaggtt gtcttggcgg 240
tgaatgttct ctatggctac caattgaagg tggtggtggt ggtggtggtg gaggtggagg 300
tggaggtgat ctattagaac ttgcaagtgg tggaagcgga cgagtacgtt ggacagaaga 360
agggacacca attataggag gaggtggagg tggtggagga ggcggaggag gtaatgagac 420
ctccttgcta ggagaaccaa acagagaggg tggtgaaggg ggagatggag ctgatgattg 480
agtgactttt atactagaaa tcacagaggc aggtgacgga ggtggtgaag gtagcggaga 540
agaagaggaa gtccttgtat cgcaaatttg aactcccttt aaacgttcag gagaaatggc 600
agtatccaat tgacagttac tttcagaaag agactgaaca ggaccaagat ctgactttga 660
aagcttcatt tgaccctcag aaatcttggg atcagaagtt ccatcagaag ctgaatcctg 720
ttcatctaaa aagttgacat ctgttgtatt agcataacta atactactag ctttctctga 780
gtccagaaaa tccaaactgt cggcaatgct cgatgcatta ttttcttctt cagaatcaaa 840
tggggatgaa tacccactca tcctactttg caaaattgac aaatctttca tatcattcag 900
caccgatagc tgtttaaaca accacaacgc agcatcatca ccagtatcaa cccaatcagc 960

```
accactaaaa agttcttgta cccttgaaaa ggcttcaata ggaagtccac cagtctcctc   1020
accattgaga gctgcagtgg gagcttttag tggagatatg ctctcaacat caccaaataa   1080
aacctgcaaa gcagaaagta taagttagag gagaaatatg aagagcaaag gtgatccaat   1140
aaaacaaaac taatcagaca gtttgtaaat aagtattcac ctcagctcga aagccttttg   1200
gatagcgtgc ctttgaatcc catagaatat ccaggttatc gcagtttaac atcaaaatgt   1260
tagagcgaat aaaagcagtg ttaaacacaa tacggaacat catgacttcc ctttcaggat   1320
ccaggtctaa gtggacacac tccaaaacta catctccttg caccaaacac tgaatatcaa   1380
tcttgatgac atcactgtcc ttctgcaaaa caataacaat catgttgcca cagagcagaa   1440
ttgaagaaga caacaaacaa gatgcagtga tagcaatttt tcacctggcg ataatgtcga   1500
aggcttctac ctttcttcgg catggagtac aacatatgag ttgacaatcc atccttgctg   1560
agaaggttcc ttccaaaaat gcgcacaatt ggcctacacc ctttttgatt gtcaaatctt   1620
ggaatggcac gaagaatgag gcaatccaga gaaagagctt gttcaggagg aggccactcg   1680
ggagatatat ttcttcttga tatatattgc aggtaacgaa gctgagaagg gaatgggttc   1740
aaaggtgaca acaattgcga taaaccttta ggtgcctcac gataaaccat ctcgagagtt   1800
tttctctctc cgctttgtaa ctttctgaaa accaagaaac tggcgaaaat gaaggctaga   1860
aggggccaac cacctctctc acagtgtaac aaaattacat tgttatgatt ttgaagagag   1920
agccaactct cacagataca tagaaaatga tgtatcaatg acaatggcag tacaggacag   1980
ccttcatatt gtcttgggta atccattaca gtcacatcat actcgcataa aatctcagca   2040
aactggctcc ttttctcgcc ttctctgaaa ttgaaagcaa gaaaggagga atctggaaat   2100
tcttcatgta gttcatttat gatttcgtgc aagtaaagct gataaattcc ctcaggcagt   2160
acttcagtcg aaaaacaaga atcaaaaact gcagatattc aacataagat aaaaagatgt   2220
tgagaaaact acaatgcact tccaatgttc aataaaaaac acattataaa gtcaaagcta   2280
gttcctttac catatactct atcatcaagt tccagcaacc catctggggg ccttctatag   2340
aaaaatctac tcaacagcga cataatactg agccaatata tcacctaaat ttacctgaca   2400
tcaaagaaat tcaaacccat tttcattcct ttggtgtccc aatatcaaaa gggtcagaga   2460
atcagctcgt acaaattcaa gaaaatgtga aattcataag aagaactcaa aattaatctc   2520
aaattcagaa tacccacaaa gctaaaaagg gattgaacta tatttcaggc gaaaaaattg   2580
gaacttgaca ccaaataaac tacaacaaga ctgaaacaca cacaaaactc acatggaaaa   2640
tatttgcata taaaacacca aaaaaggaaa tctttgaact gaagcaaacc gacagaagcc   2700
gttgaggaag gattcgagat gtgaggtgaa gaaccgacag tgttgccagt aaagttttca   2760
cctgcgcttt ccgattttag tatgaatttt tttttttttc tgattacgga tttgaactct   2820
ttggagttca aaattttggg aacgaaaaaa aaggggctga ttt                     2863
```

<210> SEQ ID NO 17
<211> LENGTH: 4781
<212> TYPE: DNA
<213> ORGANISM: Solanum habrochaites
<220> FEATURE:
<223> OTHER INFORMATION: >Genomic fragment 17

<400> SEQUENCE: 17

```
attctgactc aaaaataagt ttgattaact cttgagtcaa ttcaaacacc ctcttagttt     60
taattgacat ctataacctc taattttagg tatgtacaaa taaatactta aatttatata    120
aaaattaaac aaattaatat ttgtgatatg tgacattgca taagacaatt ttatatcaac    180
```

-continued

```
gtgatgtcct acctatatta cgccacataa attacatata tattgatctt tcaattttat    240
atcgtttaaa ttatacatat ataccctatc aaaaaagtat tatgcttgtt gaatagttct    300
aacttgtaac atccactttc ctctttccac ttcaatccca aaaacatttc ttacaaattt    360
gcaaaaaaca atgaaaagga cttaattagc aaaagagacc acaaaatgaa agggtcacat    420
ggggtgtgtt aaaactcaag cctaaaaaga ctttgttttg tttttgaata gatatatcac    480
tcaaaaaccc aaaaagcaaa ccagtaaaag gtgaccccaa aaagcttccc cacacacaca    540
ctgaagacaa ctttccagta atggcggcac atgaagaaca acaccaccat catcaacaac    600
aagaacaaga gaaccccatt tcctctttat ccttaaaacc caacaataaa cacttggaga    660
agattttctc ctcatatttg ggtctaagtt tcgctgtctt tcttgggtct ttaccaagaa    720
atgcagtttc tttggttggg agacttcaga accgtaacaa ggagctaact tttcagctta    780
ttgatacaga ggagcagtta aagcagctac ttttcaggag aaaagaggat tcaaaggcaa    840
atgcaagagt tgtggaaatc tttgcaagtc atagacatgc ctggcagcaa gaagagaaga    900
ggttgttaca gcagatcgat gagtgtgatg aagaaattgc tgagttaaga gggagagctg    960
agcagtttga gacaatggaa agtgagttga gggctaatat tgaggacttg aaaagggaga   1020
ttagtgaaag agatgaaatg ttgaacttta tgagtagaag ggttgtgag atggagaata   1080
gtactagtgg agatggtggg agtgatggtg ttggagattg ttatgctgaa atgggtttga   1140
ggtttgggaa agttgggata tctgaaggga tggatttggg ggtagggatg gaagagtgtt   1200
acttggctaa tgggattcct aatgctgaac aaatgagtgg tgtttatgga cagagtaatg   1260
ggtttaactc agaatacttg aattctgctt ctaagttttg ggctgaaaaa gctagtcctt   1320
ggcaggtatg atccattcat tatttctttt tgggaacttt tttgttcttt atagttgttg   1380
ttatttgggg ttttatagtg agtggtgtca taatgtggta aaaataaacg caaaagtcct   1440
ttccaggatc ttcatatgta ggaagaactt ggactaaagt ttgtcgcttt aatgtttgtc   1500
ttatatatgg tttttcatgg tgaaacttat gaataaagtt gcttctttta tttaaccatg   1560
ggattgtact ttaagtacta ccacctgata ttctttcttt tagtgtttat ctgtttgttc   1620
atcttgaggc tgtggaattt gtttttgtat gtgatatctg atgaaacaaa tgatccagag   1680
caattgagga tgaacgaaat taagtaataa aatgtttggc ttatagggtt cttggtgaag   1740
tacaggcctt tatgatcttt cttcacatac ctgaaaattt cacaggaata tccacttcta   1800
attgtttctg ataaagctga aatgaaggtg tttctccagg agtagttcag cgccaaattc   1860
aaattgaatt gtataatgat tacattctga gatgcttatt aatgaaatat gtagtttagt   1920
gtgtactcag tgacctccta cttgtcttgt gatttgtctt tattgttgag actcttgtct   1980
ctattatcta aaattttgaa tggtttgatc ttcttagtgg ctgctgaaag ttcaaactac   2040
ccaggatatg gttttctgtt tactgaaaga taatactcac ctcaactgtt catttttacc   2100
ctatactggt gttatggacc actgcttgaa aaccaggtca ccgttttgta cttttcttct   2160
ttcaccgttt tcgtcctatt agaggtttgc aattcttgct tcaagaatgg tccccttttgg   2220
ctgaatactt tgcatgaagg ttggtttcct ggttatgaag gaagctcaaa aaaatgtatt   2280
cgggtaactc tagaaatccg aaatccgttt aaaacggacc gttttgttgg catagaccac   2340
tgtgcctcta aaataccaac taatgacatc caattatata tccccctttgg tttgggaagt   2400
tcaattctgg ttaaaatgga tccgtatatc agcaaaggat gggctgttat cagtcaacat   2460
ctagtccatc tgttatattt ctgtttaaga ttcatcaacc tcaatggaaa gatgtcctct   2520
```

```
ccctttcttg ttgcaagctg tatcttgtcc ttgtctgtct ctgtatctta ttttccaatt   2580
acaatgttat ctttggtaat tcgttacaca tccttgaaat aaagcaaatg cctccatgaa   2640
acttgaactc cccgcggcct ctaatccagg cactaatctt tcccgttcaa aaggatcact   2700
ggaacatttt cctatacttg gtggatgtgt caaagtttgg actaggtaga gatcacacat   2760
tcaatttatg gctgtgtttt ttgtctttta tcatttttgt ctttttatat tatatagaaa   2820
agaagatctg gattttctta cccttggtac agtcaccctt ttcatttatt tggaaccaga   2880
gggaactgga gcatttcact atgttgtctt caactttaat agaaaggcta aagaaaacac   2940
acaaccttaa aaataaacct aaattgccta actattagtt gatctatgcc ttgtgagctg   3000
gttaaggatt agtcatattt acaatggtta gagcaaaaag agaaataaac atctagatca   3060
caatgcttat attctagttt caagcttgaa tggtaggaga aatgaggttc ttttgactct   3120
tattcagctt cttccttcta tgtgagatgt cctacctatc ttagtaaaac cagcttggta   3180
tttaggatgc tattgggtct taagaaaatg tgttttcttc atgcaggata tgcagtatga   3240
ttctggcgat tcacttcacc atttaaagca ttttgtagca aggtaaacat tctgtgatta   3300
gttagacaga tgcttagatg tttgcatttt gatgttgaat caactaacta gggtgagccc   3360
ttttgctttc tcagacggga ggccccttgg aagatagatg gtgaatcaac aggagtctcc   3420
tccaaactaa agttacttga gcaggagcta ctgaatttgg aaaaaattgg gaagactgat   3480
ttatctaagg taccatcatc aacgcggaag caagtgaaga gataccaagc tctagctggc   3540
aagattgatg atttatgcag aagaatggta attactgcat ctctgcaagc ttattggtta   3600
taactttagt atatggattt caaagcttgt tacatgcatg cttaggtttc tctaagaatg   3660
gacaatagtc ttgattacat ctgctaactc aaatatttag atgttgggtt atactcttag   3720
cttgcacgac taggccttac aattagcttt ttacctaaca caaacataca tctgataatg   3780
atctccctcc ctcttagcag caggccagtg atccttgcga atcaaacctg agtcctgagt   3840
tccggaccca aagacagacc gagtttttgc ttgaagcatt tcgacttcag cagcgtgcat   3900
ctgaaactgc acagaagctg atggtactac aaactgacag tggaaaaagt tattacgggg   3960
acgaatttga agggcaagcc caactagcca ctaaacgatc ctttgactcc atccggaaca   4020
acttaaaaga aatccaacgg aatttagaga tatggcttgc cagaattatt ggggatctgg   4080
agggaatcct ttctcgagat ggtgcttctc gtgtaaggga ttattacata tctagatatc   4140
cttttgttca atagttatgt cttaacatgc tcagtaaaat catgattgaa aaaatgatgt   4200
ataggtcctt cctgttatgt taacaagata gctccagctg aatgaacaat atgaggttga   4260
taagtccatt tatgcacata aatctgcttc acagaagcaa actattaatg ctaactagta   4320
ctttaaagag tgaagatttt tgacagaatt attgctggat gtcactgttc ctgatctgga   4380
tgcttgtcat ttactagttt tacttggtcc cggtctttct ggattaaaaa gttgaaagga   4440
tggtgtggcc ctttgcaact ggataaatgt catgtctaca caaatctggc aaacattaaa   4500
tatttgtgga ccaagtttac agccccattt gatttgaaat cagattgatt ttaagttgat   4560
atttgttttg atttggattc ttaagctgta ttgattattc ttaagcttag caaatgagca   4620
aatcatattt tcatgaataa gatatcaaaa tattctagga agttgaatta acaagttata   4680
tagcttcatg ttactttttt tataaataaa tatttgtaat tatatgttat tataaacttt   4740
caaatatgtt caataaacca aacaacagta atactttctt t                        4781
```

<210> SEQ ID NO 18
<211> LENGTH: 3271

<212> TYPE: DNA
<213> ORGANISM: Solanum habrochaites
<220> FEATURE:
<223> OTHER INFORMATION: >Genomic fragment 18

<400> SEQUENCE: 18
taggaagttg aattaacaag ttatatagct tcatgttact ttttttataa ataaatattt 60
gtaattatat gttattataa actttcaaat atgttcaata aaccaaacaa cagtaatact 120
ttcttttgat aaaagttatt cgcttggtac aaacaatttc ttccgctaga ttttcttttt 180
taaattttaa aattatgggt cttttcttgt aaaaattagg tttcttttc tcacctaacc 240 tagtcgtgga catgagttca taagttgaat aatctctaac taaaaggata gtcaaggatg 300
tgccaccgtc gaacaagaag gatagttaag gacactctca agcaaaggcc agtagcatgt 360
actctaaatt tagtcaaagt tccaatacaa gctttttgag cgccactgtg actttgatag 420
gtggaaaaat aattaaaatt tatctttaat atataatact cccttcattt taccacaata 480
cctattaatt gatgtaatgg cctgaggtta taacttttaa ccatctctgt tctatttatg 540
tcaagaagtg caatcaggtt ttgaaccaag tagctaatca ctcaatataa agaaaccaaa 600
ttcaaacttt tttaggggtt tattatagaa ggttcagaca tacttatagc agtaattttt 660
tttcctagcc aggaaaaggc atacacctgc tgttacacta aaatcaaaca agccacataa 720
tccaattcca ataacaattt aacaacatag atagatgagc cttatgctga agcagcacct 780
tcttccagca actgtttcac cttggtgatg tagtcgttca tggcttcatc ggtggatttt 840
cctgtcatag atgcatgcag tgcaattagt tgtgtttctc atacaaccaa gagaaaggaa 900
gtcaatctga acactgttgt tagatcacat accttcaaca gccttccatg catcccactt 960
tgctctgtct ctcatgttga aaatgccagg acggcctgcc cataagaaag ggcgtaagaa 1020
caaagtgtag ctagtttgag acagcatgta catatgcata agacatttca agcattatac 1080
tcacttgtgt tgacactgcc aacggtggct tgcttgtaaa gtccgtaaag aataagcttg 1140
ttctcattgg tggtactctc aggcaatgtc ttagctttct cagcatgtgc ttcaaattcc 1200
tcctgaaacc caaatagttc agtaaaaagg tgtggtagct gaagttacaa agataaattt 1260
ccaggtatac tttcttagtg ataaaataag gatgagaatc caacttaata gttgagatcg 1320
aaactatttg tgaattaaga gggaactgaa cttatggaaa tctaaaatac aaattgagtg 1380
ttccttcatt gggtaaatga aaagtttgca gttcaggata tcaaatatgt acgaattcat 1440
tgatggactt tagcacaagt gtacgcttag cctagcggtg aaaagggttc attctattta 1500
gccaacccga gttcaattct cgctttattt tattttataa cttgaatccg cttcgtgaaa 1560
atcctaggtc cgccactggt tagtgaaaga gtatttgcaa gaatgttaga caagaaaagc 1620
acaacaatac attcctcaac attgtaagag attctgctgg ccaacatttt gctttgacaa 1680
tgttaagacg caaattttag acacatgtgt taatcataca attctccaac cttttcctct 1740
tctagaaatg cttctattta cagatcacag tgaagcacca aaaacatcct cagataatgt 1800
attatgacct cttcagtttg tttactggtt tgccctgttt gttaccctac gattcaacca 1860
ttaccactca gtagcctaca tacttgtggt aacaggaatc cttttagtgc gaggcgattg 1920
gccaaccaac aatttttgta gtcacttaaa aataggtcag actaaattac atccactata 1980
ggttatgaac agcagagaaa tttcaaagac aggctgaaca caaagtgcac atttccttca 2040
acttttcccc ttccccaata aaagaaatat ggaagggtga tgataggttt ttgaccagga 2100
aacaaaaact agtcttggac taggcaatac aggataggaa agagaaagaa gcgggcgcta 2160
tctcatattc aatttttgct agactattta cacagaagtt ggccaatgta gcaccatata 2220
aatttgagaa agagccattt gttcactact aacattttga tggccctaac tgcacatgaa 2280
ctaatagtaa tctgattcta acatctcgtt ccctgggttt agtcatcgac ttaagcttca 2340
aagtatacac catatatata gccaataata tcaacaatct caaaaactaa aagaagaaga 2400
cattcataag atgaaatctt caaaacattg ttgaaattat ggactacttc tgggccagag 2460
acaatatata tgccttttga taaggccaaa aatgacatac acaaatccgg accaaagtac 2520
tactcatctg ccattacatt cgcactactt cttatcgaat tcagtgctta cattgctata 2580
attaccataa atctttcaac aaggccaaaa atgtacagca taattgaatt cattataaga 2640
tctatttata agatggtatg ccgccactca accacagtat gaactgctaa aaaaaaaata 2700
atcttaaaca tcaattacac caacagatca gatcaatcca atcaccgagc cttcacacta 2760
aataataacc aaacaatcct cacgtaacac agcatccaca aaattacagc acaagctgca 2820
caatcgacaa agaaaactaa cagatccgca aataccaatt gcacaaacaa cacaaaaccc 2880
agaattgaaa acgaacatta atcacagaaa aatacttttc actgtcaaaa aagattaaca 2940
ctcgcttcaa acaagataaa tacatactga aaggcaaaaa aaaaacagaa atctaaaggg 3000
gttttaaaga atttaccttc aacgccattg ttgtggaaat ctgatctggt tagcttgata 3060
aaaacgagag aaaactggag atgtgattgt gatggagatt gaagaagaag ggtgggtata 3120
tatatatagt ggagtattta gcataggaat taacgtaaaa ttcgattcga ttatgataat 3180
ctaaacaagt tgcacttgga tcacttacta gtcatagtgg acccaaaaat tgagtataga 3240
ttatggacct atactatgtg agctccacaa c 3271

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
ggtacaacaa ttgaccaagg 20

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
gctaattaaa aaggaacatc agc 23

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
gctatggcgg agaagtcaag 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
agtcacctcc atagtagacc 20

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
ggatccaagt tgtgttcgaa c 21

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
cttctcatca atgtatgtga tttc 24

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
tgtataacac ctggtgctcc 20

<210> SEQ ID NO 26
<211> LENGTH: 24
<212> TYPE: DNA
<213> ORGANISM: Artificial Sequence
<220> FEATURE:
<223> OTHER INFORMATION: Synthetic Construct

<400> SEQUENCE: 26
ccattttctg ttacaaaatt tcag 24

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
gcttcccaat ttatgctgaa g 21

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
gagcctccca ctatagtaat c 21

-continued

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
agaattatca tttgcaggat cg 22

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
ctatggttcg catgtcatgc 20

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
cacaacggca atataccttg c 21

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
tggaagtatt agaaaggtcc ag 22

<210> SEQ ID NO 33
<211> LENGTH: 22
<212> TYPE: DNA
<213> ORGANISM: Artificial Sequence
<220> FEATURE:
<223> OTHER INFORMATION: Synthetic Construct

<400> SEQUENCE: 33
ccattgagaa taactactgt ac 22

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
ccacaggatg actaacttgg 20

<210> SEQ ID NO 35
<211> LENGTH: 23
<212> TYPE: DNA
<213> ORGANISM: Artificial Sequence
<220> FEATURE:
<223> OTHER INFORMATION: Synthetic Construct

<400> SEQUENCE: 35
tgcagtattg atcgcatctt cta 23

<210> SEQ ID NO 36
<211> LENGTH: 19
<212> TYPE: DNA
<213> ORGANISM: Artificial Sequence
<220> FEATURE:
<223> OTHER INFORMATION: Synthetic Construct

<400> SEQUENCE: 36
gtttgttgct gccctcaaa 19

<210> SEQ ID NO 37
<211> LENGTH: 27
<212> TYPE: DNA
<213> ORGANISM: Artificial Sequence
<220> FEATURE:
<223> OTHER INFORMATION: Synthetic Construct

<400> SEQUENCE: 37
tgatcaagaa ttttgtttta gcataga 27

<210> SEQ ID NO 38
<211> LENGTH: 24
<212> TYPE: DNA
<213> ORGANISM: Artificial Sequence
<220> FEATURE:
<223> OTHER INFORMATION: Synthetic Construct

<400> SEQUENCE: 38
taaagcatca attttgcatt gtct 24

<210> SEQ ID NO 39
<211> LENGTH: 26
<212> TYPE: DNA
<213> ORGANISM: Artificial Sequence
<220> FEATURE:
<223> OTHER INFORMATION: Synthetic Construct

<400> SEQUENCE: 39
tcgaagacta acaaagtcct tgtaga 26

<210> SEQ ID NO 40
<211> LENGTH: 19
<212> TYPE: DNA
<213> ORGANISM: Artificial Sequence
<220> FEATURE:
<223> OTHER INFORMATION: Synthetic Construct

<400> SEQUENCE: 40
gacactccgg cagttcctt 19

<210> SEQ ID NO 41
<211> LENGTH: 23
<212> TYPE: DNA
<213> ORGANISM: Artificial Sequence
<220> FEATURE:
<223> OTHER INFORMATION: Synthetic Construct

<400> SEQUENCE: 41
ttcttatgtg aaaaattggg tgg 23

<210> SEQ ID NO 42

<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
actacgcagt cccacagctt 20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
ttgtttggtg gatccatgtg 20

<210> SEQ ID NO 44
<211> LENGTH: 18
<212> TYPE: DNA
<213> ORGANISM: Artificial Sequence
<220> FEATURE:
<223> OTHER INFORMATION: Synthetic Construct

<400> SEQUENCE: 44
agggaaaggg caaggatg 18

<210> SEQ ID NO 45
<211> LENGTH: 22
<212> TYPE: DNA
<213> ORGANISM: Artificial Sequence
<220> FEATURE:
<223> OTHER INFORMATION: Synthetic Construct

<400> SEQUENCE: 45
gatctaccaa tggctattca tc 22

<210> SEQ ID NO 46
<211> LENGTH: 21
<212> TYPE: DNA
<213> ORGANISM: Artificial Sequence
<220> FEATURE:
<223> OTHER INFORMATION: Synthetic Construct

<400> SEQUENCE: 46
gcaaaactta accggtctaa g 21

<210> SEQ ID NO 47
<211> LENGTH: 23
<212> TYPE: DNA
<213> ORGANISM: Artificial Sequence
<220> FEATURE:
<223> OTHER INFORMATION: Synthetic Construct

<400> SEQUENCE: 47
tctcgatggt tgataatttg ttc 23

<210> SEQ ID NO 48
<211> LENGTH: 21
<212> TYPE: DNA
<213> ORGANISM: Artificial Sequence
<220> FEATURE:
<223> OTHER INFORMATION: Synthetic Construct

<400> SEQUENCE: 48

-continued ggaatcgatt aacactggtt c 21

<210> SEQ ID NO 49
<211> LENGTH: 21
<212> TYPE: DNA
<213> ORGANISM: Artificial Sequence
<220> FEATURE:
<223> OTHER INFORMATION: Synthetic Construct

<400> SEQUENCE: 49
catcttattg aagctctgct g 21

<210> SEQ ID NO 50
<211> LENGTH: 21
<212> TYPE: DNA
<213> ORGANISM: Artificial Sequence
<220> FEATURE:
<223> OTHER INFORMATION: Synthetic Construct

<400> SEQUENCE: 50
caaacagtcc ctattcaaca c 21

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct

<400> SEQUENCE: 51
ggtcttgcgc taatcaaaag 20

<210> SEQ ID NO 52
<211> LENGTH: 22
<212> TYPE: DNA
<213> ORGANISM: Artificial Sequence
<220> FEATURE:
<223> OTHER INFORMATION: Synthetic Construct

<400> SEQUENCE: 52
gcgttgtggt gaaagtttta tc 22

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
cttgtttgga tggttgtcac 20

<210> SEQ ID NO 54
<211> LENGTH: 24
<212> TYPE: DNA
<213> ORGANISM: Artificial Sequence
<220> FEATURE:
<223> OTHER INFORMATION: Synthetic Construct

<400> SEQUENCE: 54
caacaaaaaa tatacaatcc gtcc 24

<210> SEQ ID NO 55
<211> LENGTH: 21
<212> TYPE: DNA

<213> ORGANISM: Artificial Sequence
<220> FEATURE:
<223> OTHER INFORMATION: Synthetic Construct

<400> SEQUENCE: 55
gagatagaag gaaacttacc g 21

<210> SEQ ID NO 56
<211> LENGTH: 20
<212> TYPE: DNA
<213> ORGANISM: Artificial Sequence
<220> FEATURE:
<223> OTHER INFORMATION: Synthetic Construct

<400> SEQUENCE: 56
caattatccc ctcagttctg 20

<210> SEQ ID NO 57
<211> LENGTH: 20
<212> TYPE: DNA
<213> ORGANISM: Artificial Sequence
<220> FEATURE:
<223> OTHER INFORMATION: Synthetic Construct

<400> SEQUENCE: 57
tatgcctgtc cctgaaaagg 20

<210> SEQ ID NO 58
<211> LENGTH: 22
<212> TYPE: DNA
<213> ORGANISM: Artificial Sequence
<220> FEATURE:
<223> OTHER INFORMATION: Synthetic Construct

<400> SEQUENCE: 58
agggtcttgg atcaaatctt ga 22

<210> SEQ ID NO 59
<211> LENGTH: 20
<212> TYPE: DNA
<213> ORGANISM: Artificial Sequence
<220> FEATURE:
<223> OTHER INFORMATION: Synthetic Construct

<400> SEQUENCE: 59
tgtggacttg gagtggtatc 20

<210> SEQ ID NO 60
<211> LENGTH: 21
<212> TYPE: DNA
<213> ORGANISM: Artificial Sequence
<220> FEATURE:
<223> OTHER INFORMATION: Synthetic Construct

<400> SEQUENCE: 60
gtagaaaggg taggcatgtt c 21

<210> SEQ ID NO 61
<211> LENGTH: 21
<212> TYPE: DNA
<213> ORGANISM: Artificial Sequence
<220> FEATURE:
<223> OTHER INFORMATION: Synthetic Construct

<400> SEQUENCE: 61
taccaaagca aacactgcca c 21

<210> SEQ ID NO 62
<211> LENGTH: 22
<212> TYPE: DNA
<213> ORGANISM: Artificial Sequence
<220> FEATURE:
<223> OTHER INFORMATION: Synthetic Construct

<400> SEQUENCE: 62
agccacgaga tatatattgg ag 22

<210> SEQ ID NO 63
<211> LENGTH: 21
<212> TYPE: DNA
<213> ORGANISM: Artificial Sequence
<220> FEATURE:
<223> OTHER INFORMATION: Synthetic Construct

<400> SEQUENCE: 63
gataagaccg ccaataacta g 21

<210> SEQ ID NO 64
<211> LENGTH: 20
<212> TYPE: DNA
<213> ORGANISM: Artificial Sequence
<220> FEATURE:
<223> OTHER INFORMATION: Synthetic Construct

<400> SEQUENCE: 64
gtgatctcca tgagcaaatg 20

<210> SEQ ID NO 65
<211> LENGTH: 21
<212> TYPE: DNA
<213> ORGANISM: Artificial Sequence
<220> FEATURE:
<223> OTHER INFORMATION: Synthetic Construct

<400> SEQUENCE: 65
tgagttgaga tgctgttcta g 21

<210> SEQ ID NO 66
<211> LENGTH: 21
<212> TYPE: DNA
<213> ORGANISM: Artificial Sequence
<220> FEATURE:
<223> OTHER INFORMATION: Synthetic Construct

<400> SEQUENCE: 66
agtccaccaa gacttaaaga g 21

<210> SEQ ID NO 67
<211> LENGTH: 20
<212> TYPE: DNA
<213> ORGANISM: Artificial Sequence
<220> FEATURE:
<223> OTHER INFORMATION: Synthetic Construct

<400> SEQUENCE: 67
gtctgccttc tcttgcatgc 20

<210> SEQ ID NO 68
<211> LENGTH: 21
<212> TYPE: DNA
<213> ORGANISM: Artificial Sequence
<220> FEATURE:

<223> OTHER INFORMATION: Synthetic Construct

<400> SEQUENCE: 68
gttgctccag acagaataag c 21

<210> SEQ ID NO 69
<211> LENGTH: 20
<212> TYPE: DNA
<213> ORGANISM: Artificial Sequence
<220> FEATURE:
<223> OTHER INFORMATION: Synthetic Construct

<400> SEQUENCE: 69
catcgaagag atgtgtaggg 20

<210> SEQ ID NO 70
<211> LENGTH: 21
<212> TYPE: DNA
<213> ORGANISM: Artificial Sequence
<220> FEATURE:
<223> OTHER INFORMATION: Synthetic Construct

<400> SEQUENCE: 70
tgcagttgaa gtagacttca g 21

<210> SEQ ID NO 71
<211> LENGTH: 22
<212> TYPE: DNA
<213> ORGANISM: Artificial Sequence
<220> FEATURE:
<223> OTHER INFORMATION: Synthetic Construct

<400> SEQUENCE: 71
tcaacgttag tggtgatgct ag 22

<210> SEQ ID NO 72
<211> LENGTH: 21
<212> TYPE: DNA
<213> ORGANISM: Artificial Sequence
<220> FEATURE:
<223> OTHER INFORMATION: Synthetic Construct

<400> SEQUENCE: 72
caattgcaga aagtgaagct g 21

<210> SEQ ID NO 73
<211> LENGTH: 22
<212> TYPE: DNA
<213> ORGANISM: Artificial Sequence
<220> FEATURE:
<223> OTHER INFORMATION: Synthetic Construct

<400> SEQUENCE: 73
gtggattcag ttaaaccaga ac 22

<210> SEQ ID NO 74
<211> LENGTH: 22
<212> TYPE: DNA
<213> ORGANISM: Artificial Sequence
<220> FEATURE:
<223> OTHER INFORMATION: Synthetic Construct

<400> SEQUENCE: 74
gacatgtgga acttgacaaa ac 22

<210> SEQ ID NO 75
<211> LENGTH: 21
<212> TYPE: DNA
<213> ORGANISM: Artificial Sequence
<220> FEATURE:
<223> OTHER INFORMATION: Synthetic Construct

<400> SEQUENCE: 75
gcgagagaaa agattctcta c 21

<210> SEQ ID NO 76
<211> LENGTH: 22
<212> TYPE: DNA
<213> ORGANISM: Artificial Sequence
<220> FEATURE:
<223> OTHER INFORMATION: Synthetic Construct

<400> SEQUENCE: 76
cattcttcac tctctcaaga tg 22

<210> SEQ ID NO 77
<211> LENGTH: 23
<212> TYPE: DNA
<213> ORGANISM: Artificial Sequence
<220> FEATURE:
<223> OTHER INFORMATION: Synthetic Construct

<400> SEQUENCE: 77
cgtttggtga tctgccttgt ctt 23

<210> SEQ ID NO 78
<211> LENGTH: 24
<212> TYPE: DNA
<213> ORGANISM: Artificial Sequence
<220> FEATURE:
<223> OTHER INFORMATION: Synthetic Construct

<400> SEQUENCE: 78
tcttcttgta gggaatccag aatc 24

<210> SEQ ID NO 79
<211> LENGTH: 21
<212> TYPE: DNA
<213> ORGANISM: Artificial Sequence
<220> FEATURE:
<223> OTHER INFORMATION: Synthetic Construct

<400> SEQUENCE: 79
gtgtcctgtg cttgttattc c 21

<210> SEQ ID NO 80
<211> LENGTH: 23
<212> TYPE: DNA
<213> ORGANISM: Artificial Sequence
<220> FEATURE:
<223> OTHER INFORMATION: Synthetic Construct

<400> SEQUENCE: 80
cctcaaacct attgcatctg aca 23

<210> SEQ ID NO 81
<211> LENGTH: 21
<212> TYPE: DNA
<213> ORGANISM: Artificial Sequence
<220> FEATURE:
<223> OTHER INFORMATION: Synthetic Construct

<400> SEQUENCE: 81
cggctcagcg aggaagtgca g 21

<210> SEQ ID NO 82
<211> LENGTH: 21
<212> TYPE: DNA
<213> ORGANISM: Artificial Sequence
<220> FEATURE:
<223> OTHER INFORMATION: Synthetic Construct

<400> SEQUENCE: 82
cgttgactgt ttttctttat g 21

<210> SEQ ID NO 83
<211> LENGTH: 20
<212> TYPE: DNA
<213> ORGANISM: Artificial Sequence
<220> FEATURE:
<223> OTHER INFORMATION: Synthetic Construct

<400> SEQUENCE: 83
gtaagctcct tcatgtcagc 20

<210> SEQ ID NO 84
<211> LENGTH: 22
<212> TYPE: DNA
<213> ORGANISM: Artificial Sequence
<220> FEATURE:
<223> OTHER INFORMATION: Synthetic Construct

<400> SEQUENCE: 84
caagtattgt ctgccgagta ac 22

<210> SEQ ID NO 85
<211> LENGTH: 23
<212> TYPE: DNA
<213> ORGANISM: Artificial Sequence
<220> FEATURE:
<223> OTHER INFORMATION: Synthetic Construct

<400> SEQUENCE: 85
gcgtacagac atatttatgc aac 23

<210> SEQ ID NO 86
<211> LENGTH: 22
<212> TYPE: DNA
<213> ORGANISM: Artificial Sequence
<220> FEATURE:
<223> OTHER INFORMATION: Synthetic Construct

<400> SEQUENCE: 86
gaacagctaa aagtaagagc ac 22

<210> SEQ ID NO 87
<211> LENGTH: 21
<212> TYPE: DNA
<213> ORGANISM: Artificial Sequence
<220> FEATURE:
<223> OTHER INFORMATION: Synthetic Construct

<400> SEQUENCE: 87
gttcatgtgt gtttatggac c 21

<210> SEQ ID NO 88
<211> LENGTH: 24

<212> TYPE: DNA
<213> ORGANISM: Artificial Sequence
<220> FEATURE:
<223> OTHER INFORMATION: Synthetic Construct

<400> SEQUENCE: 88
cttcactaaa taaataagtg gtag 24

<210> SEQ ID NO 89
<211> LENGTH: 22
<212> TYPE: DNA
<213> ORGANISM: Artificial Sequence
<220> FEATURE:
<223> OTHER INFORMATION: Synthetic Construct

<400> SEQUENCE: 89
tatggatttg tgtctcagaa ga 22

<210> SEQ ID NO 90
<211> LENGTH: 21
<212> TYPE: DNA
<213> ORGANISM: Artificial Sequence
<220> FEATURE:
<223> OTHER INFORMATION: Synthetic Construct

<400> SEQUENCE: 90
tgtggtcacc aagtgggttt c 21

<210> SEQ ID NO 91
<211> LENGTH: 23
<212> TYPE: DNA
<213> ORGANISM: Artificial Sequence
<220> FEATURE:
<223> OTHER INFORMATION: Synthetic Construct

<400> SEQUENCE: 91
gtcttccaga gcagttatgc aag 23

<210> SEQ ID NO 92
<211> LENGTH: 25
<212> TYPE: DNA
<213> ORGANISM: Artificial Sequence
<220> FEATURE:
<223> OTHER INFORMATION: Synthetic Construct

<400> SEQUENCE: 92
tgagactgct aagttgactt gtttg 25

<210> SEQ ID NO 93
<211> LENGTH: 22
<212> TYPE: DNA
<213> ORGANISM: Artificial Sequence
<220> FEATURE:
<223> OTHER INFORMATION: Synthetic Construct

<400> SEQUENCE: 93
gtacaccaaa tcacagacat cg 22

<210> SEQ ID NO 94
<211> LENGTH: 22
<212> TYPE: DNA
<213> ORGANISM: Artificial Sequence
<220> FEATURE:
<223> OTHER INFORMATION: Synthetic Construct

<400> SEQUENCE: 94

-continued cccaatttgg tttgtgttgg ac 22

<210> SEQ ID NO 95
<211> LENGTH: 20
<212> TYPE: DNA
<213> ORGANISM: Artificial Sequence
<220> FEATURE:
<223> OTHER INFORMATION: Synthetic Construct

<400> SEQUENCE: 95
gaaattcctt gcctcctctc 20

<210> SEQ ID NO 96
<211> LENGTH: 21
<212> TYPE: DNA
<213> ORGANISM: Artificial Sequence
<220> FEATURE:
<223> OTHER INFORMATION: Synthetic Construct

<400> SEQUENCE: 96
gtggaagcca tagtgtacaa g 21

<210> SEQ ID NO 97
<211> LENGTH: 23
<212> TYPE: DNA
<213> ORGANISM: Artificial Sequence
<220> FEATURE:
<223> OTHER INFORMATION: Synthetic Construct

<400> SEQUENCE: 97
catattatac agtgaaagct ttg 23

<210> SEQ ID NO 98
<211> LENGTH: 21
<212> TYPE: DNA
<213> ORGANISM: Artificial Sequence
<220> FEATURE:
<223> OTHER INFORMATION: Synthetic Construct

<400> SEQUENCE: 98
gaattgcagt tcacttgctt c 21

<210> SEQ ID NO 99
<211> LENGTH: 22
<212> TYPE: DNA
<213> ORGANISM: Artificial Sequence
<220> FEATURE:
<223> OTHER INFORMATION: Synthetic Construct

<400> SEQUENCE: 99
ccacaaagct aaaaagggat tg 22

<210> SEQ ID NO 100
<211> LENGTH: 21
<212> TYPE: DNA
<213> ORGANISM: Artificial Sequence
<220> FEATURE:
<223> OTHER INFORMATION: Synthetic Construct

<400> SEQUENCE: 100
tccatgtgag ttttgtgtgt g 21

<210> SEQ ID NO 101
<211> LENGTH: 23
<212> TYPE: DNA
<213> ORGANISM: Artificial Sequence
<220> FEATURE:
<223> OTHER INFORMATION: Synthetic Construct

<400> SEQUENCE: 101
gccacataaa ttacatatag ctg 23

<210> SEQ ID NO 102
<211> LENGTH: 23
<212> TYPE: DNA
<213> ORGANISM: Artificial Sequence
<220> FEATURE:
<223> OTHER INFORMATION: Synthetic Construct

<400> SEQUENCE: 102
gaactattca acaagcataa tac 23

<210> SEQ ID NO 103
<211> LENGTH: 21
<212> TYPE: DNA
<213> ORGANISM: Artificial Sequence
<220> FEATURE:
<223> OTHER INFORMATION: Synthetic Construct

<400> SEQUENCE: 103
accgttcaac ggcaatttag c 21

<210> SEQ ID NO 104
<211> LENGTH: 22
<212> TYPE: DNA
<213> ORGANISM: Artificial Sequence
<220> FEATURE:
<223> OTHER INFORMATION: Synthetic Construct

<400> SEQUENCE: 104
cctatacacc ttaaaaccac tg 22

<210> SEQ ID NO 105
<211> LENGTH: 24
<212> TYPE: DNA
<213> ORGANISM: Artificial Sequence
<220> FEATURE:
<223> OTHER INFORMATION: Synthetic Construct

<400> SEQUENCE: 105
gtcttacaat agtaaaatgc gcag 24

<210> SEQ ID NO 106
<211> LENGTH: 21
<212> TYPE: DNA
<213> ORGANISM: Artificial Sequence
<220> FEATURE:
<223> OTHER INFORMATION: Synthetic Construct

<400> SEQUENCE: 106
gcggttcgtt gatattccaa c 21

<210> SEQ ID NO 107
<211> LENGTH: 20
<212> TYPE: DNA
<213> ORGANISM: Artificial Sequence
<220> FEATURE:
<223> OTHER INFORMATION: Synthetic Construct

<400> SEQUENCE: 107
agcgaaagcg gaaggagtac 20

<210> SEQ ID NO 108
<211> LENGTH: 22
<212> TYPE: DNA
<213> ORGANISM: Artificial Sequence
<220> FEATURE:
<223> OTHER INFORMATION: Synthetic Construct

<400> SEQUENCE: 108
tgtggtgagt aagcaatgaa tc 22

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
gtgtataatt cgccagaata tacgg 25

<210> SEQ ID NO 110
<211> LENGTH: 29
<212> TYPE: DNA
<213> ORGANISM: Artificial Sequence
<220> FEATURE:
<223> OTHER INFORMATION: Synthetic Construct

<400> SEQUENCE: 110
cgtttagata attgtatatt acacatatg 29

<210> SEQ ID NO 111
<211> LENGTH: 26
<212> TYPE: DNA
<213> ORGANISM: Artificial Sequence
<220> FEATURE:
<223> OTHER INFORMATION: Synthetic Construct

<400> SEQUENCE: 111
caaattatta cttatgttgt gatttg 26

<210> SEQ ID NO 112
<211> LENGTH: 24
<212> TYPE: DNA
<213> ORGANISM: Artificial Sequence
<220> FEATURE:
<223> OTHER INFORMATION: Synthetic Construct

<400> SEQUENCE: 112
attaagccat gatacacaaa ttac 24

<210> SEQ ID NO 113
<211> LENGTH: 232
<212> TYPE: DNA
<213> ORGANISM: Artificial Sequence
<220> FEATURE:
<223> OTHER INFORMATION: Synthetic Construct

<400> SEQUENCE: 113
ggaagatttt aatgaaaaga ggttgataaa gaaaattgta gaatctattg aagaaaagtc 60
acttggtgac atggacttgg ctccacttca aaagaagctt caggacttgc tgaatggaaa 120
aaaatatttg cttgtcttag atgatgtttg gaatgaagat caagataagt gggctaagtt 180
aagacaagtc ttgaaggctg gagcaagtgg tgcttatgtt ctaaccacta cc 232

<210> SEQ ID NO 114
<211> LENGTH: 235
<212> TYPE: DNA
<213> ORGANISM: Artificial Sequence
<220> FEATURE:
<223> OTHER INFORMATION: Synthetic Construct

<400> SEQUENCE: 114
agaagatttt gatgagaaga agttgataaa ggcaattgtt gaatctatcg aaggaaaccc 60
acttggtgac cacatggatt tggctccact tcaaaagaag cttcaggaca tgttgaatgg 120
aaagagatac tttctcgttt tggatgatgt ttggaatgaa aatcaagaaa agtgggataa 180
gataaaagca gtcttagagg ttggagcacg aggtgcttct gttctaacca ccact 235

<210> SEQ ID NO 115
<211> LENGTH: 2940
<212> TYPE: DNA
<213> ORGANISM: Solanum habrochaites
<220> FEATURE:
<223> OTHER INFORMATION: coding sequence TBRFV resistance gene

<400> SEQUENCE: 115
atggctgaag ctttccttca aattatgtta gagaatctga cttgtttcat ccaaggggaa 60
cttggattga ttcttggttt taaggatgag ttcgaaaagc ttcaaagcac gtttactaca 120
atccaagctg tggtacaaga tgctcagttg aagcaattga aggacaaggc aattgaaaat 180
tggttgcaga aactcaatgg tgctgcatat gaagctgatg acatcttgga cgaatgtaaa 240
actgaggcac caattataca gaagaagaat aaatatgggt gttatcatcc aaacgttatc 300
actttccgtc gcaagattgg gaaaaggatg aaaaagatta tggagaaact agatgcaatt 360
gcagcggaac gaattaagtt tcatttggat gaaaggacta tagagagaca agttgctaca 420
cgccaaacag gttttgtttt aaatgaacca caagtttatg gaagagacaa agataaggat 480
gagatagtga aaatcctgat aaacaatgcc caaacacttt cagtcctccc aatacttggt 540
atggggggac taggaaagac gacccttgcc caaatggtct tcaatgatca gagagtaatt 600
gaacatttcc atcccaaaat atggatttgt gtctcggaag attttaatga aaagaggttg 660
ataaagaaaa ttgtagaatc tattgaagaa aagtcacttg gtgacatgga cttggctcca 720
cttcaaaaga agcttcagga cttgctgaat ggaaaaaaat atttgcttgt cttagatgat 780
gtttggaatg aagatcaaga taagtgggct aagttaagac aagtcttgaa ggctggagca 840
agtggtgctt atgttctaac cactacccgt cttgaaaagg ttggatcaat catggggaca 900
ttgcaaccat atgaattgtc aaatttgtct caagaagatt gttggttgtt gttcatgcaa 960
tgtgcatttg ggcaccaaga agaaatgaat cttaatctag tggctatcgg aaaggtgatt 1020
gtgaaaaaat gtggtggtgt gcctctagca gctaaaactc ttggaggtat tttgcgcttc 1080
aagagagaag aaagacagtg ggaacatgtg agagatagtg agatttggaa tttacctcaa 1140
gatgaaagtt ctattctgcc tgccctgaga cttagttacc atcaccttcc acttgatttg 1200
agacaatgct tttcatattg tgcagtattc ccaaaggata ccaaaatgga aaaggaaaat 1260
ctaatctctc tctggatggc acatggtttt cttttatcaa aaggaaactt ggagctagag 1320
gatgtaggta atgaagtatg gaatgaatta tacttgaggt ctttttttcca agagattgaa 1380 gttcaatatg atcgaactta tttcaagatg catgatctca ttcatgattt ggcaacatct 1440
ctattttcag caagcacatc aagcagcaat atccgagaaa taaatgtaga aggttaccta 1500
catatgatgt cgattggttt cgcaaaagtg gtgtcttctt actctcctcc tcacttgcaa 1560

-continued

```
aagtttgtct cattgagggt tcttaatcta agttccatgg gacttaagca gttaccgtcc   1620

tccattggag atctagtaca tttaagatac ttgaacctct ctctcaataa catgcgtact   1680

cttccaaagc agttatgcaa gcttcaaaat ctgcagactc ttaatgtaga gtattgctgg   1740

tcactttgtt gttttccaaa agaaacaagt aaacttggta gtctccgaaa tctcttactt   1800

gatggttgcg atggattgga ttctatgcca ccaaggatag gatctttgac atgccttaag   1860

actctaagtt tatttgttat tggcgagaga aaagattctc tacttggtga attacgaaac   1920

ctgaatctgt atgggtcaat tgaaatcacg catcttgaga gagtgaagaa tgatagggat   1980

gcaaaagaag ccaatttatc tgcaaaagaa aatctgcatt ctttaagcat gagatgggaa   2040

ggaccacata gatatgaatc agaagaagtt gaagtgcttg aatccctcaa accacactcc   2100

aatgtgactt gtttaacaat cactggcttc agaggaatcc gtctcccaga gtggatgaat   2160

cactcagttt tgaaaaatgt tgtctctatt gcaattagag gttgtgaaaa ctgctcatgc   2220

ttaccaccgt ttggtgatct gccttgtcta gaaagtctag agttacggag tgggtctgcg   2280

gaagtggagt atgttgaaga ttctggattc ccaacaagaa gaaggtttcc atctatgaga   2340

aaacttacta tagaaaattt tgataatctg aaaggattgc tgaaagaggc aggagaagag   2400

caattccccg tgcttgaaga gttgacaatt agatgttgtc ctgtgtttgt tattccgacc   2460

ctttcttctg tcaagaaatt ggtagttcat gggaacaagt cagatgcaat agttttgagg   2520

tccatatata atcttagggc tcttacttcc ctcaacatta gccataactt cacagctact   2580

tcgctcccag aagagatgtt caaaagcctt gcaaatctca aatacttgga aatcgctttc   2640

atctccaatc tcaaagagct gccaaacagc ctggctagtc tcaatgcttt gaagcatctg   2700

tttattaatt gttgttttgc actagagagt ctccccgagg aagcggtgaa aggtttaact   2760

tcactcacac agttatccat aacatactgt aagaggctaa aatgtttacc agagggattg   2820

cagcaactaa caaatttatc agttaggtat tgtccaacac tggccaagcg atgtgagaag   2880

ggaataggac aagactggta caaaattgct cacattcctc atctgctgat tactgattag   2940
```

```
<210> SEQ ID NO 116
<211> LENGTH: 979
<212> TYPE: PRT
<213> ORGANISM: Solanum habrochaites
<220> FEATURE:
<223> OTHER INFORMATION: TRBFV resistance protein

<400> SEQUENCE: 116

Met Ala Glu Ala Phe Leu Gln Ile Met Leu Glu Asn Leu Thr Cys Phe
1               5                   10                  15

Ile Gln Gly Glu Leu Gly Leu Ile Leu Gly Phe Lys Asp Glu Phe Glu
            20                  25                  30

Lys Leu Gln Ser Thr Phe Thr Thr Ile Gln Ala Val Val Gln Asp Ala
        35                  40                  45

Gln Leu Lys Gln Leu Lys Asp Lys Ala Ile Glu Asn Trp Leu Gln Lys
    50                  55                  60

Leu Asn Gly Ala Ala Tyr Glu Ala Asp Asp Ile Leu Asp Glu Cys Lys
65                  70                  75                  80

Thr Glu Ala Pro Ile Ile Gln Lys Lys Asn Lys Tyr Gly Cys Tyr His
                85                  90                  95

Pro Asn Val Ile Thr Phe Arg Arg Lys Ile Gly Lys Arg Met Lys Lys
            100                 105                 110

Ile Met Glu Lys Leu Asp Ala Ile Ala Ala Glu Arg Ile Lys Phe His
        115                 120                 125
```

-continued

```
Leu Asp Glu Arg Thr Ile Glu Arg Gln Val Ala Thr Arg Gln Thr Gly
    130                 135                 140

Phe Val Leu Asn Glu Pro Gln Val Tyr Gly Arg Asp Lys Asp Lys Asp
145                 150                 155                 160

Glu Ile Val Lys Ile Leu Ile Asn Asn Ala Gln Thr Leu Ser Val Leu
                165                 170                 175

Pro Ile Leu Gly Met Gly Gly Leu Gly Lys Thr Thr Leu Ala Gln Met
            180                 185                 190

Val Phe Asn Asp Gln Arg Val Ile Glu His Phe His Pro Lys Ile Trp
        195                 200                 205

Ile Cys Val Ser Glu Asp Phe Asn Glu Lys Arg Leu Ile Lys Lys Ile
    210                 215                 220

Val Glu Ser Ile Glu Glu Lys Ser Leu Gly Asp Met Asp Leu Ala Pro
225                 230                 235                 240

Leu Gln Lys Lys Leu Gln Asp Leu Leu Asn Gly Lys Lys Tyr Leu Leu
                245                 250                 255

Val Leu Asp Asp Val Trp Asn Glu Asp Gln Asp Lys Trp Ala Lys Leu
            260                 265                 270

Arg Gln Val Leu Lys Ala Gly Ala Ser Gly Ala Tyr Val Leu Thr Thr
        275                 280                 285

Thr Arg Leu Glu Lys Val Gly Ser Ile Met Gly Thr Leu Gln Pro Tyr
    290                 295                 300

Glu Leu Ser Asn Leu Ser Gln Glu Asp Cys Trp Leu Leu Phe Met Gln
305                 310                 315                 320

Cys Ala Phe Gly His Gln Glu Glu Met Asn Leu Asn Leu Val Ala Ile
                325                 330                 335

Gly Lys Val Ile Val Lys Lys Cys Gly Gly Val Pro Leu Ala Ala Lys
            340                 345                 350

Thr Leu Gly Gly Ile Leu Arg Phe Lys Arg Glu Glu Arg Gln Trp Glu
        355                 360                 365

His Val Arg Asp Ser Glu Ile Trp Asn Leu Pro Gln Asp Glu Ser Ser
    370                 375                 380

Ile Leu Pro Ala Leu Arg Leu Ser Tyr His His Leu Pro Leu Asp Leu
385                 390                 395                 400

Arg Gln Cys Phe Ser Tyr Cys Ala Val Phe Pro Lys Asp Thr Lys Met
                405                 410                 415

Glu Lys Glu Asn Leu Ile Ser Leu Trp Met Ala His Gly Phe Leu Leu
            420                 425                 430

Ser Lys Gly Asn Leu Glu Leu Glu Asp Val Gly Asn Glu Val Trp Asn
        435                 440                 445

Glu Leu Tyr Leu Arg Ser Phe Phe Gln Glu Ile Glu Val Gln Tyr Asp
    450                 455                 460

Arg Thr Tyr Phe Lys Met His Asp Leu Ile His Asp Leu Ala Thr Ser
465                 470                 475                 480

Leu Phe Ser Ala Ser Thr Ser Ser Ser Asn Ile Arg Glu Ile Asn Val
                485                 490                 495

Glu Gly Tyr Leu His Met Met Ser Ile Gly Phe Ala Lys Val Val Ser
            500                 505                 510

Ser Tyr Ser Pro Pro His Leu Gln Lys Phe Val Ser Leu Arg Val Leu
        515                 520                 525

Asn Leu Ser Ser Met Gly Leu Lys Gln Leu Pro Ser Ser Ile Gly Asp
    530                 535                 540
```

```
Leu Val His Leu Arg Tyr Leu Asn Leu Ser Leu Asn Asn Met Arg Thr
545                 550                 555                 560

Leu Pro Lys Gln Leu Cys Lys Leu Gln Asn Leu Gln Thr Leu Asn Val
                565                 570                 575

Glu Tyr Cys Trp Ser Leu Cys Cys Phe Pro Lys Glu Thr Ser Lys Leu
            580                 585                 590

Gly Ser Leu Arg Asn Leu Leu Leu Asp Gly Cys Asp Gly Leu Asp Ser
        595                 600                 605

Met Pro Pro Arg Ile Gly Ser Leu Thr Cys Leu Lys Thr Leu Ser Leu
    610                 615                 620

Phe Val Ile Gly Glu Arg Lys Asp Ser Leu Leu Gly Glu Leu Arg Asn
625                 630                 635                 640

Leu Asn Leu Tyr Gly Ser Ile Glu Ile Thr His Leu Glu Arg Val Lys
                645                 650                 655

Asn Asp Arg Asp Ala Lys Glu Ala Asn Leu Ser Ala Lys Glu Asn Leu
            660                 665                 670

His Ser Leu Ser Met Arg Trp Glu Gly Pro His Arg Tyr Glu Ser Glu
        675                 680                 685

Glu Val Glu Val Leu Glu Ser Leu Lys Pro His Ser Asn Val Thr Cys
    690                 695                 700

Leu Thr Ile Thr Gly Phe Arg Gly Ile Arg Leu Pro Glu Trp Met Asn
705                 710                 715                 720

His Ser Val Leu Lys Asn Val Val Ser Ile Ala Ile Arg Gly Cys Glu
                725                 730                 735

Asn Cys Ser Cys Leu Pro Pro Phe Gly Asp Leu Pro Cys Leu Glu Ser
            740                 745                 750

Leu Glu Leu Arg Ser Gly Ser Ala Glu Val Glu Tyr Val Glu Asp Ser
        755                 760                 765

Gly Phe Pro Thr Arg Arg Arg Phe Pro Ser Met Arg Lys Leu Thr Ile
    770                 775                 780

Glu Asn Phe Asp Asn Leu Lys Gly Leu Leu Lys Glu Ala Gly Glu Glu
785                 790                 795                 800

Gln Phe Pro Val Leu Glu Glu Leu Thr Ile Arg Cys Cys Pro Val Phe
                805                 810                 815

Val Ile Pro Thr Leu Ser Ser Val Lys Lys Leu Val Val His Gly Asn
            820                 825                 830

Lys Ser Asp Ala Ile Val Leu Arg Ser Ile Tyr Asn Leu Arg Ala Leu
        835                 840                 845

Thr Ser Leu Asn Ile Ser His Asn Phe Thr Ala Thr Ser Leu Pro Glu
    850                 855                 860

Glu Met Phe Lys Ser Leu Ala Asn Leu Lys Tyr Leu Glu Ile Ala Phe
865                 870                 875                 880

Ile Ser Asn Leu Lys Glu Leu Pro Asn Ser Leu Ala Ser Leu Asn Ala
                885                 890                 895

Leu Lys His Leu Phe Ile Asn Cys Cys Phe Ala Leu Glu Ser Leu Pro
            900                 905                 910

Glu Glu Ala Val Lys Gly Leu Thr Ser Leu Thr Gln Leu Ser Ile Thr
        915                 920                 925

Tyr Cys Lys Arg Leu Lys Cys Leu Pro Glu Gly Leu Gln Gln Leu Thr
    930                 935                 940
```

-continued

```
Asn Leu Ser Val Arg Tyr Cys Pro Thr Leu Ala Lys Arg Cys Glu Lys
945                 950                 955                 960

Gly Ile Gly Gln Asp Trp Tyr Lys Ile Ala His Ile Pro His Leu Leu
                965                 970                 975

Ile Thr Asp
```